United States Patent
Zhang et al.

(10) Patent No.: US 10,696,986 B2
(45) Date of Patent: Jun. 30, 2020

(54) PROTECTED GUIDE RNAS (PGRNAS)

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Feng Zhang, Cambridge, MA (US); Omar O. Abudayyeh, Boston, MA (US); James E. Dahlman, Cambridge, MA (US); Patrick Hsu, San Diego, CA (US); David A. Scott, Cambridge, MA (US)

(73) Assignees: THE BOARD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 57 days.

(21) Appl. No.: 15/620,098

(22) Filed: Jun. 12, 2017

(65) Prior Publication Data
US 2017/0283831 A1 Oct. 5, 2017

Related U.S. Application Data

(63) Continuation-in-part of application No. PCT/US2015/065385, filed on Dec. 11, 2015.

(60) Provisional application No. 62/180,709, filed on Jun. 17, 2015, provisional application No. 62/096,708, filed on Dec. 24, 2014, provisional application No. 62/091,455, filed on Dec. 12, 2014.

(51) Int. Cl.
| | |
|---|---|
| C12N 15/90 | (2006.01) |
| C12N 15/11 | (2006.01) |
| A01K 67/027 | (2006.01) |
| C07K 14/47 | (2006.01) |
| C12N 9/22 | (2006.01) |
| C12N 9/96 | (2006.01) |

(52) U.S. Cl.
CPC ........ *C12N 15/907* (2013.01); *A01K 67/0275* (2013.01); *C07K 14/4702* (2013.01); *C12N 9/22* (2013.01); *C12N 9/96* (2013.01); *C12N 15/11* (2013.01); *C12N 15/111* (2013.01); *C12Y 301/21004* (2013.01); *A01K 2217/07* (2013.01); *A01K 2227/105* (2013.01); *C12N 2310/20* (2017.05)

(58) Field of Classification Search
CPC .................................................. C12N 15/907
See application file for complete search history.

(56) References Cited

U.S. PATENT DOCUMENTS

| | | |
|---|---|---|
| 5,622,856 A | 4/1997 | Natsoulis |
| 6,251,677 B1 | 6/2001 | Wilson et al. |
| 7,601,492 B2 | 10/2009 | Fu et al. |
| 7,691,995 B2 | 4/2010 | Zamore et al. |
| 8,697,359 B1 | 4/2014 | Zhang |
| 8,865,406 B2 | 10/2014 | Zhang et al. |
| 8,871,445 B2 | 10/2014 | Cong et al. |
| 8,889,418 B2 | 11/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 9,549,901 B2 | 1/2017 | Shi et al. |
| 9,597,357 B2 | 3/2017 | Gregory et al. |
| 9,623,071 B2 | 4/2017 | Guo et al. |
| 9,834,791 B2 | 12/2017 | Zhang et al. |
| 2003/0186238 A1 | 10/2003 | Allawi et al. |
| 2004/0111221 A1 | 6/2004 | Beattie et al. |
| 2005/0196851 A1 | 9/2005 | Uckun |

(Continued)

FOREIGN PATENT DOCUMENTS

| | | |
|---|---|---|
| BR | 112015013784 | 7/2017 |
| CN | 101228176 | 7/2008 |

(Continued)

OTHER PUBLICATIONS

Prashant Mali et al., CAS9 Transcriptional Activators for Target Specificity Screening and Paired Nickases . . . , Nature Biotechnology (2013) vol. 31, No. 9, p. 833-838.

(Continued)

*Primary Examiner* — Thaian N. Ton
*Assistant Examiner* — David A. Montanari
(74) *Attorney, Agent, or Firm* — Foley & Lardner LLP; Sunit Talapatra; Tianran Yan

(57) ABSTRACT

The invention provides for systems, methods, and compositions for altering expression of target gene sequences and related gene products. Provided are structural information on the Cas protein of the CRISPR-Cas system, use of this information in generating modified components of the CRISPR complex, vectors and vector systems which encode one or more components or modified components of a CRISPR complex, as well as methods for the design and use of such vectors and components. Also provided are methods of directing CRISPR complex formation in eukaryotic cells and methods for utilizing the CRISPR-Cas system. In particular the present invention comprehends optimized functional CRISPR-Cas enzyme systems, wherein the guide sequence is modified by secondary structure to increase the specificity of the CRISPR-Cas system and whereby the secondary structure can protect against exonuclease activity and allow for 5' additions to the guide sequence.

29 Claims, 23 Drawing Sheets

Specification includes a Sequence Listing.

(56) References Cited

U.S. PATENT DOCUMENTS

| | | |
|---|---|---|
| 2005/0220796 A1 | 10/2005 | Dynan et al. |
| 2006/0178297 A1 | 8/2006 | Troy et al. |
| 2006/0234247 A1 | 10/2006 | Puttaraju et al. |
| 2007/0016012 A1 | 1/2007 | Hartlep et al. |
| 2007/0244031 A1 | 10/2007 | Lu et al. |
| 2010/0055798 A1 | 3/2010 | Battersby |
| 2010/0076057 A1 | 3/2010 | Sontheimer et al. |
| 2010/0081707 A1 | 4/2010 | Ali et al. |
| 2010/0093617 A1 | 4/2010 | Barrangou et al. |
| 2010/0233084 A1 | 9/2010 | Narasimhaswamy et al. |
| 2011/0016540 A1 | 1/2011 | Weinstein et al. |
| 2011/0059502 A1 | 3/2011 | Chalasani |
| 2011/0189776 A1 | 8/2011 | Terns et al. |
| 2011/0223638 A1 | 9/2011 | Wiedenheft et al. |
| 2011/0239315 A1 | 9/2011 | Bonas et al. |
| 2012/0029891 A1 | 2/2012 | Behlke et al. |
| 2013/0096182 A1 | 4/2013 | Chatterjee et al. |
| 2013/0130248 A1 | 5/2013 | Haurwitz et al. |
| 2013/0315831 A1 | 11/2013 | Shi et al. |
| 2014/0068797 A1 | 3/2014 | Doudna et al. |
| 2014/0294771 A1 | 10/2014 | Schaffer et al. |
| 2014/0295557 A1 | 10/2014 | Joung et al. |
| 2014/0315985 A1 | 10/2014 | May et al. |
| 2014/0342456 A1 | 11/2014 | Mali et al. |
| 2014/0356956 A1 | 12/2014 | Church et al. |
| 2014/0357530 A1 | 12/2014 | Zhang et al. |
| 2015/0045546 A1 | 2/2015 | Siksnys et al. |
| 2015/0071899 A1 | 3/2015 | Liu et al. |
| 2015/0071903 A1 | 3/2015 | Liu et al. |
| 2015/0071906 A1 | 3/2015 | Liu et al. |
| 2015/0232881 A1 | 8/2015 | Glucksmann et al. |
| 2015/0247150 A1 | 9/2015 | Zhang et al. |
| 2015/0291965 A1 | 10/2015 | Zhang et al. |
| 2015/0322457 A1 | 11/2015 | Kim et al. |
| 2015/0353905 A1 | 12/2015 | Weiss et al. |
| 2016/0017366 A1 | 1/2016 | Chen et al. |
| 2016/0024510 A1 | 1/2016 | Bikard et al. |
| 2016/0024524 A1 | 1/2016 | Joung et al. |
| 2016/0130609 A1 | 5/2016 | Doudna et al. |
| 2016/0237456 A1 | 8/2016 | Church et al. |
| 2016/0251648 A1 | 9/2016 | Wang et al. |
| 2016/0281072 A1 | 9/2016 | Zhang |
| 2016/0298135 A1 | 10/2016 | Chen et al. |
| 2016/0298137 A1 | 10/2016 | Chen et al. |
| 2016/0324938 A1 | 11/2016 | Bikard et al. |
| 2016/0340662 A1 | 11/2016 | Zhang et al. |
| 2017/0175144 A1 | 6/2017 | Zhang et al. |
| 2018/0127783 A1 | 5/2018 | Zhang et al. |
| 2019/0010471 A1 | 1/2019 | Zhang et al. |

FOREIGN PATENT DOCUMENTS

| | | |
|---|---|---|
| CN | 103388006 | 11/2013 |
| CN | 103668472 | 3/2014 |
| CN | 104854241 A | 8/2015 |
| EP | 2 591 770 A2 | 5/2013 |
| EP | 2 784 162 | 1/2014 |
| EP | 2 764 103 | 8/2014 |
| EP | 2 771 468 | 9/2014 |
| EP | 2 828 386 A1 | 1/2015 |
| FR | 2872170 A1 | 12/2005 |
| JP | 2004-519245 A | 7/2004 |
| JP | 2004-537285 A | 12/2004 |
| JP | 2005-509409 A | 4/2005 |
| JP | 2006-513694 A | 4/2006 |
| JP | 2006-518996 A | 8/2006 |
| JP | 2007-501626 A | 2/2007 |
| JP | 2009-502170 A | 1/2009 |
| JP | 2009-536827 A | 10/2009 |
| JP | 2010-522547 A | 7/2010 |
| JP | 2012-508235 | 4/2012 |
| JP | 2012-510812 A | 5/2012 |
| JP | 2012-511332 A | 5/2012 |
| JP | 2012-529287 A | 11/2012 |
| JP | 2013-500045 A | 1/2013 |
| JP | 2013-518602 A | 5/2013 |
| JP | 2013-544077 A | 12/2013 |
| JP | 2014-526279 A | 10/2014 |
| JP | 2015-523856 A | 8/2015 |
| JP | 2016-500003 A | 1/2016 |
| JP | 2016-500262 | 1/2016 |
| JP | 2016-501532 A | 1/2016 |
| JP | 2016-025710 A | 2/2016 |
| JP | 2016-502840 A | 2/2016 |
| JP | 2016-504026 A | 2/2016 |
| JP | 2016-093196 | 5/2016 |
| JP | 2016-516169 A | 6/2016 |
| JP | 2016-517954 A | 6/2016 |
| JP | 2016-131404 A | 7/2016 |
| JP | 2016-520317 A | 7/2016 |
| JP | 2016-521554 A | 7/2016 |
| JP | 2016-521975 A | 7/2016 |
| JP | 2016-182140 A | 10/2016 |
| JP | 2017-501151 A | 1/2017 |
| JP | 2017-501699 | 1/2017 |
| JP | 6395765 | 9/2018 |
| RU | 2009136452 A | 4/2011 |
| WO | WO-02/074968 A1 | 9/2002 |
| WO | WO-02/080851 A2 | 10/2002 |
| WO | WO-03/014318 A2 | 2/2003 |
| WO | WO-03/104414 A2 | 12/2003 |
| WO | WO-2004/029219 A2 | 4/2004 |
| WO | WO-2004/046321 A2 | 6/2004 |
| WO | WO-2004/062618 A2 | 7/2004 |
| WO | WO-2005/049642 A2 | 6/2005 |
| WO | WO-2007/014275 A2 | 2/2007 |
| WO | WO-2007/134161 A2 | 11/2007 |
| WO | WO-2008/093152 A1 | 8/2008 |
| WO | WO-2008/108989 | 9/2008 |
| WO | WO-2008/116860 A2 | 10/2008 |
| WO | WO-2010/054108 | 5/2010 |
| WO | WO-2010/065123 A1 | 6/2010 |
| WO | WO-2010/068816 A1 | 6/2010 |
| WO | WO-2010/075424 A2 | 7/2010 |
| WO | WO-2010/079430 A1 | 7/2010 |
| WO | WO-2011/011767 A1 | 1/2011 |
| WO | WO-2011/016840 A2 | 2/2011 |
| WO | WO-2011/036510 A1 | 3/2011 |
| WO | WO-2011/064736 A1 | 6/2011 |
| WO | WO-2011/076873 A1 | 6/2011 |
| WO | WO-2011/146121 A1 | 11/2011 |
| WO | WO-2012/012738 A1 | 1/2012 |
| WO | WO-2012/031205 | 3/2012 |
| WO | WO-2012/051343 A1 | 4/2012 |
| WO | WO-2012/149470 A1 | 11/2012 |
| WO | WO-2012/164565 A1 | 12/2012 |
| WO | WO-2013/044008 A2 | 3/2013 |
| WO | WO-2013/155572 | 4/2013 |
| WO | WO-2013/071440 A1 | 5/2013 |
| WO | WO-2013/078400 A1 | 5/2013 |
| WO | WO-2013/082519 A2 | 6/2013 |
| WO | WO-2013/098244 | 7/2013 |
| WO | WO-2013/130824 A1 | 9/2013 |
| WO | WO-2013/141680 A1 | 9/2013 |
| WO | WO-2013/142578 A1 | 9/2013 |
| WO | WO-2013/176772 A1 | 11/2013 |
| WO | WO-2014/165349 A1 | 3/2014 |
| WO | WO-2014/065596 A1 | 5/2014 |
| WO | WO-2014/089290 A1 | 6/2014 |
| WO | WO-2014/093479 | 6/2014 |
| WO | WO-2014/093595 | 6/2014 |
| WO | WO-2014/093622 A2 | 6/2014 |
| WO | WO-2014/093635 A1 | 6/2014 |
| WO | WO 2014/093655 A2 | 6/2014 |
| WO | WO-2014/093661 | 6/2014 |
| WO | WO-2014/093694 | 6/2014 |
| WO | WO-2014/093701 A1 | 6/2014 |
| WO | WO-2014/093709 | 6/2014 |
| WO | WO 2014/093712 A1 | 6/2014 |
| WO | WO-2014/093718 | 6/2014 |
| WO | WO-2014/099744 | 6/2014 |
| WO | WO-2014/099750 A2 | 6/2014 |
| WO | WO-2015/031775 | 8/2014 |
| WO | WO 2014/144761 A2 | 9/2014 |

(56) References Cited

FOREIGN PATENT DOCUMENTS

| WO | WO-2014/186585 | A2 | 11/2014 |
|---|---|---|---|
| WO | WO-2014/191518 | A1 | 12/2014 |
| WO | WO-2014/197568 | A2 | 12/2014 |
| WO | WO-2014/197748 | | 12/2014 |
| WO | WO-2014/204724 | A1 | 12/2014 |
| WO | WO-2014/204725 | | 12/2014 |
| WO | WO-2014/204726 | | 12/2014 |
| WO | WO-2014/204727 | A1 | 12/2014 |
| WO | WO-2014/204728 | | 12/2014 |
| WO | WO-2014/204729 | | 12/2014 |
| WO | WO-2015/006747 | A2 | 1/2015 |
| WO | WO-2015/035136 | A2 | 3/2015 |
| WO | WO-2015/048577 | | 4/2015 |
| WO | WO-2015/065964 | A1 | 5/2015 |
| WO | WO-2015/070083 | A1 | 5/2015 |
| WO | WO-2015/071474 | | 5/2015 |
| WO | WO-2015/089351 | A1 | 6/2015 |
| WO | WO-2015/089364 | | 6/2015 |
| WO | WO-2015/089419 | | 6/2015 |
| WO | WO-2015/089427 | A1 | 6/2015 |
| WO | WO-2015/113063 | A1 | 7/2015 |
| WO | WO 2016/022866 | A1 | 2/2016 |
| WO | WO-2016/141224 | A1 | 9/2016 |

OTHER PUBLICATIONS

Maeder, M.L., et al., Crispr RNA-guided Activation of Endogenous Human Genes, Nature Methods, Nature Publishing Group GB (Oct. 2013) vol. 10, No. 10, p. 977-979.

Maeder, M.L., et al., Crispr RNA-guided Activation of Endogenous Human Genes, Nature Methods, (Jul. 2013) vol. 10, No. 10, p. 977-979.

Shengdar Q. Tsai, et al., Dimeric CRISPR RNA-Guided FokI Nucleases for Highly Specific Genome Editing, Nature Biotechnology (Apr. 2014) vol. 32, No. 6, p. 569-576.

Sander, Jeffrey D., et al., CRISPR-Cas Systems for Editing, Regulating and Targeting Genomes, Nature Biotechnology (Mar. 2014) vol. 32, No. 4, p. 347-355.

Nishimasu Hiroshi, et al., Crystal Structure of Cas9 in Complex with Guide RNA and Target DNA, Cell, Cell Press, US (Feb. 2014) vol. 156, No. 5, p. 935-949.

Prashant Mali et al., Supplementary Information: CAS9 Transcriptional Activators for Target Specificity . . . , Nature Biotechnology (2013) vol. 31, No. 9, p. 833-838.

Sander, Jeffrey D., et al., Supplementary Information: CRISPR-Cas Systems for Editing, Regulating . . . , Nature Biotechnology (Mar. 2014) vol. 32, No. 4, p. 347-355.

"Crispr genome engineering" XP055167591, Oct. 5, 2013, https://web.archive.org/web/2013100500 [retrieved on Feb. 5, 2015].

"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].

"The CRISPR Revolution," Catalyst Magazine, College of Chemistry, University of California, Berkeley, http://catalyst.berkeley.edu/slideshow/the-crispr-revolution/[Dec. 19, 2014 12:40:53] (Jul. 9, 2014).

Abudayyeh, et al., "C2c2 is a single-component programmable RNA-guided RNA-targeting CRISPR effector," Science, vol. 10, dated 2016.

Addgene Materials May 2015.

Addgene Materials Oct. 2014 including Addgene News 2013.

Addgene Reagent distribution list for Zhang Lab.

Addgene, "gRNA_Cloning Vector", retrieved on Jan. 30, 2019, <https://www/addgenen.org/41824/>, 2 pages.

Al-Attar, et al., "Clustered regularly interspaced short palindromic repeats (CRISPRs): the hallmark of an ingenious antiviral defense mechanism in prokaryotes" Biol Chem., 2011, 392(4):277-289.

Alberts, et al., Molecular Biology of THE CELL, fourth edition, 2002, 671-676.

Andreas, et al. "Enhanced efficiency through nuclear localization signal fusion on phage C31-integrase: activity comparison with Cre and FLPe recombinase in mammalian cells", Nucleic Acids Research, 2002, 30(11):2299-2306.

*Arbitron, Inc.* v. *Kiefl*, No. 09-CV-04013 PAC, 2010 WL 3239414, at *1 (S.D.N.Y. Aug. 13, 2010).

Asuri, P., et al., "Directed Evolution of Adeno-Associated Virus for Enhanced Gene Delivery and Gene Targeting in Human Pluripotent Stem Cells," Molecular Therapy, vol. 30, No. 2, pp. 329-338, dated Feb. 2012, 10 pages.

Au, et al. "Characterization of a baculovirus nuclear localization signal domain in the late express factor 3 protein", Virology, 2009, 385:209-217.

Ausubel, et al. "Compendium of Methods from Current Protocols in Molecular Biology", Short Protocols in Molecular Biology, Fourth Edition, 1999, 9: 9-3-9-4.

Autofluorescence MIT Flow Cytometry Core Facility (2018), 6 pages.

Baena-Lopez, L., et al., "Accelerated homologous recombination and subsequent genome modification in *Drosophila*," Development, vol. 140, No. 23, pp. 4818-4825, dated Dec. 2013, 18 pages, including Supplementary Material.

Baiker, et al. "The Immediate-Early 63 Protein of Varicella-Zoster Virus: Analysis of Functional Domains Required for Replication In Vitro and for T-Cell and Skin Tropism in the SCIDhu Model In Vivo", Journal of Virology, 2004, 78(3):1181-1194.

Baker, M., "Gene editing at CRISPR Speed," Nature Biotechnology, vol. 32, No. 4, pp. 309-312, dated Apr. 2014, 4 pages.

Balboa et al., "Conditionally Stabilized dCas9 Activator for Controlling Gene Expression in Human Cell Reprogramming and Differentiation. (plus Supplemental Information)", Stem Cell Reports, vol. 5, No. 3, Sep. 8, 2015, pp. 448-459 16PP.

Banaszewska, A., et al. "Proprotein Convertase Subtilisin/Kexin Type 9: A New Target Molecule for Gene Therapy," Cellular & Molecular Biology Letters, vol. 17, pp. 228-239, dated Feb. 7, 2012, 12 pages.

Barrangou and Van Der Oost (Eds.), "CRISPR-Cas Systems," Springer Heidelberg (2013; written in 2012 before the publication of Cong et al.).

Barrangou, R. et al.: "CRISPR provides acquired resistance against viruses in prokaryotes," Science, vol. 315, pp. 1709-1712, dated Mar. 23, 2007, 5 pages.

Barrangou, R., "RNA-mediated programmable DNA cleavage," Nature Biotechnology, vol. 30, No. 9, pp. 836-388, dated Sep. 2012, 3 pages.

Bassett, et al. "Highly Efficient Targeted Mutagenesis of *Drosophila* with the CRISPR/Cas9 System" Cell Reports, 2013, 4:220-228.

Bassett, et al., "A Genome-Wide CRISPR Library for High-Throughput Genetic Screening in *Drosophila* Cells," Journal of Genetics and Genomics, vol. 42, pp. 301-309, dated 2015.

Bauer, et al., "An Erythroid Enhancer of BCL11A Subject to Genetic Variation Determines Fetal Hemoglobin Level," Science, vol. 342, pp. 253-257, dated 2013.

Beerli, et al. "Positive and negative regulation of endogenous genes by designed transcription factors:" PNAS, 2000, 97(4):1495-1500.

Beerli, et al. "Toward controlling gene expression at will: Specific regulation of the erbB-2/HER-2 promoter by using polydactyl zinc finger proteins constructed from modular building blocks", Proc. Natl. Acad. Sci., 1998, 95:14628-14633.

Beerli, R., et al., "Engineering polydactyl zinc-finger transcription factors," Nature Biotechnology, vol. 20, pp. 135-141, dated Feb. 2002, 7 pages.

Bennett et al., "Stable transgene expression in rod photoreceptors after recombinant adeno-associated virus-mediated gene transfer to monkey retina", Proc. Natl. Acad. Sci., USA, vol. 96, Aug. 1999, pp. 9920-9925.

Bergemann, et al. Excision of specific DNA-sequences from integrated retroviral vectors via site-specific recombination:, Nucleic Acids Res., 1995, 23(21):4451-4456.

Berns, K., et al. "A Large-Scale RNAi Screen in Human Cells Identifies New Components of the p53 Pathway," Nature 2004, vol. 428, pp. 431-437, dated Mar. 25, 2004, 7 pages.

(56) References Cited

OTHER PUBLICATIONS

Bhaya, D., et al., "CRISPR-Cas Systems in Bacteria and Archaea: Versatile Small RNAs for Adaptive Defense and Regulation," Annual Review of Genetics, vol. 45, No. 1, pp. 273-297, dated Dec. 15, 2011, 27 pages.

Bikard, et al. "CRISPR Interference Can Prevent Natural Transformation and Virulence Acquisition During In Vivo Bacterial Infection," Cell Host & Microbe, vol. 12, No. 2, pp. 177-186, dated Aug. 16, 2012, 10 pages.

Bikard, et al. Supplementary Information for: "CRISPR Interference Can Prevent Natural Transformation and Virulence Acquisition During In Vivo Bacterial Infection," Cell Host & Microbe, vol. 12, No. 2, pp. 177-186, dated Aug. 16, 2012, 10 pages.

Birch, et al. "Plant Transformation: Problems and Strategies for Practical Application", Annu. Rev. Plant Physiol. Plant Mol. Biol., 1997, 48:297-326.

Bloom et al., "Inactivation of hepatitis B virus replication in cultured cells and in vivo with engineered transcription activator-like effector nucleases", Molecular Therapy, Aug. 20, 2013, vol. 21, No. 10, pp. 1889-1897.

Bobis-Wozowicz, S., et al., "Targeted genome editing in pluripotent stem cells using zinc-finger nucleases," Methods, vol. 53, pp. 339-346, dated 2011, 8 pages.

Boch, et al. "Breaking the Code of DNA Binding Specificity of TAL-Type III Effectors". Science, 2009, 326:1509-1512.

Boch, et al. "Xanthomonas AvrBs3 Family-Type III Effectors: Discovery and Function", Annu. Rev. Phytopathol, 2010, vol. 48:419-436.

Boden, et al. "Efficient Gene Transfer of HIV-1-Specific Short Hairpin RNA into Human Lymphocytic Cells Using Recombinant Adeno-associated Virus Vectors", Molecular Therapy, 2004, 9(3):396-402.

Bogdanove, et al. "TAL Effectors: Customizable Proteins for DNA Targeting", Science, 2011, 333:1843-1846.

Bohm, "The computer program LUDI: A new method for the de novo design of enzyme inhibitors", Journal of Computer-Aided Molecular Design, 1992, vol. 6, pp. 61-78.

Bouard, et al. "Themed Section: Vector Design and Drug Delivery Review, Viral vectors: from virology to transgene expression", British Journal of Pharmacology, 2009, 157:153-165.

Boutros et al.: "Genome-wide RNAi analysis of growth and viability in Drosophila cells," Science, American Association for the Advancement of Science, vol. 303, No. 5659, pp. 832-835, dated Feb. 6, 2004, 4 pages.

Branden, C., and Tooze, J., "Prediction, Engineering, and Design of Protein Structures," Introduction to Protein Structure, Chapter 16, p. 247, Garland Publishing, Inc., New York, dated 1991, 3 pages.

Briner, et al. "Guide RNA Functional Modules Direct Cas9 Activity and Orthogonality", Molecular Cell, Oct. 2014, 56:333-339.

Brouns, S, "A Swiss Army Knife of Immunity," Science, vol. 337, No. 6096, pp. 808-809, dated Aug. 17, 2012, 3 pages.

Brouns, S., et al., "Small CRISPR RNAs Guide Antiviral Defense in Prokaryotes," Science, vol. 321, pp. 960-964, dated Aug. 15, 2008, 6 pages.

Campeau, et al. "A Versatile Viral System for Expression and Depletion of Proteins in Mammalian Cells", PLoS One, 2009, 4(8):e6529.

Canver, et al., "BCL11A enhancer dissection by Cas9-mediated in situ saturating mutagenesis," Nature, vol. 527, pp. 192-197, including Supplementary Material, dated 2015.

Carr, et al., "Genome engineering", Nature Biotechnology, 2009, 27(12):1151-1162.

Carroll, "Genome Engineering With Zing-Finger Nucleases", Genetics, 2011, 188:773.782.

Carroll, "Progress and prospects: Zinc-finger nucleases as gene therapy agents", Gene Therapy, 2008, 15:1463-1468.

Carroll, D., "A CRISPR Approach to Gene Targeting," Molecular Therapy, vol. 20, No. 9, pp. 1658-1660, dated Sep. 1, 2012, 3 pages.

Cermak, T., et al., "Efficient design and assembly of custom TALEN and other TAL Effector-Based Constructs for DNA Targeting", Nucleic Acids Research, vol. 39, No. 12, art. e82, pp. 1-11, dated Apr. 14, 2011, 11 pages.

Chan, et al. "Characterization of the Kinetochore Binding Domain of CENP-E Reveals Interactions with the Kinetochore Proteins CENP-F and hBuBR1", The Journal of Cell Biology, 1998, 143:49-63.

Chan, Wai-Ting, et al. "Toxin-Antitoxin Genes of the Gram-Positive Pathogen Streptococcus pneumoniae: So Few and Yet So Many", Microbiology and Molecular Biology Reviews, 2012, 76(4):773-791.

Chang, N., et al. "Genome editing with RNA-guided Cas9 nuclease in Zebrafish embryos", Cell Research, vol. 23, pp. 465-472, dated Mar. 26, 2013, 8 pages.

Chen, B., et al., "Dynamic Imaging of Genomic Loci in Living Human Cells by an Optimized CRISPR/Cas System," Cell, vol. 155, No. 7, pp. 1479-1491, dated Dec. 1, 2013, 25 pages.

Chen, Fuqiang et al. "High-frequency genome editing using ssDNA oligonucleotides with zinc-finger nucleases". Nature Methods, 2011, 8(9):753-755, including Supplemental Online Methods.

Chen, S., et al. "Genome-wide CRISPR Screen in a Mouse Model of Tumor Growth and Metastasis", Cell, 2015, 160:1-15, http://dx.doi.org/10.1016/j.cell.2015.02.038.

Chinnasamy, D., et al., "Multicistronic lentiviral vectors containing the FMCV 2A Cleavage factor demonstrate robust expression of encoded genes at limiting MOI," Virology Journal, vol. 3, No. 4, dated Mar. 15, 2006, 16 pages.

Chiu et al, "Engineered GFP as a vital reporter in plants", Current Biology, (1996), 6(3):325-330.

Cho, A., et al., "Generation of Transgenic Mice," Current Protocols in Cell Biology, Chapter Unit 19.11, pp. 1-29, dated Mar. 2009, 29 pages.

Chou, JY, and Mansfield, BC, "Recombinant AAV-directed gene therapy for type I glycogen storage diseases," Expert Opinion on Biological Therapy, vol. 11, No. 8, pp. 1011-1024, dated Apr. 20, 2011, 21 pages.

Choulika, et al., "Transfer of Single Gene-Containing Long Terminal Repeats into the Genome of Mammalian Cells by a Retroviral Vector Carrying the cre Gene and the loxP site", Journal of Virology, 1996, 70(3):1792-1798.

Christian, et al. "Supporting Information-Targeting DNA Double-Strand Breaks With TAL Effector Nucleases", Genetics, 2010, DOI:10.1534/110.120717:1SI-8SI.

Christian, et al. "Targeting DNA Double-Strand Breaks With TAL Effector Nucleases", Genetics, Oct. 2010, vol. 186:757-761.

Chylinski, et al. "Classification and evolution of type II CRISPR-Cas systems", Nucleic Acids Research, 2014, 42(10):6091-6105,doi:10.1093lnarlgku241.

Chylinski, K., et al. "The tracrRNA and Cas9 Families of Type II CRISPR-Cas Immunity Systems," RNA Biology, vol. 10, No. 5, pp. 726-737, dated May 2013, 13 pages.

Clark, K., et al., "A TALE of Two Nucleases: Gene Targeting for the Masses?" Zebrafish, vol. 8, No. 3, pp. 147-149, dated 2011, 3 pages.

Cockrell, "Berkeley's Wikipedian-in-residence is a first," NewsCenter, Feb. 25, 2014.

Community Corner, "CRISPR technology for gene therapy," Nature Medicine, vol. 20, No. 5, pp. 476-477, dated May 2014, 3 pages.

Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, pp. 819-823, dated Feb. 15, 2013, 36 pages.

Cong, L., et al., "Comprehensive interrogation of natural TALE DNA-binding modules and transcriptional repressor domains," Nature Communications, vol. 3, pp. 968-973, dated Jul. 24, 2012, 6 pages.

Cong, L., et al., "In Vivo Genome Engineering With AAV Vector Carrying CRISPR-Cas9 System," Molecular Therapy, vol. 22, Supplement 1, p. S214, dated May 23, 2014, 1 page.

Cong, L., et al., "Multiplex Genome Engineering Using CRISPR-Cas Systems," Science, vol. 339, pp. 819-823, dated Feb. 15, 2013.

(56) References Cited

OTHER PUBLICATIONS

Cong, L., et al., Supplementary Material for: "Multiplex Genome Engineering Using CRISPR-Cas Systems," Science Express, dated Jul. 5, 2012.
Cong, L., et al., Supplementary Material for: "Multiplex Genome Engineering Using CRISPR-Cas Systems," Science, vol. 339, pp. 819-823, dated Jan. 3, 2013, 29 pages.
Connor, S., "Scientific split—the human genome breakthrough dividing former colleagues," The Independent, http://www.independent.co.uk/news/science/scientific-split--the-human-genome-breakthrough-dividing-former-colleagues-9300456.html, dated Apr. 25, 2014, 5 pages.
Costantino, et al., "Enhanced levels of alpha Red-mediated recombinants in mismatch repair mutants", PNAS, 100(26):15748-15753.
Cotropia, et al., "Copying in Patent Law," N.C.L. Rev., Stanford Public Law Working Paper No. 1270160 (2009), 87:1421.
Cummings et al., "Fourteen and counting: unraveling trinucleotide repeat diseases", Human Molecular Genetics, 2000, vol. 9, No. 6, pp. 909-916.
Daboussi, F., et al., "Chromosomal context and epigenetic mechanisms control of efficacy of genome editing by rare-cutting designer endonucleases," Nucleic Acids Research, vol. 40, No. 13, pp. 6367-6379, dated Jul. 13, 2012, 13 pages.
Dahlman, J., et al., "In vivo endothelial siRNA delivery using polymeric nanoparticles with low molecular weight," Nature Nanotechnology, vol. 9, No. 8, pp. 648-655, dated May 11, 2014, 17 pages.
Dai, et al. "Genes:Structures and Regulation: The Transcription Factors GATA4 and dHAND Physically Interact to Synergistically Activate Cardiac Gene Expression through a p300-dependent Mechanism", J. Biol. Chem., 2002, 277:24390-24398.
Daley, J., and Wilson, T., "Rejoining of DNA Double-Strand Breaks as a Function of Overhang Length," Molecular and Cellular Biology, vol. 25, No. 3, pp. 896-906, dated Feb. 2005, 11 pages.
Damian, M., and Porteus, M., "A Crisper Look at Genome Editing: RNA-guided Genome Modification," Molecular Therapy, vol. 21, No. 4, pp. 720-722, dated Apr. 2013, 3 pages.
Database GenBank, "*Staphylococcus aureus* subsp.*aureus* ORFX gene and pseudo SCCmec-SCC-SCCCRISPR element, strain M06/0171," Accession No. HE980450, http://www.ncbi.nlm.nih.gov/nuccore/HE980450, dated Aug. 18, 2016, 22 pages.
Database GenBank: "CRISPR-associated protein, Csn1 family, *Staphylococcus pseudintermedius* ED99," Accession No. ADX75954, http://www.uniprot.org/uniprot/G1UFN3.txt?version=3, dated Nov. 21, 2011, 1 page.
Database UniProt: "CRISPR-associated endonuclease Cas9: *Staphylococcus aureus*," UniProtKB, J7RUA5 (CAS9_STAAU), XP002738511M, https://www.uniprot.org/uniprot/J7RUA5#, dated Oct. 31, 2012, 7 pages.
Database UniProtKB/TrEMBL [online], Accession No. Q0P897, "The genome sequence of the food-borne pathogen *Campylobacter jejuni* reveals hypervariable sequences," Subname: Full=Putative CRISPR-associated protein, Oct. 3, 2012 uploaded, [retrieved on Nov. 22, 2017], URL: http://www.uniprot.org/uniprot/Q0P897.txt?version=28.
Database UniProtKB/TrEMBL, Accession No. D0W2Z9, http://www.uniprot.org/uniprot/D0W2Z9.txt?version=4, dated Oct. 3, 2012, 1 page.
Database UniProtKB/TrEMBL, Accession No. G1UFN3, http://www.uniprot.org/uniprot/G1UFN3.txt?version=3, dated Oct. 3, 2012, 1 page.
Database UniProtKB/TrEMBL, Accession No. J3TRJ9, http://www.uniprot.org/uniprot/J3TRJ9.txt?version=2, dated Oct. 31, 2012, 1 page.
Database UniProtKB/TrEMBL, Accession No. Q0P897, http://www.uniprot.org/uniprot/Q0P897.txt?version=28, dated Oct. 3, 2012, 1 page.
Database UniProtKB/TrEMBL, Accession No. Q6NK13, http://www.uniprot.org/uniprot/Q6NK13.txt?version=43, dated Jun. 13, 2012, 1 page.
Database UniProtKB/TrEMBL, Accession No. Q73QW6, http://www.uniprot.org/uniprot/Q73QW6.txt?version=4, dated Nov. 28, 2012, 2 pages.
Database WPI, Week 201437 Thomson Scientific, London, GB; AN 2014-J79552, XP-002737563, 2 pages.
Datsenko, et al. "Molecular memory of prior infections activates the CRISPR/Cas adaptive bacterial immunity system", Nature Communications, Jul. 10, 2012, 3:935, DOI:10.1038/ncomms1937.
Declaration of Feng Zhang for U.S. Appl. No. 14/054,414 dated Jan. 30, 2014, 10 pages.
Declaration of Paul Simons dated Dec. 22, 2015.
Deltcheva, E., et al., "CRISPR RNA maturation by trans-encoded small RNA and host Factor RNase III," Nature, vol. 471, pp. 602-609, dated Mar. 31, 2011, 8 pages.
Deltcheva, et al. "Supplementary Information: CRISPR RNA Maturation by Trans-Encoded Small RNA and Host Factor RNase III" www.Nature.com/doi:10.1038/nature09886:1-35.
Dicarlo, et al. "Genome engineering in *Saccharomyces cerevisiae* using CRISPTR-Cas systems", Nucleic Acids Research, 2013, 41(7):4336-4343, doi:10.1093/nar/gkt135.
Dingwall, et al. "Abstract: A Polypeptide Domain That Specifies Migration of Nucleoplasmin into the Nucleus", Cell, 1982, 30(2):449-58.
Dingwall, et al. "The Nucleoplasmin Nuclear Location Sequence Is Larger and More Complex than That of SV-40 Large T Antigen", The Journal of Cell Biology, 1988, 107:841-849.
Do, et al. "Identification of multiple nuclear localization signals in murine Elf3, an ETS transcription factor" FEBS Letters, 2006, 580:1865-1871.
Doench, et al., "Rational design of highly active sgRNAs for CRISPR-Cas9-mediated gene inactivation," Nature Biotechnology, vol. 32, No. 12, pp. 1262-1267, including Supplementary Material, dated 2014.
Dominguez, et al., "Beyond editing: repurposing CRISPR-Cas 9 for precision genome regulation and interrogation" Nat Rev Mol Cell Biol., 2016, 17(1):5-15, doi:10.1038/nrm.2015.2.
Dong, et al. "The crystal structure of Cpf1 in complex with CRISPR RNA," Nature, vol. 532, pp. 523-525, including Research Letter, dated 2016.
Drittanti, et al. "High throughput production, screening and anyalysis of adeno-associated viral vectors", Gene Therapy, 2000, 7:924-929.
Dworetzky, S., et al., "The Effects of Variations in the Number and Sequence of Targeting Signals on Nuclear Uptake," The Journal of Cell Biology, vol. 107, pp. 1279-1287, dated Oct. 1988, 9 pages.
Ebina, H., et al., "Harnessing the CRISPR/Cas9 system to disrupt latent HIV-1 provirus," Scientific Reports, vol. 3, art. 2510, dated Aug. 26, 2013, 7 pages.
Ellis, B., et al., "Zinc-finger nuclease-mediated gene correction using single AAV vector transduction and enhanced by Food and Drug Administration-Approved Drugs," Gene Therapy, vol. 20, No. 1, pp. 35-42, dated Jan. 1, 2013, 8 pages.
Ellis, et al. "Macromolecular Crowding: Obvious But Underappreciated", TRENDS in Biochemical Sciences, Oct. 2001, 26(10):597-604.
Ellis, Hilary, et al. "High efficiency mutagenesis, repair, and engineering of chromosomal DNA using single-stranded oligonucleotids" PNAS, 2001, 98(12):6742-6746.
Enyeart, et al., "Biotechnological applications of mobile group II introns and their reverse transcriptases: gene targeting, RNA-seq, and non-coding RNA analysis", Mobile DNA, 2014, 5:2, http://mobilednajournal.com/content5/1/2.
Espinoza, et al., "Characterization of the structure, function, and mechanism of B2 RNA, an ncRNA repressor of RNA polymerase II transcription", RNA, 2007, 13(4):583-596.
Excerpt from Declaration of Feng Zhang, dated Sep. 9, 2015.
Federal Circuit decision in *Dow Chemical Co.* v. *Nova Chemicals Corp.*, Appeal Nos. 2014-1431, 2014-1462 (Fed. Cir. Aug. 28, 2015) (*Dow* v. *Nova*), 25 pages.
Feldgarden et al., "*Staphylococcus aureus* M0408 acrHk-supercont1.1, whole genome shotgun sequence", NCBI Reference Sequence: NK_KB821326.1, Direct Submission, Dec. 10, 2012, pp. 1-4.

(56) References Cited

OTHER PUBLICATIONS

Fieck, et al. "Modifications of the *E. coli* Lac repressor for expression in eukaryotic cells: effects of nuclear signal sequences on protein activity and nuclear accumulation", Nucleic Acids Research, 1992, 20(7):1785-1791.

Fischer-Fantuzzi, L., and Vesco, C., "Cell-dependent efficiency of reiterated nuclear signals in a mutant simian virus 40 oncoprotein targeted to the nucleus," Molecular and Cellular Biology, vol. 8, No. 12, pp. 5495-5503, dated 1988, 10 pages.

Fleming, J., et al.: "Adeno-Associated Virus and Lentivirus Vectors Mediate Efficient and Sustained Transduction of Cultured Mouse and Human Dorsal Root Ganglia Sensory Neurons," Human Gene Therapy, vol. 12, pp. 77-86, dated Jan. 1, 2001, 10 pages.

Foecking, et al. "Powerful and versatile enhance-promoter unit for mammalian expression vectors", Gene, 1986, 101-105.

Fonfara et al., "Phylogeny of Cas9 determines functional exchangeability of dual-RNA and Cas9 among orthologous type II CRISPR-Cas systems", Nucleic Acids Research, 2014, vol. 42, No. 4, pp. 2577-2590.

Freitas, et al. "Mechanisms and Signals for the Nuclear Import of Proteins", Current Genomics, 2009, 10:550-557.

Fu et al, "Targeted genome editing in human cells using CRISPR/Cas nucleases and truncated guide RNAsc", Jan. 1, 2014, The Use of CRISPR/Cas9 ZFNs and Talens in Generating Site-Specific Genome Alterations; Methods in Enzymology; ISSN 1557-7988, vol. 546, Elsevier, NL, pp. 21-45.

Fu, et al. "High-frequency off-target mutagenesis induced by CRISPR-Cas nucleases in human cells", Nature Biotechnology, 2013, 31(9):822-826.

Gabriel, R., et al., "An unbiased genome-wide analysis of zinc-finger nuclease specificity," Nature Biotechnology, vol. 29, No. 9, pp. 816-823, dated Aug. 7, 2011, 10 pages.

Gaj, T., et al., "Targeted Gene knockout by direct delivery of zinc-finger nuclease proteins," Nature Methods, vol. 9, No. 8, pp. 805-807, dated Aug. 2012, 5 pages.

Gaj, T., et al., "ZFN, TALEN, and CRISPR/Cas-Based Methods for Genome Engineering," Trends in Biotechnology, vol. 31, No. 7, pp. 397-405, dated Jul. 2013, 9 pages.

Gama Sosa, M., et al., "Animal transgenesis: an overview," Brain Structure and Function, vol. 214, pp. 91-109, dated 2010, 19 pages.

Gao, et al. "Engineered Cpf1 Enzymes with Altered PAM Specificities", BioRxiv Preprint, XP-002769442, 2016, doi:http://dx.doi.org/10.1101/091611, 1-13, including Figure Legends.

Gao, et al. "Engineered Cpf1 variants with altered PAM specificities", Nature Biotechnology, 2017, 1-4, doi:10.1038/nbt.3900, advanced online publication including Supplementary Information.

Garcia-Bustos, et al. "Nuclear protein localization", Biochimica et Biophysica Acta, 1991, 1071:83-101.

Gardlik, R., et al., "Vectors and delivery systems in gene therapy," Medical Science Monitor, vol. 11, No. 4, pp. RA110-121, dated Apr. 1, 2005, 12 pages.

Garg, et al. "Engineering synthetic TAL effectors with orthogonal target sites", Nucleic Acids Research, 2012, 40(15):7584-7595, doi:10.1093/nar/gks404.

Garneau, et al. "The CRISPR-Cas bacterial immune systems cleaves bacteriophage and plasmid DNA", Nature, Nov. 2010, 468:67-71.

Garriga-Canut, M., et al., "Synthetic zinc finger repressors reduce mutant huntingtin expression in the brain of R6/2 mice," Proceedings of the National Academy of Sciences, vol. 109, No. 45, pp. E3136-E3145, dated Nov. 6, 2012, 10 pages.

Gasiunas, G, et al, "Cas9-crRNA ribonucleoprotein complex mediates specific DNA cleavage for adaptive immunity in bacteria," Proceedings of the National Academy of Sciences, v.109, n.39, p. E2579-2586, dated Sep. 4, 2012, 8 pages.

Geibler, et al. "Trancscriptional Activators of Human Genes with Programmable DNA-Specificity", PLone, 2011, 6(5):e19509. Doi:10.1371/hournal.pone.0019509.

Geisinger et al., "In vivo blunt-end cloning through CRISPR/CAS9-facilitated non-homologous end-joining", Nucleic Acid Research Advance Access, Jan. 13, 2016, pp. 1-15.

Gilbert, L., et al., "CRISPR-Mediated Modular RNA-Guided Regulation of Transcription in Eukaryotes," Cell, vol. 154, No. 2, pp. 442-451, dated Jul. 1, 2013, 15 pages.

Goldfarb, et al. "Synthetic peptides as nuclear localization signals", Nature, Aug. 1986, 322(14):641-644.

Gomaa, et al. "Programmable removal of bacterial strains by use of genome-targeting CRISPR-Cas systems", MBio., 2014, 5(1):e00928-13.

Goncalves, M., et al., "Concerted nicking of donor and chromosomal acceptor DNA promotes homology-directed gene targeting in Human Cells," Nucleic Acids Research, vol. 40, No. 8, pp. 3443-3455, dated Dec. 20, 2011, 13 pages.

Gratz, et al. "Genome Engineering of *Drosophila* with the CRISPR RNA-Guide Cas9 Nuclease", Genetics, 2013, 194:1029-1035.

Greenspan, et al. "Two Nuclear Location Signals in the Influenza Virus NS1 Nonstructural Protein", Journal of Virology, 1988, 62(8):3020-3026.

Grens, "Enzyme Improves CRISPR A smaller Cas9 protein enables in vivo genome engineering via viral vectors", The Scientist, Apr. 1, 2015.

Grieger, J., and Samulski, R., "Packaging Capacity of Adeno-Associated Virus Serotypes: Impact of Larger Genomes on Infectivity and Postentry Steps," Journal of Virology, vol. 79, No. 15, pp. 9933-9944, dated Aug. 2005, 12 pages.

Grissa, I., et al., "CRISPRFinder: a web tool to identify clustered regularly interspaced short palindromic repeats," Nucleic Acids Research, vol. 35, pp. W52-W57, dated 2007, 6 pages.

Guan, et al. "Heritable endogenous gene regulation in plants with designed polydactyl zinc finger transcription factors", PNAS, 2002, 99(20):13296-13301.

Gustafsson, et al. "Codon Bias and heterologous protein expression", TRENDS in Biotechnology, Jul. 2004, 22(7):346-353.

Habib, N., Assignment to Broad Institute, dated Jun. 9, 2014, 4 pages.

Haft, D., et al., "A Guild of 45 CRISPR-Associated (Cas) Protein Families and Multiple CRISPR/Cas Subtypes Exist in Prokaryotic Genomes," PLoS Computational Biology, vol. 1, No. 6, pp. 0474-0483, dated Nov. 2005, 10 pages.

Haft, D.H., "HMM Summary Page TIGR04330", 2012, XP-002757584, http://jcvi.org/cgi-bin/tigrfams/HmmReportPage.cgi?acc=TIGR04330.

Hale, et al. "Essential Features and Rational Design of CRISPR RNAs that Function With the Cas RAMP Module Complex to Cleave RNAs", Molecular Cell, 2012, 45(3):292-302.

Hale, et al. "Prokaryotic siliencing (psi) RNAs in Pyrococcus furiosus", RNA, 2008, 14:2572-2579.

Hale, et al. "RNA-Guided RNA Cleavage by a CRISPR RNA-Cas Protein Complex", Cell, 2009, 139:945-956.

Hall, B., et al., "Overview: Generation of Gene Knockout Mice," Current Protocols in Cell Biology, unit 19.12, suppl. 44, pp. 1-17, dated 2009, 17 pages.

Handel, E., et al., "Versatile and Efficient Genome Editing in Human Cells by Combining Zinc-Finger Nucleases With Adeno-Associated Viral-Vectors," Human Gene Therapy, vol. 23, No. 3, pp. 321-329, dated Mar. 2012, 9 pages.

Harrison et al., "A CRISPR view of development", Genes & Development, vol. 28, No. 17, Sep. 1, 2014, pp. 1859-1872.

Heintze, et al. "A CRISPR CASe for high-throughput silencing", Frontiers in Genetics, Oct. 2013, 4(193): DOI:10.3389/gfene.2013.00193.

Hibbitt, O., et al. "RNAi-mediated knockdown of HMG CoA reductase enhances gene expression from physiologically regulated low-density lipoprotein receptor therapeutic vectors in vivo," Gene Therapy, vol. 19, pp. 463-467, dated 2012, 5 pages.

Hicks, et al. "Protein Import Into the Nucleus: An Integrated View", Annu. Rev. Cell Dev. Biol., 1995, 11:155-188.

Ho, et al, "Targeting non-coding RNAs with the CRISPR/Cas9 system in human cell lines," Nucleic Acids Research, vol. 43, No. 3, p. e17, dated 2015.

Hockemeyer, et al. "Highly efficient gene targeting of expressed and silent genes in human ESCs and iPSCs using zinc finger nucleases", Nat Biotechnol., 2009, 27(9):851-857, doi:10.1038/nbt.1562.

(56) References Cited

OTHER PUBLICATIONS

Holkers, M., et al., "Adenoviral vector DNA for accurate genome editing with engineered nucleases," Nature Methods, vol. 11, No. 10, pp. 1051-1057, Aug. 24, 2014, 8 pages (Only Abstract Available).
Holmes, "CRISPR Genome Engineering Resources" XP055167586, Oct. 2, 2013, https://groups.google/forum/#!top1c/crispr/5BpJj_Y3yIG [retrieved on Feb. 5, 2015].
Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-l/rziHxKT76pYJ [retrieved on Feb. 6, 2015].
Horvath, P., and Barrangou, R., "RNA-guidded genome editing a la carte," Cell Research, vol. 23, No. 6, pp. 733-734, dated Jun. 2013, 2 pages.
Hou, Z., et al., "Efficient genome engineering in human pluripotent stem cells using Cas9 from Neisseria meningitides," Proceedings of the National Academy of Sciences, vol. 110, No. 39, pp. 15644-15649, dated Aug. 12, 2013, 6 pages.
Houdebine, L., "The methods to generate transgenic animals and to control transgene expression," Journal of Biotechnology, vol. 98, pp. 145-160, dated 2002, 16 pages.
Hsu et al., "DNA targeting specificity of RNA-guided Cas9 nucleases," Nature Biotechnology, 2013, 31(9):827-834.
Hsu et al., "Supplementary Information-DNA targeting specificity of RNA-guided Cas9 nucleases," Nature Biotechnology, 2013, doi:10.1038/nbt.2647.
Hsu, P., et al., "Development and Applications of CRISPR-Cas9 for Genome Engineering," Cell, vol. 157, No. 6, pp. 1262-1278, dated Jun. 5, 2014, 17 pages.
*Huang v. California Institute of Technology*, 2004 WL 2296330 (C.D. Cal. Feb. 18, 2004).
Hung, S., et al., "AAV-Mediated CRISPR/Cas Gene Editing of Retinal Cells In Vivo," Investigative Ophthalmology & Visual Science, vol. 57, No. 7, pp. 3470-3476, dated Jun. 2016, 7 pages.
Hwang W., et al., "Efficient genome editing in zebrafish using a CRISPR-Cas System," Nature Biotechnology, vol. 31, No. 3, pp. 227-229, dated Jan. 29, 2013, 12 pages.
Hwang Woong, et al. "Efficient In Vivo Genome Editing Using RNA-Guided Nucleases", Nat. Biotechnol., 2013, 31(3):227.229. doi. 1.1038/mbt.2501.
Imagawa, et al. "Two nuclear localization signals are required for nuclear translocation of nuclear factor 1-A", FEBS Letters, 2000, 484118-124.
Incontro, S., et al., "Efficient, Complete Deletion of Synaptic Proteins using CRISPR," Neuron, vol. 83, No. 5, pp. 1051-1057, dated Sep. 3, 2014, 13 pages.
Iwamoto et al., "A General Chemical Method to Regulate Protein Stability in the Mammalian Central Nervous System", Chemistry and Biology, Current Biology, London, GB, vol. 17, No. 9, Sep. 24, 2010, pp. 981-988.
Jackson, A., et al. "Widespread siRNA "off-target" transcript silencing mediated by seed region sequence complementarity," RNA 2006, vol. 12, No. 7, dated Mar. 16, 2006, 10 pages.
Janssen, et al., "Mouse Models of K-ras-lnitiated Carcinogenesis", Biochimicia et Biophysica Acta, 2005, 1756:145-154.
Jao, et al. "Efficient multiplex biallelic zebrafish genome editing using a CRISPR nuclease system", Proceeding of the National Academy of Sciences, 2013, www.pnas.org/cgi/doi/10.1073/pnas.1308335110.
Jiang, W., et al., "RNA-guided editing of bacterial genomes using CRISPR-Cas systems," Nature Biotechnology, vol. 31, No. 3, pp. 233-239, dated Mar. 2013, 30 pages, including Supplementary Materials.
Jieliang Chen, et al. "An Efficient Antiviral Strategy for Targeting Hepatitis B Virus Genome Using Transcription Activator-Like Effector Nucleases", Molecular Therapy, 2014, 22(2):303-311.
Jinek, M., et al, "A programmable Dual-RNA-Guided DNA Endonuclease in adaptive bacterial immunity," Science, vol. 337, n.6096, pp. 816-821, dated Aug. 17, 2012, 7 pages.

Jinek, M., et al., "A Programmable Dual-RNA-Guided DNA Endonuclease in Adaptive Bacterial Immunity," Science, vol. 337, pp. 816-821, dated Aug. 17, 2012, Including Supplementary Material, 45 pages.
Jinek, M., et al., "RNA-programmed genome editing in human cells", eLIFE, vol. 2, No. e00471, dated Jan. 29, 2013, 9 pages.
Jinek, M., et al., Figures and figure supplements for: "RNA-programmed genome editing in human cells," eLIFE, vol. 2, No. e00471, dated Jan. 29, 2013, 5 pages.
Jinek, M., et al., Supplementary Materials for: "A Programmable Dual-RNA-Guided DNA Endonuclease in Adaptive Bacterial Immunity," Science, vol. 337, No. 6096, pp. 816-821, dated Jun. 28, 2012, 38 pages.
Joseph, T., and Osman, R., "Thermodynamic basis of selectivity in guide-target-mismatched RNA interference," Proteins, vol. 80, No. 5, pp. 1283-1298, dated May 2012, 26 pages.
Joshi, et al., "Evolution of I-Scel homing endonucleases with increased DNA recognition site specificity", Journal of Molecular Biology, 2011, 405(1):185-200; ePub: Oct. 26, 2010.
Joung, et al. "TALENs: a widely applicable technology for targeted genome editing", Nat Ref. Mol. Cell Biol., 2013, 14(1):49-55. doi:10.1038/nrm3586.
Kalderon, et al. "A short Amino Acid Sequence Able to Specify Nuclear Location", Cell, 1984, 39:499-509.
Kanasty, R., et al., "Delivery materials for siRNA therapeutics," Nature Materials, vol. 12, No. 11, pp. 967-977, dated Oct. 23, 2013, 11 pages.
Karvelis, et al. "crRNA and tracrRNA guide Cas9-mediated DNA interference in *Streptococcus thermophiles*" RNA Biology, 2013, 10(5):841-851.
Karvelis, et al. "Supplemental Material to: crRNA and tracrRNA guide Cas9-mediated DNA interference in *Streptococcus thermophiles*", Landes Bioscience, 2013, 10(5), http://dx.doi.org/10.4161/rna.24203.
Kiani, et al. "CAS9 gRNA engineering for genome editing, activation and repression", Nature Methods, Advanced Online Publication, 2015, DOI:10.1038/NMETH.3580.
Kim et al., "High Cleavage Efficiency of a 2A Peptide Derived from Porcine Teschovirus-1 in Human Cell Lines, Zebrafish and Mice," PLoS One, 6(4):el 8556, (2011).
Kim, E., et al., "Precision genome engineering with programmable DNA-nicking enzymes," Genome Research, vol. 22, pp. 1327-1333, dated 2012, 8 pages.
Kim, et al. "Crystal structure of Cas1 from Archaeoglobus fulgidus and characterization of its nucleolytic activity", Biochemical and Biophysical Research Communications, 2013, 441:720-725.
Kim, S., et al., "CRISPER RNAs trigger innate immune responses in human cells," Genome Research, pp. 1-7, dated Feb. 22, 2018, 8 pages.
Kinnevery, P., et al., "Emergence of Sequence Type 779 Methicillin-Resistant *Staphylococcus aureus* Harboring a Novel Pseudo *Staphylococcal* Cassette Chromosome mec (SCCmec)-SCC-SCC CRISPR Composite Element in Irish Hospitals," Antimicrobial Agents and Chemotherapy, vol. 57, No. 1, pp. 524-531, dated Jan. 2013, 8 pages.
Kleinstiver et al., "High-fidelity CRISP-Cas9 nucleases with no detectable genome-wide off-target effects", Nature, vol. 529, No. 7587, Jan. 28, 2016, pp. 490-495.
Kleinstiver, et al. "Engineered CRISPR-Cas9 nucleases with altered PAM specificities," Nature, vol. 523, pp. 481-485, including Research Letter, dated 2015.
Kondo, et al. "Highly Improved Gene Targeting by Germline-Specific Cas9 Expression in *Drosphila*", Genetics, 2013, 195:715-721.
Konermann, et al, "Genome-scale transcriptional activation by an engineered CRISPR-Cas9 complex", Nature, 2015, 517:583-588.
Koo et al., "Measuring and Reducing Off-Target Activities of Programmable Nucleases Including CRISPR-Cas9", Molecules and Cells, vol. 38, No. 6, May 19, 2015, pp. 475-481.
Koornneef, A., et al., "Apolioprotein B Knockdown by AAV-Delivered shRNA Lowers Plasma Cholesterol in Mice," Molecular Therapy, vol. 19, No. 4, pp. 731-740, dated Apr. 2011, 10 pages.

(56) References Cited

OTHER PUBLICATIONS

Kosugi, et al. "Six Classes of Nuclear Localization Signals Specific to Different Binding Grooves of Importin a . . . " The Journal of Biological Chemistry, 2009, 284(1):478-485.
Kowalski, Thomas J., PowerPoint Presentation, "Interview Sep. 9, 2015.".
Krauer, et al. "Identification of the nuclear localization signals within the Epstein-Barr virus EBNA-6 protein", Journal of General Virology, 2004, 85:165-172.
Kuhlman, et al. "A place for everything$201 D Chromosomal intergration of large constructs", Bioengineered Bugs, Jul./Aug. 2010, 1(4)296-299.
Kuhlman, et al. "Site-specific chromosomal integration of large synthetic constructs", Nucleic Acids Research, 2010, 38(6):1-10, doi:10.1093/nar/gkp1193.
Kumar, M., et al., "Systematic Determination of the Packaging Limit of Lentiviral Vectors," Human Gene Therapy, vol. 12, pp. 1893-1905, dated Oct. 10, 2001, 21 pages.
Kuwayama, H., "Enhancement of Homologous Recombination Efficiency by Homologous Oligonucleotides," Cell Interaction Sivakumar Gowder, IntechOpen, DOI: 10.5772/47779, dated Oct. 10, 2012, 12 pages.
Lambowitz, et al. "Group II Introns: Mobile Ribozymes that Invade DNA", Cold Spring Harb Perspect Biol., 2011, 3:a003616.
Lanford, et al. "Induction of Nuclear Transport with a Synthetic Peptide Homologous to the SV40 T Antigen Transport Signal", Cell, 1986, 46:575-582.
Lange, et al. "Classical Nuclear Localization Signals: Definition, Function, and Interaction with Importin$2026" J. Biol. Chem., 2007, 282(8):5101-5105.
Larson, et al. "CRISPR interference (CRISPRi) for sequence-specific control of gene expression", Nature Protocols, 2013, 8(11):2180-2196.
Lebherz, C., et al., "Gene therapy with novel adeno-associated virus vectors substantially diminished atherosclerosis in a murine model of familial hypercholesterolemia," The Journal of Gene Medicine, vol. 6, pp. 663-672, dated Mar. 2, 2004, 10 pages.
Lee, C., et al., "Correction of the F508 Mutation in the Cystic Fibrosis Transmembrane Conductance Regulator Gene by Zinc-Finger Nuclease Homology-Directed Repair," Bioresearch Open Access, vol. 1, No. 3, pp. 99-108, dated 2012, 12 pages.
Leenay, et al. "Identifying and Visualizing Functional PAM Diversity across CRISPR-Cas Systems", Molecular Cell, 2016, 62:137-147.
Lemay, et al. "Folding of the Adenine Riboswitch", Chemistry & Biology, 2006, 13:857-868.
Levitt, J., et al., "Intrinsic fluorescence and redox changes associated with apoptosis of primary human epithelial cells," Journal of Biomedical Optics, vol. 11, No. 6, pp. 064012 1-10, dated Nov./Dec. 2006, 10 pages.
Lewin, et al. "Nuclear localization sequences target proteins to the nucleus" Cells, 2006, 5:224.
Lewis, et al., "The c-myc and PyMT oncogenes induce different tumor types in a somatic mouse model for pancreatic cancer" Genes & Development, 2003, 17:3127-3138.
Li et al., "Coevolution of CRISPR-Cas system with bacteria and phages", Hereditas, vol. 33, No. 3, Mar. 31, 2011, pp. 213-218.
Li, et al. "In vivo genome editing restores hemostasis in a mouse model of hemophilia" Nature, 2011, 475(7355):217-221. doi: 10.1038/nature10177.
Li, et al. "Multiplex and homologous recombination-mediated genome editing in *Arabidopsis* and Nicotaina benthamiana using guide RNA and Cas9" Nature Biotechnology, 2013, 31(9):688-691.
Li, P., et al., "Biallelic knockout of alpha-1,3 galactosyltransferase gene in porcine liver-derived cells using zing finger nucleases," Journal of Surgical Research, vol. 181, No. 1, pp. E39-E45, dated Jul. 3, 2012, 7 pages.
Li, Ting, et al. "Modularly assembled designer TAL effector nucleases for targeted gene knockout and gene replacement in eukaryotes" Nucleic Acids Research, 2011, 39(14):6315-6325.

Liu, et al. "Epstein-Barr Virus DNase Contains Two Nuclear Localization Signals Which Are Different in Sensitivity to the Hydrophobic Regions" Virology, 1998, 247:62-73.
Lombardo, A., et al., "Gene editing in human stem cells using zinc finger nucleases and integrase-defective lentiviral vector delivery," Nature Biotechnology, vol. 25, No. 11, pp. 1298-1306, dated Nov. 1, 2007, 9 pages.
Los, et al. "Halotag Technology: Cell Imaging and Protein Analysis" Cell Notes, 2006, 14:10-14.
Luo, B., et al., "Highly parallel identification of essential genes in cancer cells," Proceeding of the National Academy of Sciences, vol. 105, No. 51, pp. 20380-20385, dated Dec. 23, 2008, 6 pages.
Luo, Ming, et al. "Multiple Nuclear Localization Sequences Allow Modulation of 5-Lipoxygenase Nuclear Import" Traffic, 2004, 5:847-854.
Lyssenko, et al. "Cognate putative nuclear localization signal effects strong nuclear localization of a GFP reporter and facilitates gene expression studies in Caenorhabditis elegans" BioTechniques, 2007, 43:596-600.
Ma, M., et al., "A Guide RNA Sequence Design Platform for the CRISPR/Cas9 System for Model Organism Genomes," Hindawi, vol. 2013, art. 270805, BioMed Research International, dated Sep. 13, 2013, 5 pages.
Ma, M., et al., "A Guide RNA Sequence Design Platform for the CRISPR/Cas9 System for Model Organism Genomes," BioMed Research International, vol. 31, No. 3, pp. 822-824, dated Nov. 2013, 4 pages.
Maczuga, P., et al., "Embedding siRNA sequences targeting Apolipoprotein B100 in shRNA and miRNA scaffolds results in differential processing and in vivo efficacy," Molecular Therapy, vol. 21, No. 1, pp. 217-227, dated Jan. 2013, 11 pages.
Madisen et al., "A robust and high-throughput Cre reporting and characterization system for the whole mouse brain," Nat. Neurosci., 13(1):133-140, (2010) (author manuscript; available in PMC Jul. I, 2010).
Maeder, M., and Gersbach, C., "Genome-editing Technologies for Gene and Cell Therapy," Molecular Therapy, vol. 24, No. 3, pp. 430-446, dated Mar. 2016, 17 pages.
Maeder, M., et al., "Robust, synergistic regulation of human gene expression using TALE activators," Nature Methods, vol. 10, No. 3, pp. 243-245, dated Mar. 2013, 9 pages.
Mahfouz, et al. "Targeted transcriptional repression using a chimeric TALE-SRDX repressor protein" Plant Mol Biol, 2012, 78:311-321.
Mahfouz, M., et al., "De novo-engineered transcription activator-like effector (TALE) hybrid nuclease with novel DNA binding specificity creates double-strand breaks," Proceedings of the National Academy of Science, vol. 108, No. 6, pp. 2623-2628, dated Feb. 8, 2011, 6 pages.
Makarova, et al. "An updated evolutionary classification of CRISPR-Cas systems" Nature Reviews—Microbiology, 2015, 13:722-736.
Makarova, K., et al., "Evolution and classification of the CRISPR-CAS Systems," Nature Reviews Microbiology, vol. 9, No. 6, pp. 467-477, dated Jun. 2011, 23 pages.
Makarova, K., et al., "Unification of Cas protein families and a simple scenario for the origin and evolution of CRISPR-Cas systems," Biology Direct, vol. 6, No. 38, dated 2011, 27 pages.
Mali et al., "CAS9 transcriptional activators for target specificity screening and paired nickases for cooperative genome engineering", Nature Biotechnology, Sep. 2013, vol. 31, No. 9, pp. 833-837.
Mali, et al, Supplementary Information for "Use of adjacent sgRNA: Cas9 complexes for transcriptional activation and genome engineering," Nature Biotechnology, doi:10.1037/nbt.2675.
Mali, et al. "RNA-Guided Human Genome engineering Via Cas9" Science, vol. 339, pp. 823-826, dated Feb. 15, 2013, 41 pages (Includes Supplemental Information).
Mali, et al.: "Supplementary Materials for-RNA-Guided Human Genome Engineering Via Cas9" Science, vol. 339, art. 6121, pp. 823-826, dated Feb. 15, 2013, 8 pages.
Mali, P., et al., "CAS9 transcriptional activators for target specificity screening and paired nickases for cooperative genome engineering," Nature Biotechnology, vol. 31, No. 9, pp. 833-838, dated Aug. 1, 2013, 44 pages (Includes Supplemental Information).

(56) References Cited

OTHER PUBLICATIONS

Mali, P., et al., Supplementary Information for: "RNA-Guided Human Genome Engineering via Cas9," Science, vol. 339, pp. 823-826, dated Feb. 15, 2013, 36 pages.

Malina, A., et al., "Repurposing CRISPR/Cas9 for in situ functional assays," Genes & Development, vol. 27, No. 23, pp. 2602-2614, dated Dec. 1, 2013, 14 pages.

Manjunath, N., et al., "Newer Gene Editing Technologies toward HIV Gene Therapy," Viruses, vol. 5, No. 11, pp. 2748-2766, dated Nov. 14, 2013, 19 pages.

*Manning v. Paradis*, 296 F.3d 1098 (Fed. Cir. 2012).

Marraffini, L., "CRISPR-Cas Immunity against Phages: Its Effects on the Evolution and Survival of Bacterial Pathogens," PLOS, Pathogens, dated Dec. 12, 2013, 6 pages.

Marraffini, L., Assignment to Rockefeller University, dated Dec. 12, 2013, 3 pages.

Marraffini, L., et al., "Self vs. non-self discrimmination during CRISPR RNA-directed immunity," Nature, vol. 463, No. 7280, pp. 568-571, dated Jan. 28, 2010, 13 pages.

Mastroianni, et al. "Group II Intron-Based Gene Targeting Reactions in Eukaryotes" Plos One, 2008, 3(9):e3121. DOI:10.1371/journal.pone.0003121.

*Maxwell v. The Stanley Works*, 2006 WL 1967012, *5 (M.D. Tenn. Jul. 11, 2006).

Meshorer, et al. "Chromatin in pluripotent embryonic stem cells and differentiation" Nature Reviews Molecular Cell Biology, 2006, 7:540-546.

Miller, et al. "A TALE nuclease architecture for efficient genome editing" Nature Biotechnology, 2011, 29(2):143-150.

Mincer, J., and Simon, S., "Simulations of nuclear pore transport yield mechanistic insights and quantitative predictions," Proceedings of the National Academy of Science, vol. 108, No. 31, pp. E351-E358, dated Aug. 2, 2011, 8 pages.

Minton, "How can biochemical reactions within cells differ from those in test tubes?" Journal of Cell Science, 2006, 119:2863-2869.

Mojica, F. J., et al., "Short motif sequences determine the targets of the prokaryotic CRISPR defence system," Microbiology, vol. 155, No. 3, pp. 733-740, dated Mar. 1, 2009, 8 pages.

Mojica, F. J., et al., Supplementary Material for: "Short motif sequences determine the targets of the prokaryotic CRISPR defence system," Microbiology, vol. 155, No. 3, pp. 733-740, dated Mar. 1, 2009, 8 pages.

Morbitzer, et al. "Assembly of custom TALE-type DNA binding domains by modular cloning" 2011, 39(13):5790-5799.

Morbitzer, et al. "Regulation of selected genome loci using de novo-engineered transcription activator-like effector (TALE)-type transcription factors" PNAS, 2010, 108(50):21617-21622.

Morgan, et al. "Inducible Expression and Cytogenetic Effects of the EcoRI Restriction Endonuclease in Chinese Hamster Ovary Cells" Molecular and Cellular Biology, 1988, 8(10):4204-4211.

Morin, et al. "Nuclear Localization of the Adenovirus DNA-Binding Protein: Requirement for Two Signals and Complementation during Viral Infection" Molecular and Cellular Biology, 1989, 9(10):4372-4380.

Morris et al., "Distributed automated docking of flexible ligands to proteins: Parallel applications of AutoDock 2.4*", Journal of Computer-Aided Molecular Design, 1996, vol. 10, pp. 293-304.

Moscou, et al. "A Simple Cipher Governs DNA Regognition by TAL Effectors" Science, 2009, 326:1501.

Mukhopadyay, R., "On the Same Wavelength," ASBMB Today, http://www.asbmb.org/asbmbtoday/201408/Features/Doudna/, dated Aug. 2014, 6 pages.

Mussolino, et al. "TALE nucleases: tailored genome engineering made easy" Current Opinion in Biotechnology, 2012, 23(5):644-650.

Musunuru, "Abstract 18593: Use of a CRISPR/Cas System for Cardiovascualr Disease Modeling and Therapeutic Applications", Circulation, vol. 128, No. 22, Suppl. 1, Nov. 26, 2013, 4 pages (Meeting info: American Heart Association, 2013 Scientific Sessions and Resuscitation Science Symposium, Dallas, TX, US, Nov. 16-20, 2013).

Muther, N., et al.: "Viral Hybrid Vectors for Somatic Integration—Are They the Better Solution?" Viruses, vol. 1, pp. 1295-1324, dated Dec. 15, 2009, 30 pages.

Nagarajan, et al. "A Hierarchy of Nuclear Localization Signals Governs the Import of the Regulatory Factor X Complex Subunits and MHC Class II Expression" The Journal of Immunology, 2004, 173:410.419.

Nakai, et al. "PSORT: a program for detecting sorting signals in proteins and predicting their subcellular localization" Trends in Biochem Sciences, 1999 24:34-35.

Nakamura, et al. "Codon usage tabulated from international DNA sequence databases: status for the year 2000" Nucleic Acids Research, 2000, 28(1): 292.

Nishimasu, H., et al., "Crystal Structure of *Staphylococcus aureus* Cas9," Cell, vol. 162, pp. 1113-1126, dated Aug. 27, 2015, 15 pages.

Noguchi, et al. "PDX-1 Protein Containing Its Own Antennapedia-Like Protein Transduction Domain Can Transduce Pancreatic Duct and Islet Cells" Diabetes, 2003, 52:1732-1737.

Nomura, S., et al., "Low-density lipoprotein receptor gene therapy using helper-dependent adenovirus produces long-term protection against atherosclerosis in a mouse model of familial hypercholesterolemia," Gene Therapy, vol. 11, No. 20, pp. 1540-1548, dated Oct. 22, 2004, 10 pages.

Notice of Opposition filed Aug. 11, 2017 by Schlich against EP Patent No. 2840140.

Notice of Opposition filed Aug. 14, 2017 by Grund against EP Patent No. 2840140.

Notice of Opposition filed Aug. 16, 2017 by Mathys & Squire LLP against EP Patent No. 2840140.

Notice of Opposition filed by Aug. 16, 2017 by Vossius against EP Patent No. 2840140.

O'Hare, et al. "Transformation of mouse fibroblasts to methotrexate resistance by a recombinant plasmid expressing a prokaryotic dihydrofolate reductase" Proc. Natl. Acad. Sci., 1981, 78(3):1527-1531.

Oost, "New Tool for Genome Surgery" Science, Feb. 15, 2013, 399:768-770.

Opposition Against Appl. Ser. No. EP13818570.7 submitted by Schlich dated Oct. 26, 2015, 8 pages.

Opposition Against EP Appl. Ser. No. 2771468-B1 dated Oct. 26, 2015.

Ozawa, K., "Gene therapy using AAV," Uirusu, vol. 57, No. 1, pp. 47-55 dated Nov. 27, 2007, 13 pages (with English Abstract; No English Translation).

Pandika, et al., www.ozy.com/rising-stars-and-provocateurs/jennifer-doudna-crispr-code-killer/4690; 2014 (Jul. 1, 2014).

Panyam, J., and Labhasetwar, V., "Biodegradable nanoparticles for drug and gene delivery to cells and tissue," Advanced Drug Delivery Reviews, vol. 55, No. 3, pp. 329-347, dated Feb. 24, 2003, 19 pages.

Park, et al. "Regulation of Ribosomal S6 Kinase 2 by Mammalian Target of Rapamycin", The Journal of Biological Chemistry, 2002, 277(35):31423-31429.

Pattanayak, et al., "High-throughput profiling of off-target DNA cleavage reveals RNA-programmed Cas9 nuclease specificity," Nature Biotechnology, vol. 31, No. 9, pp. 839-843, dated 2013, including Supplementary Materials.

Patterson, et al. "Codon optimization of bacterial luciferase (lux) for expression in mammalian cells" J. Ind. Microbio. Biotechnology, 2005, 32:115-123.

Perez-Pinera, et al. "Advances in Targeted Genome Editiong" Curr Opin Chem Biol., 2012, 16(3-4):268.277, doi:10.1016/j.cbpa.2012.06.007.

Perez-Pinera, et al. "RNA-guided gene activation by CRISPR-Cas9-based transcription factors" Nature Methods, 2013, 10(10):973-976 (12 pages).

Phillips, A., "The challenge of gene therapy and DNA delivery," The Journal of Pharmacy and Pharmacology, vol. 53, pp. 1169-1174, dated 2001, 6 pages.

(56) References Cited

OTHER PUBLICATIONS

Planey, et al. "Mechanisms of Signal Transduction: Inhibition of Glucocorticoid-induced Apoptosis in 697 Pre-B Lymphocytes by the Mineralocorticoid Receptor N-terminal Domain", J. Biol. Chem., 2002, 277:42188-42196.

Platt, R., et al., "CRISPR-Cas9 Knockin Mice for Genome Editing and Cancer Modeling," Cell, vol. 159, No. 2, pp. 440-455, dated Oct. 9, 2014, 16 pages.

Porteus, et al. "Gene targeting using zinc finger nucleases" Nature Biotechnology, 2005, 23(8):967-973.

Porteus, M., and Balitmore, D., "Chimeric Nucleases Stimulate Gene Targeting in Human Cells," Science, vol. 300, p. 763, dated May 2, 2003, 2 pages.

Posfai, et al. "Markerless gene replacement in *Escherichia coli* stimulated by a double-strand break in the chromosome" Nucleic Acids Resarch, 1999, 27(22):4409-4415.

Pougach, et al. "Transcription, Processing and Function of CRISPR Cassettes in *Escherichia coli*" Mol. Microbiol, 2010, 77(6):1367-1379.

Pougach, K.S., et al.: "CRISPR Adaptive Immunity Systems of Prokaryotes," Molecular Biology, vol. 46, No. 2, Apr. 2012, pp. 195-203, 1 page (English Abstract).

PowerPoint slide entitled "Development and Applications of CRISPR-Cas9 for Genome Editing" dated Sep. 9, 2015.

Pride, D., et al., "Analysis of *Streptococcal* CRISPRs from Human Saliva Reveals Substantial Sequence Diversity Within and Between Subjects Over Time," Genome Research, vol. 21, No. 1, pp. 126-136, dated Jan. 2011, 11 pages.

Primo, et al. "Lentiviral vectors for cutaneous RNA managing" Experimental Dermatology, 2012, 21:162-170.

Qi, et al. "Repurposing CRISPR as an RNA-Guided Platform for Sequence-Specific Control of Gene Expression" Cell, 2013, 152(5):1173-1183.

Qi, J., et al., "microRNAs regulate human embryonic stem cell division," Cell Cycle, vol. 8, No. 22, pp. 3729-3741, dated Nov. 15, 2009, 13 pages.

Radecke, S., et al., "Zinc-finger Nuclease-induced Gene Repair With Oligodeoxynucleotides: Wanted and Unwanted Target Locus Modifications," Molecular Therapy, vol. 18, No. 4, pp. 743-753, dated Apr. 2010, 11 pages.

Radulovich, et al. "Modified gateway system for double shRNA expression and Cre/lox based gene expression" BMC Biotechnology, 2011, 11(24):1-9.

Ran et al., "Double Nicking by RNA-guided CRISPR Cas9 for enhanced genome editing specificity", Cell, Sep. 2013, vol. 154, pp. 1380-1389.

Ran, et al., "Double Nicking by RNA-Guided CRISPR Cas9 for Enhanced Genome Editing Specificity," Cell 154, 1-10, Sep. 12, 2013.

Ran, F., et al, "In vivo genome editing using *Staphylococcus aureus* Cas9," Nature, vol. 520, pp. 186-191, dated Apr. 2015, 18 pages.

Ran, F., et al., "Genome engineering using the CRISPR-Cas9 system," Nature Protocols, vol. 8, No. 11, pp. 2281-2308, dated 2013, 28 pages.

Rand, et al. "Argonaute2 Cleaves the Anti-Guide Strand of siRNA during RISC Activation" Cell, 2005, 123:621-629.

Raymond, et al. "High-Efficiency FLP and φC31 Site-Specific Recombination in Mammalian Cells" PLoS ONE, 2007, 2(1):e162. Doi. 10.1371/journal.pone.0000162.

Rebar, et al. "Induction of angiogenesis in a mouse model using engineered transcription factors" Nature Medicine, Dec. 2002, 8(12):1427-1432.

Redeclaration—37 C.F.R. 41.203(c); filed Mar. 17, 2016.

Reiss, et al. "RecA protein stimulates homologous recombination in plants" Proc. Natl. Acad. Sci. USA, 1996, 93:3094-3098.

Response to Third Party Observations in EP No. 13824232.6 filed Oct. 2, 2014, with Redlined and Clean Amended Claims.

Rho, M., et al., "Diverse CRISPRs Evolving in Human Microbiomes," PLOS Genetics, vol. 8, No. 6, pp. e1002441, dated Jun. 2012, 12 pages.

Rhun, A., and Charpentier, E., "Small RNAs in streptococci," RNA Biology, vol. 9, No. 4, pp. 414-426, dated Apr. 2012, 13 pages.

Roberts, et al. "Nuclear location signal-mediated protein transport" Biochimica et Biophysica Acta, 1989, 1008:263-280.

Roberts, et al. "The Effect of Protein Content on Nuclear Location Signal Function" Cell, 1987, 50:465-475.

Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-institute-mit-and-harvard-announce-update-crispr-cas9, 3 pages.

Rodrigues, et al. "Red Fluorescent Protein (DsRed) as a Reporter in Saccharomyces cerevisiae" Journal of Bacteriology, 2001, 183(12):3791-3794.

Rodriguez et al., "AAV-CRISPR: A New Therapeutic Approach to Nucleotide Repeat Diseases", Molecular Therapy, vol. 22, Supplement 1, Abstract 247, May 2014, p. S94.

Rolling, "Recombinant AAV-mediated gene transfer to the retina: gene therapy perspectives", Gene Therapy, Vo. 11, 2004, pp. S26-S32.

*Rubin v. The General Hospital Corp.*, 2011-1439 (Fed. Cir. Mar. 28, 2013).

Sadowski, M., and Jones, D., "The sequence-structure relationship and protein function prediction," Current Opinion in Structural Biology, vol. 19, pp. 357-362, dated May 4, 2009, 6 pages.

Sambrook, et al., Molecular Cloning, A Laboratory Manual on the Web, 2001, Chapter 16.

Sander, et al., "CRISPR-Cas systems for editing, regulating and targeting genomes," Nature Biotechnology, vol. 32, pp. 347-355, dated 2014.

Sanders, et al. "Use of a macromolecular crowding agent to dissect interactions and define functions in transcriptional activation by a DNA-tracking protein: Bacteriophage T4 gene 45 protein and late transcription" PNAS, 1994, 9:7703-7707.

Sanders, UC Berkeley Jan. 7, 2013 Press Release, available at http://newscenter.berkeley.edu/2013/01/07/cheap-and-easy-technique-to-snip-dna-could-revolutionize-gene-therapy/.

Sanjana, et al., "Improved vectors and genome-wide libraries for CRISPR screening," HHS Public Access Author Manuscript, 2014, 11(8):2145-2148.

Sanjana, N., et al., "A Transcription Activator-Like Effector (TALE) Toolbox for Genome Engineering," Nature Protocols, vol. 7, No. 1, pp. 171-192, dated Jan. 1, 2012, 39 pages.

Sapranauskas, R., et al., "The *Streptococcus thermophilus* CRISPR-Cas system provides immunity in *Escherichia coli*," Nucleic Acids Research, vol. 3, No. 21, pp. 9275-9282, dated Aug. 3, 2011, 8 pages.

Sato, et al. "Generation of Adeno-Associated Virus Vector Enabling Functional Expression of Oxytocin Receptor and Fluorescence Marker Genes Using the Human eIF4G Internal Ribosome Entry Site Elemet" Biosci. Biotechno. Biochem, 2009, 73(9):2145-2148.

Sauer, "Functional Expression of the cre-lox Site-Specific Recombination System in the Yeast *Saccharomyces cerevisiae*" Mol. Cell. Biol., 1987, 7(6):2087-2096.

Sauer, et al. "Site-specific DNA recombination in mammalian cells by the Cre recombinase of bacteriophage P1" Proc. Natl. Acad. Sci. U.S.A., 1988, 85:5166-5170.

Schiffer, et al. "Predictors of Hepatitis B Cure Using Gene Therapy to Deliver DNA Cleavage Enzymes: A Mathematical Modeling Approach" PLOS Computational Biology, 2013, 9(7):e1003131. www.ploscompbiol.org.

Scholze, et al. "TAL effector-DNA specificity" Virulence, 2010, 1(5):428-432, DOI:10.4161/viru.1.5.12863.

Schramm et al. "Recruitment of RNA polymerase III to its target promoters" Genes & Development, 2002, 16:2593-2620.

Schunder et al., "First indication for a functional CRISPR/Cas system in Francisella tularensis", International Journal of Medical Microbiology, 2013, vol. 303, pp. 51-60.

Sebastiani, et al., "BCL11A enhancer haplotypes and fetal hemoglobin in sickle cell anemia," Blood Cells, vol. 54, No. 3, pp. 1079-9796, dated 2015.

(56) References Cited

OTHER PUBLICATIONS

Sebo, et al. "A simplified and efficient germline-specific CRISPR/Cas9 system for Drosophila genomic engineering" Fly, 2014, 8(1):52-57.
Seffernick, J., et al., "Melamine Deaminase and Atrazine Chlorohydrolase: 98 Percent Identical but Functionally Different," Journal of Bacteriology, vol. 183, No. 8, pp. 2405-2410, dated Apr. 2001, 6 pages.
Senis, E., et al., "CRISPR/Cas9-mediated genome engineering: An adeno-associated viral (AAV) vector toolbox," Biotechnology Journal, vol. 9, No. 11, Sp. Iss. SI, pp. 1402-1412, dated Sep. 4, 2014, 12 pages.
Senturk et al., "A rapid and tunable method to temporally control cas9 expression enables the identification of essential genes and the interrogation of functional gene interactions in vitro and in vivo", Jul. 28, 2015, pp. 1-27, XP002756303, doi:10.1101/023366, Retrieved from the Internet: URL:http://biorxiv.org/content/early/2015/07/28/023366 [retrieved on Apr. 11, 2016).
Seung Woo Cho, et al. "Analysis off-target effects of CRISPR/Cas-derived RNA-guided endonucleases and nickases" Genome Research, Nov. 2014, 24:132-141.
Shalem, et al., "High-throughput functional genomics using CRISP-Cas9," Nature Reviews Genetics, vol. 16, No. 5, pp. 1471-0056, dated 2015.
Shalem, O., et al., "Genome-Scale CRISPR-Cas9 Knockout Screening in Human Cells," Science, vol. 343, pp. 84-87, dated Jan. 3, 2014, 5 pages.
Sharan, et al. "Recombineering: A Homologous Recombination-Based Method of Genetic Engineering" Nat. Protoc., 2009, 4(2):206-223, doi:10.1038/nprot.2008.227.
Shen, B., et al. "Generation of gene-modified mice via Cas9/RNA-mediated gene targeting," Cell Research, vol. 23, No. 5, pp. 720-723, dated May 2013, 4 pages.
Shen, et al. "Efficient genome modification by CRISPR-Cas9 mickase with minimal off-target effects" 2014, Nature Methods, 11(4):399-404.
Shieh, et al. "Nuclear Targeting of the Maize R. Protein Requires Two Nuclear Localization Sequences" Plant Physiol, 1993, 101:353-361.
Siegl, et al. "I-Scel endonuclease: a new tool for DNA repair studies and genetic manipulations in streptomycetes" Appl Microbiol Bitotechnol, 2010, 87:1525-1532.
Sims, D., et al., "High-throughput RNA interference screening using pooled shRNA libraries and next generation sequencing," Genome Biology, vol. 12, No. 10, p. R104, dated Oct. 21, 2011, 13 pages.
Singer, et al. "Applications of Lentiviral Vectors for shRNA Delivery and Transgenesis" Curr Gene Ther., 2008, 8(6):483-488.
Slaymaker et al., Rationally engineered Cas9 nucleases with improved specificity, Science, American Association for the Advancement of Science, US, vol. 351, No. 6268, Jan. 1, 2016, pp. 84-88.
Sontheimer, "Project 7: Establishing RNA-Directed DNA Targeting in Eukaryotic Cells" Physical Sciences-Onc., Nov. 16, 2011-Dec. 31, 2012, htt://groups.molbiosci.northwestern.edu/sontheimer/Sontheimer_cv.php) Molecular Biosciences.
Stolfi, et al, "Tissue-specific genome editing in Ciona embryos by CRISPR/Cas9," Development, 2014, 141:4115-4120 doi:10.1242/dev.114488.
Stoller, J. and Aboussouan, L., "Alpha1-antitrypsin deficiency," The Lancet, Seminar, vol. 365, No. 9478, pp. 2225-2236, dated Jun. 25, 2005, 12 pages
Stratikopoulos, E., et al., "The hormonal action of IGF1 in postnatal mouse growth," Proceedings of the National Academy of Sciences, vol. 105, No. 49, pp. 19378-19383, dated Dec. 9, 2008, 6 pages.
Straub, C., et al., "CRISPR/Cas9-Mediated Gene Knock-Down in Post-Mitotic Neurons," PLOS One, vol. 9, No. 8, art. E105584, pp. 1-5, dated Aug. 2014, 6 pages.
Sung, et al. "An rpsL Cassette, Janus, for Gene Replacement through Negative Selectionin Streptococcus pneumoniae" Applied and Environmental Microbiology, 2001, 67(11):5190-5196.

Sung, M., et al., "The importance of valency in enhancing the import and cell routing potential of protein transduction domain-containing molecules," Biochimica et Biophysica Aeta, vol. 1758, pp. 355-363, dated 2006, 9 pages.
Sung, Young Hoon, et al. "Mouse genetics: Catalogue and scissors" BMB Reports, 2012, 45(12):686-692.
Suzuki, K., et al., "In vivo genome editing via CRISPR/Cas9 mediated homology-independent targeted integration," Nature, vol. 540, art. 7631, pp. 144-149, dated Dec. 1, 2016, 44 pages.
Swarthout, J., et al., "Zinc Finger Nucleases: A new era for transgenic animals," Annals of Neurosciences, vol. 18, No. 1, pp. 25-28, dated Jan. 2011, 4 pages.
Swiech et al., "CRISPR-Mediated Genome Editing in the Mammalian Brain", Molecular Therapy, vol. 22, 749, May 2012, p. S289.
Swiech, L., et al., "In vivo interrogation of gene function in the mammalian brain using CRISPR-Cas9," Nature Biotechnology, vol. 33, pp. 102-106, dated Oct. 19, 2014, 9 pages.
Tang, T., et al., "A mouse knockout library for secreted and transmembrane proteins," Nature Biotechnology, vol. 28, No. 7, pp. 749-755, dated Jul. 2010, 9 pages.
Terns, M., and Terns, R., "CRISPR-based adaptive immune systems," Current Opinion in Microbiology, vol. 14, pp. 321-327, dated 2011, 8 pages.
The Broad Inst. v. The Regents of University of UCA—Decision on Motions for Patent Interference No. 106,048 filed Feb. 15, 2017.
Third Party Observation for Application No. EP20130824232 filed Sep. 22, 2014.
Third Party Observations Concerning App. No. GB1420270.9 dated Jun. 30, 2015.
Third Party Observations Concerning Appl. No. EP2800811, dated Jul. 24, 2015.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13824232.6, Pub. No. EP2764103A, Mar. 25, 2015.
Third Party Observations submitted by Broad Institute Inc. Concerning Appl. Ser. No. EP13793997.1 dated Jul. 24, 2015, 108 pages.
Third Party Observations submitted by Broad Institute Inc. Concerning Appl. Ser. No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, Feb. 16, 2015.
Third-Party Observation for Application No. EP20130824232 Aug. 9, 2014.
Tinland, et al. "The T-DNA-linked VirD2 protein contains two distinct functional nuclear localization signals" Proc. Natl. Acad. Sci, 1992, 89:7442-7446.
Tiscornia, et al. "Development of Lentiviral Vectors Expressing siRNA" Gene Transfer-Delivery and Expression of DNA and RNA—A Laboratory Manual, 2007, Chapter 3:23-34.
Tolia, et al. "Slicer and the Argonautes" Nature Chemical Biology, 2007, 3(1):36-43.
Trafton, A., "CRISPR-carrying nanoparticles edit the genome," MIT News, dated Nov. 13, 2017, 3 pages.
Trevino, et al. "Genome Editing Using Cas9 Nickases" Methods in Enxymology, 2014, 546:161-174.
Tulpan, D., et al., "Free energy estimation of short DNA duplex hybridizations," BMC Bioinformatics, vol. 11, pp. 105-127, dated 2012, 22 pages.
Type V CRISPR-associated protein Cpfi [Acidaminococcus sp. Bv3L6], 2017, NCBI Reference Sequence: WP_02173622.1, Non-redundant Protein Sequence.
Ultra-Precision Mfg. Ltd. v. Ford Motor Co., 2004 WL 3507671, *7, *11-12 (E.D. Mich. Mar. 30, 2004).
Urnov, et al. "Highly efficient endogenous human gene correction using designed zinc-finger nucleases" Nature, 2005, 435:646-651.

(56) References Cited

OTHER PUBLICATIONS

Urnov, F., et al., "Genome editing with engineered zinc finger nucleases," Nature Reviews, Genetics, vol. 11, pp. 637-646, dated Sep. 2010, 11 pages.

Urrutia, et al. "KRAB-containing zing finger repressor proteins" Genome Biology, 2003, 4(10):231-231.8.

Van Den Ackerveken, et al. "Recognition of the Bacterial Avirulence Protein AvrBs3 Occurs inside the Host Plant Cell" Cell, 1996, 87:1307-1316.

Van Der Oost, "New tool for genome surgery", Science, Feb. 2013, vol. 339, pp. 768-770.

Van Nierop, G., et al., "Stimulation of homology-directed gene targeting at an endogenous human locus by a nicking endonuclease," Nucleic Acids Research, vol. 37, No. 17, pp. 5725-5736, dated Aug. 3, 2009, 12 pages.

Venken et al., "P[acman]: A BAC Transgenic Platform for Targeted Insertion of Large DNA Fragments in *D. melanogaster*", Science, vol. 314, No. 5806, Nov. 30, 2006, pp. 1747-1751.

Vestergaard et al., "CRISPR adaptive immune systems of Archaea", RNA Biology, 2014, vol. 11, No. 2, pp. 156-167.

Villion, et al. "The double-edged sword of CRISPR-Cas systems" Cell Research, 2013, 23:15-17.

Wang, et al. "Genetic Screens in Human Cells Using the CRISPR-Cas9 System", Science, 2014, 343:80-84.

Wang, H., et al. "One-Step Generation of Mice Carrying Mutations in Multiple Genes by CRISPR/Cas-Mediated Genome Engineering," Cell, vol. 153, No. 4, pp. 910-918, dated May 9, 2013, 9 pages.

Weber et al., "TALENs Targeting HBV: Designer Endonuclease Therapies for Viral Infections", Molecular Therapy, vol. 21, No. 10, Oct. 2013, pp. 1819-1821.

Welch, et al. "Designing Genes for Successful Protein Expression" Methods in Enzymology, 2011, 498:43-66, DOI: 10.1016/B978-0-12-385120-8.00003-6.

Wiedenheft, B., et al., "RNA-guided genetic silencing systems in bacteria and archaea," Nature, vol. 482, pp. 331-338, dated Feb. 16, 2012, 8 pages.

Wienert, B., et al., "In vitro transcribed guide RNAs trigger an innate immune response via the RIG-I pathway," BioRxiv Preprint, dated Mar. 3, 2018, 28 pages.

Witkowski, A., et al., "Conversion of a Beta-Ketoacyl Synthase to a Malonyl Decarboxylase by Replacement of the Active-Site Cysteine with Glutamine," Biochemistry, vol. 38, pp. 11643-11650, dated Aug. 18, 1999, 8 pages.

Wittmann et al., "Engineered riboswitches: Expanding researchers' toolbox with synthetic RNA regulators", FEBS Letters, vol. 586, No. 15, Feb. 28, 2012, pp. 2076-2083.

Wolff, et al. "Nuclear security breached" Nature Biotechnology, 2001, 19:1118-1120.

Woo Cho, S., et al., "Targeted genome engineering in human cells with the Cas9 RNA-guided endonuclease," Nature Biotechnology, vol. 31, No. 3, pp. 230-232, dated Jan. 29, 2013, including Supplementary Information, 14 pages.

Wu, X., et al., "Genome-wide binding of the CRISPR endonuclease Cas9 in mammalian cells," Nature Biotechnology, Advance Online Publication, dated Apr. 20, 2014, 9 pages.

Wu, Y., et al., "Correction of a Genetic Disease in Mouse via Use of CRISPR-Cas9," Cell Stem Cell, vol. 13, No. 6, pp. 659-662, dated Dec. 5, 2013, 4 pages.

Wu, Z., et al., "Effect of Genome Size on AAV Vector Packaging," The American Society of Gene & Cell Therapy, vol. 18, No. 1, pp. 80-86, dated Jan. 2010, 7 pages.

Xiao, et al. "Chromosomal deletions and inversions mediated by TALENs and CRIPPR/Cas in zebrafish" Nucleic Acids Research, 2013, 41(14):E141. doi:10.1093/nar/gkt464.

Xiao, et al. "Production of High-Titer Recombinant Adeno-Associated Virus Vectors in the Absence of Helper Adenovirus" Journal of Virology, 1998, 72(3):2224-2232.

Xie, et al. "RNA-Guided Genome Editing in Plants Using a CRISPR-Cas System" Molecular Plant, 2013, 6(6):1975-1983.

Yaghmai, et al. "Optimized Regulation of Gene Expression Using Artificial Transcription Factors", Molecular Therapy, 2002, 5(6):685-694.

Yamano, et al. "Crystal Structure of Cpf1 in Complex with Guide RNA and Target DNA" Cell, 2016, 165:949-962.

Yanfang Fu et al., "Improving CRISPR-Cas nuclease specificity using truncated guide RNAs" (with Supplement Table), Nature Biotechnology, vol. 32, No. 3, Jan. 26, 2014, pp. 279-284.

Yang et al., "HIV-1 TAT-mediated protein transduction and subcellular localization using novel expression vectors," FEBS Letters 532:36-44, (2002).

Yang, H., et al., "One-Step Generation of Mice Carrying Reporter and Conditional Alleles by CRISPR/Cas-Mediated Genome Engineering," Cell, vol. 154, No. 6, pp. 1370-1379, dated Sep. 12, 2013, 14 pages.

Yi, et al. "Current Advances in Retroviral Gene Therapy" Current Gene Therapy, 2011, 11:218:228.

Yin, H., et al., "Structure-guided chemical modification of guide RNA enables potent non-viral in vivo genome editing," Nature Biotechnology, vol. 35, pp. 1179-1187, dated Nov. 13, 2017, 22 pages.

Yu, et al. "An efficient recombination system for chromosome engineering in *Escherichia coli*" PNAS, 2000, 97(11):5978-5983.

Yu, W., et al., "Nrl knockdown by AAV-delivered CRISPR/Cas9 prevents retinal degeneration in mice," Nature Communications, vol. 8, art. 14716, dated Mar. 14, 2017, 15 pages.

Yu, Zhongshen, et al. "Highly Efficient Genome Modifications Mediated by CRISPR/Cas9 in *Drosophila*" Genetics, 2013, 195:289-291.

Yusuke Miyazaki et al., Destabilizing Domains Derived from the Human Estrogen Receptor:, Journal of the American Chemical Society, vol. 134, No. 9, Mar. 7, 2012, pp. 3942-3945.

Zetsche et al. "A split-Cas9 architecture for inducible genome editing and transcription modulation" Nature biotechnology, 2015, 33(2): 139-142.

Zetsche et al., "Cpf1 is a single RNA-guided endonuclease of a class 2 CRISPR-Cas system", Cell, Oct. 1, 2015, vol. 163, No. 3, pp. 759-771.

Zhang, "Processing-Independent CRISPR RNAs Limit Natural Transformation in Neisseria meningitidis", Molecular Cell, vol. 50, May 23, 2013. pp. 488-503.

Zhang, et al. "Optogenetic interrogation of neural circuits: technology for probing mammalian brain structures" Nat Protoc., 2010, 5(3):439-456, doi:10.1038/nprot.2009.226.

Zhang, et al. "Efficient construction of sequence-specific TAL effectors for modulating mammalian transcription" nature biotechnology, 2011, 29(2):149-154.

Zhang, et al., "Optimized CRISPR Design", MIT, XP055167487, Oct. 23, 2013, URL:http//crispr.mit.edu/about[retrieved on Feb. 5, 2015].

Zhang, F., PowerPoint Presentation: "Development and Applications of CRISPR-Cas9 for Genome Editing," Broad Institute/MIT, dated Sep. 9, 2015, 50 pages.

Zhang, L., et al., "Efficient Expression of CFTR Function with Adeno-Associated Virus Vectors that Carry Shortened CFTR Genes," Proceedings of the National Academy of Science USA, vol. 95, pp. 10158-10163, dated Aug. 1998, 6 pages.

Zhang, X. D., et al., "cSSMD: assessing collective activity for addressing off-target effects in genome-scale RNA interference screens," Bioinformatics, vol. 27, No. 20, pp. 2775-2781, dated Oct. 2011, 7 pages.

Zhou, et al., "High-throughput screening of a CRISPR/Cas9 library for functional genomics in human cells," Nature, vol. 509, pp. 487-491, dated 2014.

Zhu, et al. "Crystal structure of Cmr2 suggests a nucleotide cyclase-related enzyme in type III CRISPR-Cas sytems" FEBS Letters, 2012, 939-945. Doi:10.1016/j.febslet2012.02.036.

Zolkiewska, et al. "ADAM Proteases:Ligand Processing and Modulation of the Notch Pathway" Cell Mol Life Sci, 2008, 65(13):2056-2068.

(56) References Cited

OTHER PUBLICATIONS

Zuris, et al., "Cationic lipid-mediated delivery of proteins enables efficient protein-based genome editing in vitro and in vivo" Nature Biotechnology, 2014, Advanced Online publication, doi:10.1038/nbt.3081.

Zuris, et al., Supplementary Information—"Cationic lipid-mediated delivery proteins enables efficient protein-based genome editing in vitro and in vivo" Nature Biotechnology, 2014, Advanced Online publication, doi:10.1038/nbt.3081.

Allen, et al., "Liposomal drug delivery systems: From concept to clinical applications" Advanced Drug Delivery Reviews, vol. 65, 2013, pp. 36-48, 13 pages.

Botta, S. et al, "Transcriptional Repression with Zinc-Finger and Tale Protein Scaffold", Molecular Therapy, 2013, Supplement 1, p. S208, Abstract No. 539.

Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.

Cho, Minseon, et al., "Quantitative selection and parallel characterization of aptamers," PNAS, vol. 110, Nov. 12, 2013, pp. 18460-18465.

Dean., "Recent Advances in Drug Design Methods: Where Will They Lead?", BioEssays, vol. 16, Sep. 1994, pp. 683-687.

Esvelt et. al., "Orthogonal Cas9 proteins for RNA-guided gene regulation and editing", Nature Methods, vol. 10, No. 11, Nov. 2013 (available online Sep. 29, 2013), pp. 1116-1123.

Flannery, J. G., "Ribozyme-Mediated Gene Therapy for Autosomal Dominant Retinal Degeneration", Retinal Degenerative Diseases and Experimental Therapy, 1999, pp. 277-291.

Gao, et al., "A Sustained, Cytoplasmic Transgene Expression System delivered by Cationic Liposomes", Biochemical and Biophysical Research Communications, vol. 200, May 16, 1994, pp. 1201-1206.

Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.

Grosse, et al. "Meganuclease-medicated Inhibition of HSV1 Infection in Cultured Cells", Molecular Therapy, vol. 19, No. 4, Apr. 1, 2011, pp. 694-702.

Sarra, G., et al., "Gene replacement therapy in the retinal degeneration slow (rds) mouse: the effect on retinal degeneration following partial transduction of the retina", Human Molecular Genetics, vol. 10, 2001, pp. 2353-2361, 9 pages.

Schiffer, et al. "Targeted DNA Mutagenesis for the Cure of Chronic Viral Infections" Journal of Virology, vol. 86, No. 17, Jun. 20, 2012, pp. 8920-8936.

Spencer, J.M., et al., "Development of a Nuclease Screen to Improve Cas9 Targeting Specificity", Molecular Therapy, May 2015, vol. 23, Suppl. 1, S136(340).

Symington et al., "Double-Strand Break End Resection and Repair Pathway Choice", Annual Review of Genetics, vol. 45, 2011, pp. 247-271, 25 pages.

Takara Bio USA, Inc., "Lenti-X™ Tet-On © 3G CRISPR/Cas9 System User Manual", 2016, pp. 1-35.

Third Party Observation in Application No. PCT/US2013/074819 dated Apr. 10, 2015, 10 pages.

Third Party Observation Under Article 115 EPC in Application No. 13818570.7 dated Oct. 1, 2014.

Wayengera, M., "Identity of zinc finger nucleases with specificity to herpes simplex virus type II genomic DNA; novel HSV-2 vaccine/therapy precursors", Theoretical Biology and Medical Modelling, vol. 8, No. 1, Jun. 24, 2011, p. 23.

Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.

Xu, Zhi-Li et al., "Regulated gene expression from adenovirus vectors: a systematic comparison of various inducible systems," Gene, vol. 309, 2003, pp. 145-151, 7 pages.

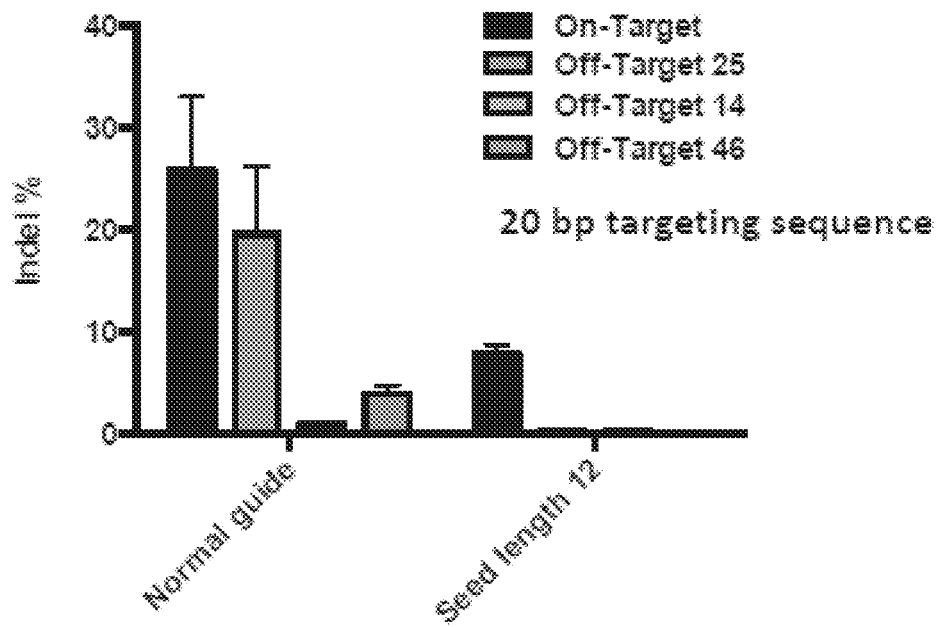
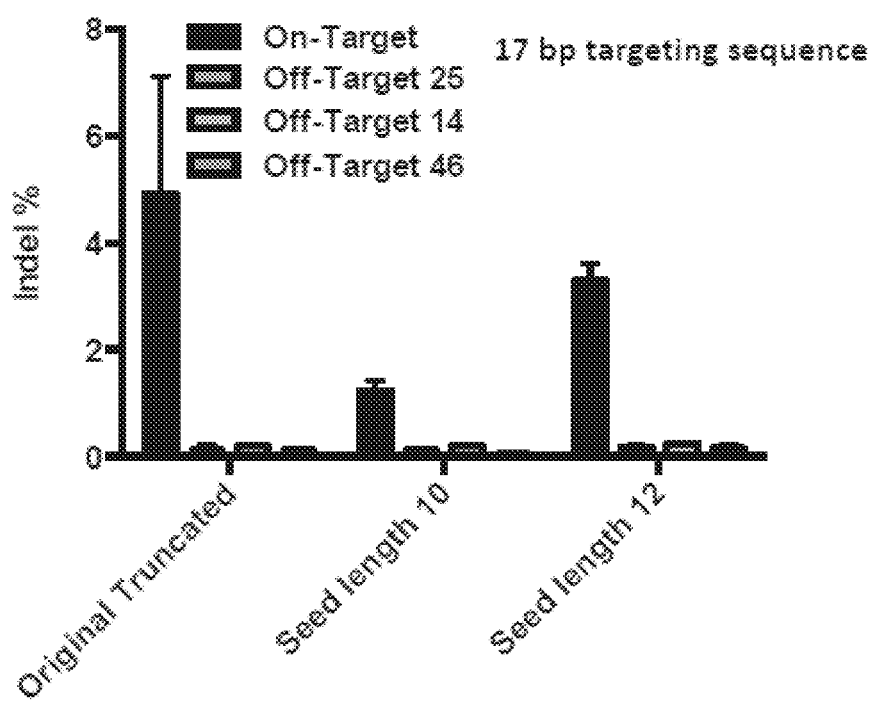
Fig. 6

FIG. 9A

20nt spacer (X=20)

```
                                                    PAM
CAAACGGCAGAAGCTGGAGGAGGAAGGGCCTGAGTCCGAGCAGAAGAAGAAGGGCTCCCAT
| | | | | | | | | | | | | | | | | | | | | | | | | | | | | | | | | | | | | | | | | | | | |  | | | | | | | |
GTTTGCCGTCTTCGACCTCCTCCTTCCCGGACTCAGGCTCGTCTTCTTCTTCCCGAGGGTA
                                    | | | | | | | | | | | | | | | | | | | | |
On-target                           GAGTCCGAGCAGAAGAAGAA
                                                        +85 sgRNA
```

```
                                                    PAM
GCAAATAGAGCCCTTTATTCATAGTAGACAAGAGTCTAAGCAGAAGAAGAAGAGAGCCACT
| | | | | | | | | | | | | | | | | | | | | | | | | | | | | | | | | | | | | | | | | | | | | | | | | | | | | | |
CGTTTATCTCGGGAAATAAGTATCATCTGTTCTCAGATTCGTCTTCTTCTTCTCTCGGTGA
                                | | | |   | | | | | | | | | | |
Off-target                      GAGTCCGAGCAGAAGAAGAA
                                                        +85 sgRNA
```

FIG. 9B

20nt spacer with distal matching extension (X=20, Z=10)

```
                                                    PAM
CAAACGGCAGAAGCTGGAGGAGGAAGGGCCTGAGTCCGAGCAGAAGAAGAAGGGCTCCCAT
| | | | | | | | | | | | | | | | | | | |              | | | | | | | | | | | | | | | | | | | | | |
GTTTGCCGTCTTCGACCTCCTCCTTCCCGGACTCAGGCTCGTCTTCTTCTTCCCGAGGGTA
                          | | | | | | | | | | | | | | | | | | | | | | | | | | | | | |
On-target                 GGAAGGGCCTGAGTCCGAGCAGAAGAAGAA
                                                        +85 sgRNA
```

```
                                                    PAM
GCAAATAGAGCCCTTTATTCATAGTAGACAAGAGTCTAAGCAGAAGAAGAAGAGAGCCACT
| | | | | | | | | | | | | | | | | | | | | | | | | | | | |    | | | | | | | | | | | | | | | | |
CGTTTATCTCGGGAAATAAGTATCATCTGTTCTCAGATTCGTCTTCTTCTTCTCTCGGTGA
                       | |   | | | |   | | | | | | | | | | |
Off-target              GGAAGGGCCTGAGTCCGAGCAGAAGAAGAA
                                                        +85 sgRNA
```

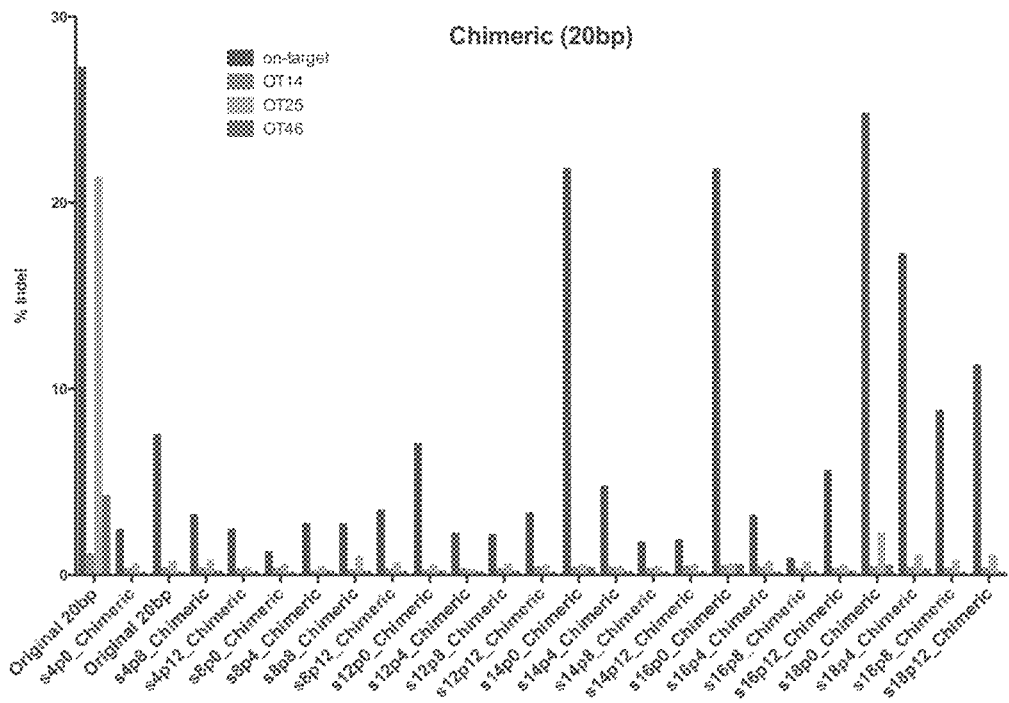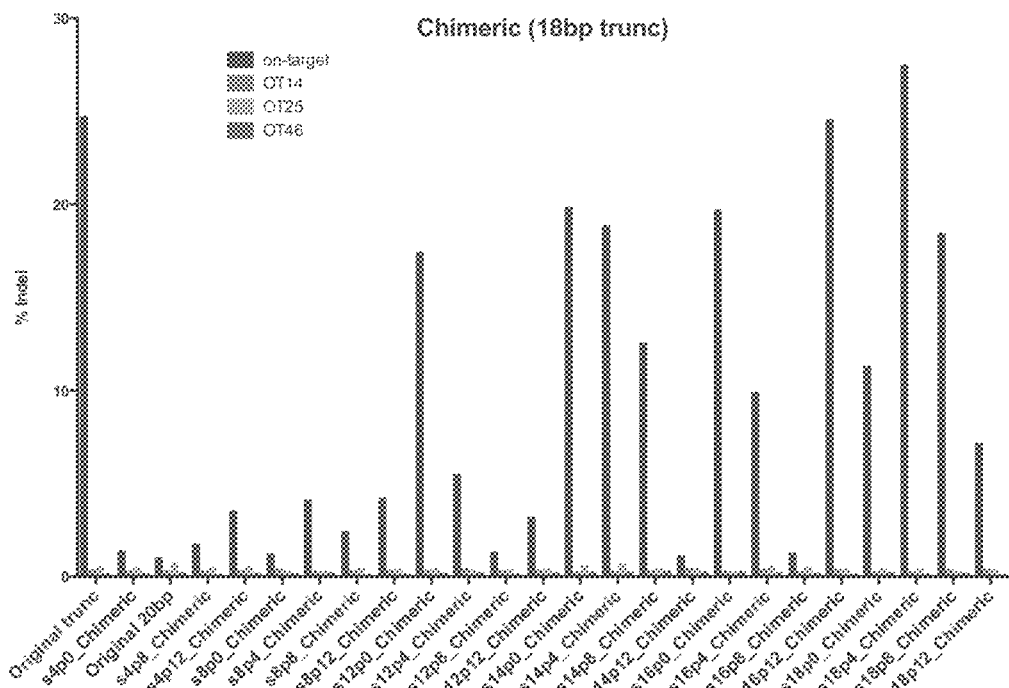
Fig. 16

US 10,696,986 B2

PROTECTED GUIDE RNAS (PGRNAS)

RELATED APPLICATIONS AND INCORPORATION BY REFERENCE

This application is a continuation-in-part to international patent application Serial No. PCT/US2015/065385 filed Dec. 11, 2015 and published as PCT Publication No. WO2016/094867 on Jun. 16, 2016 and claims priority from U.S. application Ser. No. 62/091,455, filed Dec. 12, 2014, U.S. application Ser. No. 62/096,708, filed Dec. 24, 2014, and U.S. application Ser. No. 62/180,709, filed Jun. 17, 2015.

STATEMENT AS TO FEDERALLY SPONSORED RESEARCH

This invention was made with government support under Grant Nos. MH100706 and MH110049 awarded by the National Institutes of Health. The government has certain rights in the invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

Mention is also made of U.S. applications 62/091,462, filed Dec. 12, 2014, 62/096,324, filed Dec. 23, 2014, 62/180,681, filed Jun. 17, 2015 62/237,496, filed Oct. 5, 2015, and PCT/US2015/065393, entitled DEAD GUIDES FOR CRISPR TRANSCRIPTION FACTORS. Mention is also made of U.S. applications 62/091,456, filed Dec. 12, 2014, 62/180,692, filed Jun. 17, 2015, and PCT/US2015/065396, entitled ESCORTED AND FUNCTIONALIZED GUIDES FOR CRISPR-CAS SYSTEMS.

SEQUENCE LISTING

The instant application contains a Sequence Listing which has been submitted electronically in ASCII format and is hereby incorporated by reference in its entirety. Said ASCII copy, created on Feb. 29, 2016, is named 47627.99.2001_SL.txt and is 23 bytes in size.

FIELD OF THE INVENTION

The present invention generally relates to systems, methods and compositions used for the control of gene expression involving sequence targeting, such as perturbation of gene transcripts or nucleic acid editing, that may use vector systems related to Clustered Regularly Interspaced Short Palindromic Repeats (CRISPR) and components thereof. In particular the present invention comprehends optimized functional CRISPR-Cas9 enzyme systems.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that employ novel strategies and molecular mechanisms and are affordable, easy to set up, scalable, and amenable to targeting multiple positions within the eukaryotic genome. This would provide a major resource for new applications in genome engineering and biotechnology.

Citation or identification of any document in this application is not an admission that such document is available as prior art to the present invention.

SUMMARY OF THE INVENTION

There exists a pressing need for alternative and robust systems and techniques for sequence targeting with a wide array of applications. This invention addresses this need and provides related advantages. The CRISPR/Cas9 or the CRISPR-Cas9 system (both terms are used interchangeably throughout this application) does not require the generation of customized proteins to target specific sequences but rather a single Cas9 enzyme can be programmed by a short RNA molecule to recognize a specific DNA target, in other words the Cas9 enzyme can be recruited to a specific DNA target using said short RNA molecule. Adding the CRISPR-Cas9 system to the repertoire of genome sequencing techniques and analysis methods may significantly simplify the methodology and accelerate the ability to catalog and map genetic factors associated with a diverse range of biological functions and diseases. To utilize the CRISPR-Cas9 system effectively for genome editing without deleterious effects, it is critical to understand aspects of engineering and optimization of these genome engineering tools, which are aspects of the claimed invention. The terms 'CRISPR-Cas9 or 'CRISPR-Cas9 system' and 'nucleic acid-targeting system' may be used interchangeably. The terms 'CRISPR complex' and 'nucleic acid-targeting complex' be used interchangeably. Where reference is made herein to a 'target locus,' for example a target locus of interest, then it will be appreciated that this may be used interchangeably with the phrase 'sequences associated with or at a target locus of interest.'

In particular the present invention comprehends optimized CRISPR-Cas systems comprising a CRISPR-Cas9 enzyme or functionalized CRISPR-Cas9 enzyme or proteins. In an aspect, the invention provides guide RNAs for optimizing specificity of the CRISPR-Cas system which may also be protected against exonuclease activity. In an aspect, the invention provides guide RNAs which comprise additional nucleotides at the 5' end of the guide sequence.

In one aspect, the invention provides a method for altering or modifying expression of a gene product. The method may comprise introducing into a cell containing and expressing a DNA molecule encoding the gene product an engineered, non-naturally occurring CRISPR-Cas system comprising a Cas9 protein and guide RNA that targets the DNA molecule, whereby the guide RNA targets the DNA molecule encoding the gene product and the Cas9 protein cleaves the DNA molecule encoding the gene product, whereby expression of the gene product is altered; and, wherein the Cas9 protein and the guide RNA do not naturally occur together. The invention comprehends the guide RNA comprising a guide sequence fused to a tracr sequence. The invention further comprehends the Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In particular, an object of the current invention is to further enhance the specificity of Cas9 given individual guide RNAs through thermodynamic tuning of the binding specificity of the guide RNA to target DNA.

In one aspect, the invention provides for the guide sequence being modified by secondary structure to increase the specificity of the CRISPR-Cas9 system and whereby the secondary structure can protect against exonuclease activity and allow for 5' additions to the guide sequence.

In one aspect, the invention provides for hybridizing a "protector RNA" to a guide sequence, wherein the "protector RNA" is an RNA strand complementary to the 5' end of the sgRNA, to thereby generate a partially double-stranded sgRNA. In an embodiment of the invention, wherein nucleotides at the 5' end of an sgRNA match a target sequence but contain mismatches with respect to an off-target sequence, protecting mismatched bases of the sgRNA with a perfectly complementary protector sequence decreases the likelihood of target DNA binding to mismatched base pairs at the 5' end. In embodiments of the invention, additional sequences comprising an extended length may also be present.

In one aspect, the invention provides an sgRNA which comprises a protector polynucleotide located 5' to the guide sequence. In an embodiment of the invention, there is provided a protected guide RNA (pgRNA) which comprises (a) a protector sequence, (b) a guide sequence capable of hybridizing to a target sequence in a eukaryotic cell, (c) a tracr mate sequence, and (d) a tracr sequence wherein (a), (b), (c) and (d) are arranged in a 5' to 3' orientation, wherein when transcribed, the tracr mate sequence hybridizes to the tracr sequence and the guide sequence directs sequence-specific binding of a CRISPR complex to the target sequence, wherein the CRISPR complex comprises a Type II Cas9 protein complexed with (1) the guide sequence that is hybridized to the target sequence, and (2) the tracr mate sequence that is hybridized to the tracr sequence and wherein in the polynucleotide sequence, one or more of the guide, tracr and tracr mate sequences are modified. In an embodiment of the invention, the protector sequence comprises nucleotides that are complementary to the guide sequence. In an embodiment of the invention, the protector sequence comprises nucleotides that are not complementary to the target sequence. In an embodiment of the invention, the protector sequence comprises two or more nucleotides that are non-complementary to the target sequence. In an embodiment of the invention, the modification of one or more of the guide, tracr, and tracr mate sequences is an engineered secondary structure. In an embodiment of the invention, the engineered secondary structure comprises nucleotides of the protector sequence and polynucleotides of the guide. In an embodiment of the invention, the guide RNA comprising the protector sequence has improved target specificity as compared to a guide RNA without the protector sequence. In an embodiment of the invention, a CRISPR-Cas9 complex comprising the the protected modified guide has improved stability as compared to a CRISPR-Cas9 complex lacking the protector sequence.

In an embodiment of the invention, the protected guide comprises a protector sequence of length between 3 and 120 nucleotides and comprises 3 or more contiguous nucleotides complementary to another sequence within the guide or protector wherein the modification comprises or allows for hairpin formation. In another embodiment, the protector sequence length is 10-30 nucleotides long. In an embodiment of the invention, the protected guide comprises a protected sequence and an exposed sequence. In certain embodiments, the exposed sequence is 1 to 19 nucleotides. In an embodiment, the exposed sequence is at least 75%, at least 90% or about 100% complementary to the target sequence.

In an embodiment of the invention, the guide sequence is at at least 90% or about 100% complementary to the protector strand. In an embodiment of the invention, the guide sequence is at least 75%, at least 90% or about 100% complementary to the target sequence. In an embodiment of the invention, the tracr mate sequence is at least 75%, at least 90% or about 1000/0 complementary to the tracr sequence.

In an embodiment of the invention, the RNA comprising a guide sequence and protector sequence further comprises an extension sequence. In certain embodiments, the extension sequence is operably linked to the 5' end of the protected guide sequence, and optionally directly linked to the 5' end of the protected guide sequence. In certain embodiments, the extension sequence is 0-12 nucleotides. In certain embodiments, the extension sequence is operably linked to the guide sequence at the 5' end of the protected guide sequence and the 3' end of the protector strand and optionally directly linked to the 5' end of the protected guide sequence and the 3' end of the protector strand, wherein the extension sequence is a linking sequence between the protected sequence and the protector strand. In certain embodiments, the extension sequence is 100% not complementary (0% complementary) to the protector strand, optionally at least 95%, at least 90%, at least 80%, at least 70%, at least 60%, or at least 50% not complementary to the protector strand.

In certain embodiments, the guide sequence further comprises mismatches appended to the end of the guide sequence, wherein the mismatches thermodynamically optimize specificity.

In an aspect, the invention provides a non-naturally occurring or engineered CRISPR-Cas complex composition comprising (I) a protected guide RNA (pgRNA) which comprises (a) a protector sequence, (b) a guide sequence capable of hybridizing to a target sequence in a eukaryotic cell, (c) a tracr mate sequence, and (d) a tracr sequence wherein (a), (b), (c) and (d) are arranged in a 5' to 3' orientation, wherein when transcribed, the tracr mate sequence hybridizes to the tracr sequence and the guide sequence directs sequence-specific binding of a CRISPR complex to the target sequence, wherein the CRISPR complex comprises a Type II Cas9 protein complexed with (1) the guide sequence that is hybridized to the target sequence, and (2) the tracr mate sequence that is hybridized to the tracr sequence and wherein in the polynucleotide sequence, one or more of the guide, tracr and tracr mate sequences are modified, and (II) a CRISPR-Cas9 enzyme, wherein optionally the CRISPR-Cas9 enzyme comprises at least one mutation, such that the CRISPR-Cas9 enzyme has no more than 5% of the nuclease activity of the CRISPR-Cas9 enzyme not having the at least one mutation, and optionally comprising at least one or more nuclear localization sequences.

In certain embodiments of the invention, the non-naturally occurring or engineered composition comprises two or more adaptor proteins, wherein each protein is associated with one or more functional domains and wherein the adaptor protein binds to the distinct RNA sequence(s) inserted into the at least one loop of the sgRNA.

In embodiments of the invention, the non-naturally occurring or engineered composition comprises a protected guide RNA (pgRNA), and a CRISPR-Cas90 enzyme comprising at least one or more nuclear localization sequences, wherein the CRISPR enzyme comprises at least one mutation, such that the CRISPR enzyme has no more than 5% of the nuclease activity of the CRISPR enzyme not having the at least one mutation.

In certain embodiments, the CRISPR-Cas9 enzyme has a diminished nuclease activity of at least 97° %, or 100% as compared with the CRISPR-Cas9 enzyme not having the at least one mutation.

In certain embodiments, the CRISPR-Cas9 enzyme comprises two or more mutations wherein two or more of D10, E762, H840, N854, N863, or D986 according to SpCas9 protein or any corresponding ortholog are mutated, or the CRISPR-Cas9 enzyme comprises at least one mutation wherein at least H840 is mutated. In certain embodiments, the CRISPR-Cas9 enzyme two or more mutations comprising D10A, E762A, H840A, N854A, N863A or D986A according to SpCas9 protein or any corresponding ortholog, or at least one mutation comprising H840A. In certain embodiments, the CRISPR-Cas9 enzyme comprises H840A, or D10A and H840A, or D10A and N863A, according to SpCas9 protein or any corresponding ortholog.

In certain embodiments, in a composition comprising a protected guide RNA (pgRNA), and a CRISPR-Cas9 enzyme, the CRISPR-Cas9 enzyme is associated with one or more functional domains. In certain embodiments, the functional domains associated with the adaptor protein is a heterologous functional domain. In certain embodiments, the one or more functional domains associated with the CRISPR enzyme is a heterologous functional domain.

In an embodiment of the invention, the adaptor protein is a fusion protein comprising the functional domain. In an embodiment of the invention, the one or more functional domains associated with the adaptor protein is a transcriptional activation domain. In an embodiment of the invention, the one or more functional domains associated with the CRISPR enzyme is a transcriptional activation domain. In another embodiment of the invention, the one or more functional domains associated with the adaptor protein is a transcriptional activation domain comprising VP64, p65, MyoD1 or HSF1. In another embodiment, the one or more functional domains associated with the CRISPR enzyme is a transcriptional activation domain comprises VP64, p65, MyoD1 or HSF1. In yet another embodiment, the one or more functional domains associated with the adaptor protein is a transcriptional repressor domain. In another embodiment, the one or more functional domains associated with the CRISPR enzyme is a transcriptional repressor domain. In one such embodiment, transcriptional repressor domain is a KRAB domain. In another embodiment, the transcriptional repressor domain is a SID domain or a SID4X domain.

In an embodiment of the invention, at least one of the one or more functional domains associated with the adaptor protein have one or more activities comprising methylase activity, demethylase activity, transcription activation activity, transcription repression activity, transcription release factor activity, histone modification activity, RNA cleavage activity, DNA cleavage activity or nucleic acid binding activity. In an embodiment of the invention, the one or more functional domains associated with the CRISPR enzyme have one or more activities comprising methylase activity, demethylase activity, transcription activation activity, transcription repression activity, transcription release factor activity, histone modification activity, RNA cleavage activity, DNA cleavage activity, nucleic acid binding activity, or molecular switch activity or chemical inducibility or light inducibility. In one such embodiment, the DNA cleavage activity is due to a Fok1 nuclease.

In certain embodiments, the one or more functional domains is attached to the CRISPR enzyme so that upon binding to the sgRNA and target the functional domain is in a spatial orientation allowing for the functional domain to function in its attributed function. In certain embodiments, the sgRNA is modified so that, after sgRNA binds the adaptor protein and further binds to the CRISPR enzyme and target, the functional domain is in a spatial orientation allowing for the functional domain to function in its attributed function. In certain embodiments, the one or more functional domains associated with the CRISPR enzyme is attached to the Rec1 domain, the Rec2 domain, the HNH domain, or the PI domain of the SpCas9 protein or any ortholog corresponding to these domains. In certain embodiments, the one or more functional domains associated with the CRISPR enzyme is attached to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains. In certain embodiments the one or more functional domains associated with the CRISPR enzyme is attached to the Rec1 domain or the Rec2 domain, of the SpCas9 protein or any ortholog corresponding to these domains. In certain embodiments the one or more functional domains associated with the CRISPR enzyme is attached to the Rec2 domain of the SpCas9 protein or any ortholog corresponding to this domain. In certain embodiments the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s or PRR1.

In an aspect, the invention provides a cell or progeny thereof which comprises a non-naturally occurring or engineered CRISPR-Cas complex composition as described herein. In an embodiment, the cell is a eukaryotic cell or progeny thereof. In an embodiment, the eukaryotic cell is a mammalian cell or progeny thereof. In an embodiment, the mammalian cell is a human cell or progeny thereof.

In certain embodiment, there is a first adaptor protein associated with a p65 domain and a second adaptor protein associated with a HSF1 domain. In certain embodiments there is a composition which comprises a CRISPR-Cas complex having at least three functional domains, at least one of which is associated with the CRISPR enzyme and at least two of which are associated with sgRNA.

In an aspect, the invention provides a method for introducing a genomic locus event comprising the administration to a host or expression in a host in vivo of one or more of the aforementioned compositions. In an embodiment of the invention, the genomic locus event comprises affecting gene activation, gene inhibition, or cleavage in the locus. In one such embodiment, the host is a eukaryotic cell or progeny thereof. In one such embodiment, the host is a mammalian cell or progeny thereof. In one such embodiment, the host is a non-human eukaryote or progeny thereof. In one such embodiment the non-human eukaryote is a non-human mammal or progeny thereof. In one such embodiment the non-human mammal is a mouse or progeny thereof.

In an aspect, the invention provides a method of modifying a genomic locus of interest to change gene expression in a cell or progeny thereof by introducing or expressing in a cell any one of the aforementioned compositions.

In an embodiment of the invention, the extension of a pgRNA comprises chemically modified bases. In an embodiment of the invention, the protector sequence of the pgRNA comprises chemically modified bases. In an embodiment of the invention, the guide sequence comprise chemically modified bases. In another embodiment of the invention, both the extension sequence and the protector sequence comprise chemically modified bases. In another embodiment of the invention, the extension sequence, the protector sequence, and the guide sequence comprise chemically modified bases.

In an embodiment of the invention, binding free energy of the protector sequence is designed so that the overall free energy of the reaction is in a range of no more than +/−10% from zero. In another embodiment of the invention, the binding free energy of the protector sequence is designed so that the overall free energy of the reaction is in a range of no more than +/−5% from zero. In another embodiment, the binding free energy of the protector sequence is designed so that the overall free energy of the reaction is in a range of no more than +/−2% from zero. In another embodiment of the invention, the binding free energy of the protector sequence is designed so that the overall free energy of the reaction is zero.

While in certain aspects the invention is set forth in the context of protecting bases of an sgRNA that are mismatched with respect to off-target sequences, in certain embodiments, the invention does not require identification of such off-targets or their sequences. It will be generally understood that a perfectly complementary protector sequence can potentially reduce off-target effects by a guide RNA, to one extent or another throughout the genome depending on the nature and number of mismatches at each potential off-target. Off target activity and reduction thereof can measured at off-target loci of known sequence or by less biased methods that detect double stranded breaks (DSBs) throughout the genome. See, e.g., Ran et al., 2015, Nature 520(7546):186-91.

In one aspect, the invention provides for enhanced Cas9 specificity wherein the double stranded 5' end of the protected guide RNA (pgRNA) allows for two possible outcomes: (1) the guide RNA-protector RNA to guide RNA-target DNA strand exchange will occur and the guide will fully bind the target (i.e. strand exchange will occur as the protector RNA dissociates from the [guide RNA-protector RNA] duplex, and the guide RNA associates with target DNA; or (2) the guide RNA will fail to fully bind the target and because Cas9 target cleavage is a multiple step kinetic reaction that requires guide RNA:target DNA binding to activate Cas9-catalyzed DSBs (Double-Strand Breaks), Cas9 cleavage does not occur if the guide RNA does not properly bind. In one aspect, the invention provides an engineered, non-naturally occurring CRISPR-Cas9 system comprising a Cas9 protein and a guide RNA that targets a DNA molecule encoding a gene product in a cell, whereby the guide RNA targets the DNA molecule encoding the gene product and the Cas9 protein cleaves the DNA molecule encoding the gene product, whereby expression of the gene product is altered; and, wherein the Cas9 protein and the guide RNA do not naturally occur together. The invention comprehends the guide RNA comprising a guide sequence fused to a tracr sequence. The invention further comprehends the Cas9 protein being codon optimized for expression in a eukaryotic cell. In a preferred embodiment the Eukaryotic cell is a mammalian cell and in a more preferred embodiment the mammalian cell is a human cell. In a further embodiment of the invention, the expression of the gene product is decreased.

As mentioned, the invention contemplates nucleotide additions to the 5' end of a guide sequence. As disclosed in further detail herein, the additions can be to normal (i.e., about 20 nt in length), truncated, or extended sgRNAs, and can match, mismatch or partially mismatch a target sequence, and/or can be partially or fully self-complementary or complementary to a guide sequence. It will be apparent, that the additional nucleotides can operate as protectors. (see e.g., FIG. 2). In an aspect, the invention also provides protectors that are partially or perfectly complementary to such nucleotide additions.

In another aspect, the invention provides an engineered, non-naturally occurring vector system comprising one or more vectors comprising (a) a first regulatory element operably linked to a CRISPR-Cas9 system protected guide RNA that targets a DNA molecule encoding a gene product and (b) a second regulatory element operably linked to a Cas9 protein. Components (a) and (b) may be located on same or different vectors of the system. The guide RNA targets the DNA molecule encoding the gene product in a cell and the Cas9 protein cleaves the DNA molecule encoding the gene product, whereby expression of the gene product is altered; and, wherein the Cas9 protein and the guide RNA do not naturally occur together. The invention comprehends the guide RNA comprising a guide sequence fused to a tracr sequence. The invention further comprehends the Cas9 protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and (b) a second regulatory element operably linked to an enzyme-coding sequence encoding said CRISPR enzyme comprising a nuclear localization sequence; wherein components (a) and (b) are located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned.

Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan. In some embodiments, the CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for CRISPR complex activity in eukaryotes, but that including such sequences enhances activity of the system, especially as to targeting nucleic acid molecules in the nucleus. In some embodiments, the CRISPR enzyme is a type II CRISPR system enzyme. In some embodiments, the CRISPR enzyme is a Cas9 enzyme. In some embodiments, the Cas9 enzyme is S. pneumoniae, S. pyogenes, or S. thermophilus Cas9, and may include mutated Cas9 derived from these organisms. The enzyme may be a Cas9 homolog or ortholog. In some embodiments, the CRISPR-Cas9 enzyme is codon-optimized for expression in a eukaryotic cell. In some embodiments, the CRISPR-Cas9 enzyme directs cleavage of one or two strands at the location of the target sequence. In some embodiments, the first regulatory element is a polymerase I promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Vectors for and that result in expression in a eukaryotic cell can be referred to herein as "eukaryotic expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol I promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a tracr mate sequence and one or more insertion sites for inserting one or more guide sequences (the one or more guide sequences each having their respective protector sequence(s)) upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. The enzyme may be a Cas9 homolog or ortholog. In some embodiments, the CRISPR-Cas9 enzyme is codon-optimized for expression in a eukaryotic cell. In some embodiments, the CRISPR-Cas9 enzyme directs cleavage of one or two strands at the location of the target sequence. In some embodiments, the CRISPR-Cas9 enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

With respect to use of the CRISPR-Cas9 system generally, mention is made of the documents, including patent applications, patents, and patent publications cited throughout this disclosure as embodiments of the invention can be used as in those documents. CRISPR-Cas9 system(s) (e.g., single or multiplexed) can be used in conjunction with recent advances in crop genomics. Such CRISPR-Cas9 system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas9 system(s) can be used with regard to plants in Site-Directed Integration (SDI) or Gene Editing (GE) or any Near Reverse Breeding (NRB) or Reverse Breeding (RB) techniques. With respect to use of the CRISPR-Cas system in plants, mention is made of the University of Arizona website "CRISPR-PLANT" (http://www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi: 10.1186/1746-4811-9-39); Brooks, "Efficient gene editing in tomato in the first generation using the CRISPR-Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 November; 6(6): 1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial Populus reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061-*Agrobacterium*-Mediated Plant Transformation Method; U.S. Pat. No. 7,868,149-Plant Genome Sequences and Uses Thereof and US 2009/0100536-Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences (the one or more guide sequences each having their respective protector sequence(s)) upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the kit comprises components (a) and (b) located on the same or different vectors of the system. In some embodiments, component (a) further comprises the tracr sequence downstream of the tracr mate sequence under the control of the first regulatory element. In some embodiments, component (a) further comprises two or more guide sequences (the two or more guide sequences each having their respective protector sequence(s)) operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is S. pneumoniae, S. pyogenes or S. thermophilus Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a protected guide sequence hybridized to a target sequence within said target polynucleotide, wherein said guide sequence comprises a protector sequence and is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence comprises a protector sequence and is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a CRISPR enzyme, a guide sequence comprising a protector sequence, and linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a CRISPR complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a CRISPR enzyme, a guide sequence comprising a protector sequence, linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more cell(s) in which one or more mutations have been introduced to be selected. In a preferred embodiment, the CRISPR enzyme is Cas9. In another preferred embodiment of the invention the cell to be selected may be a eukaryotic cell. Aspects of the invention allow for selection of specific cells without requiring a selection marker or a two-step process that may include a counter-selection system.

With respect to mutations of the CRISPR enzyme, when the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. In an aspect the invention provides as to any or each or all embodiments herein-discussed wherein the CRISPR enzyme comprises at least one or more, or at least two or more mutations, wherein the at least one or more mutation or the at least two or more mutations is as to D10, E762, H840, N854, N863, or D986 according to SpCas9 protein, e.g., D10A, E762A, H840A, N854A, N863A and/or D986A as to SpCas9, or N580 according to SaCas9, e.g., N580A as to SaCas9, or any corresponding mutation(s) in a Cas9 of an ortholog to Sp or Sa, or the CRISPR enzyme comprises at least one mutation wherein at least H840 or N863A as to Sp Cas9 or N580A as to Sa Cas9 is mutated; e.g., wherein the CRISPR enzyme comprises H840A, or D10A and H840A, or D10A and N863A, according to SpCas9 protein, or any corresponding mutation(s) in a Cas9 of an ortholog to Sp protein or Sa protein.

In a further aspect, the invention involves a computer-assisted method for identifying or designing potential compounds to fit within or bind to CRISPR-Cas9 system or a functional portion thereof or vice versa (a computer-assisted method for identifying or designing potential CRISPR-Cas9 systems or a functional portion thereof for binding to desired compounds) or a computer-assisted method for identifying or designing potential CRISPR-Cas9 systems (e.g., with regard to predicting areas of the CRISPR-Cas9 system to be able to be manipulated—for instance, based on crystal structure data or based on data of Cas9 orthologs, or with respect to where a functional group such as an activator or repressor can be attached to the CRISPR-Cas9 system, or as to Cas9 truncations or as to designing nickases), said method comprising:

using a computer system, e.g., a programmed computer comprising a processor, a data storage system, an input device, and an output device, the steps of:

(a) inputting into the programmed computer through said input device data comprising the three-dimensional co-ordinates of a subset of the atoms from or pertaining to the CRISPR-Cas9 crystal structure, e.g., in the CRISPR-Cas9 system binding domain or alternatively or additionally in domains that vary based on variance among Cas9 orthologs or as to Cas9s or as to nickases or as to functional groups, optionally with structural information from CRISPR-Cas9 system complex(es), thereby generating a data set;

(b) comparing, using said processor, said data set to a computer database of structures stored in said computer data storage system, e.g., structures of compounds that bind or putatively bind or that are desired to bind to a CRISPR-Cas9 system or as to Cas9 orthologs (e.g., as Cas9s or as to domains or regions that vary amongst Cas9 orthologs) or as to the CRISPR-Cas9 crystal structure or as to nickases or as to functional groups;

(c) selecting from said database, using computer methods, structure(s)—e.g., CRISPR-Cas9 structures that may bind to desired structures, desired structures that may bind to certain CRISPR-Cas9 structures, portions of the CRISPR-Cas9 system that may be manipulated, e.g., based on data from other portions of the CRISPR-Cas9 crystal structure and/or from Cas9 orthologs, truncated Cas9s, novel nickases or particular functional groups, or positions for attaching functional groups or functional-group-CRISPR-Cas9 systems;

(d) constructing, using computer methods, a model of the selected structure(s); and (e) outputting to said output device the selected structure(s);

and optionally synthesizing one or more of the selected structure(s);

and further optionally testing said synthesized selected structure(s) as or in a CRISPR-Cas9 system;

or, said method comprising: providing the co-ordinates of at least two atoms of the CRISPR-Cas9 crystal structure, e.g., at least two atoms of the herein Crystal Structure Table of the CRISPR-Cas9 crystal structure or co-ordinates of at least a sub-domain of the CRISPR-Cas9 crystal structure ("selected co-ordinates"), providing the structure of a candidate comprising a binding molecule or of portions of the CRISPR-Cas9 system that may be manipulated, e.g., based on data from other portions of the CRISPR-Cas9 crystal structure and/or from Cas9 orthologs, or the structure of functional groups, and fitting the structure of the candidate to the selected co-ordinates, to thereby obtain product data comprising CRISPR-Cas9 structures that may bind to desired structures, desired structures that may bind to certain CRISPR-Cas9 structures, portions of the CRISPR-Cas9 system that may be manipulated, truncated Cas9s, novel nickases, or particular functional groups, or positions for attaching functional groups or functional-group-CRISPR-Cas9 systems, with output thereof; and optionally synthesizing compound(s) from said product data and further optionally comprising testing said synthesized compound(s) as or in a CRISPR-Cas9 system.

The testing can comprise analyzing the CRISPR-Cas9 system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (e.g. POWERPOINT), internet, email, documentary communication such as a computer program (e.g. WORD) document and the like. Accordingly, the invention also comprehends computer readable media containing: atomic co-ordinate data according to the herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The computer readable media can also contain any data of the foregoing methods. The invention further comprehends methods a computer system for generating or performing rational design as in the foregoing methods containing either: atomic co-ordinate data according to herein-referenced Crystal Structure, said data defining the three dimensional structure of CRISPR-Cas9 or at least one sub-domain thereof, or structure factor data for CRISPR-Cas9, said structure factor data being derivable from the atomic co-ordinate data of herein-referenced Crystal Structure. The invention further comprehends a method of doing business comprising providing to a user the computer system or the media or the three dimensional structure of CRISPR-Cas9 or at least one sub-domain thereof, or structure factor data for CRISPR-Cas9, said structure set forth in and said structure factor data being derivable from the atomic co-ordinate data of herein-referenced Crystal Structure, or the herein computer media or a herein data transmission.

A "binding site" or an "active site" comprises or consists essentially of or consists of a site (such as an atom, a functional group of an amino acid residue or a plurality of such atoms and/or groups) in a binding cavity or region, which may bind to a compound such as a nucleic acid molecule, which is/are involved in binding.

By "fitting", is meant determining by automatic, or semi-automatic means, interactions between one or more atoms of a candidate molecule and at least one atom of a structure of the invention, and calculating the extent to which such interactions are stable. Interactions include attraction and repulsion, brought about by charge, steric considerations and the like. Various computer-based methods for fitting are described further By "root mean square (or rms) deviation", Applicants mean the square root of the arithmetic mean of the squares of the deviations from the mean.

By a "computer system", is meant the hardware means, software means and data storage means used to analyze atomic coordinate data. The minimum hardware means of the computer-based systems of the present invention typically comprises a central processing unit (CPU), input means, output means and data storage means. Desirably a display or monitor is provided to visualize structure data. The data storage means may be RAM or means for accessing computer readable media of the invention. Examples of such systems are computer and tablet devices running Unix, Windows or Apple operating systems.

By "computer readable media", is meant any medium or media, which can be read and accessed directly or indirectly by a computer e.g., so that the media is suitable for use in the above-mentioned computer system. Such media include, but are not limited to: magnetic storage media such as floppy discs, hard disc storage medium and magnetic tape; optical storage media such as optical discs or CD-ROM; electrical storage media such as RAM and ROM; thumb drive devices; cloud storage devices and hybrids of these categories such as magnetic/optical storage media.

In particular embodiments of the invention, the conformational variations in the crystal structures of the CRISPR-Cas9 system or of components of the CRISPR-Cas9 provide important and critical information about the flexibility or movement of protein structure regions relative to nucleotide (RNA or DNA) structure regions that may be important for CRISPR-Cas system function. The structural information provided for Cas9 (e.g., *S. pyogenes* Cas9) as the CRISPR enzyme in the present application may be used to further engineer and optimize the CRISPR-Cas9 system and this may be extrapolated to interrogate structure-function relationships in other CRISPR enzyme systems as well, e.g, other Type II CRISPR enzyme systems.

The invention comprehends optimized functional CRISPR-Cas9 enzyme systems. In particular the CRISPR enzyme comprises one or more mutations that converts it to a DNA binding protein to which functional domains exhibiting a function of interest may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain.

The structural information provided herein allows for interrogation of sgRNA (or chimeric RNA) interaction with the target DNA and the CRISPR enzyme (e.g., Cas9) permitting engineering or alteration of sgRNA structure to optimize functionality of the entire CRISPR-Cas system. For example, loops of the sgRNA may be extended, without colliding with the Cas9 protein by the insertion of adaptor proteins that can bind to RNA. These adaptor proteins can further recruit effector proteins or fusions which comprise one or more functional domains.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (e.g. SID4X). In some embodiments, the functional domain is an epigenetic modifying domain, such that an epigenetic modifying enzyme is provided. In some embodiments, the functional domain is an activation domain, which may be the P65 activation domain.

Aspects of the invention encompass a non-naturally occurring or engineered composition that may comprise a protected guide RNA (sgRNA) comprising a guide sequence (including its protector sequence, as described herein) capable of hybridizing to a target sequence in a genomic locus of interest in a cell and a CRISPR enzyme that may comprise at least one or more nuclear localization sequences, wherein the CRISPR enzyme comprises two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous functional domains. In an embodiment of the invention the CRISPR enzyme comprises two or more mutations in a residue selected from the group comprising, consisting essentially of, or consisting of D10, E762, H840, N854, N863, or D986. In a further embodiment the CRISPR enzyme comprises two or more mutations selected from the group comprising D10A, E762A, H840A, N854A, N863A or D986A. In another embodiment, the functional domain is a transcriptional activation domain, e.g., VP64. In another embodiment, the functional domain is a transcriptional repressor domain, e.g., KRAB domain, SID domain or a SID4X domain. In embodiments of the invention, the one or more heterologous functional domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. In another embodiment, the at least one loop of the sgRNA is tetraloop and/or loop2. An aspect of the invention encompasses methods of modifying a genomic locus of interest to change gene expression in a cell by introducing into the cell any of the compositions described herein.

An aspect of the invention is that the above elements are comprised in a single composition or comprised in individual compositions. These compositions may advantageously be applied to a host to elicit a functional effect on the genomic level.

In general, the sgRNA are modified in a manner that provides specific binding sites (e.g., aptamers) for adapter proteins comprising one or more functional domains (e.g., via fusion protein) to bind to. The modified sgRNA are modified such that once the sgRNA forms a CRISPR complex (i.e. CRISPR enzyme binding to sgRNA and target) the adapter proteins bind and, the functional domain on the adapter protein is positioned in a spatial orientation which is advantageous for the attributed function to be effective. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target.

The skilled person will understand that modifications to the sgRNA which allow for binding of the adapter+functional domain but not proper positioning of the adapter+functional domain (e.g., due to steric hindrance within the three dimensional structure of the CRISPR complex) are modifications which are not intended. The one or more modified sgRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). In some cases it is advantageous that additionally at least one NLS is provided. In some instances, it is advantageous to position the NLS at the N terminus. When more than one functional domain is included, the functional domains may be the same or different.

The sgRNA may be designed to include multiple binding recognition sites (e.g., aptamers) specific to the same or different adapter protein. The sgRNA may be designed to bind to the promoter region −1000−+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified sgRNA may be one or more modified sgRNAs targeted to one or more target loci (e.g., at least 1 sgRNA, at least 2 sgRNA, at least 5 sgRNA, at least 10 sgRNA, at least 20 sgRNA, at least 30 sg RNA, at least 50 sgRNA) comprised in a composition.

Further, the CRISPR enzyme with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a Cas9 enzyme or CRISPR enzyme having advantageously about 0% of the nuclease activity of the non-mutated or wild type Cas9 enzyme or CRISPR enzyme, or no more than about 3% or about 5% or about 10% of the nuclease activity of the non-mutated or wild type Cas9 enzyme or CRISPR enzyme). This is possible by introducing mutations into the RuvC and HNH nuclease domains of the SpCas9 and orthologs thereof. For example utilizing mutations in a residue selected from the group comprising, consisting essentially of, or consisting of D10, E762, H840, N854, N863, or D986 and more preferably introducing one or more of the mutations selected from the group comprising, consisting essentially of, or consisting of D10A, E762A, H840A, N854A, N863A or D986A. A preferable pair of mutations is D10A with H840A, more preferable is D10A with N863A of SpCas9 and orthologs thereof.

The inactivated CRISPR enzyme may have associated (e.g., via fusion protein) one or more functional domains, like for example as described herein for the modified sgRNA adaptor proteins, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1 and MyoD1. In the event that Fok1 is provided, it is advantageous that multiple Fok1 functional domains are provided to allow for a functional dimer and that sgRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases it is advantageous that additionally at least one NLS is provided. In some instances, it is advantageous to position the NLS at the N terminus. When more than one functional domain is included, the functional domains may be the same or different.

In general, the positioning of the one or more functional domains on the inactivated CRISPR enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR enzyme.

Due to crystal structure experiments, the Applicant has identified that positioning the functional domain in the Rec1 domain, the Rec2 domain, the HNH domain, or the PI domain of the SpCas9 protein or any ortholog corresponding to these domains is advantageous. Positioning of the functional domains to the Rec1 domain or the Rec2 domain, of the SpCas9 protein or any ortholog corresponding to these domains, in some instances may be preferred. Positioning of the functional domains to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains, in some instances may be preferred. Fok1 functional domain may be attached at the N terminus. When more than one functional domain is included, the functional domains may be the same or different.

The adaptor protein may be any number of proteins that binds to an aptamer or recognition site introduced into the modified sgRNA and which allows proper positioning of one or more functional domains, once the sgRNA has been incorporated into the CRISPR complex, to affect the target with the attributed function. As explained in detail in this application such may be coat proteins, preferably bacteriophage coat proteins. The functional domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1 and MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains.

Thus, the modified protector sgRNA, the inactivated CRISPR enzyme (with or without functional domains), and the binding protein with one or more functional domains, may each individually be comprised in a composition and administered to a host individually or collectively. Alternatively, these components may be provided in a single composition for administration to a host. Administration to a host may be performed via viral vectors known to the skilled person or described herein for delivery to a host (e.g., lentiviral vector, adenoviral vector, AAV vector). As explained herein, use of different selection markers (e.g., for lentiviral sgRNA selection) and concentration of sgRNA (e.g., dependent on whether multiple sgRNAs are used) may be advantageous for eliciting an improved effect.

On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function, gain-of-function modeling; loss-of-function modeling; the use the compositions of the invention to establish cell lines and transgenic animals for optimization and screening purposes).

The current invention comprehends the use of the compositions of the current invention to establish and utilize conditional or inducible CRISPR transgenic cell/animals. (See, e.g., Platt et al., Cell (2014), 159(2): 440-455, or PCT patent publications cited herein, such as WO 2014/093622 (PCT/US2013/074667), which are not believed prior to the present invention or application). For example, the target cell comprises CRISPR enzyme (e.g., Cas9) conditionally or inducibly (e.g., in the form of Cre dependent constructs) and/or the adapter protein conditionally or inducibly and, on expression of a vector introduced into the target cell, the vector expresses that which induces or gives rise to the condition of CRISPR enzyme (e.g., Cas9) expression and/or adaptor expression in the target cell. By applying the teaching and compositions of the current invention with the known method of creating a CRISPR complex, inducible genomic events affected by functional domains are also an aspect of the current invention. One mere example of this is the creation of a CRISPR knock-in/conditional transgenic animal (e.g., mouse comprising e.g., a Lox-Stop-polyA-Lox (LSL) cassette) and subsequent delivery of one or more compositions providing one or more modified sgRNA (e.g., −200 nucleotides to TSS of a target gene of interest for gene activation purposes) as described herein (e.g., modified sgRNA with one or more aptamers recognized by coat proteins, e.g., MS2), one or more adapter proteins as described herein (MS2 binding protein linked to one or more VP64) and means for inducing the conditional animal (e.g., Cre recombinase for rendering Cas9 expression inducible). Alternatively, the adaptor protein may be provided as a conditional or inducible element with a conditional or inducible CRISPR enzyme to provide an effective model for screening purposes, which advantageously only requires minimal design and administration of specific sgRNAs for a broad number of applications.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6: Increasing the seed length improves on-target guide activity without sacrificing specificity in both the original 20 bp and truncated 17 bp designs.

FIG. 9A-9D: sgRNA extension and mismatch strategies for specificity enhancement. A) EMX1.3 20nt sgRNA spacer compulsory schematic at on and off-target loci (SEQ ID NOS 59, 68, 60 and 68, respectively, in order of appearance). B) Extension of the sgRNA with matching sequence spacer seed length (X)=20, extension (Z)=10 (SEQ ID NOS 59, 61, 60 and 61, respectively, in order of appearance). C) Addition of mismatched bases (Y=3) to the distal end of the 20nt spacer sequence (X=17) (SEQ ID NOS 59, 62, 60 and 62, respectively, in order of appearance). D) Extension sgRNA with mismatched bases (X=17, Y=3, Z=2) (SEQ ID NOS 59, 63, 60 and 63, respectively, in order of appearance).

FIG. 16: The indel formation percent at the EMX1.3 on-target site and three off-target sites (OT14, 25, and 46). Results are shown for both the EMX1.3 original 20 bp (top) and truncated 18 bp (bottom). The nomenclature used to name the constructs is as follows: 's' refers to the exposed length and 'p' refers to the extended length.

Figure 1:
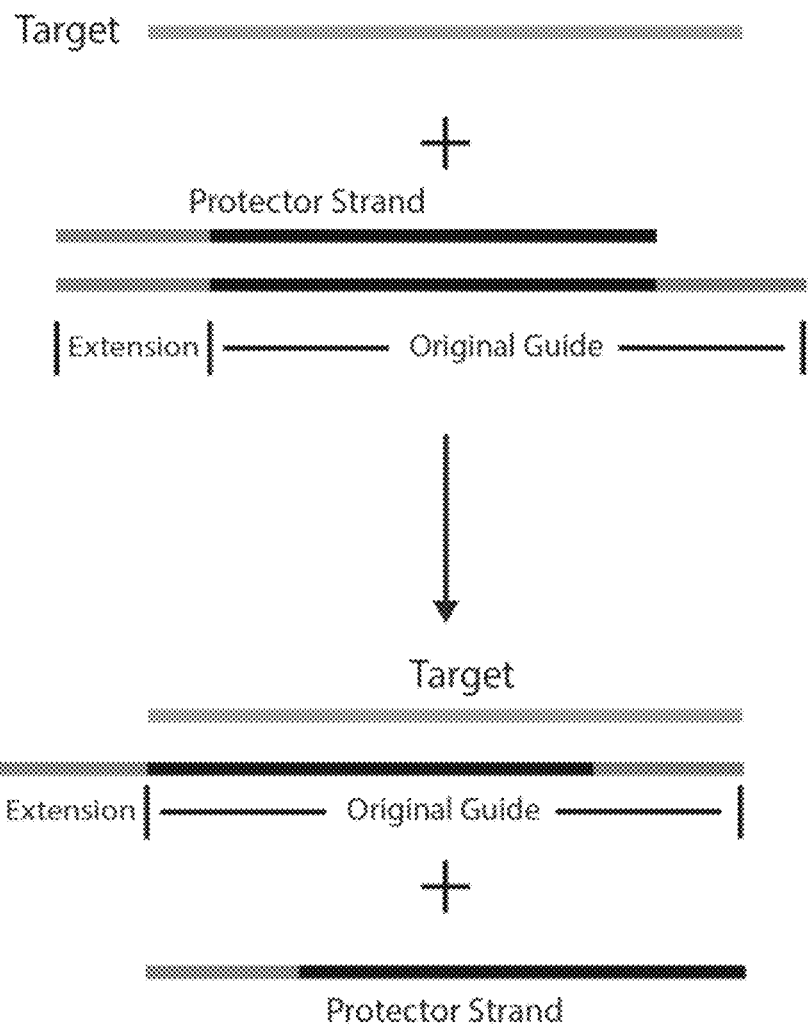
FIG. 1: Protected guide RNA (pgRNA) design. In the top cartoon, an original guide is paired with a complementary protector strand. Also depicted is an optional extension sequence at the 5' end of the original guide based on thermodynamic modeling, shown in pink. The target is shown in green. The seed sequence is shown in blue. The bottom cartoon depicts disruption of the guide:protector duplex in conjunction with binding of the guide to the target.

s14=14 nucleotide seed sequence (i.e. 14 exposed nucleotides);

p0=total length of 18 nucleotides, so that ratio is 14/18=0.77;

Chimeric=has a GAAA loop so that this is one contiguous construct;

The s14p0_ExtCompChimericControl is a typical EMX1.3 20 bp guide.

The s14p0_ExtCompChimericTruControl is a typical EMX1.3 18 bp truGuide. GFP is Green Fluorescent Protein.

The figures herein are for illustrative purposes only and are not necessarily drawn to scale.

DETAILED DESCRIPTION OF THE INVENTION

In general, the CRISPR-Cas, CRISPR-Cas9 or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, in particular a Cas9 gene in the case of CRISPR-Cas9, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell, and may include nucleic acids in or from mitochondrial, organelles, vesicles, liposomes or particles present within the cell. In some embodiments, especially for non-nuclear uses, NLSs are not preferred. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas system, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the protected guide RNA (capable of guiding Cas9 to a target locus) may comprise (1) a guide sequence (including its protector sequence) capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR-Cas9 complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas9 mRNA and guide RNA delivered. Optimal concentrations of Cas9 mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas9 nickase mRNA (for example S. pyogenes Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas9 proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas9 is advantageously codon optimized Cas9. An example of a codon optimized sequence, is in this instance a sequence optimized for expression in a eukaryote, e.g., humans (i.e. being optimized for expression in humans), or for another eukaryote, animal or mammal as herein discussed, see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas9 is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas9 correspond to the most frequently used codon for a particular amino acid.

In certain embodiments, the methods as described herein may comprise providing a Cas9 transgenic cell in which one or more nucleic acids encoding one or more guide RNAs are provided or introduced operably connected in the cell with a regulatory element comprising a promoter of one or more gene of interest. As used herein, the term "Cas9 transgenic cell" refers to a cell, such as a eukaryotic cell, in which a Cas9 gene has been genomically integrated. The nature, type, or origin of the cell are not particularly limiting according to the present invention. Also the way in which the Cas9 transgene is introduced in the cell may vary and can be any method as is known in the art. In certain embodiments, the Cas9 transgenic cell is obtained by introducing the Cas9 transgene in an isolated cell. In certain other embodiments, the Cas9 transgenic cell is obtained by isolating cells from a Cas9 transgenic organism. By means of example, and without limitation, the Cas9 transgenic cell as referred to herein may be derived from a Cas9 transgenic eukaryote, such as a Cas9 knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas9 system of the present invention. Methods of US Patent Publication No. 20130236946 assigned to Cellectis directed to targeting the Rosa locus may also be modified to utilize the CRISPR Cas9 system of the present invention. By means of further example reference is made to Platt et. al. (Cell; 159(2):440-455 (2014)), describing a Cas9 knock-in mouse, which is incorporated herein by reference. The Cas9 transgene can further comprise a Lox-Stop-polyA-Lox(LSL) cassette thereby rendering Cas9 expression inducible by Cre recombinase. Alternatively, the Cas9 transgenic cell may be obtained by introducing the Cas9 transgene in an isolated cell. Delivery systems for transgenes are well known in the art. By means of example, the Cas9 transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas9 transgenic cell, as referred to herein may comprise further genomic alterations besides having an integrated Cas9 gene or the mutations arising from the sequence specific action of Cas9 when complexed with RNA capable of guiding Cas9 to a target locus, such as for instance one or more oncogenic mutations, as for instance and without limitation described in Platt et al. (2014), Chen et al., (2014) or Kumar et al. (2009).

In some embodiments, the Cas9 sequence is fused to one or more nuclear localization sequences (NLSs), such as about or more than about 1, 2, 3, 4, 5, 6, 7, 8, 9, 10, or more NLSs. In some embodiments, the Cas9 comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas9 comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 1); the NLS from nucleoplasmin (e.g. the nucleoplasmin bipartite NLS with the sequence KRPAATKKAGQAKKKK) (SEQ ID NO: 2); the c-myc NLS having the amino acid sequence PAAKRVKLD (SEQ ID NO: 3) or RQRRNELKRSP (SEQ ID NO: 4); the hRNPA1 M9 NLS having the sequence NQSSNFGPMKGGNFGGRSSGPYGGGGQYFAKPRNQGGY(SEQ ID NO: 5); the sequence RMRIZFKNKGKDTAELRRRRVEVSVELRKAKKDEQILKRRNV (SEQ ID NO: 6) of the IBB domain from importin-alpha; the sequences VSRKRPRP (SEQ ID NO: 7) and PPKKARED (SEQ ID NO: 8) of the myoma T protein; the sequence PQPKKKPL (SEQ ID NO: 9) of human p53; the sequence SALIKKKKMAP (SEQ ID NO: 10) of mouse c-abl IV; the sequences DRLRR (SEQ ID NO: 11) and PKQKKRK (SEQ ID NO: 12) of the influenza virus NS1; the sequence RKLKKKIKKL (SEQ ID NO: 13) of the Hepatitis virus delta antigen; the sequence REKKKFLKRR (SEQ ID NO: 14) of the mouse Mx1 protein; the sequence KRKGDEVDGVDEVAKKKSKK (SEQ ID NO: 15) of the human poly(ADP-ribose) polymerase; and the sequence RKCLQAGMNLEARKTKK (SEQ ID NO: 16) of the steroid hormone receptors (human) glucocorticoid. In general, the one or more NLSs are of sufficient strength to drive accumulation of the Cas9 in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas9 enzyme activity), as compared to a control no exposed to the Cas9 or complex, or exposed to a Cas9 lacking the one or more NLSs. In other embodiments, no NLS is required.

In certain aspects the invention involves vectors, e.g. for delivering or introducing in a cell Cas9 and/or RNA capable of guiding Cas9 to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas9 encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (http://www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., http://nar.oxfordjournals.org/content/34/7/e53.short, http://www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters-especially as to the numbers of RNAs or guides or sgRNAs discussed herein, without any undue experimentation.

The guide RNA(s), e.g., sgRNA(s) encoding sequences and/or Cas9 encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the 3-actin promoter, the phosphoglycerol kinase (PGK) promoter, and the EF1α promoter. An advantageous promoter is the promoter is U6.

As used herein, the term "crRNA" or "guide RNA" or "single guide RNA" or "sgRNA" or "one or more nucleic acid components" of a Type II CRISPR-Cas9 locus effector protein comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence, and hence a nucleic acid-targeting guide RNA may be selected to target any target nucleic acid sequence. The target sequence may be DNA. The target sequence may be any DNA that encodes an RNA sequence. In some embodiments, the target sequence may be a sequence that encodes an RNA molecule selected from messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some embodiments, the target sequence may be a DNA sequence encoding a sequence within an RNA molecule selected from mRNA, pre-mRNA, and rRNA. In some embodiments, the target sequence may encode a sequence within a RNA molecule selected from ncRNA, and lncRNA. In some embodiments, the target sequence may encode a sequence within an mRNA molecule or a pre-mRNA molecule.

In some embodiments, a nucleic acid-targeting guide RNA is selected to reduce the degree secondary structure within the DNA-targeting guide RNA. In some embodiments, about or less than about 75° %, 50%, 40%, 30%, 25%, 20%, 150%, 10%, 5%, 1° %, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

The "tracrRNA" sequence or analogous terms includes any polynucleotide sequence that has sufficient complementarity with a crRNA sequence to hybridize. In general, degree of complementarity is with reference to the optimal alignment of the tracr-mate sequence and tracr sequence, along the length of the shorter of the two sequences. Optimal alignment may be determined by any suitable alignment algorithm, and may further account for secondary structures, such as self-complementarity within either the tracr-mate sequence or tracr sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG (SEQ ID NO: 17) where NNNNNNNNNNNNXGG (SEQ ID NO: 18) (N is A, G, T, or C; and X can be anything) has a single occurrence in the genome. A unique target sequence in a genome may include an S. pyogenes Cas9 target site of the form MMMMMMMMMNNNNNNNNNNNXGG (SEQ ID NO: 19) where NNNNNNNNNNNXGG (SEQ ID NO: 20) (N is A, G, T, or C; and X can be anything) has a single occurrence in the genome. For the S. thermophilus CRISPR1 Cas9, a unique target sequence in a genome may include a Cas9 target site of the form MMMMMM-MMNNNNNNNNNNNNXXAGAAW (SEQ ID NO: 21) where NNNNNNNNNNNNXXAGAAW (SEQ ID NO: 22) (N is A, G, T, or C; X can be anything; and W is A or T) has a single occurrence in the genome. A unique target sequence in a genome may include an S. thermophilus CRISPR1 Cas9 target site of the form MMMMMMM-MMNNNNNNNNNNNXXAGAAW (SEQ ID NO: 23) where NNNNNNNNNNNXXAGAAW (SEQ ID NO: 24) (N is A, G, T, or C; X can be anything; and W is A or T) has a single occurrence in the genome. For the S. pyogenes Cas9, a unique target sequence in a genome may include a Cas9 target site of the form MMMMMM-MMNNNNNNNNNNNNXGGXG (SEQ ID NO: 25) where NNNNNNNNNNNNXGGXG (SEQ ID NO: 26) (N is A, G, T, or C; and X can be anything) has a single occurrence in the genome. A unique target sequence in a genome may include an S. pyogenes Cas9 target site of the form MMM-MMMMMMNNNNNNNNNNNXGGXG (SEQ ID NO: 27) where NNNNNNNNNNNXGGXG (SEQ ID NO: 28) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

An object of the current invention is to further enhance the specificity of Cas9 given individual guide RNAs through thermodynamic tuning of the binding specificity of the guide RNA to target DNA.

Figure 10A:
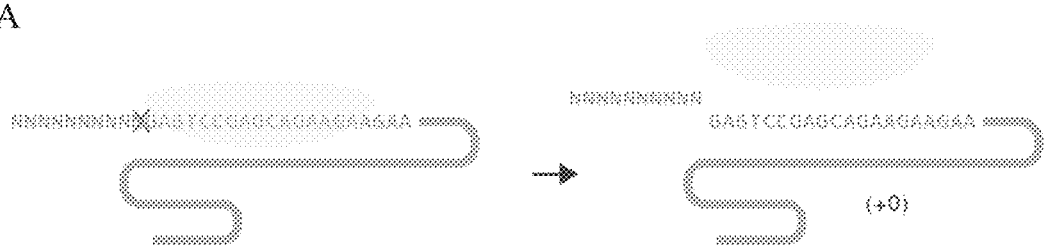
FIG. 10A-10C: Possibilities for processing of extended sgRNAs. A) Extended sgRNA spacer is truncated to 20nt (SEQ ID NOS 64 and 68, respectively, in order of appearance). B) Short extensions to the 20nt spacer sequence are not truncated (SEQ ID NOS 65, 65, 66 and 68, respectively, in order of appearance). C) Stabilized sgRNA spacer extension matching target sequence distal of sgRNA. Specific sgRNA spacer length extensions demonstrate thermodynamic states, which result in secondary structure that protects the spacer length extension from truncation. Protective secondary structures show preserved on-target cutting, and diminished offs-target cutting, indicating that the target-bound state is thermodynamically favorable to the protected structure of the unbound pgRNA (SEQ ID NOS 67, 67, 67 and 67, respectively, in order of appearance).
Figure 10B:
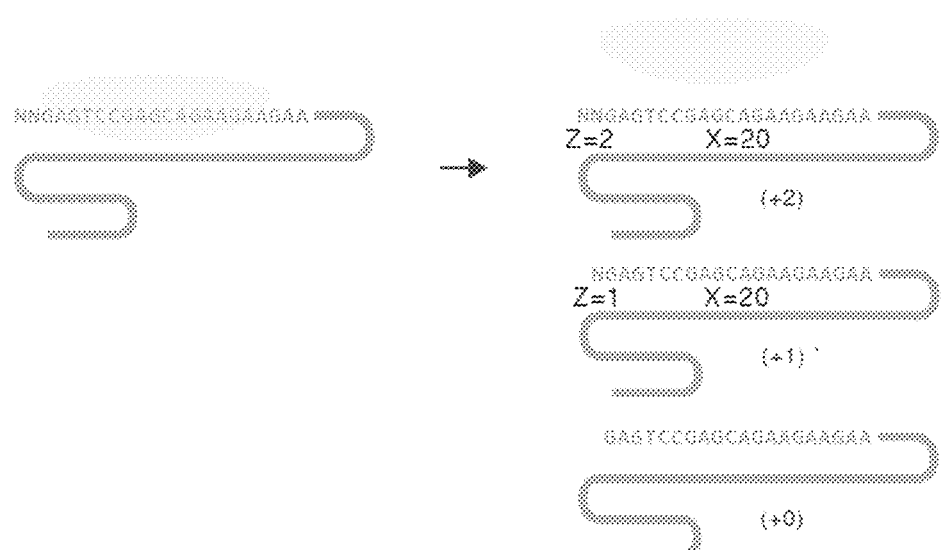
Figure 10C:
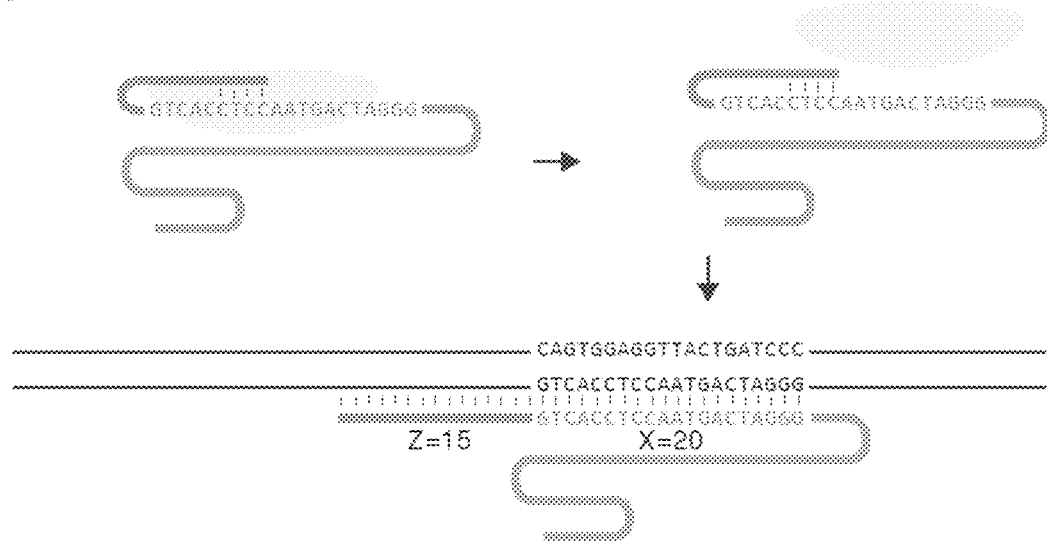
Figure 12A:
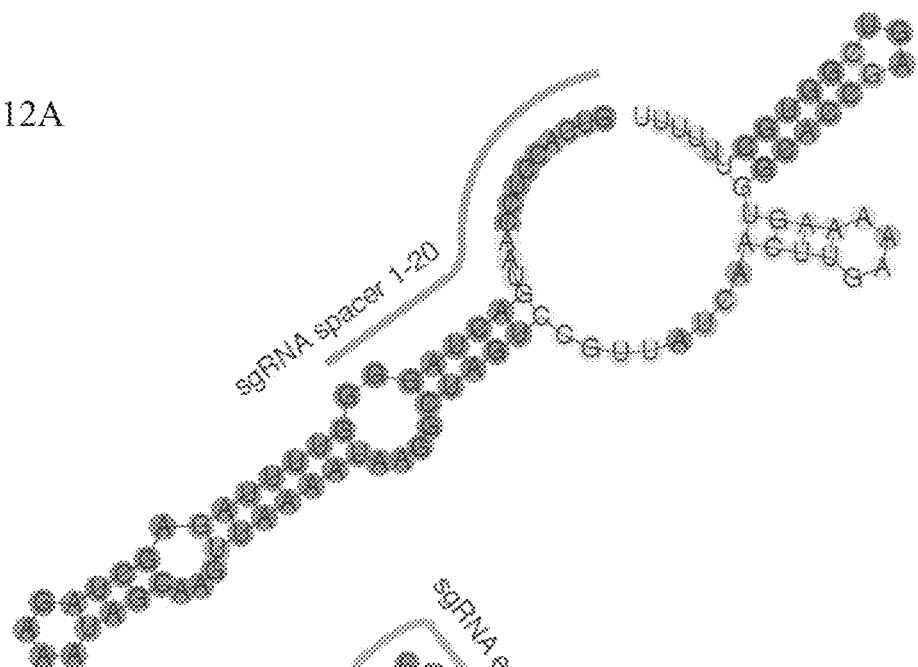
FIG. 12A-12B: Protection of target-matching extensions to sgRNA spacer. A) Structural prediction of EMX1.1 WT sgRNA containing a 20nt spacer (X=20) (SEQ ID NO: 69). B) Structural modeling of EMX1.1 sgRNA containing a 20nt spacer with a 15nt extension matching the genomic target sequence distal of the sgRNA spacer (X=20, Z=15) predicts a protected structure for the sgRNA extension due to interaction of the sgRNA extension and spacer seed (SEQ ID NO: 70).
Figure 12B:
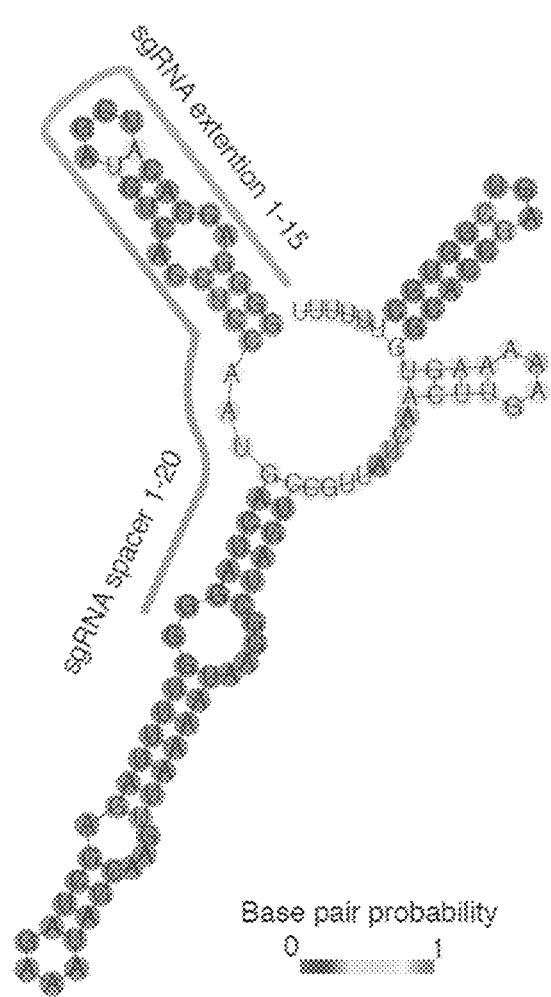
Figure 13A:
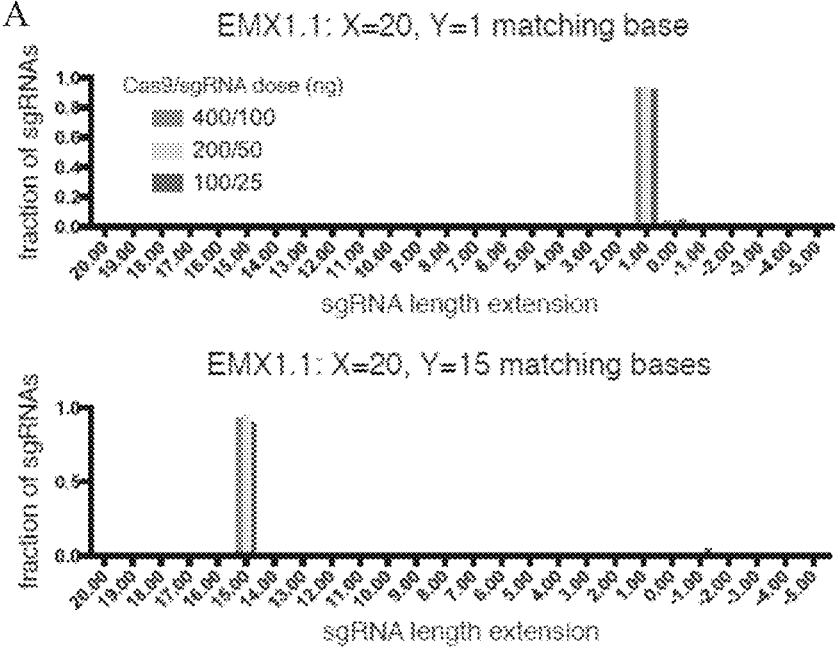
FIG. 13A-13C: Specificity of target-matching extensions to sgRNA spacer. A) RNA sequencing of extended sgRNAs. Nucleotide resolution sgRNA sequencing shows that specific sgRNA length extensions are preserved (top: EMX1.1; X=20, Z=1), (bottom: EMX1.1; X=20, Z=15) as shown in FIG. 2 b,c and FIG. 4. B) EMX1.1 on-target and off-target cutting is reduced for extended sgRNAs. C) EMX1.1 length extensions show significantly enhanced specificity compared to WT sgRNA.
Figure 13B:
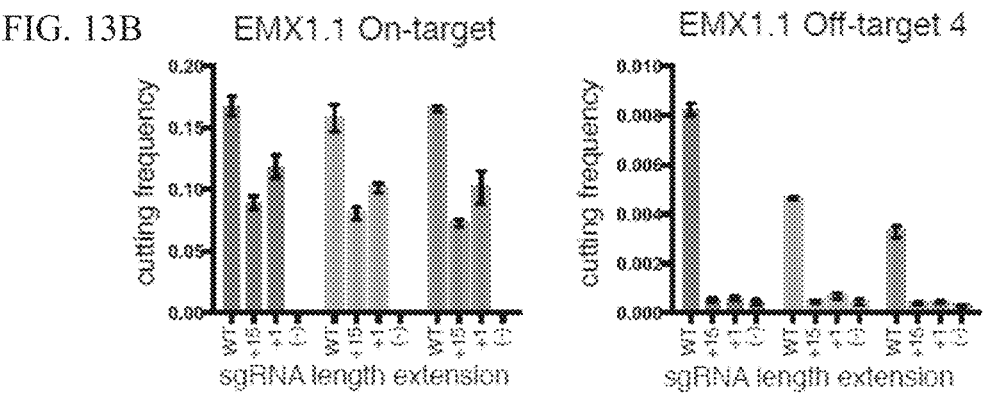
Figure 13C:
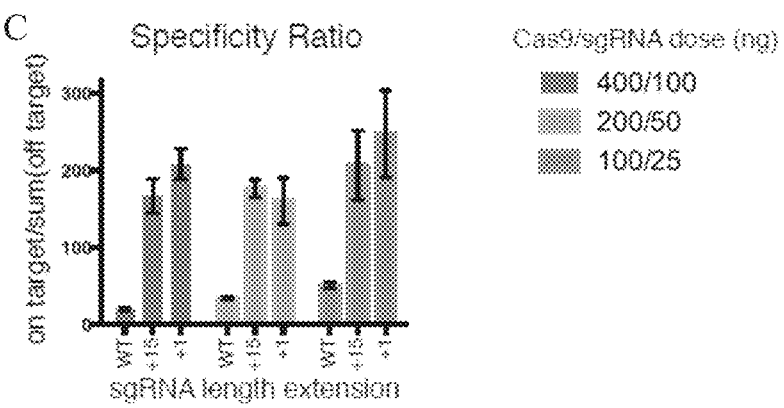

A further aspect is the general approach of introducing mismatches, elongation or truncation of the guide sequence to increase/decrease the number of complimentary bases vs. mismatched bases shared between a genomic target and its potential off-target loci. These principles are intended to give thermodynamic advantage to targeted genomic loci over genomic off-targets. As a result, improved specificity may be achieved while maximizing the versatility of Cas9 target selection and cutting efficiencies. Such approaches use, for example, a single sgRNA or a single sgRNA expression product. Specificity of Cas9 can be optimized against potential genomic off-targets by, for example, altering 1-3 distal bases in the sgRNA, preferably 1-2 bases. This provides the ability to possibly maximize the number of mismatches between the genomic target and potential off-target loci.

sgRNA extensions matching the genomic target provide sgRNA protection and enhance specificity. Extension of the sgRNA with matching sequence distal to the end of the spacer seed for individual genomic targets demonstrates enhanced specificity (FIG. 10c; FIGS. 13b and 13c). Matching sgRNA extensions that enhance specificity can be observed in cells without truncation (FIG. 13a). Prediction of sgRNA structure accompanying these stable length extensions shows that stable forms arise from protective states, where the extension forms a closed loop with the sgRNA seed due to complimentary sequences in the spacer extension and the spacer seed (FIG. 12). These results demonstrate that the protected guide concept also includes sequences matching the genomic target sequence distal of the 20mer spacer-binding region. Thermodynamic prediction (as shown in FIG. 12) can be used to predict completely matching or partially matching guide extensions that result in protected sgRNA states. This extends the concept of protected sgRNAs to interaction between X and Z (FIG. 3), where X will generally be of length 17-20nt and Z is of length 1-30nt (FIG. 10c; FIG. 12). Thermodynamic prediction can be used to determine the optimal extension state for Z, potentially introducing small numbers of mismatches in Z to promote the formation of protected conformations between X and Z as shown in FIG. 10c. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and EL are used interchangeably to correspond to the term extended length (ExL) which represents the number of nucleotides by which the target sequence is extended.

Figure 5:
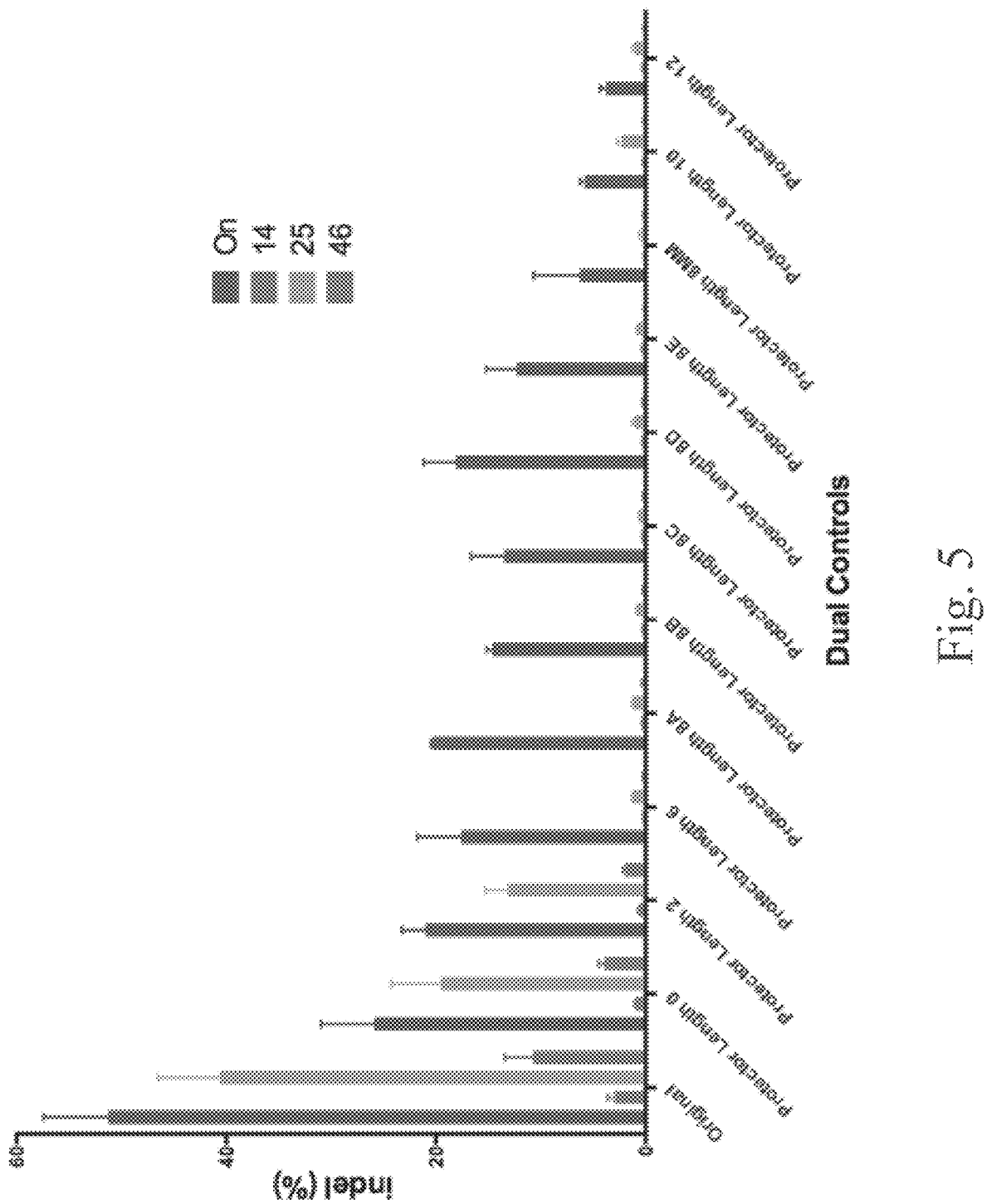
FIG. 5: Extended dual guides without protector are transfected in HEK293 cells and demonstrate increased specificity. The extensions, increase in length from 0 to 12 and are the same extended guides used in the dual experiments when a protector is also transfected. Extended guides alone improve specificity.
Figure 9C:
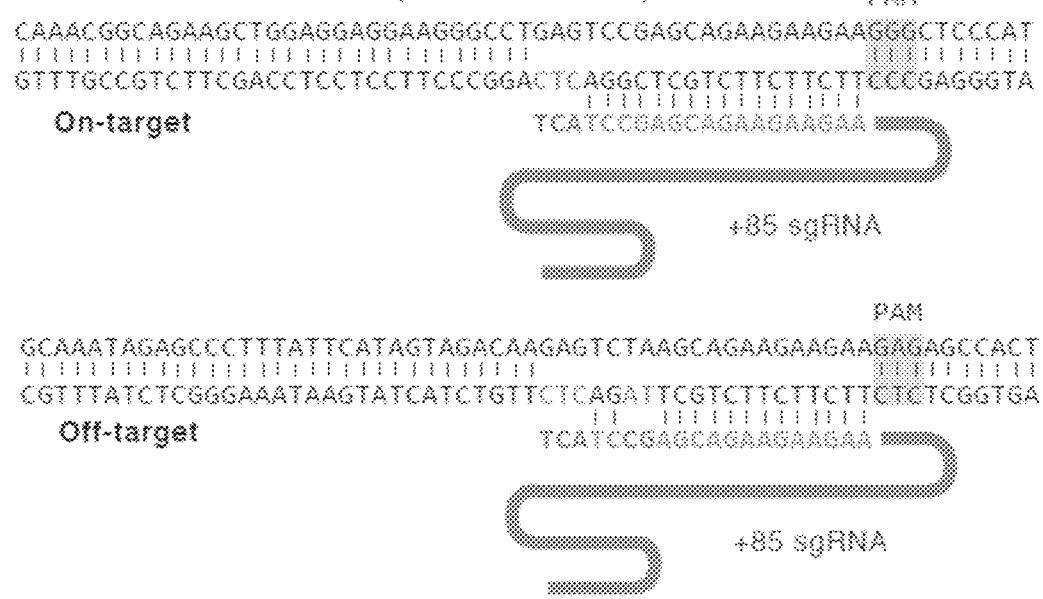
Figure 9D:
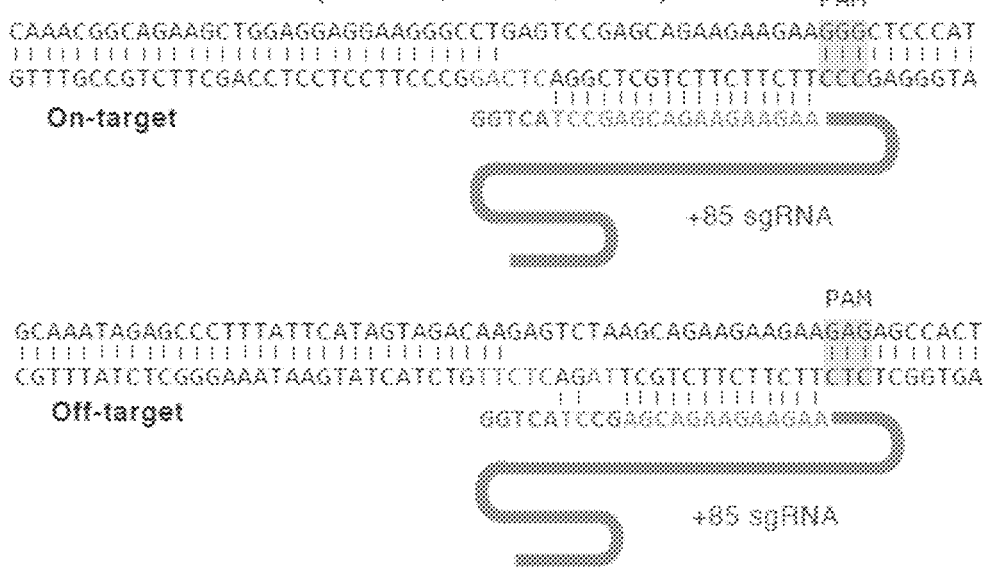
Figure 11:
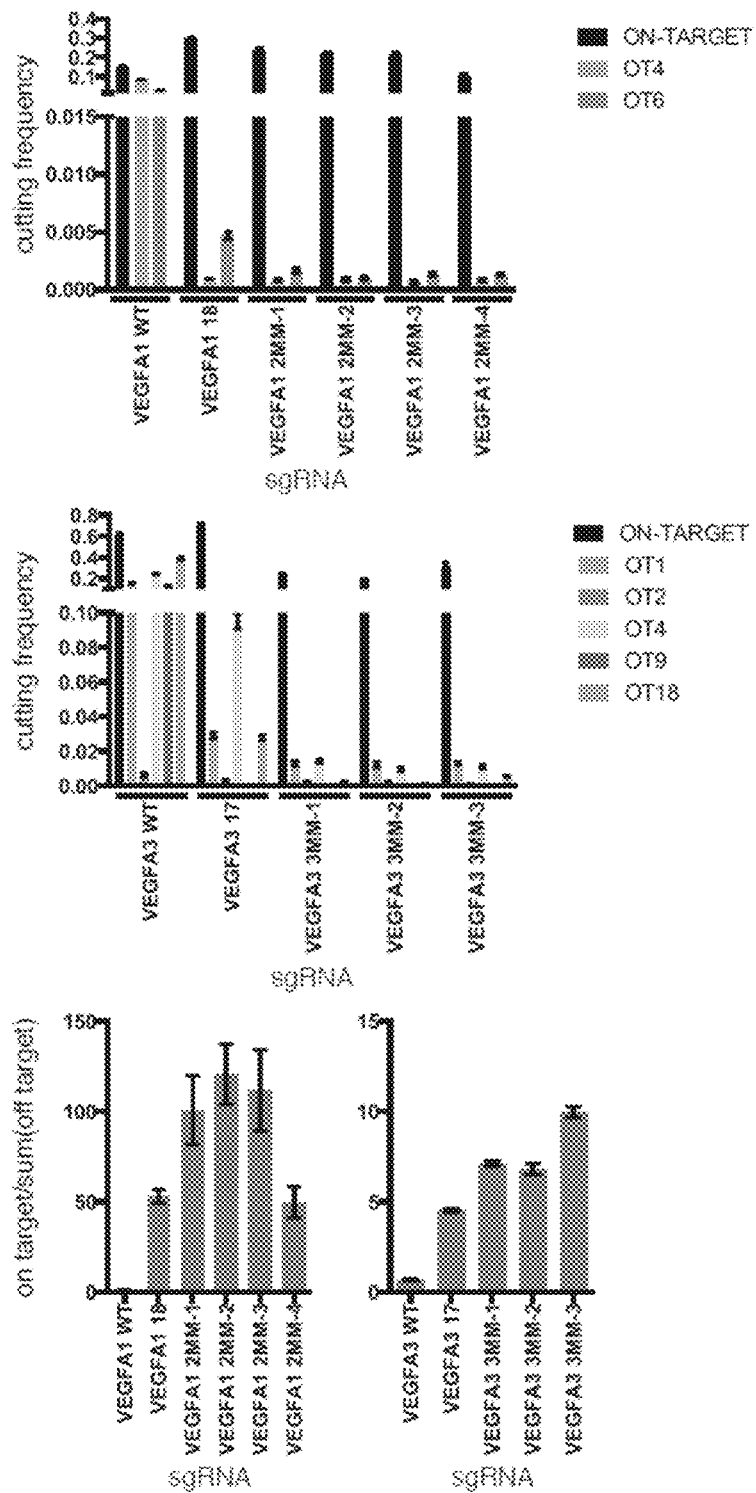
FIG. 11: Comparison of tru sgRNA and truncated sgRNA spacer with mismatched extension. A) VEGFA1 results show that tru sgRNA (VEGFA1 18) and truncated sgRNA with mismatch extension (VEGFA1 2MM-1, 2MM-2, 2MM-3, 2MM-4; X=18, Y=2) result in increased cutting compared to WT sgRNA (VEGFA1). Mismatch extended sgRNAs show decreased off-target cutting compared to tru sgRNA. B) VEGFA3 results show that truncated sgRNAs with mismatched extensions (VEGFA1 3MM-1, 3MM-2, 3MM-3) resulted in decreased on-target cutting compared to WT (VEGFA3) and tru (VEGFA3 17) sgRNAs. Truncated spacers with mismatched extensions showed diminished off-target activity compared to both WT and tru sgRNAs. C) Specificity ratio comparisons between WT, tru, and mismatch extended sgRNAs shows that specific mismatched sgRNAs significantly enhance specificity over WT and tru sgRNAs.

Addition of sgRNA mismatches to the distal end of the sgRNA demonstrates enhanced specificity. The introduction of unprotected distal mismatches in Y or extension of the sgRNA with distal mismatches (Z) demonstrates enhanced specificity (FIG. 9 (c,d) and FIG. 11). This concept, as mentioned, is tied to X, Y, and Z components used in protected sgRNAs, which is touched on in FIG. 5. The unprotected mismatch concept may be further generalized to the concepts of X, Y, and Z described for protected sgRNAs as elaborated in FIG. 9 (c,d) and FIG. 11.

Without wishing to be bound by theory, protecting the mismatched bases with a perfectly complementary protector sequence could decrease the likelihood of target DNA binding to the mismatched base pairs at the 5' end (FIG. 1). As the double-stranded DNA target is unwound, Cas9 eventually attempts to interrogate the PAM-distal, 5' end of the target for guide sequence complementarity. However, because the 5' end of the protected guide RNA (pgRNA) is double-stranded, there may be two possible outcomes: 1) guide RNA-protector RNA to guide RNA-target DNA strand exchange will occur and the guide will fully bind the target or 2) the guide RNA will fail to fully bind the target. Because Cas9 target cleavage is a multiple step kinetic reaction that requires guide RNA:target DNA binding to activate Cas9-catalyzed DSBs, Cas9 cleavage should not occur if the guide RNA does not properly bind.

One aspect is a non-naturally occurring or engineered composition comprising a protected guide RNA (pgRNA) comprising a guide sequence capable of hybridizing to a target sequence in a genomic locus of interest in a cell and a protector strand, wherein the protector strand is optionally complementary to the guide sequence and wherein the guide sequence may in part be hybridizable to the protector strand. The pgRNA optionally includes an extension sequence.

One aspect is a non-naturally occurring or engineered CRISPR-Cas9 complex composition comprising the pgRNA of the current invention and a CRISPR enzyme, wherein optionally the CRISPR enzyme comprises at least one mutation, such that the CRISPR enzyme has no more than 5% of the nuclease activity of the CRISPR enzyme not having the at least one mutation, and optionally one or more comprising at least one or more nuclear localization sequences.

One aspect is a non-naturally occurring or engineered composition comprising the protected guide RNA (pgRNA) of the current invention, a CRISPR enzyme comprising at least one or more nuclear localization sequences, wherein the CRISPR enzyme comprises at least one mutation, such that the CRISPR enzyme has no more than 5% of the nuclease activity of the CRISPR enzyme not having the at least one mutation.

One aspect is a method for introducing a genomic locus event comprising the administration to a host or expression in a host in vivo of one or more of the compositions of the current invention.

One aspect is a method of modifying a genomic locus of interest to change gene expression in a cell by introducing or expressing in a cell the composition of the current invention.

Figure 2:
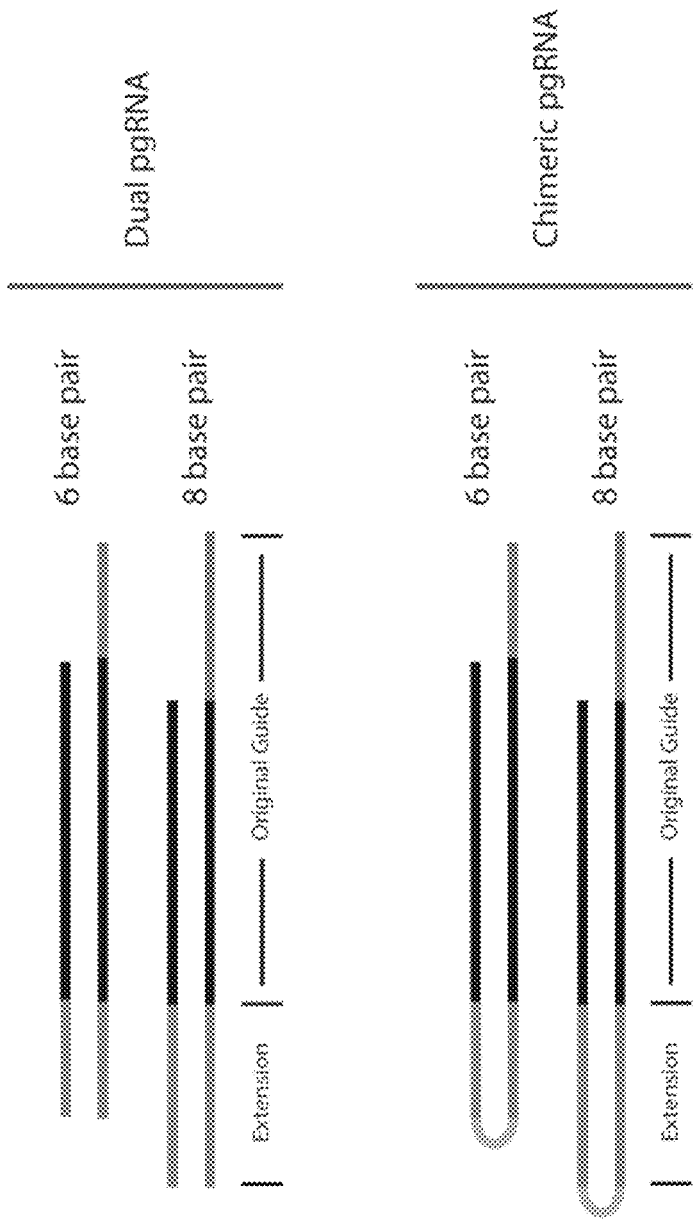
FIG. 2: Initial protected guide design parameters. Dual and chimeric versions were cloned and tested for extension lengths of 6 and 8 (pink). The seed sequence (i.e. the unprotected, unpaired region at the 3' end of the original guide) is shown in blue and the chimeric hairpin, in this instance formed by nucleotides of the extension, is shown in green.

The thermodynamics of the pgRNA-target DNA hybridization will be determined by the number of bases complementary between the guide RNA and target DNA. By employing 'thermodynamic protection,' specificity of sgRNA can be improved by adding a protector sequence. One aspect includes strategies for implementing the protected guide RNA. For example, one method adds a complementary protector strand of varying lengths to the 5' end of the guide sequence within the sgRNA. As a result, the protector strand is bound to at least a portion of the sgRNA and provides for a protected sgRNA (pgRNA). In turn, the sgRNA references herein may be easily protected using the described embodiments, resulting in pgRNA. The protector strand can be either a separate RNA transcript or strand (also referred to herein as dual pgRNA) or a chimeric version joined to the 5' end of the sgRNA guide sequence (e.g., FIG. 2). Herein the terms "protector strand", "protector sequence", "protecting sequence", "protector RNA", and "protector" are used interchangeably.

A second strategy uses thermodynamic modeling to add mismatched base pairs to the 5' end of the guide. The binding free energy of the protector sequence is carefully designed to optimize the overall free energy of the reaction to be close to zero (which is predicted to be the free energy at which optimal specificity occurs). The current invention provides several design parameters that can be adjusted to achieve improved on-target activity as well as improved specificity desired (e.g., FIG. 3). In general, the pgRNA of the current invention may be designed so that the binding free energy of the protector sequence results in an overall free energy of the reaction in a range of no more than +/−10% from zero, no more than +/−5% from zero, preferably no more than +/−2% from zero, and most preferably the overall free energy of the reaction is zero.

TABLE 1

Figure 3:
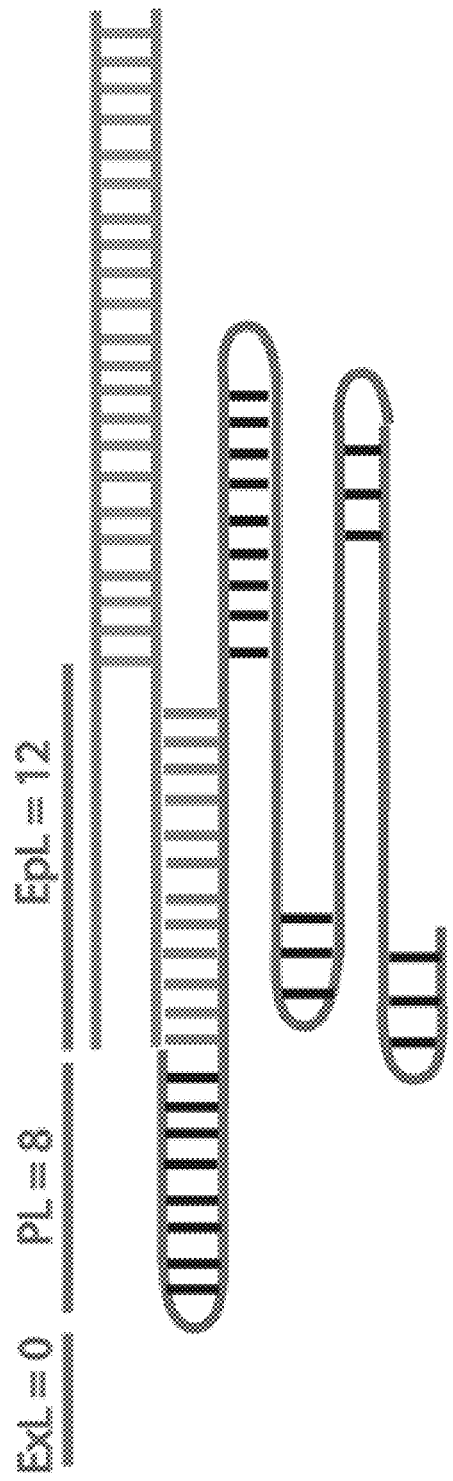
FIG. 3: The adjustable design parameters for protected guides. The Exposed Length (EpL) as used in this application corresponds to the number of nucleotides available for target DNA to bind. The terms "X" or seed length (SL) have been previously used to refer to the EpL and may be used interchangeably with the term EpL herein. The Protector Length (PL) as used in this application corresponds to the length of the protector on the original guide and the term "Y" has been previously used to refer to the PL and may be used interchangeably with the term PL herein. The cartoon depicts a protector adjacent to the targeting sequence of the guide. There is sufficient complementarity of the protector with the 5' end of the targeting sequence of the guide to form a hybrid with 5' end of the guide. In particular, an 8 nt protector is depicted adjacent to an 20 nt guide, or which 12 nt are immediately available to bind target DNA and 8 nt are protected. There is no extension (ExL). Optionally, an extension can be present between the protector and the guide (see FIG. 2, bottom). The Extended Length (ExL) as used in this application corresponds to the number of nucleotides by which the target sequence is extended. The terms "E", "E", "Z" or "EL" have been previously used to refer to or correspond to the ExL and may be used interchangeably with the term ExL herein. A=the presence of mismatches, deletions, or insertions in the PL region. B=the presence of modified nucleotides in the sgRNA.

Designs with different X (EpL) and Z (ExL) lengths (see FIG. 3 for X and Z definitions; X and Z correspond to EpL and ExL respectively). Shown in the table are the lengths of double stranded protection for each construct to determine the best possible construct.

|        | X = 4 | X = 8 | X = 12 | X = 14 | X = 16 | X = 18 |
|--------|-------|-------|--------|--------|--------|--------|
| Z = 0  | 16    | 12    | 8      | 6      | 4      | 2      |
| Z = 4  | 20    | 16    | 12     | 10     | 8      | 6      |
| Z = 8  | 24    | 20    | 16     | 14     | 12     | 10     |
| Z = 12 | 28    | 24    | 20     | 18     | 16     | 14     |

TABLE 2

Designs with different X (EpL) and Z (ExL) lengths (see FIG. 3 for EpL and ExL definitions). Shown in the table are the ratios of double stranded protection to the exposed sequence length for each construct.

|        | X = 4 | X = 8 | X = 12 | X = 14 | X = 16 | X = 18 |
|--------|-------|-------|--------|--------|--------|--------|
| Z = 0  | 4     | 1.5   | 0.67   | 0.43   | 0.25   | 0.11   |
| Z = 4  | 5     | 2     | 1      | 0.72   | 0.5    | 0.33   |
| Z = 8  | 6     | 2.5   | 1.33   | 1      | 0.75   | 0.55   |
| Z = 12 | 7     | 3     | 1.67   | 1.29   | 1      | 0.78   |

Figure 4A:
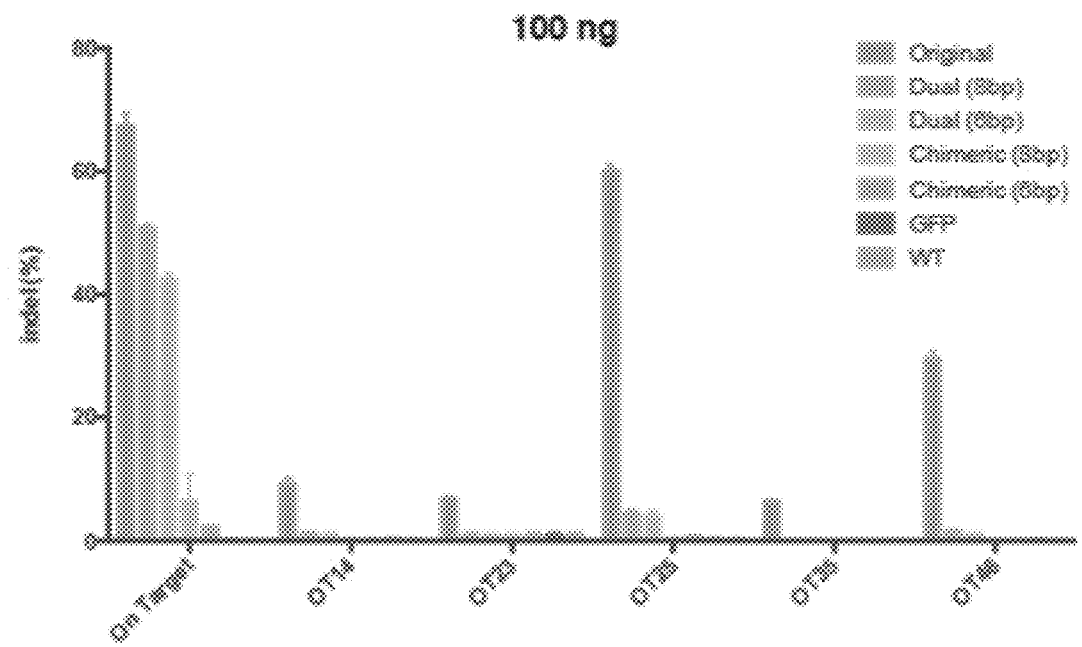
FIG. 4A-4B: Improved specificity by pgRNA at the human EMX1.3 target site in HEK 293FT cells. (a) 100 ng of pgRNA transfected. (b) 250 ng of pgRNA transfected.
Figure 4B:
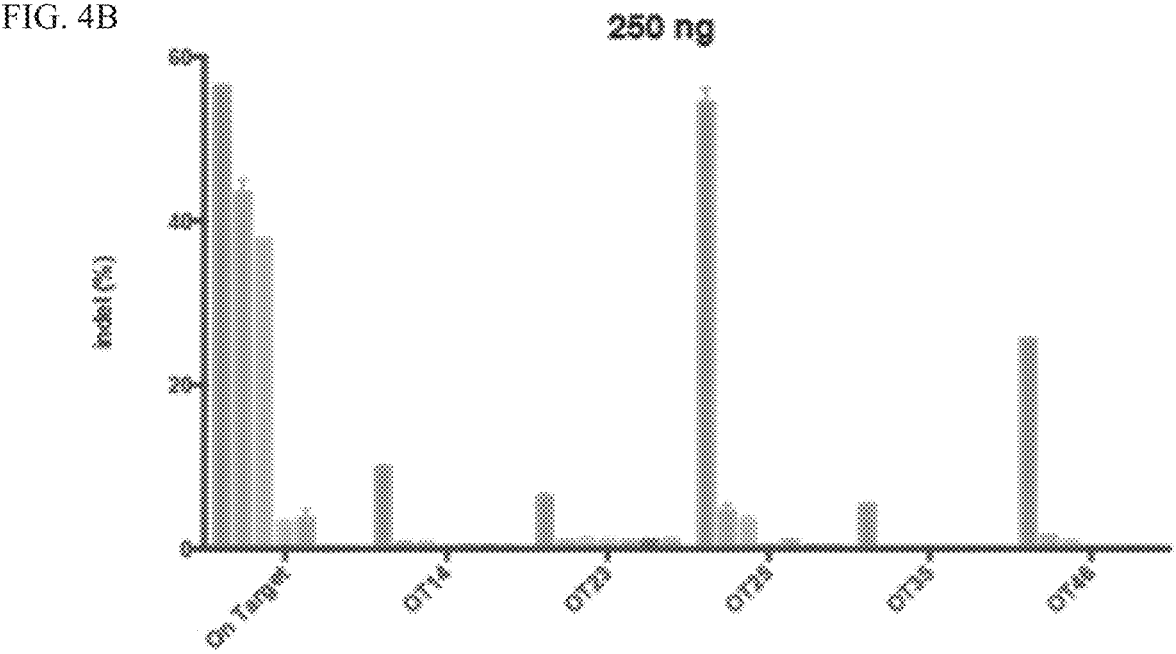

Dual and chimeric pgRNA forms were tested for possible improvement of Cas9 cleavage specificity at the human EMX1.3 target site and 5 known off-target sites (Hsu et al. NBT 2013). 100 and 250 ng of pgRNA were transfected to test if the relative ratio of pgRNA to Cas9 can also affect Cas9 specificity (see FIG. 4). Here, in particular, the dual pgRNA strategy showed dramatically improved off-target activity with only modest loss in overall on-target indel efficiency.

In the follow-up experiments, the parameters that govern the specificity of a protected guide were further investigated. Seed and extension protector lengths and mismatches at the seed end of the protector were tested. Over 72 designs involving both the dual and chimeric constructs for the original and truncated forms of the EMX1.3 guide. In general:

1) An extended guide (containing complementarity to the protector sequence) but without the protector RNA yields greater specificity than the wild-type sgRNA,
2) Protected guides have improved specificity,
3) Longer seed lengths or exposed sequence lengths further promote greater on-target activity without sacrificing specificity,
4) Mismatches on the exposed sequence-side of the protector promote greater on-target activity by increasing the effective length of the exposed sequences, and
5.) Short exposed sequence lengths (EpL) and long protected lengths inhibited on-target activity.

Figure 8:
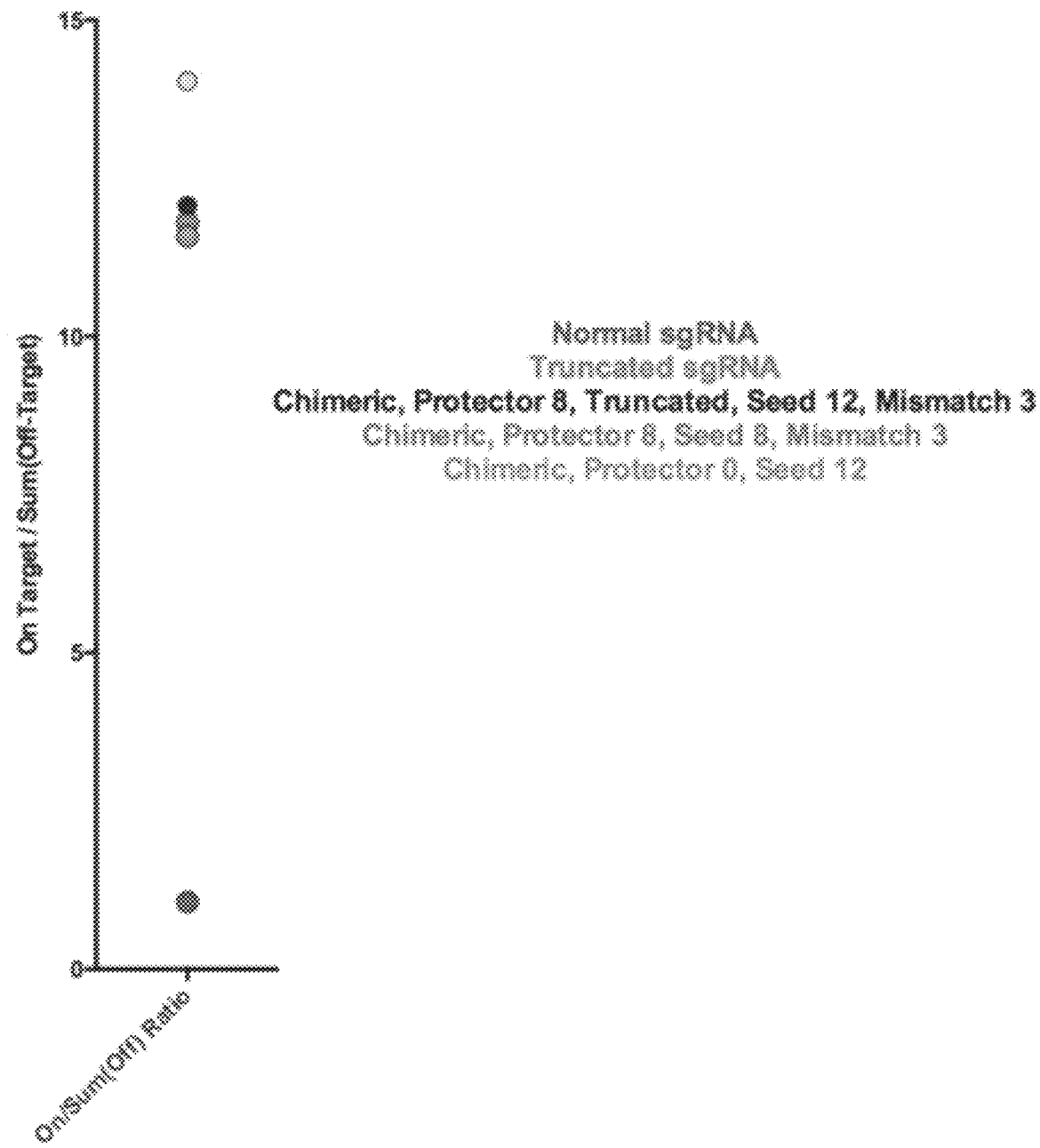
FIG. 8: On-target to off-target ratio scores for all constructs tested. The normal 20 bp guide (blue) is located towards the bottom end of the distribution while the chimeric protected guide with mismatches (Chimeric, Protector 8, Seed 8, Mismatch 3) ranks the highest (grey). The truncated guide (red) without protection ranks third from the top, lower than the chimeric protected guides (both the chimeric original (20 bp Chimeric, Protector 8, Seed 8, Mismatch 3; grey) and a truncated form (Chimeric, Protector8, Truncated, Seed 12, Mismatch3; black).

The above was identified, inter alia, by analyzing the controls where the extended guide was transfected only (i.e. without any protector). On-target activity of an extended guide alone, without a protector, decreases as the extension increases. On-target to off-target ratio score is improved in the protected cases (see FIG. 8).

Figure 7:
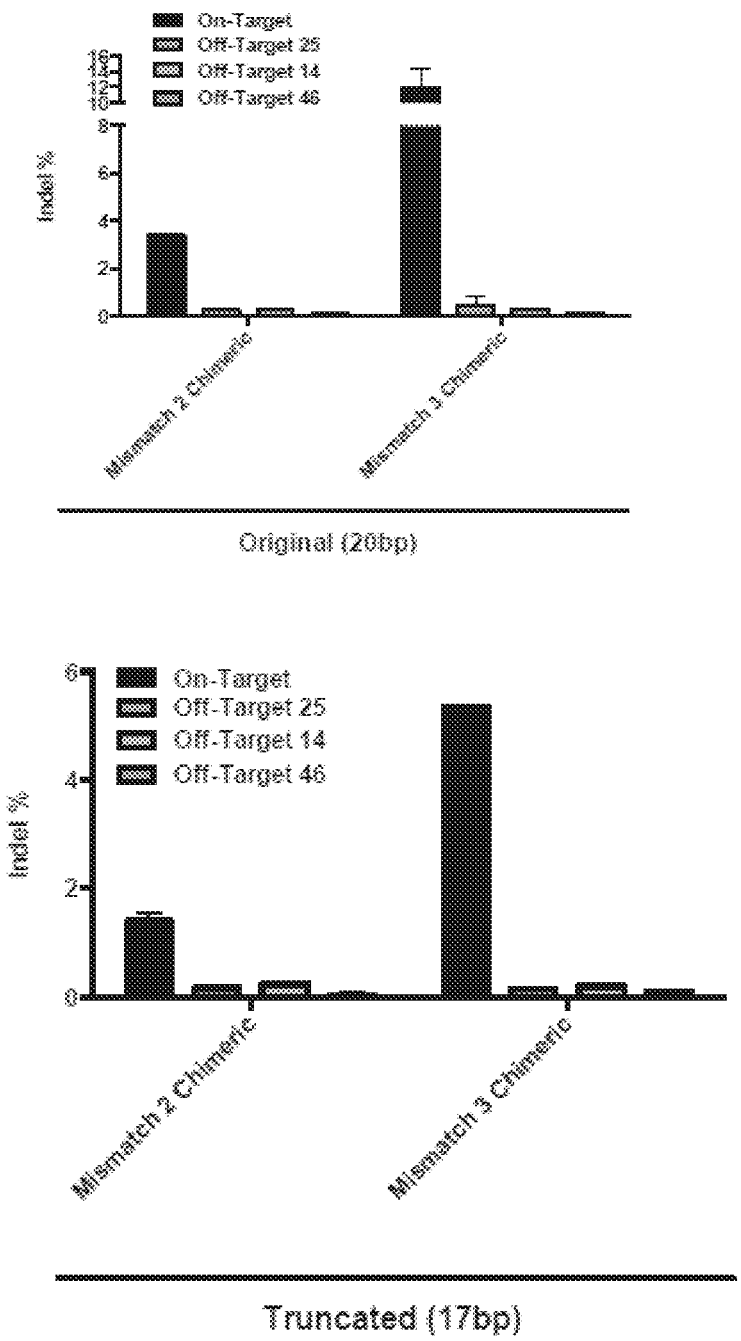
FIG. 7: Increasing the number of mismatches improves the on-target guide activity without sacrificing the specificity in both the chimeric 20 bp and truncated 17 bp designs. Mismatch 0=no mismatches, Mismatch 1=2 bp, Mismatch 2=4 bp, and Mismatch 3=6 bp.

Additionally, chimeric protected guides have improved specificity over the wild-type sgRNA. By titrating both the seed length and the number of mismatches, a greater seed length and number of mismatches was identified to correlate with greater on-target to off-target scores by increasing the on-target activity (see FIGS. 6-7). These are two important design rules on account that not only is it desired to achieve a high on-target to off-target ratio, but it is also advantageous for on-target activity to be as close as possible to the original (e.g., 20-bp guide's activity). The mismatch trend was observed in both the original 20 bp and truncated chimeric guides (see FIG. 7). The seed length effect was also readily observable in both the original and truncated guides for the chimeric constructs (see FIG. 6). Here the seed length corresponds to the exposed length (EpL).

Figure 21:
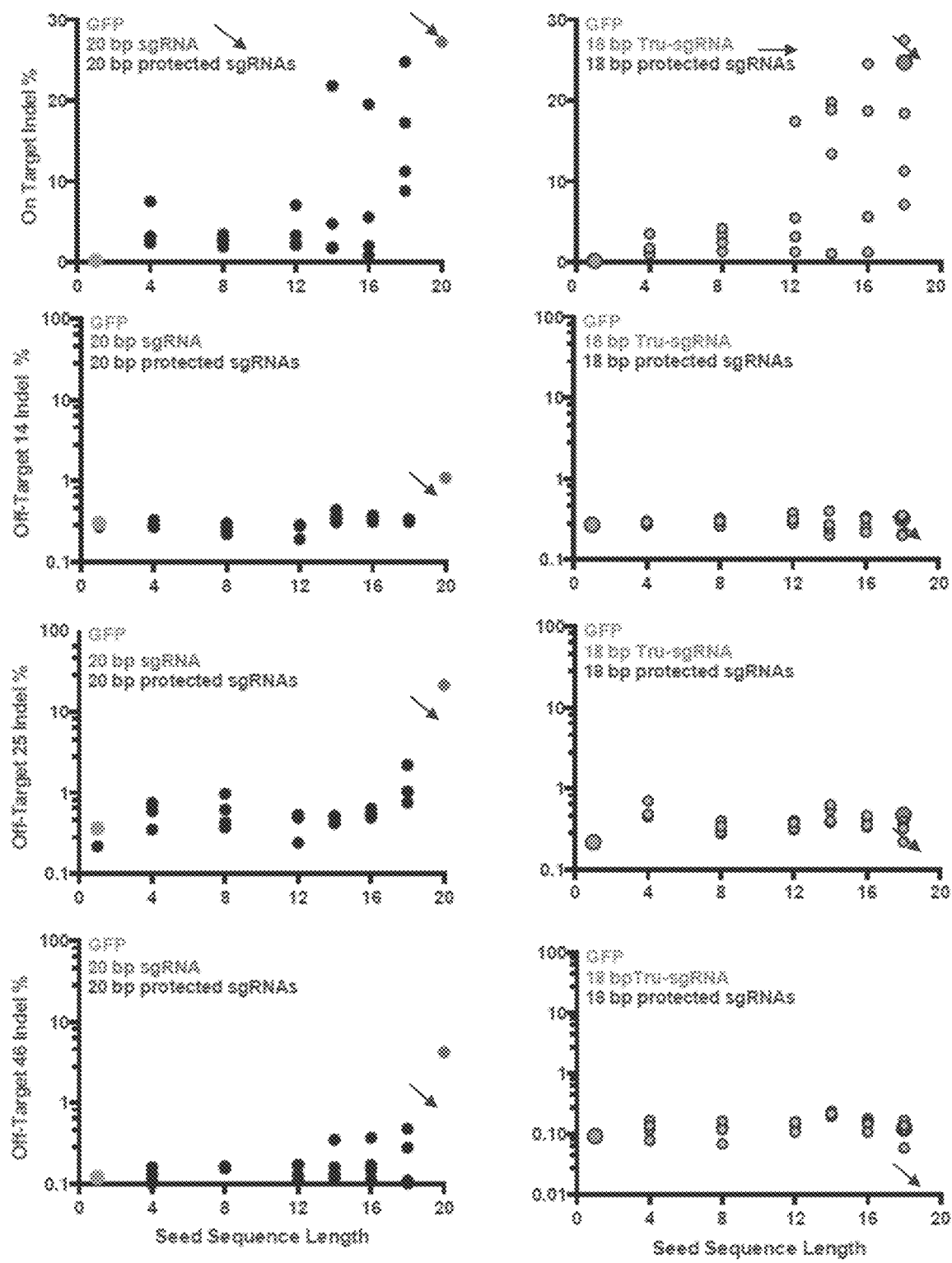
FIG. 21: Is a series of 8 plots in two columns. The Column 1 of 4 plots on the left provides results illustrative of the effects of a 20 bp protected sgRNA. The Column 2 of 4 plots on the right provides results illustrative of the effects of a 18 bp protected sgRNA. The results shown in Column 1 illustrate that there are many 20 bp protected-guide sgRNA constructs that reduce off-target activity compared to a typical 20 bp EMX1.3 sgRNA. Data points from unprotected guides are identified by arrows, and from GFP are shown lighter and larger. The results shown in Column 2 illustrate that there is one 18 bp protected sgRNA construct that has lower off target indel activity than an 18 bp Tru-sgRNA construct. These results also show that increasing the seed sequence length can improve specificity.

FIG. 21 provides a further illustration of aspects of the invention in which a double stranded region at the 5' end of a sgRNA increases the specificity of the construct. To obtain the data illustrated in FIG. 21, HEK.293 cells were cultured in DMEM and 10% FBS. Cells were transfected with 100 ng PX165 spCas9 and 100 ng PCR product with different constructs. 48 hours later, DNA was isolated with Quick Extract, and prepared for MiSeq analysis. MiSeq analysis was used to quantify cutting efficiency. The data plotted in FIG. 21 illustrate the following: the On target indel cutting for EMX1.3, or the Off target cutting at 3 sites known to have off-target effects for EMX1.3. The cutting is plotted as a function of the seed sequence, the unbound and single stranded part of the sgRNA. The data illustrate that, in these embodiments, increasing this unexposed seed region drastically increases the amount of on target cutting, but does not drastically increase the amount of off-target cutting. This data also illustrates that protecting the 5' end of an sgRNA does increase specificity, which is evident in Column 1 showing that there are many protected-guide sgRNA constructs that reduce off-target activity compared to the typical 20 bp EMX1.3 guide. This is also evident in Column 2-showing that there is one construct that has lower off target activity than the 18 bp Tru-sgRNA.

Figure 22:
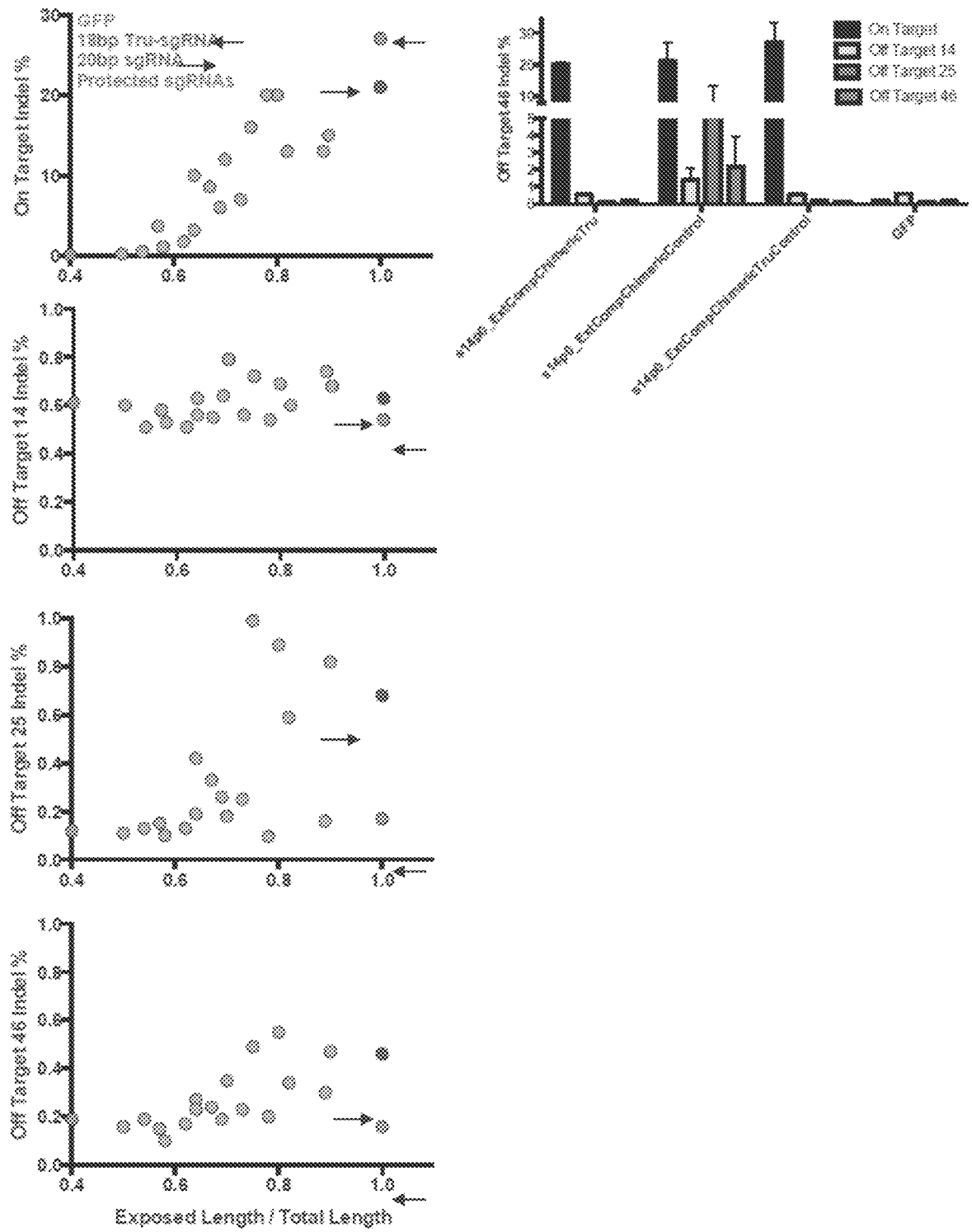
FIG. 22: is a series of plots in the left column and a graph in the right column, further illustrating that increasing the seed sequence length can improve specificity, and highlighting aspects of guide construct optimization. The left column plots On Target EMX1.3 cutting, as well as off-target EMX1.3 cutting, for different sgRNAs. The efficacy of cutting is plotted against the following ratio: Seed Sequence/Total sgRNA Length. The graph in the right column highlights an optimized construct: the s14p0_ExtCompChimericTru construct. In the graph, this construct is compared to a typical 18 bp EMX1.3 TruGuide, a regular 20 bp EMX1.3 guide, and GFP. On Target cutting and Off-target cutting is measured at three sites known to have significant EMX1.3 off target cutting. As illustrated, the "s14p0_ExtCompChimericTru" means.

Building on the foregoing results which show that increasing the seed sequence length improves specificity, and using the experimental protocols as set out above, a second illustrative panel of protected sgRNAs was developed. These sgRNAs had relatively long seed sequences, as set out in the plots in FIG. 22. The data in FIG. 22 further confirms that increasing the seed sequence tends to increase cutting efficacy, and that employing a 5' protection sequence improves specificity. FIG. 22 also illustrates an approach to optimization of constructs. FIG. 22 plots On Target EMX1.3 cutting, as well as off-target EMX1.3 cutting, for different sgRNAs. The efficacy of cutting is plotted against the following ratio: Seed Sequence/Total sgRNA Length. For example, given the following sgRNA targeting sequence (the Total sgRNA Length that attacks DNA): 5' ATCGATC-GATCGATCGATCG 3' (SEQ ID NO: 29) (which has 20 nucleotides), and if the protected sgRNA sequence is: 5'-CGATCGATCGATCG 3' (SEQ ID NO: 30), then there are 14 exposed nucleotides in the Seed Sequence, with 6 nucleotides that are bound by the protected region. As plotted in FIG. 22, this construct would have a position on the X axis of 14/20=0.7. Notably, in practice, the actual sequence would have a GAAA loop secondary structure with the guide RNA folding back on itself to provide the 6 nucleotides that bind to the 5' end, and protect it (GAAATAGCTA (SEQ ID NO: 31)). Thus, in some embodiments, the chimeric pgRNA comprises a loop to join the 5' end of the guide sequence (including the protected guide sequence) to the 3' end of the protector sequence. The loop optionally comprises or consists of GAAA. The data set out in FIG. 22 illustrate that increasing this ratio increases specificity. Information of this kind can also be used to optimize guide constructs. For example, in the illustrated embodiments, one optimized construct is selected on the right: the s14p0_ExtCompChimericTru construct. In the graph, this construct is compared to a typical 18 bp EMX1.3 TruGuide, a regular 20 bp EMX1.3 guide, and GFP. On Target cutting and Off-target cutting is measured at three sites known to have significant EMX1.3 off target cutting. As illustrated, the "s14p0_ExtCompChimericTru" means:

s14=14 nucleotide seed sequence (i.e. 14 exposed nucleotides);
p0=total length of 18 nucleotides, so that ratio is 14/18=0.77;
Chimeric=has a GAAA loop so that this is one contiguous construct;
The s14p0_ExtCompChimericControl is a typical EMX1.3 20 bp guide.

The s14p0_ExtCompChimericTruControl is a typical EMX1.3 18 bp truGuide.

GFP is Green Fluorescent Protein.

The current invention concerns a partially double stranded nucleotide sequence either comprising consisting essentially of, or consisting of a guide sequence. Preferably the guide sequence is 10 to 30 nucleotides long. More preferably the guide sequence is 10 to 30 nucleotides long and operably linked to a tracr mate sequence. Most preferably the guide sequence is 10 to 30 nucleotides long and has attached to its 3' end a tracr mate sequence. As explained in more detail below, a protector sequence may be designed to optionally have desired complementarity to either a portion of three or more contiguous base pairs of the protector sequence itself (i.e., the protector comprises regions of self-complementarity), the guide sequence or both. Advantageously there are three or four to thirty or more, e.g., about 10 or more, contiguous base pairs having complementarity to the protector sequence, the guide sequence or both. It is advantageous that the protected portion does not impede thermodynamics of the CRISPR-Cas9 system interacting with its target. By providing such an extension including a partially double stranded guide sequence, the guide sequence is considered protected (i.e. pgRNA) and results in improved specific binding of the CRISPR-Cas9 complex, while maintaining specific activity.

Such a technical effect is surprising and unexpected. For example, in general, even small changes to nucleotide sequences, and in particular to RNA sequences, are known to entirely change their binding characteristics and prevent effective use. An illustrative example is from microRNA targeting (e.g., Fougerolles et al. Nature Reviews Vol 6, pp. 443-453; Schirle et al. Science, Vol 346, 6209; pp. 608-613; Patel, Vol 346, 6209; pp. 542-543). In microRNA targeting, particular spatial and structural conditions are provided for in a RISC complex in which the miRNA and targeted mRNA can bind (e.g., "guide-target groove"). Modifications, and in particular the addition of a protector strand on the miRNA, would, expectedly, result in a non-functional miRNA. In the same manner, in consideration of the crystal structure of Cas9/sgRNA/target DNA (e.g., Nishimasu et al. Cell 156, pp. 935-949), it would be expected that the addition of a protector would also result in a nonfunctional guide RNA.

For matters of explanation, a guide sequence may be considered to comprise, consist essentially of or consist of a protected guide sequence and an exposed sequence. The protected length (PL) is the length of the protector that covers the guide sequence and protects it. The exposed length (EpL) is a series of unprotected bases, which are available for the target DNA to bind. For example, given a 20 nucleotide targeting sequence, the exposed sequence may be 1 to 19 nucleotides in length and is complementary to the target. In an embodiment, the exposed sequence which corresponds to the EpL is 14 to 18 nucleotides in length. In further preferred embodiments the EpL can be 14 nucleotides, 16 nucleotides, or 18 nucleotides in length. The EpL or the exposed sequence may be at least 75% complementary to the target sequence, in preferred cases at least 90% complementary, and most preferably 100% complementary to the target sequence. The exposed sequence may be 100% complementary in the first 50/o portion of the region most 3' with 50% complementarity in the second 50% portion of the region most 5' (i.e., distal). For example, if the exposed portion is 12 nucleotides in length, the 6 nucleotides of the exposed portion most 3' (with respect to the pgRNA) are 100% complementary to the target and the 6 nucleotides most 5' are 50% complementary to the target (i.e. 3 of 6 nucleotides are complementary to the target).

In an embodiment the protected guide sequence is advantageously directly attached to the exposed sequence at the 5' end of the exposed sequence. The protected guide sequence may be 1 to 29 nucleotides in length and is complementary to at least some of the target. The protected guide sequence is the portion of the guide sequence which serves as a template to which a protecting sequence may bind. As a result the protected guide may be at least partially double stranded, as shown in FIG. 1, when bound to a protecting sequence, i.e., the "Protector Strand" (FIG. 1 top), or with the target sequence when the Protector Strand (FIG. 1 bottom) is displaced. The protected guide sequence may be 100% complementary to the protecting sequence at least at the two nucleotides most 5' and 3', and is further at least 90% complementary with the protecting sequence. Preferably the protected sequence is 100% complementary to the protecting sequence. The protecting sequence may be an individual sequence specifically the length of the protected sequence. Preferably, the protecting sequence is comprised in a longer sequence. The protected guide sequence may be at least 75% complementary to the target sequence, in preferred cases at least 90% complementary, and most preferably 100% complementary to the target sequence. The protected guide sequence may be 100% complementary in the first 50% portion of the region most 3' with 50% complementarity in the second 50% portion of the region most 5'. For example, if the protected guide sequence is 8 nucleotides in length, the 4 nucleotides most 3' are 100% complementary to the target and the 4 nucleotides most 5' are 50% complementary to the target (i.e. 2 of 4 nucleotides are complementary to the target). For matters of completeness, the protecting sequence cannot be considered the target sequence.

An extension sequence which corresponds to the extended length (ExL) may optionally be attached directly to the guide sequence at the 5' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence.

An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence.

In one aspect, the partially double stranded nucleotide sequence comprising a guide sequence of the invention may be generated using a vector system as described herein. For example, one or more vectors comprising at least one regulatory element operably linked to a nucleotide sequence encoding a CRISPR-Cas9 system as described herein may be used to generate the partially double stranded nucleotide sequence comprising a guide sequence of the invention. The nucleotide sequence encoding the partially double stranded nucleotide sequence comprising a guide sequence of the invention may be introduced into such a vector system. The guide sequence as described with a 1) exposed sequence and 2) a protected sequence is generated as described herein for a guide sequence. If an extension sequence is desired, this may be introduced into the encoding sequence, as may be an extension sequence followed by a protecting sequence. The protecting sequence may be generated from the same or on a different vector.

By designing a protecting sequence with the desired complementarity to the guide sequence, any guide sequence may be protected in the form of a partially double stranded guide sequence. Thus the invention provides both 1) partially double stranded nucleotide sequence comprising a guide sequence, and 2) a partially double stranded nucleotide sequence comprising, consisting essentially of, or consisting of a guide sequence. Such may be generated using in vitro methods. It may also be generated using synthetic means. The partially double stranded nucleotide sequence may be DNA, a chimeric DNA/RNA (i.e. the guide sequence is RNA and the protecting sequence is DNA), a chimeric RNA/DNA (i.e. the guide sequence is DNA and the protecting sequence is RNA), or RNA. Preferably the partially double stranded nucleotide sequence is RNA.

One aspect is a partially double stranded nucleotide sequence comprising a guide sequence which is 100% complementary to the target wherein the guide sequence is 10 to 30 nucleotides in length and comprises, consists essentially of, or consists of an exposed sequence in length in nucleotides (corresponding in length to the EpL) of 1-19 and a double stranded protected guide sequence in length in nucleotides (also referred to as "dsPG" which also corresponds to the protector length (PL) of 1-29.

Exemplary, partially double stranded nucleotide sequences are partially double stranded nucleotide sequences comprising a guide sequence which is 100% complementary to the target wherein the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 16; or an S of 4 and a dsPG of 20; or an S of 4 and a dsPG of 24; or an S of 4 and a dsPG of 28; or an S of 8 and a dsPG of 12; or an S of 8 and a dsPG of 16; or an S of 8 and a dsPG of 20; or an S of 8 and a dsPG of 24; or an S of 8 and a dsPG of 12; or an S of 12 and a dsPG of 12; or an S of 12 and a dsPG of 16; or an S of 12 and a dsPG of 20; or an S of 14 and a dsPG of 6; or an S of 14 and a dsPG of 10; or an S of 14 and a dsPG of 14; or an S of 14 and a dsPG of 18; or an S of 16 and a dsPG of 4; or an S of 16 and a dsPG of 8; or an S of 16 and a dsPG of 12; or an S of 16 and a dsPG of 16; or an S of 18 and a dsPG of 2; or an S of 18 and a dsPG of 6; or an S of 18 and a dsPG of 10; or an S of 18 and a dsPG of 14. One aspect is a partially double stranded nucleotide sequence comprising a guide sequence which is at least 90% complementary to the target wherein the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29.

Exemplary, partially double stranded nucleotide sequences are partially double stranded nucleotide sequences comprising a guide sequence which is at least 90% complementary to the target wherein the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 16; or an S of 4 and a dsPG of 20; or an S of 4 and a dsPG of 24; or an S of 4 and a dsPG of 28; or an S of 8 and a dsPG of 12; or an S of 8 and a dsPG of 16; or an S of 8 and a dsPG of 20; or an S of 8 and a dsPG of 24; or an S of 8 and a dsPG of 12; or an S of 12 and a dsPG of 12; or an S of 12 and a dsPG of 16; or an S of 12 and a dsPG of 20; or an S of 14 and a dsPG of 6; or an S of 14 and a dsPG of 10; or an S of 14 and a dsPG of 14; or an S of 14 and a dsPG of 18; or an S of 16 and a dsPG of 4; or an S of 16 and a dsPG of 8; or an S of 16 and a dsPG of 12; or an S of 16 and a dsPG of 16; or an S of 18 and a dsPG of 2; or an S of 18 and a dsPG of 6; or an S of 18 and a dsPG of 10; or an S of 18 and a dsPG of 14.

One aspect is a partially double stranded nucleotide sequence comprising a guide sequence which is 100% complementary to the target wherein the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29 and directly attached to the 5' end of the guide sequence as an extension sequence in length in nucleotides (also referred to as E and corresponds to the extended length (ExL)) of 2 to 12.

Exemplary, partially double stranded nucleotide sequences are partially double stranded nucleotide sequences comprising a guide sequence which is 100% complementary to the target wherein the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 20 and directly attached to the 5' end of the guide sequence is an extension sequence in length in nucleotides (also referred to as E and corresponds to the extended length (ExL)) of 4; or an S of 4, a dsPG of 24 and an E of 8; or an S of 4, a dsPG of 28 and an E of 12; or an S of 8, a dsPG of 16 and an E of 4, or an S of 8, a dsPG of 20 and an E of 8; or an S of 8, a dsPG of 24 and an E of 12; or an S of 12, a dsPG of 12 and an E of 4; or an S of 12, a dsPG of 16 and an E of 8; or an S of 12, a dsPG of 20 and an E of 12; or an S of 14, a dsPG of 10 and an E of 4; or an S of 14, a dsPG of 14 and an E of 8; or an S of 14, a dsPG of 18 and an E of 12; or an S of 16, a dsPG of 8 and an E of 4; or an S of 16, a dsPG of 12 and an E of 8; or an S of 16, a dsPG of 16 and an E of 12; or an S of 18, a dsPG of 6 and an E of 4; or an S of 18, a dsPG of 10 and an E of 8; or an S of 18, a dsPG of 14 and an E of 12.

One aspect is a partially double stranded nucleotide sequence comprising a guide sequence which is at least 90% complementary to the target wherein the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29 and directly attached to the 5' end of the guide sequence is an extension sequence in length in nucleotides (also referred to as E and corresponds to the extended length (ExL)) of 2 to 12.

Exemplary, partially double stranded nucleotide sequences are partially double stranded nucleotide sequences comprising a guide sequence which is at least 90% complementary to the target wherein the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 20 and directly attached to the 5' end of the guide sequence is an extension sequence in length in nucleotides (also referred to as E and corresponds to the extended length (ExL)) of 4; or an S of 4, a dsPG of 24 and an E of 8; or an S of 4, a dsPG of 28 and an E of 12; or an S of 8, a dsPG of 16 and an E of 4; or an S of 8, a dsPG of 20 and an E of 8; or an S of 8, a dsPG of 24 and an E of 12; or an S of 12, a dsPG of 12 and an E of 4; or an S of 12, a dsPG of 16 and an E of 8; or an S of 12, a dsPG of 20 and an E of 12; or an S of 14, a dsPG of 10 and an E of 4; or an S of 14, a dsPG of 14 and an E of 8; or an S of 14, a dsPG of 18 and an E of 12; or an S of 16, a dsPG of 8 and an E of 4; or an S of 16, a dsPG of 12 and an E of 8; or an S of 16, a dsPG of 16 and an E of 12: or an S of 18, a dsPG of 6 and an E of 4; or an S of 18, a dsPG of 10 and an E of 8; or an S of 18, a dsPG of 14 and an E of 12.

One aspect is a partially double stranded nucleotide sequence comprising a guide sequence which is 100% complementary to the target wherein the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29 and directly attached to the 5' end of the guide sequence is an extension sequence which is further directly attached to the 3' end of a protecting sequence and has a length in nucleotides (also referred to as E and corresponds to the extended length (ExL)) of 2 to 12.

Exemplary, partially double stranded nucleotide sequences are partially double stranded nucleotide sequences comprising a guide sequence which is 100% complementary to the target wherein the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 20 and directly attached to the 5' end of the guide sequence is an extension sequence which is further directly attached to the 3' end of a protecting sequence and has a length in nucleotides (also referred to as E' and corresponds to the extended length (ExL)) of 4; or an S of 4, a dsPG of 24 and an E' of 8; or an S of 4, a dsPG of 28 and an E' of 12; or an S of 8, a dsPG of 16 and an E' of 4; or an S of 8, a dsPG of 20 and an E' of 8; or an S of 8, a dsPG of 24 and an E' of 12; or an S of 12, a dsPG of 12 and an E' of 4; or an S of 12, a dsPG of 16 and an E' of 8; or an S of 12, a dsPG of 20 and an E' of 12; or an S of 14, a dsPG of 10 and an E' of 4; or an S of 14, a dsPG of 14 and an E' of 8; or an S of 14, a dsPG of 18 and an E' of 12; or an S of 16, a dsPG of 8 and an E' of 4; or an S of 16, a dsPG of 12 and an E' of 8; or an S of 16, a dsPG of 16 and an E' of 12; or an S of 18, a dsPG of 6 and an E' of 4; or an S of 18, a dsPG of 10 and an E' of 8; or an S of 18, a dsPG of 14 and an E' of 12.

One aspect is a partially double stranded nucleotide sequence comprising a guide sequence which is at least 90% complementary to the target wherein the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29 and directly attached to the 5' end of the guide sequence is an extension sequence which is further directly attached to the 3' end of a protecting sequence and has a length in nucleotides (also referred to as E' and corresponds to the extended length (ExL)) of 2 to 12.

Exemplary, partially double stranded nucleotide sequences are partially double stranded nucleotide sequences comprising a guide sequence which is at least 90% complementary to the target wherein the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 20 and directly attached to the 5' end of the guide sequence is an extension sequence which is further directly attached to the 3' end of a protecting sequence and has a length in nucleotides (also referred to as E' and corresponds to the extended length (ExL)) of 4; or an S of 4, a dsPG of 24 and an E' of 8: or an S of 4, a dsPG of 28 and an E' of 12; or an S of 8, a dsPG of 16 and an E' of 4; or an S of 8, a dsPG of 20 and an E' of 8; or an S of 8, a dsPG of 24 and an E' of 12; or an S of 12, a dsPG of 12 and an E' of 4; or an S of 12, a dsPG of 16 and an E' of 8; or an S of 12, a dsPG of 20 and an E' of 12; or an S of 14, a dsPG of 10 and an E' of 4; or an S of 14, a dsPG of 14 and an E' of 8; or an S of 14, a dsPG of 18 and an E' of 12; or an S of 16, a dsPG of 8 and an E' of 4; or an S of 16, a dsPG of 12 and an E' of 8; or an S of 16, a dsPG of 16 and an E' of 12; or an S of 18, a dsPG of 6 and an E' of 4; or an S of 18, a dsPG of 10 and an E' of 8; or an S of 18, a dsPG of 14 and an E' of 12.

One aspect is a partially double stranded nucleotide sequence comprising a guide sequence which is 100% complementary to the target wherein the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0.

Exemplary, partially double stranded nucleotide sequences are partially double stranded nucleotide sequences comprising a guide sequence which is 100% complementary to the target wherein the guide sequence comprises, consists essentially of, or consists of a ratio of the double stranded protected guide sequence length (dsPG which also corresponds to the protector length (PL)) to the seed sequence length of at least 0.1; or of at least 0.2; or of at least 0.3; or of at least 0.4; or of at least 0.5; or of at least 0.6; or of at least 0.7; or of at least 0.8; or of at least 0.9; or of at least 1.0; or of at least 1.1; or of at least 1.2; or of at least 1.3; or of at least 1.5; or of at least 1.6; or of at least 1.7; or of at least 2.0; or of at least 2.5; or of at least 3.0; or of at least 4.0; or of at least 5.0; or of at least 6.0; or of at least 7.0.

One aspect is a partially double stranded nucleotide sequence comprising a guide sequence which is at least 90% complementary to the target wherein the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0.

Exemplary, partially double stranded nucleotide sequences are partially double stranded nucleotide sequences comprising a guide sequence which is at least 90% complementary to the target wherein the guide sequence comprises, consists essentially of, or consists of a ratio of the double stranded protected guide sequence length (dsPG which also corresponds to the protector length (PL)) to the seed sequence length (which corresponds to the exposed length (EpL) of at least 0.1; or of at least 0.2; or of at least 0.3; or of at least 0.4; or of at least 0.5; or of at least 0.6; or of at least 0.7; or of at least 0.8; or of at least 0.9; or of at least 1.0; or of at least 1.1; or of at least 1.2; or of at least 1.3; or of at least 1.5; or of at least 1.6; or of at least 1.7; or of at least 2.0; or of at least 2.5; or of at least 3.0; or of at least 4.0; or of at least 5.0; or of at least 6.0; or of at least 7.0.

One aspect is a partially double stranded nucleotide sequence comprising a guide sequence which is 100% complementary to the target wherein the guide sequence is 10 to 30 nucleotides in length and comprises, consists essentially of, or consists of a ratio of the double stranded protected guide sequence length (dsPG) to the seed sequence length of 0.1 to 7.0 and directly attached to the 5' end of the guide sequence is an extension sequence in length in nucleotides (also referred to as E or EL and corresponds to the extended length (ExL)) of 2 to 12.

Exemplary, partially double stranded nucleotide sequences are partially double stranded nucleotide sequences comprising a guide sequence which is 100% complementary to the target wherein the guide sequence comprises, consists essentially of, or consists of a ratio of the double stranded protected guide sequence length (dsPG) to the seed sequence length of at least 0.3 and directly attached to the 5' end of the guide sequence is an extension sequence in length in nucleotides (also referred to as E or EL and corresponds to the extended length (ExL)) of 4; or of at least 0.5 with an E of 4; or of at least 0.5 with an E of 8; or of at least 0.7 with an E of 4; or of at least 0.7 with an E of 12; or of at least 0.8 with an E of 12; or of at least 1.0 with an E of 4; or of at least 1.0 with an E of 8; or of at least 1.0 with an E of 12; or of at least 1.2 with an E of 12; or of at least 1.3 with an E of 8; or of at least 1.3 with an E of 12; or of at least 1.4 with an E of 8; or of at least 1.6 with an E of 12; or of at least 1.7 with an E of 12; or of at least 2.0 with an E of 4; or of at least 2.5 with an E of 8; or of at least 3.0 with an E of 12; or of at least 5.0 with an E of 4; or of at least 6.0 with an E of 8; or of at least 7.0 with an E of 12.

One aspect is a partially double stranded nucleotide sequence comprising a guide sequence which is at least 90% complementary to the target wherein the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0 and directly attached to the 5' end of the guide sequence is an extension sequence in length in nucleotides (also referred to as E and corresponds to the extended length (ExL)) of 2 to 12.

Exemplary, partially double stranded nucleotide sequences are partially double stranded nucleotide sequences comprising a guide sequence which is at least 90% complementary to the target wherein the guide sequence comprises, consists essentially of, or consists of a ratio of the double stranded protected guide sequence length (dsPG which also corresponds to the protector length (PL)) to the seed sequence length of at least 0.3 and directly attached to the 5' end of the guide sequence is an extension sequence in length in nucleotides (also referred to as E) of 4; or of at least 0.5 with an E of 4; or of at least 0.5 with an E of 8; or of at least 0.7 with an E of 4; or of at least 0.7 with an E of 12; or of at least 0.8 with an E of 12; or of at least 1.0 with an E of 4; or of at least 1.0 with an E of 8; or of at least 1.0 with an E of 12; or of at least 1.2 with an E of 12; or of at least 1.3 with an E of 8; or of at least 1.3 with an E of 12; or of at least 1.4 with an E of 8; or of at least 1.6 with an E of 12; or of at least 1.7 with an E of 12; or of at least 2.0 with an E of 4; or of at least 2.5 with an E of 8; or of at least 3.0 with an E of 12; or of at least 5.0 with an E of 4; or of at least 6.0 with an E of 8; or of at least 7.0 with an E of 12.

One aspect is a partially double stranded nucleotide sequence comprising a guide sequence which is 100% complementary to the target wherein the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0 and directly attached to the 5' end of the guide sequence is an extension sequence which is further directly attached to the 3' end of a protecting sequence and has a length in nucleotides (also referred to as E' or EL and corresponds to the extended length (ExL)) of 2 to 12.

Exemplary, partially double stranded nucleotide sequences are partially double stranded nucleotide sequences comprising a guide sequence which is 100% complementary to the target wherein the guide sequence comprises, consists essentially of, or consists of a ratio of the double stranded protected guide sequence length (dsPG which also corresponds to the protector length (PL)) to the seed sequence length of at least 0.3 and directly attached to the 5' end of the guide sequence is an extension sequence which is further directly attached to the 3' end of a protecting sequence and has a length in nucleotides (also referred to as E' and corresponds to the extended length (ExL)) of 4; or of at least 0.5 with an E' of 4; or of at least 0.5 with an E' of 8; or of at least 0.7 with an E' of 4; or of at least 0.7 with an E' of 12; or of at least 0.8 with an E' of 12; or of at least 1.0 with an E' of 4; or of at least 1.0 with an E' of 8; or of at least 1.0 with an E' of 12; or of at least 1.2 with an E' of 12; or of at least 1.3 with an E' of 8; or of at least 1.3 with an E' of 12; or of at least 1.4 with an E' of 8; or of at least 1.6 with an E' of 12; or of at least 1.7 with an E' of 12; or of at least 2.0 with an E' of 4; or of at least 2.5 with an E' of 8; or of at least 3.0 with an E' of 12; or of at least 5.0 with an E' of 4; or of at least 6.0 with an E' of 8; or of at least 7.0 with an E' of 12.

One aspect is a partially double stranded nucleotide sequence comprising a guide sequence which is at least 90% complementary to the target wherein the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0 and directly attached to the 5' end of the guide sequence is an extension sequence which is further directly attached to the 3' end of a protecting sequence and has a length in nucleotides (also referred to as E' or EL and corresponds to the extended length (ExL)) of 2 to 12.

Exemplary, partially double stranded nucleotide sequences are partially double stranded nucleotide sequences comprising a guide sequence which is at least 90% complementary to the target wherein the guide sequence comprises, consists essentially of, or consists of a ratio of the double stranded protected guide sequence length (dsPG which also corresponds to the protector length (PL)) to the seed sequence length of at least 0.3 and directly attached to the 5' end of the guide sequence is an extension sequence which is further directly attached to the 3' end of a protecting sequence and has a length in nucleotides (also referred to as E' and corresponds to the extended length (ExL)) of 4; or of at least 0.5 with an E' of 4; or of at least 0.5 with an E' of 8; or of at least 0.7 with an E' of 4; or of at least 0.7 with an E' of 12; or of at least 0.8 with an E' of 12; or of at least 1.0 with an E' of 4; or of at least 1.0 with an E' of 8; or of at least 1.0 with an E' of 12; or of at least 1.2 with an E' of 12; or of at least 1.3 with an E' of 8; or of at least 1.3 with an E' of 12; or of at least 1.4 with an E' of 8; or of at least 1.6 with an E' of 12; or of at least 1.7 with an E' of 12; or of at least 2.0 with an E' of 4: or of at least 2.5 with an E' of 8; or of at least 3.0 with an E' of 12; or of at least 5.0 with an E' of 4; or of at least 6.0 with an E' of 8; or of at least 7.0 with an E' of 12.

One aspect is a partially double stranded nucleotide sequence comprising a guide sequence which is 100% complementary to the target wherein the guide sequence is linked to a tracr mate sequence at the 3' end of the seed sequence and the guide sequence is 10 to 30 nucleotides in length and comprises, consists essentially of, or consists of a seed sequence in length in nucleotides (also referred to as S and corresponds to the exposed length (EpL)) of 1-19 and a double stranded protected guide sequence in length in nucleotides (also referred to as dsPG which also corresponds to the protector length (PL)) of 1-29.

Exemplary, partially double stranded nucleotide sequences are partially double stranded nucleotide sequences comprising a guide sequence which is 100% complementary to the target wherein the guide sequence is linked to a tracr mate sequence at the 3' end of the seed sequence and the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 16; or an S of 4 and a dsPG of 20; or an S of 4 and a dsPG of 24; or an S of 4 and a dsPG of 28; or an S of 8 and a dsPG of 12; or an S of 8 and a dsPG of 16; or an S of 8 and a dsPG of 20; or an S of 8 and a dsPG of 24; or an S of 8 and a dsPG of 12; or an S of 12 and a dsPG of 12; or an S of 12 and a dsPG of 16; or an S of 12 and a dsPG of 20; or an S of 14 and a dsPG of 6; or an S of 14 and a dsPG of 10; or an S of 14 and a dsPG of 14; or an S of 14 and a dsPG of 18; or an S of 16 and a dsPG of 4; or an S of 16 and a dsPG of 8; or an S of 16 and a dsPG of 12; or an S of 16 and a dsPG of 16; or an S of 18 and a dsPG of 2; or an S of 18 and a dsPG of 6; or an S of 18 and a dsPG of 10; or an S of 18 and a dsPG of 14.

One aspect is a partially double stranded nucleotide sequence comprising a guide sequence which is at least 90% complementary to the target wherein the guide sequence is linked to a tracr mate sequence at the 3' end of the seed sequence and the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29.

Exemplary, partially double stranded nucleotide sequences are partially double stranded nucleotide sequences comprising a guide sequence which is at least 90% complementary to the target wherein the guide sequence is linked to a tracr mate sequence at the 3' end of the seed sequence and the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 16; or an S of 4 and a dsPG of 20; or an S of 4 and a dsPG of 24; or an S of 4 and a dsPG of 28; or an S of 8 and a dsPG of 12; or an S of 8 and a dsPG of 16; or an S of 8 and a dsPG of 20; or an S of 8 and a dsPG of 24; or an S of 8 and a dsPG of 12; or an S of 12 and a dsPG of 12; or an S of 12 and a dsPG of 16; or an S of 12 and a dsPG of 20; or an S of 14 and a dsPG of 6; or an S of 14 and a dsPG of 10; or an S of 14 and a dsPG of 14; or an S of 14 and a dsPG of 18; or an S of 16 and a dsPG of 4; or an S of 16 and a dsPG of 8; or an S of 16 and a dsPG of 12; or an S of 16 and a dsPG of 16; or an S of 18 and a dsPG of 2; or an S of 18 and a dsPG of 6; or an S of 18 and a dsPG of 10; or an S of 18 and a dsPG of 14.

One aspect is a partially double stranded nucleotide sequence comprising a guide sequence which is 100% complementary to the target wherein the guide sequence is linked to a tracr mate sequence at the 3' end of the seed sequence and the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29 and directly attached to the 5' end of the guide sequence is an extension sequence in length in nucleotides (also referred to as E) of 2 to 12.

Exemplary, partially double stranded nucleotide sequences are partially double stranded nucleotide sequences comprising a guide sequence which is 100% complementary to the target wherein the guide sequence is linked to a tracr mate sequence at the 3' end of the seed sequence and the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 20 and directly attached to the 5' end of the guide sequence is an extension sequence in length in nucleotides (also referred to as E or EL and corresponds to the extended length (ExL)) of 4; or an S of 4, a dsPG of 24 and an E of 8; or an S of 4, a dsPG of 28 and an E of 12; or an S of 8, a dsPG of 16 and an E of 4; or an S of 8, a dsPG of 20 and an E of 8; or an S of 8, a dsPG of 24 and an E of 12; or an S of 12, a dsPG of 12 and an E of 4; or an S of 12, a dsPG of 16 and an E of 8; or an S of 12, a dsPG of 20 and an E of 12; or an S of 14, a dsPG of 10 and an E of 4; or an S of 14, a dsPG of 14 and an E of 8; or an S of 14, a dsPG of 18 and an E of 12; or an S of 16, a dsPG of 8 and an E of 4; or an S of 16, a dsPG of 12 and an E of 8; or an S of 16, a dsPG of 16 and an E of 12; or an S of 18, a dsPG of 6 and an E of 4; or an S of 18, a dsPG of 10 and an E of 8; or an S of 18, a dsPG of 14 and an E of 12.

One aspect is a partially double stranded nucleotide sequence comprising a guide sequence which is at least 90% complementary to the target wherein the guide sequence is linked to a tracr mate sequence at the 3' end of the seed sequence and the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29 and directly attached to the 5' end of the guide sequence is an extension sequence in length in nucleotides (also referred to as E and corresponds to the extended length (ExL)) of 2 to 12.

Exemplary, partially double stranded nucleotide sequences are partially double stranded nucleotide sequences comprising a guide sequence which is at least 90% complementary to the target wherein the guide sequence is linked to a tracr mate sequence at the 3' end of the seed sequence and the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 20 and directly attached to the 5' end of the guide sequence is an extension sequence in length in nucleotides (also referred to as E or EL and corresponds to the extended length (ExL)) of 4; or an S of 4, a dsPG of 24 and an E of 8; or an S of 4, a dsPG of 28 and an E of 12; or an S of 8, a dsPG of 16 and an E of 4; or an S of 8, a dsPG of 20 and an E of 8; or an S of 8, a dsPG of 24 and an E of 12; or an S of 12, a dsPG of 12 and an E of 4; or an S of 12, a dsPG of 16 and an E of 8; or an S of 12, a dsPG of 20 and an E of 12; or an S of 14, a dsPG of 10 and an E of 4; or an S of 14, a dsPG of 14 and an E of 8; or an S of 14, a dsPG of 18 and an E of 12; or an S of 16, a dsPG of 8 and an E of 4; or an S of 16, a dsPG of 12 and an E of 8; or an S of 16, a dsPG of 16 and an E of 12; or an S of 18, a dsPG of 6 and an E of 4; or an S of 18, a dsPG of 10 and an E of 8; or an S of 18, a dsPG of 14 and an E of 12.

One aspect is a partially double stranded nucleotide sequence comprising a guide sequence which is 100% complementary to the target wherein the guide sequence is linked to a tracr mate sequence at the 3' end of the seed sequence and the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29 and directly attached to the 5' end of the guide sequence is an extension sequence which is further directly attached to the 3' end of a protecting sequence and has a length in nucleotides (also referred to as E' or EL and corresponds to the extended length (ExL)) of 2 to 12.

Exemplary, partially double stranded nucleotide sequences are partially double stranded nucleotide sequences comprising a guide sequence which is 100% complementary to the target wherein the guide sequence is linked to a tracr mate sequence at the 3' end of the seed sequence and the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 20 and directly attached to the 5' end of the guide sequence is an extension sequence which is further directly attached to the 3' end of a protecting sequence and has a length in nucleotides (also referred to as E' and corresponds to the extended length (ExL)) of 4; or an S of 4, a dsPG of 24 and an E' of 8; or an S of 4, a dsPG of 28 and an E' of 12; or an S of 8, a dsPG of 16 and an E' of 4; or an S of 8, a dsPG of 20 and an E' of 8; or an S of 8, a dsPG of 24 and an E' of 12; or an S of 12, a dsPG of 12 and an E' of 4; or an S of 12, a dsPG of 16 and an E' of 8; or an S of 12, a dsPG of 20 and an E' of 12; or an S of 14, a dsPG of 10 and an E' of 4; or an S of 14, a dsPG of 14 and an E' of 8; or an S of 14, a dsPG of 18 and an E' of 12; or an S of 16, a dsPG of 8 and an E' of 4; or an S of 16, a dsPG of 12 and an E' of 8; or an S of 16, a dsPG of 16 and an E' of 12; or an S of 18, a dsPG of 6 and an E' of 4; or an S of 18, a dsPG of 10 and an E' of 8; or an S of 18, a dsPG of 14 and an E' of 12.

One aspect is a partially double stranded nucleotide sequence comprising a guide sequence which is at least 90% complementary to the target wherein the guide sequence is linked to a tracr mate sequence at the 3' end of the seed sequence and the guide sequence is 10 to 30 nucleotides in length and comprises, consists essentially of, or consists of a seed sequence in length in nucleotides (also referred to as S and corresponds to the exposed length (EpL)) of 1 to 19 and a double stranded protected guide sequence in length in nucleotides (also referred to as dsPG which also corresponds to the protector length (PL)) of 1 to 29 and directly attached to the 5' end of the guide sequence is an extension sequence which is further directly attached to the 3' end of a protecting sequence and has a length in nucleotides (also referred to as E' and corresponds to the extended length (ExL)) of 2 to 12.

Exemplary, partially double stranded nucleotide sequences are partially double stranded nucleotide sequences comprising a guide sequence which is at least 90% complementary to the target wherein the guide sequence is linked to a tracr mate sequence at the 3' end of the seed sequence and the guide sequence comprises, consists essentially of, or consists of a seed sequence in length in nucleotides (also referred to as S and corresponds to the exposed length (EpL)) of 4 and a double stranded protected guide sequence in length in nucleotides (also referred to as dsPG which also corresponds to the protector length (PL)) of 20 and directly attached to the 5' end of the guide sequence is an extension sequence which is further directly attached to the 3' end of a protecting sequence and has a length in nucleotides (also referred to as E' and corresponds to the extended length (ExL)) of 4; or an S of 4, a dsPG of 24 and an E' of 8; or an S of 4, a dsPG of 28 and an E' of 12; or an S of 8, a dsPG of 16 and an E' of 4; or an S of 8, a dsPG of 20 and an E' of 8; or an S of 8, a dsPG of 24 and an E' of 12; or an S of 12, a dsPG of 12 and an E' of 4; or an S of 12, a dsPG of 16 and an E' of 8; or an S of 12, a dsPG of 20 and an E' of 12; or an S of 14, a dsPG of 10 and an E' of 4; or an S of 14, a dsPG of 14 and an E' of 8; or an S of 14, a dsPG of 18 and an E' of 12; or an S of 16, a dsPG of 8 and an E' of 4; or an S of 16, a dsPG of 12 and an E' of 8; or an S of 16, a dsPG of 16 and an E' of 12; or an S of 18, a dsPG of 6 and an E' of 4; or an S of 18, a dsPG of 10 and an E' of 8; or an S of 18, a dsPG of 14 and an E' of 12.

One aspect is a partially double stranded nucleotide sequence comprising a guide sequence which is 100% complementary to the target wherein the guide sequence is linked to a tracr mate sequence at the 3' end of the seed sequence and the guide sequence is 10 to 30 nucleotides in length and comprises, consists essentially of, or consists of a ratio of the double stranded protected guide sequence length (dsPG which also corresponds to the protector length (PL)) to the seed sequence length (corresponds to the exposed length (EpL) of 0.1 to 7.0.

Exemplary, partially double stranded nucleotide sequences are partially double stranded nucleotide sequences comprising a guide sequence which is 100% complementary to the target wherein the guide sequence is linked to a tracr mate sequence at the 3' end of the seed sequence and the guide sequence comprises, consists essentially of, or consists of a ratio of the double stranded protected guide sequence length (dsPG which also corresponds to the protector length (PL)) to the seed sequence length of at least 0.1; or of at least 0.2; or of at least 0.3; or of at least 0.4; or of at least 0.5; or of at least 0.6; or of at least 0.7; or of at least 0.8; or of at least 0.9; or of at least 1.0; or of at least 1.1; or of at least 1.2; or of at least 1.3; or of at least 1.5; or of at least 1.6; or of at least 1.7; or of at least 2.0; or of at least 2.5; or of at least 3.0; or of at least 4.0; or of at least 5.0; or of at least 6.0; or of at least 7.0.

One aspect is a partially double stranded nucleotide sequence comprising a guide sequence which is at least 90% complementary to the target wherein the guide sequence is linked to a tracr mate sequence at the 3' end of the seed sequence and the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0.

Exemplary, partially double stranded nucleotide sequences are partially double stranded nucleotide sequences comprising a guide sequence which is at least 90% complementary to the target wherein the guide sequence is linked to a tracr mate sequence at the 3' end of the seed sequence and the guide sequence comprises, consists essentially of, or consists of a ratio of the double stranded protected guide sequence length (dsPG which also corresponds to the protector length (PL)) to the seed sequence length of at least 0.1; or of at least 0.2; or of at least 0.3; or of at least 0.4; or of at least 0.5; or of at least 0.6; or of at least 0.7; or of at least 0.8; or of at least 0.9; or of at least 1.0; or of at least 1.1; or of at least 1.2; or of at least 1.3; or of at least 1.5; or of at least 1.6; or of at least 1.7; or of at least 2.0; or of at least 2.5; or of at least 3.0; or of at least 4.0; or of at least 5.0; or of at least 6.0; or of at least 7.0.

One aspect is a partially double stranded nucleotide sequence comprising a guide sequence which is 100% complementary to the target wherein the guide sequence is linked to a tracr mate sequence at the 3' end of the seed sequence and the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0 and directly attached to the 5' end of the guide sequence is an extension sequence in length in nucleotides (also referred to as E and corresponds to the extended length (ExL)) of 2 to 12.

Exemplary, partially double stranded nucleotide sequences are partially double stranded nucleotide sequences comprising a guide sequence which is 100% complementary to the target wherein the guide sequence is linked to a tracr mate sequence at the 3' end of the seed sequence and the guide sequence comprises, consists essentially of, or consists of a ratio of the double stranded protected guide sequence length (dsPG which also corresponds to the protector length (PL)) to the seed sequence length of at least 0.3 and directly attached to the 5' end of the guide sequence is an extension sequence in length in nucleotides (also referred to as E and corresponds to the extended length (ExL)) of 4; or of at least 0.5 with an E of 4; or of at least 0.5 with an E of 8; or of at least 0.7 with an E of 4; or of at least 0.7 with an E of 12; or of at least 0.8 with an E of 12; or of at least 1.0 with an E of 4; or of at least 1.0 with an E of 8; or of at least 1.0 with an E of 12; or of at least 1.2 with an E of 12; or of at least 1.3 with an E of 8; or of at least 1.3 with an E of 12; or of at least 1.4 with an E of 8; or of at least 1.6 with an E of 12; or of at least 1.7 with an E of 12; or of at least 2.0 with an E of 4; or of at least 2.5 with an E of 8; or of at least 3.0 with an E of 12; or of at least 5.0 with an E of 4; or of at least 6.0 with an E of 8; or of at least 7.0 with an E of 12.

One aspect is a partially double stranded nucleotide sequence comprising a guide sequence which is at least 90% complementary to the target wherein the guide sequence is linked to a tracr mate sequence at the 3' end of the seed sequence and the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0 and directly attached to the 5' end of the guide sequence is an extension sequence in length in nucleotides (also referred to as E and corresponds to the extended length (ExL)) of 2 to 12.

Exemplary, partially double stranded nucleotide sequences are partially double stranded nucleotide sequences comprising a guide sequence which is at least 90% complementary to the target wherein the guide sequence is linked to a tracr mate sequence at the 3' end of the seed sequence and the guide sequence comprises, consists essentially of, or consists of a ratio of the double stranded protected guide sequence length (dsPG which also corresponds to the protector length (PL)) to the seed sequence length of at least 0.3 and directly attached to the 5' end of the guide sequence is an extension sequence in length in nucleotides (also referred to as E and corresponds to the extended length (ExL)) of 4; or of at least 0.5 with an E of 4; or of at least 0.5 with an E of 8; or of at least 0.7 with an E of 4; or of at least 0.7 with an E of 12; or of at least 0.8 with an E of 12; or of at least 1.0 with an E of 4; or of at least 1.0 with an E of 8; or of at least 1.0 with an E of 12; or of at least 1.2 with an E of 12; or of at least 1.3 with an E of 8; or of at least 1.3 with an E of 12; or of at least 1.4 with an E of 8; or of at least 1.6 with an E of 12; or of at least 1.7 with an E of 12; or of at least 2.0 with an E of 4; or of at least 2.5 with an E of 8; or of at least 3.0 with an E of 12; or of at least 5.0 with an E of 4; or of at least 6.0 with an E of 8; or of at least 7.0 with an E of 12.

One aspect is a partially double stranded nucleotide sequence comprising a guide sequence which is 100% complementary to the target wherein the guide sequence is linked to a tracr mate sequence at the 3' end of the seed sequence and the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0 and directly attached to the 5' end of the guide sequence is an extension sequence which is further directly attached to the 3' end of a protecting sequence and has a length in nucleotides (also referred to as E' and corresponds to the extended length (ExL)) of 2 to 12.

Exemplary, partially double stranded nucleotide sequences are partially double stranded nucleotide sequences comprising a guide sequence which is 100% complementary to the target wherein the guide sequence is linked to a tracr mate sequence at the 3' end of the seed sequence and the guide sequence comprises, consists essentially of, or consists of a ratio of the double stranded protected guide sequence length (dsPG which also corresponds to the protector length (PL)) to the seed sequence length of at least 0.3 and directly attached to the 5' end of the guide sequence is an extension sequence which is further directly attached to the 3' end of a protecting sequence and has a length in nucleotides (also referred to as E' and corresponds to the extended length (ExL)) of 4; or of at least 0.5 with an E' of 4; or of at least 0.5 with an E' of 8; or of at least 0.7 with an E' of 4; or of at least 0.7 with an E' of 12; or of at least 0.8 with an E' of 12; or of at least 1.0 with an E' of 4; or of at least 1.0 with an E' of 8; or of at least 1.0 with an E' of 12; or of at least 1.2 with an E' of 12; or of at least 1.3 with an E' of 8; or of at least 1.3 with an E' of 12; or of at least 1.4 with an E' of 8; or of at least 1.6 with an E' of 12; or of at least 1.7 with an E' of 12; or of at least 2.0 with an E' of 4; or of at least 2.5 with an E' of 8; or of at least 3.0 with an E' of 12; or of at least 5.0 with an E' of 4; or of at least 6.0 with an E' of 8; or of at least 7.0 with an E' of 12.

One aspect is a partially double stranded nucleotide sequence comprising a guide sequence which is at least 90% complementary to the target wherein the guide sequence is linked to a tracr mate sequence at the 3' end of the seed sequence and the guide sequence is 10 to 30 nucleotides in length and comprises, consists essentially of, or consists of a ratio of the double stranded protected guide sequence length (dsPG which also corresponds to the protector length (PL)) to the seed sequence length of 0.1 to 7.0 and directly attached to the 5' end of the guide sequence is an extension sequence which is further directly attached to the 3' end of a protecting sequence and has a length in nucleotides (also referred to as E' and corresponds to the extended length (ExL)) of 2 to 12.

Exemplary, partially double stranded nucleotide sequences are partially double stranded nucleotide sequences comprising a guide sequence which is at least 90% complementary to the target wherein the guide sequence is linked to a tracr mate sequence at the 3' end of the seed sequence and the guide sequence comprises, consists essentially of, or consists of a ratio of the double stranded protected guide sequence length (dsPG which also corresponds to the protector length (PL)) to the seed sequence length of at least 0.3 and directly attached to the 5' end of the guide sequence is an extension sequence which is further directly attached to the 3' end of a protecting sequence and has a length in nucleotides (also referred to as E' and corresponds to the extended length (ExL)) of 4; or of at least 0.5 with an E' of 4; or of at least 0.5 with an E' of 8; or of at least 0.7 with an E' of 4; or of at least 0.7 with an E' of 12; or of at least 0.8 with an E' of 12; or of at least 1.0 with an E' of 4; or of at least 1.0 with an E' of 8; or of at least 1.0 with an E' of 12; or of at least 1.2 with an E' of 12; or of at least 1.3 with an E' of 8; or of at least 1.3 with an E' of 12; or of at least 1.4 with an E' of 8, or of at least 1.6 with an E' of 12; or of at least 1.7 with an E' of 12; or of at least 2.0 with an E' of 4; or of at least 2.5 with an E' of 8; or of at least 3.0 with an E' of 12; or of at least 5.0 with an E' of 4; or of at least 6.0 with an E' of 8; or of at least 7.0 with an E' of 12.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNgttttgtactctcaagatttaGAAAtaaatcttgcagaagctacaaagataa ggct-tcatgccgaaatcaacaccctgtcatttatggcagggtgttttcgttatt-taaTTTTTT (SEQ ID NO: 32); (2) NNNNNNNNNNNNNNNNNNNNgttttgtactctcaGAAAt-gcagaagctacaaagataaggcttcatgccg aaatcaacaccctgtcatttatg-gcagggtgttttcgttatttaaTTTTTT (SEQ ID NO: 33); (3) NNNNNNNNNNNNNNNNNNNNgttttgtactctcaGAAAtgca-gaagctacaaagataaggcttcatgccg aaatcaacaccctgtcatttatggca-gggtgtTTTTTT (SEQ ID NO: 34); (4) NNNNNNNNNNNNNNNNNNNNgttttagagctaGAAAtag-caagttaaaataaggctagtccgttatcaactt gaaaaagtggcaccgagtcggt-gcTTTTTT (SEQ ID NO: 35); (5) NNNNNNNNNNNNNNNNNNNNgttttagagcta-GAAATAGcaagttaaaataaggctagtccgttatcaac ttgaaaaagt-gTTTTTT (SEQ ID NO: 36); and (6) NNNNNNNNNNNNNNNNNNNNgttttagagctagAAATAG-caagttaaaataaggctagtccgttataTT TTTTTT (SEQ ID NO: 37). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 38) in the EMX1 gene of the human genome, deep sequencing can be used to assess the level of modification at the following two off-target loci, 1: 5'-GAGTC-CTAGCAGGAGAAGAA-3' (SEQ ID NO: 39) and 2: 5'-GAGTCTAAGCAGAAGAAGAA-3' (SEQ ID NO: 40). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

The term "nucleic acid-targeting system", wherein nucleic acid is DNA or RNA, and in some aspects may also refer to DNA-RNA hybrids or derivatives thereof, refers collectively to transcripts and other elements involved in the expression of or directing the activity of DNA or RNA-targeting CRISPR-associated ("Cas") genes, which may include sequences encoding a DNA or RNA-targeting Cas9 protein and a DNA or RNA-targeting guide RNA comprising a CRISPR RNA (crRNA) sequence and (in some but not all systems) a trans-activating CRISPR-Cas9 system RNA (tracrRNA) sequence, or other sequences and transcripts from a DNA or RNA-targeting CRISPR locus. In general, a RNA-targeting system is characterized by elements that promote the formation of a DNA or RNA-targeting complex at the site of a target DNA or RNA sequence. In the context of formation of a DNA or RNA-targeting complex, "target sequence" refers to a DNA or RNA sequence to which a DNA or RNA-targeting guide RNA is designed to have complementarity, where hybridization between a target sequence and a RNA-targeting guide RNA promotes the formation of a RNA-targeting complex. In some embodiments, a target sequence is located in the nucleus or cytoplasm of a cell.

In an aspect of the invention, novel DNA targeting systems also referred to as DNA-targeting CRISPR-Cas9 or the CRISPR-Cas9 DNA-targeting system of the present application are based on identified Type II Cas9 proteins which do not require the generation of customized proteins to target specific DNA sequences but rather a single effector protein or enzyme can be programmed by a RNA molecule to recognize a specific DNA target, in other words the enzyme can be recruited to a specific DNA target using said RNA molecule. Aspects of the invention particularly relate to DNA targeting RNA-guided Cas9 CRISPR systems.

In an aspect of the invention, novel RNA targeting systems also referred to as RNA- or RNA-targeting CRISPR-Cas9 or the CRISPR-Cas9 system RNA-targeting system of the present application are based on identified Type II Cas9 proteins which do not require the generation of customized proteins to target specific RNA sequences but rather a single enzyme can be programmed by a RNA molecule to recognize a specific RNA target, in other words the enzyme can be recruited to a specific RNA target using said RNA molecule.

The nucleic acids-targeting systems, the vector systems, the vectors and the compositions described herein may be used in various nucleic acids-targeting applications, altering or modifying synthesis of a gene product, such as a protein, nucleic acids cleavage, nucleic acids editing, nucleic acids splicing; trafficking of target nucleic acids, tracing of target nucleic acids, isolation of target nucleic acids, visualization of target nucleic acids, etc.

Aspects of the invention also encompass methods and uses of the compositions and systems described herein in genome engineering, e.g. for altering or manipulating the expression of one or more genes or the one or more gene products, in prokaryotic or eukaryotic cells, in vitro, in vivo or ex vivo.

The CRISPR system is derived advantageously from a type II CRISPR system. In some embodiments, one or more elements of a CRISPR system is derived from a particular organism comprising an endogenous CRISPR system, such as *Streptococcus pyogenes*. The CRISPR system is a type II CRISPR system and the Cas enzyme is Cas9, which catalyzes DNA cleavage. Other non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In an embodiment, the Cas9 protein may be an ortholog of an organism of a genus which includes but is not limited to *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter*. Species of an organism of such a genus can be as otherwise herein discussed.

Some methods of identifying orthologs of CRISPR-Cas9 system enzymes may involve identifying tracr sequences in genomes of interest. Identification of tracr sequences may relate to the following steps: Search for the direct repeats or tracr mate sequences in a database to identify a CRISPR region comprising a CRISPR enzyme. Search for homologous sequences in the CRISPR region flanking the CRISPR enzyme in both the sense and antisense directions. Look for transcriptional terminators and secondary structures. Identify any sequence that is not a direct repeat or a tracr mate sequence but has more than 50% identity to the direct repeat or tracr mate sequence as a potential tracr sequence. Take the potential tracr sequence and analyze for transcriptional terminator sequences associated therewith.

It will be appreciated that any of the functionalities described herein may be engineered into CRISPR enzymes from other orthologs, including chimeric enzymes comprising fragments from multiple orthologs. Examples of such orthologs are described elsewhere herein. Thus, chimeric enzymes may comprise fragments of CRISPR enzyme orthologs of an organism which includes but is not limited to *Corynebacter, Sutterella, Legionella, Treponema, Filifactor, Eubacterium, Streptococcus. Lactobacillus, Myco-* plasma. Bacteroides, Flaviivola Flavobacterium, Sphaerochaeta, Azospirillum, Gluconacetobacter, Neisseria, Roseburia, Parvibaculum, Staphylococcus, Nitratifractor, Mycoplasma and Campylobacter. A chimeric enzyme can comprise a first fragment and a second fragment, and the fragments can be of CRISPR enzyme orthologs of organisms of genuses herein mentioned or of species herein mentioned; advantageously the fragments are from CRISPR enzyme orthologs of different species In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.10%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR-Cas9 locus in *Streptococcus pyogenes*. However, it will be appreciated that this invention includes many more Cas9s from other species of microbes, such as SpCas9., SaCa9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archaea, Mole Cell 2010, Jan. 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target comprising, consisting essentially of, or consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array comprising, consisting essentially of, or consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas9 proteins) results in cleavage of one or both strands in or near (e.g., within 1, 2, 3, 4, 5, 6, 7, 8, 9, 10, 20, 50, or more base pairs from) the target sequence. Without wishing to be bound by theory, the tracr sequence, which may comprise, consist essentially of, or consist of all or a portion of a wild-type tracr sequence (e.g., about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 1); the NLS from nucleoplasmin (e.g., the nucleoplasmin bipartite NLS with the sequence KRPAATKKAGQAKKKK (SEQ ID NO: 2)); the c-myc NLS having the amino acid sequence PAAKRVKLD (SEQ ID NO: 3) or RQRRNELKRSP (SEQ ID NO: 4); the hRNPA1 M9 NLS having the sequence NQSSNFGPMKGGNFGGRSSGPYGGGGQYFAKPRNQGGY (SEQ ID NO: 5); the sequence RMRIZFKNKGKDTAELRRRRVEVSVELRKAKKDEQILKRRNV (SEQ ID NO: 6) of the IBB domain from importin-alpha; the sequences VSRKRPRP (SEQ ID NO: 7) and PPKKARED (SEQ ID NO: 8) of the myoma T protein; the sequence PQPKKKPL (SEQ ID NO: 9) of human p53; the sequence SALIKKKKKMAP (SEQ ID NO: 10) of mouse c-abl IV; the sequences DRLRR (SEQ ID NO: 11) and PKQKKRK (SEQ ID NO: 12) of the influenza virus NS1; the sequence RKLKKKIKKL (SEQ ID NO: 13) of the Hepatitis virus delta antigen; the sequence REKKKFLKRR (SEQ ID NO: 14) of the mouse Mx1 protein; the sequence KRKGDEVDGVDEVAKKKSKK (SEQ ID NO: 15) of the human poly(ADP-ribose) polymerase; and the sequence RKCLQAGMNLEARKTKK (SEQ ID NO: 16) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or CRISPR enzyme activity), as compared to a control not exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of the same vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g., about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas9 enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9; or an animal or mammal that is otherwise expressing Cas9 or has cells containing Cas9, such as by way of prior administration thereto of a vector or vectors that code for and express in vivo Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas9 protein. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96°%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). The target can be a control element or a regulatory element or a promoter or an enhancer or a silencer. The promoter may, in some embodiments, be in the region of +200 bp or even +1000 bp from the TTS. In some embodiments, the regulatory region may be an enhancer. The enhancer is typically more than +1000 bp from the TTS. More in particular, expression of eukaryotic protein-coding genes generally is regulated through multiple cis-acting transcription-control regions. Some control elements are located close to the start site (promoter-proximal elements), whereas others lie more distant (enhancers and silencers) Promoters determine the site of transcription initiation and direct binding of RNA polymerase II. Three types of promoter sequences have been identified in eukaryotic DNA. The TATA box, the most common, is prevalent in rapidly transcribed genes. Initiator promoters infrequently are found in some genes, and CpG islands are characteristic of transcribed genes. Promoter-proximal elements occur within =200 base pairs of the start site. Several such elements, containing up to ≈20 base pairs, may help regulate a particular gene. Enhancers, which are usually ≈100-200 base pairs in length, contain multiple 8- to 20-bp control elements. They may be located from 200 base pairs to tens of kilobases upstream or downstream from a promoter, within an intron, or downstream from the final exon of a gene. Promoter-proximal elements and enhancers may be cell-type specific, functioning only in specific differentiated cell types. However, any of these regions can be the target sequence and are encompassed by the concept that the target can be a control element or a regulatory element or a promoter or an enhancer or a silencer.

Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

The invention relates to the engineering and optimization of systems, methods and compositions used for the control of gene expression involving sequence targeting, such as genome perturbation or gene-editing, that relate to the CRISPR-Cas9 system and components thereof. An advantage of the present methods is that the CRISPR system minimizes or avoids off-target binding and its resulting side effects. This is achieved using systems arranged to have a high degree of sequence specificity for the target DNA.

In relation to a CRISPR-Cas9 complex or system preferably, the tracr sequence has one or more hairpins and is 30 or more nucleotides in length, 40 or more nucleotides in length, or 50 or more nucleotides in length, the guide sequence is between 10 to 30 nucleotides in length, the CRISPR/Cas enzyme is a Type II Cas9 enzyme.

One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:
Guide 1-MS2 aptamer-----MS2 RNA-binding protein-----VP64 activator; and
Guide 2-PP7 aptamer----PP7 RNA-binding protein-----SID4x repressor.

The present invention also relates to orthogonal PP7/MS2 gene targeting. In this example, sgRNA targeting different loci are modified with distinct RNA loops in order to recruit MS2-VP64 or PP7-SID4X, which activate and repress their target loci, respectively. PP7 is the RNA-binding coat protein of the bacteriophage Pseudomonas. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as Q-beta.

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g., using the Alu repressor (in RNA) that interferes with RNA polymerase II in mammalian cells). The Alu RNA sequence was located: in place of the MS2 RNA sequences as used herein (e.g., at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker).

The use of two different aptamers (each associated with a distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for example 10 or 20 or 30 and so forth, whilst only one (or at least a minimal number) of Cas9s to be delivered, as a comparatively small number of Cas9s can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, whilst the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the GlySer linker.

It is also envisaged that the enzyme-guide complex as a whole may be associated with two or more functional domains. For example, there may be two or more functional domains associated with the enzyme, or there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS (SEQ ID NO: 41) can be used. They can be used in repeats of 3 ((GGGGS)$_3$ (SEQ ID NO: 42)) or 6 (SEQ ID NO: 43), 9 (SEQ ID NO: 44) or even 12 (SEQ ID NO: 45) or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

The invention comprehends a CRISPR Cas9 complex comprising a CRISPR enzyme and a guide RNA (sgRNA), wherein the CRISPR enzyme comprises at least one mutation, such that the CRISPR enzyme has no more than 5% of the nuclease activity of the CRISPR enzyme not having the at least one mutation and, optional, at least one or more nuclear localization sequences; the guide RNA (sgRNA) comprises a guide sequence capable of hybridizing to a target sequence in a genomic locus of interest in a cell; and wherein: the CRISPR enzyme is associated with two or more functional domains; or at least one loop of the sgRNA is modified by the insertion of distinct RNA sequence(s) that bind to one or more adaptor proteins, and wherein the adaptor protein is associated with two or more functional domains; or the CRISPR enzyme is associated with one or more functional domains and at least one loop of the sgRNA is modified by the insertion of distinct RNA sequence(s) that bind to one or more adaptor proteins, and wherein the adaptor protein is associated with one or more functional domains.

In an embodiment, nucleic acid molecule(s) encoding a CRISPR-Cas9 or an ortholog or homolog thereof, may be codon-optimized for expression in a eukaryotic cell. A eukaryote can be as herein discussed. Nucleic acid molecule(s) can be engineered or non-naturally occurring.

In an embodiment, the CRISPR-Cas9 effector protein may comprise one or more mutations. The mutations may be artificially introduced mutations and may include but are not limited to one or more mutations in a catalytic domain, to provide a nickase, for example. Examples of catalytic domains with reference to a Cas9 enzyme may include but are not limited to RuvC I, RuvC II, RuvC III, and HNH domains.

In an embodiment, the CRISPR-Cas9 effector protein may be used as a generic nucleic acid binding protein with fusion to or being operably linked to a functional domain. Exemplary functional domains may include but are not limited to translational initiator, translational activator, translational repressor, nucleases, in particular ribonucleases, a spliceosome, beads, a light inducible/controllable domain or a chemically inducible/controllable domain.

In some embodiments, the CRISPR-Cas9 effector protein may have cleavage activity. In some embodiments, the CRISPR-Cas9 effector protein may direct cleavage of one or both nucleic acid strands at the location of or near a target sequence, such as within the target sequence and/or within the complement of the target sequence or at sequences associated with the target sequence. In some embodiments, the Cas9 effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be blunt, i.e., generating blunt ends. In some embodiments, the cleavage may be staggered, i.e., generating sticky ends. In some embodiments, the cleavage may be a staggered cut with a 5' overhang, e.g., a 5' overhang of 1 to 5 nucleotides. In some embodiments, the cleavage may be a staggered cut with a 3' overhang, e.g., a 3' overhang of 1 to 5 nucleotides. In some embodiments, a vector encodes a nucleic acid-targeting Cas9 protein that may be mutated with respect to a corresponding wild-type enzyme such that the mutated nucleic acid-targeting Cas9 protein lacks the ability to cleave one or both DNA or RNA strands of a target polynucleotide containing a target sequence. As a further example, two or more catalytic domains of Cas9 (RuvC I, RuvC II, and RuvC III or the HNH domain) may be mutated to produce a mutated Cas9 substantially lacking all RNA cleavage activity. As described herein, corresponding catalytic domains of a Cas9 effector protein may also be mutated to produce a mutated Cas9 lacking all DNA cleavage activity or having substantially reduced DNA cleavage activity. In some embodiments, a nucleic acid-targeting effector protein may be considered to substantially lack all RNA cleavage activity when the RNA cleavage activity of the mutated enzyme is about no more than 25%, 10%, 5%, 1%, 0.1%, 0.01%, or less of the nucleic acid cleavage activity of the non-mutated form of the enzyme, an example can be when the nucleic acid cleavage activity of the mutated form is nil or negligible as compared with the non-mutated form. An effector protein may be identified with reference to the general class of enzymes that share homology to the biggest nuclease with multiple nuclease domains from the Type II CRISPR system. Most preferably, the effector protein is a Type II protein such as Cas9. By derived, Applicants mean that the derived enzyme is largely based, in the sense of having a high degree of sequence homology with, a wildtype enzyme, but that it has been mutated (modified) in some way as known in the art or as described herein.

Again, it will be appreciated that the terms Cas and CRISPR enzyme and CRISPR protein and Cas9 protein are generally used interchangeably and at all points of reference herein refer by analogy to novel CRISPR-Cas9 effector proteins further described in this application, unless otherwise apparent, such as by specific reference to Cas9. As mentioned above, many of the residue numberings used herein refer to the effector protein from the Type II CRISPR locus. However, it will be appreciated that this invention includes many more effector proteins from other species of microbes.

In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic nucleic acid binding protein.

Typically, in the context of an endogenous nucleic acid-targeting system, formation of a nucleic acid-targeting complex (comprising a guide RNA hybridized to a target sequence and complexed with one or more nucleic acid-targeting effector proteins) results in cleavage of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest).

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667) as an example of a codon optimized sequence (from knowledge in the art and this disclosure, codon optimizing coding nucleic acid molecule(s), especially as to effector protein (e.g., Cas9) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA-targeting Cas9 protein is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a DNA-targeting Cas9 protein corresponds to the most frequently used codon for a particular amino acid.

In one aspect, the invention provides methods for using one or more elements of a nucleic acid-targeting system. The nucleic acid-targeting complex of the invention provides an effective means for modifying a target DNA (double stranded, linear or super-coiled). The nucleic acid-targeting complex of the invention has a wide variety of utility including modifying (e.g., deleting, inserting, translocating, inactivating, activating) a target DNA in a multiplicity of cell types. As such the nucleic acid-targeting complex of the invention has a broad spectrum of applications in, e.g., gene therapy, drug screening, disease diagnosis, and prognosis. An exemplary nucleic acid-targeting complex comprises a DNA-targeting effector protein complexed with a guide RNA hybridized to a target sequence within the target locus of interest.

In some embodiments, the method may comprise allowing a nucleic acid-targeting complex to bind to the target DNA to effect cleavage of said target DNA thereby modifying the target DNA, wherein the nucleic acid-targeting complex comprises a nucleic acid-targeting effector protein complexed with a guide RNA hybridized to a target sequence within said target DNA. In one aspect, the invention provides a method of modifying expression of DNA in a eukaryotic cell. In some embodiments, the method comprises allowing a nucleic acid-targeting complex to bind to the DNA such that said binding results in increased or decreased expression of said DNA; wherein the nucleic acid-targeting complex comprises a nucleic acid-targeting effector protein complexed with a guide RNA. Similar considerations and conditions apply as above for methods of modifying a target DNA. In fact, these sampling, culturing and re-introduction options apply across the aspects of the present invention. In one aspect, the invention provides for methods of modifying a target DNA in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the nucleic acid-targeting complex may comprise a nucleic acid-targeting effector protein complexed with a guide RNA hybridized to a target sequence.

The invention relates to the engineering and optimization of systems, methods and compositions used for the control of gene expression involving DNA sequence targeting, that relate to the nucleic acid-targeting system and components thereof. An advantage of the present methods is that the CRISPR system minimizes or avoids off-target binding and its resulting side effects. This is achieved using systems arranged to have a high degree of sequence specificity for the target DNA.

In relation to a nucleic acid-targeting complex or system preferably, the tracr sequence has one or more hairpins and is 30 or more nucleotides in length, 40 or more nucleotides in length, or 50 or more nucleotides in length; the crRNA sequence is between 10 to 30 nucleotides in length, the nucleic acid-targeting effector protein is a Type II Cas9 effector protein.

Crystallization of CRISPR-Cas9 and Characterization of Crystal Structure

The crystals of the Cas9 can be obtained by techniques of protein crystallography, including batch, liquid bridge, dialysis, vapor diffusion and hanging drop methods. Generally, the crystals of the invention are grown by dissolving substantially pure CRISPR-Cas9 and a nucleic acid molecule to which it binds in an aqueous buffer containing a precipitant at a concentration just below that necessary to precipitate. Water is removed by controlled evaporation to produce precipitating conditions, which are maintained until crystal growth ceases. The crystal structure information is described in U.S. provisional applications 61/915,251 filed Dec. 12, 2013, 61/930,214 filed on Jan. 22, 2014, 61/980,012 filed Apr. 15, 2014 and international application PCT/US2014/069925, filed Dec. 12, 2014; and Nishimasu et al, "Crystal Structure of Cas9 in Complex with Guide RNA and Target DNA," Cell 156(5):935-949, DOI: http://dx.doi.org/10 1016/j.cell 2014 02 001 (2014), each and all of which are incorporated herein by reference.

Uses of the Crystals, Crystal Structure and Atomic Structure Co-Ordinates: The crystals of the Cas9, and particularly the atomic structure co-ordinates obtained therefrom, have a wide variety of uses. The crystals and structure co-ordinates are particularly useful for identifying compounds (nucleic acid molecules) that bind to CRISPR-Cas9, and CRISPR-Cas9s that can bind to particular compounds (nucleic acid molecules). Thus, the structure co-ordinates described herein can be used as phasing models in determining the crystal structures of additional synthetic or mutated CRISPR-Cas9s, Cas9s, nickases, binding domains. The provision of the crystal structure of CRISPR-Cas9 complexed with a nucleic acid molecule as applied in conjunction with the herein teachings provides the skilled artisan with a detailed insight into the mechanisms of action of CRISPR-Cas9. This insight provides a means to design modified CRISPR-Cas9s, such as by attaching thereto a functional group, such as a repressor or activator. While one can attach a functional group such as a repressor or activator to the N or C terminal of CRISPR-Cas9, the crystal structure demonstrates that the N terminal seems obscured or hidden, whereas the C terminal is more available for a functional group such as repressor or activator. Moreover, the crystal structure demonstrates that there is a flexible loop between approximately CRISPR-Cas9 (S. pyogenes) residues 534-676 which is suitable for attachment of a functional group such as an activator or repressor. Attachment can be via a linker, e.g., a flexible glycine-serine (GlyGlyGlySer (SEQ ID NO: 41)) or (GGGS)$_3$ (SEQ ID NO: 46) or a rigid alpha-helical linker such as (Ala(GluAlaAlaAlaLys)Ala (SEQ ID NO: 47)). In addition to the flexible loop there is also a nuclease or H3 region, an H2 region and a helical region. By "helix" or "helical", is meant a helix as known in the art, including, but not limited to an alpha-helix. Additionally, the term helix or helical may also be used to indicate a c-terminal helical element with an N-terminal turn.

The provision of the crystal structure of CRISPR-Cas9 complexed with a nucleic acid molecule allows a novel approach for drug or compound discovery, identification, and design for compounds that can bind to CRISPR-Cas9 and thus the invention provides tools useful in diagnosis, treatment, or prevention of conditions or diseases of multi-cellular organisms, e.g., algae, plants, invertebrates, fish, amphibians, reptiles, avians, mammals; for example domesticated plants, animals (e.g., production animals such as swine, bovine, chicken, companion animal such as felines, canines, rodents (rabbit, gerbil, hamster); laboratory animals such as mouse, rat), and humans.

In any event, the determination of the three-dimensional structure of CRISPR-Cas9 (S. pyogenes Cas9) complex provides a basis for the design of new and specific nucleic acid molecules that bind to CRISPR-Cas9 (e.g., S. pyogenes Cas9), as well as the design of new CRISPR-Cas9 systems, such as by way of modification of the CRISPR-Cas9 system to bind to various nucleic acid molecules, by way of modification of the CRISPR-Cas9 system to have linked thereto to any one or more of various functional groups that may interact with each other, with the CRISPR-Cas9 (e.g., an inducible system that provides for self-activation and/or self-termination of function), with the nucleic acid molecule nucleic acid molecules (e.g., the functional group may be a regulatory or functional domain which may be selected from the group consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase; and, in some aspects, the functional domain is an epigenetic regulator, see, e.g., Zhang et al., U.S. Pat. No. 8,507,272, and it is again mentioned that it and all documents cited herein and all appln cited documents are hereby incorporated herein by reference), by way of modification of Cas9, by way of novel nickases). Indeed, the herewith CRISPR-Cas9 (S. pyogenes Cas9) crystal structure has a multitude of uses. For example, from knowing the three-dimensional structure of CRISPR-Cas9 (S. pyogenes Cas9) crystal structure, computer modelling programs may be used to design or identify different molecules expected to interact with possible or confirmed sites such as binding sites or other structural or functional features of the CRISPR-Cas9 system (e.g., S. pyogenes Cas9). Compound that potentially bind ("binder") can be examined through the use of computer modeling using a docking program. Docking programs are known; for example GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders ascertain how well the shape and the chemical structure of the potential binder will bind to a CRISPR-Cas9 system (e.g., *S. pyogenes* Cas9). Computer-assisted, manual examination of the active site or binding site of a CRISPR-Cas9 system (e.g., *S. pyogenes* Cas9) may be performed. Programs such as GRID (P. Goodford, J. Med. Chem, 1985, 28, 849-57)—a program that determines probable interaction sites between molecules with various functional groups—may also be used to analyze the active site or binding site to predict partial structures of binding compounds. Computer programs can be employed to estimate the attraction, repulsion or steric hindrance of the two binding partners, e.g., CRISPR-Cas9 system (e.g., *S. pyogenes* Cas9) and a candidate nucleic acid molecule or a nucleic acid molecule and a candidate CRISPR-Cas9 system (e.g., *S. pyogenes* Cas9); and the CRISPR-Cas9 crystal structure (*S. pyogenes* Cas9) herewith enables such methods. Generally, the tighter the fit, the fewer the steric hindrances, and the greater the attractive forces, the more potent the potential binder, since these properties are consistent with a tighter binding constant. Furthermore, the more specificity in the design of a candidate CRISPR-Cas9 system (e.g., *S. pyogenes* Cas9), the more likely it is that it will not interact with off-target molecules as well. Also, "wet" methods are enabled by the instant invention. For example, in an aspect, the invention provides for a method for determining the structure of a binder (e.g., target nucleic acid molecule) of a candidate CRISPR-Cas9 system (e.g., *S. pyogenes* Cas9) bound to the candidate CRISPR-Cas9 system (e.g., *S. pyogenes* Cas9), said method comprising, (a) providing a first crystal of a candidate CRISPR-Cas9 system (*S. pyogenes* Cas9) according to the invention or a second crystal of a candidate a candidate CRISPR-Cas9 system (e.g., *S. pyogenes* Cas9), (b) contacting the first crystal or second crystal with said binder under conditions whereby a complex may form; and (c) determining the structure of said a candidate (e.g., CRISPR-Cas9 system (e.g., *S. pyogenes* Cas9) or CRISPR-Cas9 system (*S. pyogenes* Cas9) complex. The second crystal may have essentially the same coordinates discussed herein, however due to minor alterations in CRISPR-Cas9 system (e.g., from the Cas9 of such a system being e.g., *S. pyogenes* Cas9 versus being *S. pyogenes* Cas9), wherein "e.g., *S. pyogenes* Cas9" indicates that the Cas9 is a Cas9 and can be of or derived from *S. pyogenes* or an ortholog thereof), the crystal may form in a different space group.

The invention further involves, in place of or in addition to "in silico" methods, other "wet" methods, including high throughput screening of a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)), to select compounds with binding activity. Those pairs of binder and CRISPR-Cas9 system which show binding activity may be selected and further crystallized with the CRISPR-Cas9 crystal having a structure herein, e.g., by co-crystallization or by soaking, for X-ray analysis. The resulting X-ray structure may be compared with that of the Cas9 Crystal Structure for a variety of purposes, e.g., for areas of overlap. Having designed, identified, or selected possible pairs of binder and CRISPR-Cas9 system by determining those which have favorable fitting properties, e.g., predicted strong attraction based on the pairs of binder and CRISPR-Cas9 crystal structure data herein, these possible pairs can then be screened by "wet" methods for activity. Consequently, in an aspect the invention can involve: obtaining or synthesizing the possible pairs; and contacting a binder (e.g., target nucleic acid molecule) and a candidate CRISPR-Cas9 system (e.g., *S. pyogenes* Cas9), or a candidate binder (e.g., target nucleic acid molecule) and a CRISPR-Cas9 system (e.g., *S. pyogenes* Cas9), or a candidate binder (e.g., target nucleic acid molecule) and a candidate CRISPR-Cas9 system (e.g., *S. pyogenes* Cas9) (the foregoing CRISPR-Cas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex(es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate CRISPR-Cas9 system or components thereof. These steps may be repeated and re-repeated as necessary. Alternatively or additionally, potential CRISPR-Cas9 systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom.

The invention further involves a method of determining three dimensional structures of CRISPR-Cas systems or complex(es) of unknown structure by using the structural co-ordinates of the Cas9 Crystal Structure. For example, if X-ray crystallographic or NMR spectroscopic data are provided for a CRISPR-Cas system or complex of unknown crystal structure, the structure of a CRISPR-Cas9 complex may be used to interpret that data to provide a likely structure for the unknown system or complex by such techniques as by phase modeling in the case of X-ray crystallography. Thus, an inventive method can comprise: aligning a representation of the CRISPR-Cas system or complex having an unknown crystal structure with an analogous representation of the CRISPR-Cas9 system and complex of the crystal structure herein to match homologous or analogous regions (e.g., homologous or analogous sequences); modeling the structure of the matched homologous or analogous regions (e.g., sequences) of the CRISPR-Cas9 system or complex of unknown crystal structure based on the structure of the Cas9 Crystal Structure of the corresponding regions (e.g., sequences); and, determining a conformation (e.g. taking into consideration favorable interactions should be formed so that a low energy conformation is formed) for the unknown crystal structure which substantially preserves the structure of said matched homologous regions. "Homologous regions" describes, for example as to amino acids, amino acid residues in two sequences that are identical or have similar, e.g., aliphatic, aromatic, polar, negatively charged, or positively charged, side-chain chemical groups. Homologous regions as to nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art. Homology modeling is a technique that is well known to those skilled in the art (see, e.g., Greer, Science vol. 228

(1985) 1055, and Blundell et al. Eur J Biochem vol 172 (1988), 513). The computer representation of the conserved regions of the CRISPR-Cas9 crystal structure and those of a CRISPR-Cas9 system of unknown crystal structure aid in the prediction and determination of the crystal structure of the CRISPR-Cas9 system of unknown crystal structure.

Further still, the aspects of the invention which employ the CRISPR-Cas9 crystal structure in silico may be equally applied to new CRISPR-Cas9 crystal structures divined by using the herein-referenced CRISPR-Cas9 crystal structure. In this fashion, a library of CRISPR-Cas9 crystal structures can be obtained. Rational CRISPR-Cas9 system design is thus provided by the instant invention. For instance, having determined a conformation or crystal structure of a CRISPR-Cas9 system or complex, by the methods described herein, such a conformation may be used in a computer-based methods herein for determining the conformation or crystal structure of other CRISPR-Cas9 systems or complexes whose crystal structures are yet unknown. Data from all of these crystal structures can be in a database, and the herein methods can be more robust by having herein comparisons involving the herein crystal structure or portions thereof be with respect to one or more crystal structures in the library. The invention further provides systems, such as computer systems, intended to generate structures and/or perform rational design of a CRISPR-Cas9 system or complex. The system can contain: atomic co-ordinate data according to the herein-referenced Crystal Structure or be derived therefrom e.g., by modeling, said data defining the three-dimensional structure of a CRISPR-Cas9 system or complex or at least one domain or sub-domain thereof, or structure factor data therefor, said structure factor data being derivable from the atomic co-ordinate data of the herein-referenced Crystal Structure. The invention also involves computer readable media with: atomic co-ordinate data according to the herein-referenced Crystal Structure or derived therefrom e.g., by homology modeling, said data defining the three-dimensional structure of a CRISPR-Cas9 system or complex or at least one domain or sub-domain thereof, or structure factor data therefor, said structure factor data being derivable from the atomic co-ordinate data of the herein-referenced Crystal Structure. "Computer readable media" refers to any media which can be read and accessed directly by a computer, and includes, but is not limited to: magnetic storage media; optical storage media; electrical storage media; cloud storage and hybrids of these categories. By providing such computer readable media, the atomic co-ordinate data can be routinely accessed for modeling or other "in silico" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of CRISPR-Cas9 systems or complexes; advantageously, the three-dimensional structure being as defined by the atomic co-ordinate data according to the herein-referenced Crystal Structure. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The herein-referenced Crystal Structure gives atomic co-ordinate data for a CRISPR-Cas9 (*S. pyogenes*), and lists each atom by a unique number, the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms$^2$) which accounts for movement of the atom around its atomic center, and atomic number.

In particular embodiments of the invention, the conformational variations in the crystal structures of the CRISPR-Cas9 system or of components of the CRISPR-Cas9 provide important and critical information about the flexibility or movement of protein structure regions relative to nucleotide (RNA or DNA) structure regions that may be important for CRISPR-Cas9 system function. The structural information provided for Cas9 (e.g. *S. pyogenes* Cas9) as the CRISPR enzyme in the present application may be used to further engineer and optimize the CRISPR-Cas9 system and this may be extrapolated to interrogate structure-function relationships in other CRISPR enzyme systems as well. An aspect of the invention relates to the crystal structure of *S. pyogenes* Cas9 in complex with sgRNA and its target DNA at 2.4 Å resolution. The structure revealed a bilobed architecture composed of target recognition and nuclease lobes, accommodating a sgRNA:DNA duplex in a positively-charged groove at their interface. The recognition lobe is essential for sgRNA and DNA binding and the nuclease lobe contains the HNH and RuvC nuclease domains, which are properly positioned for the cleavage of complementary and non-complementary strands of the target DNA, respectively. This high-resolution structure and the functional analyses provided herein elucidate the molecular mechanism of RNA-guided DNA targeting by Cas9, and provides an abundance of information for generating optimized CRISPR-Cas9 systems and components thereof.

In particular embodiments of the invention, the crystal structure provides a critical step towards understanding the molecular mechanism of RNA-guided DNA targeting by Cas9. The structural and functional analyses herein provide a useful scaffold for rational engineering of Cas9-based genome modulating technologies and may provide guidance as to Cas9-mediated recognition of PAM sequences on the target DNA or mismatch tolerance between the sgRNA: DNA duplex. Aspects of the invention also relate to truncation mutants, e.g. an *S. pyogenes* Cas9 truncation mutant may facilitate packaging of Cas9 into size-constrained viral vectors for in vivo and therapeutic applications. Similarly, future engineering of the PAM Interacting (PI) domain may allow programing of PAM specificity, improve target site recognition fidelity, and increase the versatility of the Cas9 genome engineering platform. Accordingly, while the herein-referenced crystal structure may be used in conjunction with the herein disclosure, and in conjunction with the herein invention, the herein invention of protected guides and the utility thereof could not have been predicted from the herein-referenced crystal structure.

The invention comprehends optimized functional CRISPR-Cas9 enzyme systems. In particular the CRISPR enzyme comprises one or more mutations that converts it to a DNA binding protein to which functional domains exhibiting a function of interest may be recruited or appended or inserted or attached. In certain embodiments, the CRISPR enzyme comprises one or more mutations which include but are not limited to D10A, E762A, H840A, N854A, N863A or D986A (based on the amino acid position numbering of a *S. pyogenes* Cas9) and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain.

The structural information provided herein allows for interrogation of sgRNA (or chimeric RNA) interaction with the target DNA and the CRISPR enzyme (e.g. Cas9) permitting engineering or alteration of sgRNA structure to optimize functionality of the entire CRISPR-Cas9 system. For example, loops of the sgRNA may be extended, without colliding with the Cas9 protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes, inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

In one aspect surveyor analysis is used for identification of indel activity/nuclease activity. In general survey analysis includes extraction of genomic DNA, PCR amplification of the genomic region flanking the CRISPR target site, purification of products, re-annealing to enable heteroduplex formation. After re-annealing, products are treated with SURVEYOR nuclease and SURVEYOR enhancer S (Transgenomics) following the manufacturer's recommended protocol. Analysis may be performed with poly-acrylamide gels according to known methods. Quantification may be based on relative band intensities.

Delivery Generally

Gene Editing or Altering a Target Loci with Cas9

The double strand break or single strand break in one of the strands advantageously should be sufficiently close to target position such that correction occurs. In an embodiment, the distance is not more than 50, 100, 200, 300, 350 or 400 nucleotides. While not wishing to be bound by theory, it is believed that the break should be sufficiently close to target position such that the break is within the region that is subject to exonuclease-mediated removal during end resection. If the distance between the target position and a break is too great, the mutation may not be included in the end resection and, therefore, may not be corrected, as the template nucleic acid sequence may only be used to correct sequence within the end resection region.

In an embodiment, in which a guide RNA and a Type II molecule, in particular Cas9Cas9 or an ortholog or homolog thereof, preferably a Cas9 nuclease induce a double strand break for the purpose of inducing HDR-mediated correction, the cleavage site is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position. In a further embodiment, two or more guide RNAs complexing with Cas9 or an ortholog or homolog thereof, may be used to induce multiplexed breaks for purpose of inducing HDR-mediated correction.

The homology arm should extend at least as far as the region in which end resection may occur, e.g., in order to allow the resected single stranded overhang to find a complementary region within the donor template. The overall length could be limited by parameters such as plasmid size or viral packaging limits. In an embodiment, a homology arm may not extend into repeated elements. Exemplary homology arm lengths include a least 50, 100, 250, 500, 750 or 1000 nucleotides.

Target position, as used herein, refers to a site on a target nucleic acid or target gene (e.g., the chromosome) that is modified by a Type II, in particular Cas9 or an ortholog or homolog thereof, preferably Cas9 molecule-dependent process. For example, the target position can be a modified Cas9 molecule cleavage of the target nucleic acid and template nucleic acid directed modification, e.g., correction, of the target position. In an embodiment, a target position can be a site between two nucleotides, e.g., adjacent nucleotides, on the target nucleic acid into which one or more nucleotides is added. The target position may comprise one or more nucleotides that are altered, e.g., corrected, by a template nucleic acid. In an embodiment, the target position is within a target sequence (e.g., the sequence to which the guide RNA binds). In an embodiment, a target position is upstream or downstream of a target sequence (e.g., the sequence to which the guide RNA binds).

A template nucleic acid, as that term is used herein, refers to a nucleic acid sequence which can be used in conjunction with a Type II molecule, in particular Cas9 or an ortholog or homolog thereof, preferably a Cas9 molecule and a guide RNA molecule to alter the structure of a target position. In an embodiment, the target nucleic acid is modified to have some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA.

In an embodiment, the template nucleic acid alters the structure of the target position by participating in homologous recombination. In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas9 mediated cleavage event. In an embodiment, the template nucleic acid may include sequence that corresponds to both, a first site on the target sequence that is cleaved in a first Cas9 mediated event, and a second site on the target sequence that is cleaved in a second Cas9 mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

A template nucleic acid comprises the following components: [5' homology arm]-[replacement sequence]-[3' homology arm]. The homology arms provide for recombination into the chromosome, thus replacing the undesired element, e.g., a mutation or signature, with the replacement sequence. In an embodiment, the homology arms flank the most distal cleavage sites. In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, or 2000 nucleotides 5' from the 5' end of the replacement sequence. In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, or 2000 nucleotides 3' from the 3' end of the replacement sequence.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In certain embodiments, a template nucleic acids for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Cas9 Effector Protein Complex System Promoted Non-Homologous End-Joining

In certain embodiments, nuclease-induced non-homologous end-joining (NHEJ) can be used to target gene-specific knockouts. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily be greater than 50 bp, e.g., they can easily reach greater than about 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it may also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving Type II molecule, in particular Cas9 or an ortholog or homolog thereof, preferably Cas9 molecules and single strand, or nickase, Type II molecule, in particular Cas9 or an ortholog or homolog thereof, preferably Cas9 molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In an embodiment, in which a guide RNA and Type II molecule, in particular Cas9 or an ortholog or homolog thereof, preferably Cas9 nuclease generate a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two guide RNAs complexing with Type II molecules, in particular Cas9 or an ortholog or homolog thereof, preferably Cas9 nickases induce two single strand breaks for the purpose of inducing NHEJ-mediated indels, two guide RNAs may be configured to position two single-strand breaks to provide for NHEJ repair a nucleotide of the target position.

Cas9 Effector Protein Complexes can Deliver Functional Effectors

Unlike CRISPR-Cas-mediated gene knockout, which permanently eliminates expression by mutating the gene at the DNA level, CRISPR-Cas9 knockdown allows for temporary reduction of gene expression through the use of artificial transcription factors. Mutating key residues in both DNA cleavage domains of the Cas9 protein results in the generation of a catalytically inactive Cas9. A catalytically inactive Cas9 complexes with a guide RNA and localizes to the DNA sequence specified by that guide RNA's targeting domain, however, it does not cleave the target DNA. Fusion of the inactive Cas9 protein to an effector domain, e.g., a transcription repression domain, enables recruitment of the effector to any DNA site specified by the guide RNA. In certain embodiments, Cas9 may be fused to a transcriptional repression domain and recruited to the promoter region of a gene. Especially for gene repression, it is contemplated herein that blocking the binding site of an endogenous transcription factor would aid in downregulating gene expression. In another embodiment, an inactive Cas9 can be fused to a chromatin modifying protein. Altering chromatin status can result in decreased expression of the target gene.

In an embodiment, a guide RNA molecule can be targeted to a known transcription response elements (e.g., promoters, enhancers, etc.), a known upstream activating sequences, and/or sequences of unknown or known function that are suspected of being able to control expression of the target DNA.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In certain embodiments, the CRISPR enzyme comprises one or more mutations selected from the group consisting of D917A, E1006A and D1225A and/or the one or more mutations is in a RuvC domain of the CRISPR enzyme or is a mutation as otherwise as discussed herein. In some embodiments, the CRISPR enzyme has one or more mutations in a catalytic domain, wherein when transcribed, the direct repeat sequence forms a single stem loop and the guide sequence directs sequence-specific binding of a CRISPR complex to the target sequence, and wherein the enzyme further comprises a functional domain. In some embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

Delivery of the CRISPR-Cas9 Complex or Components Thereof

Through this disclosure and the knowledge in the art, TALEs, CRISPR-Cas9 system, specifically the novel CRISPR systems described herein, or components thereof or nucleic acid molecules thereof (including, for instance HDR template) or nucleic acid molecules encoding or providing components thereof may be delivered by a delivery system herein described both generally and in detail.

Vector delivery, e.g., plasmid, viral delivery: The CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^5$ particles (e.g., about $1 \times 10^8$-$1 \times 10^{11}$ particles or about $1 \times 10^8$-$1 \times 10^{12}$ particles), and most preferably at least about $1 \times 10^0$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{10}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^{11}$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^{50}$ to $1 \times 10^{16}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter, (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver Cas9 and gRNA (and, for instance, HR repair template) into cells using liposomes or particles/nanoparticles. Thus delivery of the CRISPR enzyme, such as a Cas9 and/or delivery of the RNAs of the invention may be in RNA form and via microvesicles, liposomes or particles/nanoparticles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via particles/nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E ($\alpha$-tocopherol) may be conjugated with CRISPR Cas9 and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas9 conjugated to $\alpha$-tocopherol and co-administered with HDL targeted to the brain may be contemplated for humans in the present invention, for example, about 3 nmol to about 3 µmol of CRISPR Cas9 targeted to the brain may be contemplated. Zou et al. ((HUMAN GENE THERAPY 22:465-475 (April 2011)) describes a method of lentiviral-mediated delivery of short-hairpin RNAs targeting PKC$\gamma$ for in vivo gene silencing in the spinal cord of rats. Zou et al. administered about 10 µl of a recombinant lentivirus having a titer of $1 \times 10^9$ transducing units (TU)/ml by an intrathecal catheter. A similar dosage of CRISPR Cas9 expressed in a lentiviral vector targeted to the brain may be contemplated for humans in the present invention, for example, about 10-50 ml of CRISPR Cas9 targeted to the brain in a lentivirus having a titer of $1 \times 10^9$ transducing units (TU)/ml may be contemplated.

In terms of local delivery to the brain, this can be achieved in various ways. For instance, material can be delivered intrastriatally e.g., by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package Cas9 coding nucleic acid molecules, e.g., DNA, into vectors, e.g., viral vectors, to mediate genome modification in vivo include:

To achieve NHEJ-mediated gene knockout:
  Single virus vector:
    Vector containing two or more expression cassettes:
    Promoter-Cas9 coding nucleic acid molecule-terminator
    Promoter-guide RNA1-terminator
    Promoter-guide RNA2-terminator
    Promoter-guide RNA(N)-terminator (up to size limit of vector)
  Double virus vector:
    Vector 1 containing one expression cassette for driving the expression of Cas9
    Promoter-Cas9 coding nucleic acid molecule-terminator
    Vector 2 containing one more expression cassettes for driving the expression of one or more guide RNAs
    Promoter-guide RNA1-terminator
    Promoter-guide RNA(N)-terminator (up to size limit of vector)

To mediate homology-directed repair.
  In addition to the single and double virus vector approaches described above, an additional vector is used to deliver a homology-direct repair template.

The promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9.

For ubiquitous expression, can use promoters: CMV, CAG, CBh, PGK, SV40, Ferritin heavy or light chains, etc.

For brain or other CNS expression, can use promoters: SynapsinI for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can use OG-2.

The promoter used to drive guide RNA can include:
  Pol III promoters such as U6 or H1
  Use of Pol II promoter and intronic cassettes to express guide RNA
    Adeno Associated Virus (AAV)

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cas9 can be driven by a cell-type specific promoter. For example, liver-specific

| Species | Cas9 Size |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species with respect to both AAV delivery and in general.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND | expression might use the Albumin promoter and neuron-specific expression (e.g., for targeting CNS disorders) might use the Synapsin I promoter.

In terms of in vivo delivery, AAV is advantageous over other viral vectors for a couple of reasons:
  Low toxicity (this may be due to the purification method not requiring ultra centrifugation of cell particles that can activate the immune response)
  Low probability of causing insertional mutagenesis because it doesn't integrate into the host genome.

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquotted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas9 system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas9 system of the present invention. A minimum of $2.5 \times 10^6$ CD34+ cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm$^2$ tissue culture flasks coated with fibronectin (25 mg/cm$^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g., using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g., diameter) of less than 100 microns (µm). In some embodiments, inventive particles have a greatest dimension of less than 10 µm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas9 system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

CRISPR enzyme mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1X PBS; and separately, DOTAP, DMPC, PEG, and cholesterol as applicable for the formulation are dissolved in alcohol, e.g., 100% ethanol; and, the two solutions are mixed together to form particles containing the complexes).

Nucleic acid-targeting effector proteins (such as a Type H protein such as Cas9) mRNA and guide RNA may be delivered simultaneously using particles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver RNA to a cancer cell to stop tumor growth developed by Dan Anderson's lab at MIT may be used/and or adapted to the CRISPR Cas9 system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CRISPR Cas9 system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas9 system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas9 system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas9 to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml of LNP or CRISPR-Cas9 RNA in or associated with the LNP may be contemplated, especially for a formulation containing DLinKC2-DMA.

Preparation of LNPs and CRISPR Cas9 encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR Cas9 RNA may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a CRISPR-Cas9 system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano Z S, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-μm syringe filter.

Spherical Nucleic Acid (SNA™) constructs and other nanoparticles (particularly gold nanoparticles) are also contemplated as a means to delivery CRISPR-Cas9 system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas9 is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHSester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a RNA clinical trial that uses a targeted nanoparticle-delivery system (clinical trial registration number NCT00689065).

Patients with solid cancers refractory to standard-of-care therapies are administered doses of targeted nanoparticles on days 1, 3, 8 and 10 of a 21-day cycle by a 30-min intravenous infusion. The nanoparticles comprise, consist essentially of, or consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumors, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the CRISPR Cas9 system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

In terms of this invention, it is preferred to have one or more components of CRISPR complex, e.g., CRISPR enzyme or mRNA or guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm.

Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 µm and 30 µm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable nanoparticles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas9 system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). C71 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the CRISPR-Cas9 system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport RNAs and proteins, and which can deliver RNA to the brain and other target organs. To reduce immunogenicity, Alvarez- Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 μg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 pF resulted in the greatest retention of RNA and was used for all subsequent experiments.

Alvarez-Erviti et al. administered 150 μg of each BACE1 siRNA encapsulated in 150 μg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas9 system of the present invention to therapeutic targets, especially neurodegenerative diseases. A dosage of about 100 to 1000 mg of CRISPR Cas9 encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas9 into exosomes may be conducted similarly to siRNA. The exosomes may be co-cultured with monocytes and lymphocytes isolated from the peripheral blood of healthy donors. Therefore, it may be contemplated that exosomes containing CRISPR Cas9 may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi: 10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi: 10.1155/2011/469679 for review].

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at http://cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CRISPR Cas9 system or components thereof may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas9 targeted in a SNALP are contemplated. The daily treatment may be over about three days and then weekly for about five weeks. In another embodiment, a specific CRISPR Cas9 encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1,2-dimyristyloxy-propylamine (PEG-C-DMA), 1,2-dilinoley-loxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas9 per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl) aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTROI was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 µm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas9 system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas9 or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the CRISPR Cas9 system of the present invention or component(s) thereof or nucleic acid molecule(s) coding therefor to form lipid nanoparticles (LNPs). Lipids include, but are not limited to, DLin-KC2-DMA4, C12-200 and colipids disteroylphosphatidyl choline, cholesterol, and PEG-DMG may be formulated with CRISPR Cas9 instead of siRNA (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90%° entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901, 708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The CRISPR Cas9 system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumors, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine and phosphorous containing compounds with a mixture of amine/amide or $N-P(O_2)S$ as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumors, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumor activity may complement the activity of the agent to be delivered." The disclosures of these patent publications may be employed in conjunction with herein teachings for delivery of CRISPR Cas9 system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of CRISPR Cas9 system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified+36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and RNA should be performed to optimize the procedure for specific cell lines.

(1) One day before treatment, plate $1\times10^5$ cells per well in a 48-well plate.

(2) On the day of treatment, dilute purified +36 GFP protein in serum free media to a final concentration 200 nM. Add RNA to a final concentration of 50 nM. Vortex to mix and incubate at room temperature for 10 min.

(3) During incubation, aspirate media from cells and wash once with PBS.

(4) Following incubation of +36 GFP and RNA, add the protein-RNA complexes to cells.

(5) Incubate cells with complexes at 37° C. for 4 h.

(6) Following incubation, aspirate the media and wash three times with 20 U/mL heparin PBS. Incubate cells with serum-containing media for a further 48 h or longer depending upon the assay for activity.

(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1 \times 10^5$ per well in a 48-well plate.

(2) On the day of treatment, dilute purified b36 GFP protein in serumfree media to a final concentration 2 mM. Add 1 mg of plasmid DNA. Vortex to mix and incubate at room temperature for 10 min.

(3) During incubation, aspirate media from cells and wash once with PBS.

(4) Following incubation of b36 GFP and plasmid DNA, gently add the protein-DNA complexes to cells.

(5) Incubate cells with complexes at 37 C for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas9 system of the present invention. These systems of Dr. Lui and documents herein in conjunction with herein teachings can be employed in the delivery of CRISPR Cas9 system(s) or component(s) thereof or nucleic acid molecule(s) coding therefor.

Cell Penetrating Peptides (CPPs)

In yet another embodiment, cell penetrating peptides (CPPs) are contemplated for the delivery of the CRISPR Cas9 system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles including nanoparticles, liposomes, chromophores, small molecules and radioactive materials. In aspects of the invention, the cargo may also comprise any component of the CRISPR Cas9 system or the entire functional CRISPR Cas9 system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CRISPR-Cas9 system or components thereof. That CPPs can be employed to deliver the CRISPR-Cas9 system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the CRISPR Cas9 system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the CRISPR Cas9 system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

US Patent Publication 20110195123 provides a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 $m^3$ to 1000 $mm^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system of US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear-auditory system, labyrinth of the inner ear, vestibular system; 11. Intra tracheal; 12. Intracardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23.

Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas9 system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the CRISPR Cas9 system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas9 system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the CRISPR Cas9 system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable device technology herein discussed can be employed with herein teachings and hence by this disclosure and the knowledge in the art, CRISPR-Cas9 system or components thereof or nucleic acid molecules thereof or encoding or providing components may be delivered via an implantable device.

Patient-Specific Screening Methods

A nucleic acid-targeting system that targets D NA, e.g., trinucleotide repeats can be used to screen patients or patent samples for the presence of such repeats. The repeats can be the target of the RNA of the nucleic acid-targeting system, and if there is binding thereto by the nucleic acid-targeting system, that binding can be detected, to thereby indicate that such a repeat is present. Thus, a nucleic acid-targeting system can be used to screen patients or patient samples for the presence of the repeat. The patient can then be administered suitable compound(s) to address the condition; or, can be administered a nucleic acid-targeting system to bind to and cause insertion, deletion or mutation and alleviate the condition.

CRISPR Effector Protein mRNA and Guide RNA

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

The CRISPR effector protein of the present invention, i.e. a Cas9 effector protein is sometimes referred to herein as a CRISPR Enzyme. It will be appreciated that the effector protein is based on or derived from an enzyme, so the term 'effector protein' certainly includes 'enzyme' in some embodiments. However, it will also be appreciated that the effector protein may, as required in some embodiments, have DNA or RNA binding, but not necessarily cutting or nicking, activity, including a dead-Cas9 effector protein function.

Additional administrations of CRISPR enzyme mRNA and/or guide RNA might be useful to achieve the most efficient levels of genome modification. In some embodiments, phenotypic alteration is preferably the result of genome modification when a genetic disease is targeted, especially in methods of therapy and preferably where a repair template is provided to correct or alter the phenotype.

In some embodiments diseases that may be targeted include those concerned with disease-causing splice defects.

In some embodiments, cellular targets include Hemopoietic Stem/Progenitor Cells (CD34+); Human T cells; and Eye (retinal cells)—for example photoreceptor precursor cells.

In some embodiments Gene targets include: Human Beta Globin—HBB (for treating Sickle Cell Anemia, including by stimulating gene-conversion (using closely related HBD gene as an endogenous template)); CD3 (T-Cells); and CEP920-retina (eye).

In some embodiments disease targets also include: cancer; Sickle Cell Anemia (based on a point mutation); HIV; Beta-Thalassemia; and ophthalmic or ocular disease—for example Leber Congenital Amaurosis (LCA)-causing Splice Defect.

In some embodiments delivery methods include: Cationic Lipid Mediated "direct" delivery of Enzyme-Guide complex (RiboNucleoProtein) and electroporation of plasmid DNA.

Inventive methods can further comprise delivery of templates, such as repair templates, which may be dsODN or ssODN, see below. Delivery of templates may be via the cotemporaneous or separate from delivery of any or all the CRISPR enzyme, guide, tracr mate or tracrRNA and via the same delivery mechanism or different. In some embodiments, it is preferred that the template is delivered together with the guide, tracr mate and/or tracrRNA and, preferably, also the CRISPR enzyme. An example may be an AAV vector where the CRISPR enzyme is SaCas9 (with the N580 mutation).

Inventive methods can further comprise: (a) delivering to the cell a double-stranded oligodeoxynucleotide (dsODN) comprising overhangs complimentary to the overhangs created by said double strand break, wherein said dsODN is integrated into the locus of interest; or —(b) delivering to the cell a single-stranded oligodeoxynucleotide (ssODN), wherein said ssODN acts as a template for homology directed repair of said double strand break. Inventive methods can be for the prevention or treatment of disease in an individual, optionally wherein said disease is caused by a defect in said locus of interest. Inventive methods can be conducted in vivo in the individual or ex vivo on a cell taken from the individual, optionally wherein said cell is returned to the individual.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or animal model and using deep sequencing the analyze the extent of modification at potential off-target genomic loci. For example, for the guide sequence targeting 5'-GAGTC-CGAGCAGAAGAAGAA-3' (SEQ ID NO: 38) in the EMX1 gene of the human genome, deep sequencing can be used to assess the level of modification at the following two off-target loci, 1: 5'-GAGTCCTAGCAGGAGAAGAA-3' (SEQ ID NO: 39) and 2: 5'-GAGTCTAAGCA-GAAGAAGAA-3' (SEQ ID NO: 40). The concentration that gives the highest level of on-target modification while minimizing the level of off-target modification should be chosen for in vivo delivery.

Inducible Systems

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465, U.S. 61/721,283 and WO 2014/018423, which is hereby incorporated by reference in its entirety.

Self-Inactivating Systems

Once all copies of a gene in the genome of a cell have been edited, continued CRISRP-Cas9 expression in that cell is no longer necessary. Indeed, sustained expression would be undesirable in case of off-target effects at unintended genomic sites, etc. Thus time-limited expression would be useful. Inducible expression offers one approach, but in addition Applicants have engineered a Self-Inactivating CRISPR-Cas9 system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self inactivating CRISPR-Cas9 system includes additional RNA (i.e., guide RNA) that targets the coding sequence for the CRISPR enzyme itself or that targets one or more non-coding guide target sequences complementary to unique sequences present in one or more of the following:

(a) within the promoter driving expression of the non-coding RNA elements,
(b) within the promoter driving expression of the Cas9 gene,
(c) within 100 bp of the ATG translational start codon in the Cas9 coding sequence,
(d) within the inverted terminal repeat (iTR) of a viral delivery vector, e.g., in the AAV genome.

Furthermore, that RNA can be delivered via a vector, e.g., a separate vector or the same vector that is encoding the CRISPR complex. When provided by a separate vector, the CRISPR RNA that targets Cas9 expression can be administered sequentially or simultaneously. When administered sequentially, the CRISPR RNA that targets Cas9 expression is to be delivered after the CRISPR RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas9 enzyme associates with a first gRNA/chiRNA capable of hybridizing to a first target, such as a genomic locus or loci of interest and undertakes the function(s) desired of the CRISPR-Cas9 system (e.g., gene engineering); and subsequently the Cas9 enzyme may then associate with the second gRNA/chiRNA capable of hybridizing to the sequence comprising at least part of the Cas9 or CRISPR cassette. Where the gRNA/chiRNA targets the sequences encoding expression of the Cas9 protein, the enzyme becomes impeded and the system becomes self inactivating. In the same manner, CRISPR RNA that targets Cas9 expression applied via, for example liposome, lipofection, particles, microvesicles as explained herein, may be administered sequentially or simultaneously. Similarly, self-inactivation may be used for inactivation of one or more guide RNA used to target one or more targets.

In some aspects, a single gRNA is provided that is capable of hybridization to a sequence downstream of a CRISPR enzyme start codon, whereby after a period of time there is a loss of the CRISPR enzyme expression. In some aspects, one or more gRNA(s) are provided that are capable of hybridization to one or more coding or non-coding regions of the polynucleotide encoding the CRISPR-Cas9 system, whereby after a period of time there is a inactivation of one or more, or in some cases all, of the CRISPR-Cas9 system. In some aspects of the system, and not to be limited by theory, the cell may comprise a plurality of CRISPR-Cas9 complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas9 system, wherein the first subset of CRISPR-Cas9 complexes mediate editing of the targeted genomic locus or loci and the second subset of CRISPR complexes eventually inactivate the CRISPR-Cas9 system, thereby inactivating further CRISPR-Cas9 expression in the cell.

Thus the invention provides a CRISPR-Cas9 system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence, The first and second complexes can use the same tracr and tracr mate, thus differing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence and (b) a CRISPR enzyme bound to a guide RNA, such that a guide RNA can hybridize to its target sequence; and the second CRISPR complex inactivates the CRISPR-Cas9 system to prevent continued expression of the CRISPR enzyme by the cell.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr and tracr mate) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

The first guide RNA can target any target sequence of interest within a genome, as described elsewhere herein. The second guide RNA targets a sequence within the vector which encodes the CRISPR Cas9 enzyme, and thereby inactivates the enzyme's expression from that vector. Thus the target sequence in the vector must be capable of inactivating expression. Suitable target sequences can be, for instance, near to or within the translational start codon for the Cas9 coding sequence, in a non-coding sequence in the promoter driving expression of the non-coding RNA elements, within the promoter driving expression of the Cas9 gene, within 100 bp of the ATG translational start codon in the Cas9 coding sequence, and/or within the inverted terminal repeat (iTR) of a viral delivery vector, e.g., in the AAV genome. A double stranded break near this region can induce a frame shift in the Cas9 coding sequence, causing a loss of protein expression. An alternative target sequence for the "self-inactivating" guide RNA would aim to edit/inactivate regulatory regions/sequences needed for the expression of the CRISPR-Cas9 system or for the stability of the vector. For instance, if the promoter for the Cas9 coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, polyadenylation sites, etc.

Furthermore, if the guide RNAs are expressed in array format, the "self-inactivating" guide RNAs that target both promoters simultaneously will result in the excision of the intervening nucleotides from within the CRISPR-Cas9 expression construct, effectively leading to its complete inactivation. Similarly, excision of the intervening nucleotides will result where the guide RNAs target both ITRs, or targets two or more other CRISPR-Cas9 components simultaneously. Self-inactivation as explained herein is applicable, in general, with CRISPR-Cas9 systems in order to provide regulation of the CRISPR-Cas9. For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cas9 shutdown.

In one aspect of the self-inactivating AAV-CRISPR-Cas9 system, plasmids that co-express one or more sgRNA targeting genomic sequences of interest (e.g. 1-2, 1-5, 1-10, 1-15, 1-20, 1-30) may be established with "self-inactivating" sgRNAs that target an SpCas9 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an sgRNA. The U6-driven sgRNAs may be designed in an array format such that multiple sgRNA sequences can be simultaneously released. When first delivered into target tissue/cells (left cell) sgRNAs begin to accumulate while Cas9 levels rise in the nucleus. Cas9 complexes with all of the sgRNAs to mediate genome editing and self-inactivation of the CRISPR-Cas9 plasmids.

One aspect of a self-inactivating CRISPR-Cas9 system is expression of singly or in tandam array format from 1 up to 4 or more different guide sequences; e.g. up to about 20 or about 30 guides sequences. Each individual self inactivating guide sequence may target a different target. Such may be processed from, e.g. one chimeric pol3 transcript. Pol3 promoters such as U6 or H1 promoters may be used. Pol12 promoters such as those mentioned throughout herein. Inverted terminal repeat (iTR) sequences may flank the Pol3 promoter—sgRNA(s)-Pol2 promoter-Cas9.

One aspect of a chimeric, tandem array transcript is that one or more guide(s) edit the one or more target(s) while one or more self inactivating guides inactivate the CRISPR-Cas9 system. Thus, for example, the described CRISPR-Cas9 system for repairing expansion disorders may be directly combined with the self-inactivating CRISPR-Cas9 system described herein. Such a system may, for example, have two guides directed to the target region for repair as well as at least a third guide directed to self-inactivation of the CRISPR-Cas9. Reference is made to Application Ser. No. PCT/US2014/069897, entitled "Compositions And Methods Of Use Of Crispr-Cas Systems In Nucleotide Repeat Disorders," published Dec. 12, 2014 as WO/2015/089351.

The guideRNA may be a control guide. For example it may be engineered to target a nucleic acid sequence encoding the CRISPR Enzyme itself, as described in US2015232881A1, the disclosure of which is hereby incorporated by reference. In some embodiments, a system or composition may be provided with just the guideRNA engineered to target the nucleic acid sequence encoding the CRISPR Enzyme. In addition, the system or composition may be provided with the guideRNA engineered to target the nucleic acid sequence encoding the CRISPR Enzyme, as well as nucleic acid sequence encoding the CRISPR Enzyme and, optionally a second guide RNA and, further optionally, a repair template. The second guideRNA may be the primary target of the CRISPR system or composition (such a therapeutic, diagnostic, knock out etc. as defined herein). In this way, the system or composition is self-inactivating. This is exemplified in relation to Cas9 in US2015232881A1 (also published as WO2015070083 (A1), referenced elsewhere herein).

Kits

In one aspect, the invention provides kits containing any one or more of the elements disclosed in the above methods and compositions. In some embodiments, the kit comprises a vector system as taught herein and instructions for using the kit. Elements may be provided individually or in combinations, and may be provided in any suitable container, such as a vial, a bottle, or a tube. The kits may include the sgRNA and the unbound protector strand as described herein. The kits may include the sgRNA with the protector strand bound to at least partially to the guide sequence (i.e. pgRNA). Thus the kits may include the pgRNA in the form of a partially double stranded nucleotide sequence as described here. In some embodiments, the kit includes instructions in one or more languages, for example in more than one language. The instructions may be specific to the applications and methods described herein.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allow to provide all elements of the systems of the invention.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR effector protein complexed with a guide sequence hybridized to a target sequence within the target polynucleotide. In certain embodiments, a direct repeat sequence is linked to the guide sequence.

In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell.

The break created by the CRISPR complex can be repaired by a repair processes such as the error prone non-homologous end joining (NHEJ) pathway or the high fidelity homology directed repair (HDR). During these repair process, an exogenous polynucleotide template can be introduced into the genome sequence. In some methods, the HDR process is used to modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome.

Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 10% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In an exemplary method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template.

In other embodiments, this invention provides a method of modifying expression of a polynucleotide in a eukaryotic cell. The method comprises increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). In some methods, the inactivation of a target sequence results in "knockout" of the target sequence.

Exemplary Methods of Using of CRISPR Cas9 System

The invention provides a non-naturally occurring or engineered composition, or one or more polynucleotides encoding components of said composition, or vector or delivery systems comprising one or more polynucleotides encoding components of said composition for use in a modifying a target cell in vivo, ex vivo or in vitro and, may be conducted in a manner alters the cell such that once modified the progeny or cell line of the CRISPR modified cell retains the altered phenotype. The modified cells and progeny may be part of a multi-cellular organism such as a plant or animal with ex vivo or in vivo application of CRISPR system to desired cell types. The CRISPR invention may be a therapeutic method of treatment. The therapeutic method of treatment may comprise gene or genome editing, or gene therapy.

Modifying a Target with CRISPR-Cas9 System or Complex

In one aspect, the invention provides for methods of modifying a target polynucleotide in a eukaryotic cell, which may be in vivo. ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized or hybridizable to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized or hybridizable to a target sequence, wherein said guide sequence may be linked to a tracr mate sequence which in turn may hybridize to a tracr sequence.

Similar considerations and conditions apply as above for methods of modifying a target polynucleotide. Thus in any of the non-naturally-occurring CRISPR enzymes described herein comprise at least one modification and whereby the enzyme has certain improved capabilities. In particular, any of the enzymes are capable of forming a CRISPR complex with a guide RNA. When such a complex forms, the guide RNA is capable of binding to a target polynucleotide sequence and the enzyme is capable of modifying a target locus. In addition, the enzyme in the CRISPR complex has reduced capability of modifying one or more off-target loci as compared to an unmodified enzyme.

In addition, the modified CRISPR enzymes described herein encompass enzymes whereby in the CRISPR complex the enzyme has increased capability of modifying the one or more target loci as compared to an unmodified enzyme. Such function may be provided separate to or provided in combination with the above-described function of reduced capability of modifying one or more off-target loci. Any such enzymes may be provided with any of the further modifications to the CRISPR enzyme as described herein, such as in combination with any activity provided by one or more associated heterologous functional domains, any further mutations to reduce nuclease activity and the like.

In advantageous embodiments of the invention, the modified CRISPR enzyme is provided with reduced capability of modifying one or more off-target loci as compared to an unmodified enzyme and increased capability of modifying the one or more target loci as compared to an unmodified enzyme. In combination with further modifications to the enzyme, significantly enhanced specificity may be achieved. For example, combination of such advantageous embodiments with one or more additional mutations is provided wherein the one or more additional mutations are in one or more catalytically active domains. Such further catalytic mutations may confer nickase functionality as described in detail elsewhere herein. In such enzymes, enhanced specificity may be achieved due to an improved specificity in terms of enzyme activity.

Modifications to reduce off-target effects and/or enhance on-target effects as described above may be made to amino acid residues located in a positively-charged region/groove situated between the RuvC-III and HNH domains. It will be appreciated that any of the functional effects described above may be achieved by modification of amino acids within the aforementioned groove but also by modification of amino acids adjacent to or outside of that groove.

Additional functionalities which may be engineered into modified CRISPR enzymes as described herein include the following. 1. modified CRISPR enzymes that disrupt DNA: protein interactions without affecting protein tertiary or secondary structure. This includes residues that contact any part of the RNA:DNA duplex. 2. modified CRISPR enzymes that weaken intra-protein interactions holding Cas9 in conformation essential for nuclease cutting in response to DNA binding (on or off target). For example: a modification that mildly inhibits, but still allows, the nuclease conformation of the HNH domain (positioned at the scissile phosphate).

3. modified CRISPR enzymes that strengthen intra-protein interactions holding Cas9 in a conformation inhibiting nuclease activity in response to DNA binding (on or off targets). For example: a modification that stabilizes the HNH domain in a conformation away from the scissile phosphate. Any such additional functional enhancement may be provided in combination with any other modification to the CRISPR enzyme as described in detail elsewhere herein.

Any of the herein described improved functionalities may be made to any CRISPR enzyme, such as a Cas9 enzyme. Cas9 enzymes described herein are derived from Cas9 enzymes from S. pyogenes and S. aureus. However, it will be appreciated that any of the functionalities described herein may be engineered into Cas9 enzymes from other orthologs, including chimeric enzymes comprising fragments from multiple orthologs.

Nucleic Acids, Amino Acids and Proteins. Regulatory Sequences. Vectors. Etc

The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridizing to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 650° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life-eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In aspects of the invention the term "guide RNA", refers to the polynucleotide sequence comprising one or more of a putative or identified tracr sequence and a putative or identified crRNA sequence or guide sequence. In particular embodiments, the "guide RNA" comprises a putative or identified crRNA sequence or guide sequence. In further embodiments, the guide RNA does not comprise a putative or identified tracr sequence.

As used herein the term "wild type" is a term of the art understood by skilled persons and means the typical form of an organism, strain, gene or characteristic as it occurs in nature as distinguished from mutant or variant forms. A "wild type" can be a base line.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. In all aspects and embodiments, whether they include these terms or not, it will be understood that, preferably, the may be optional and thus preferably included or not preferably not included. Furthermore, the terms "non-naturally occurring" and "engineered" may be used interchangeably and so can therefore be used alone or in combination and one or other may replace mention of both together. In particular, "engineered" is preferred in place of "non-naturally occurring" or "non-naturally occurring and/or engineered."

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4$^{th}$ Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50, FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

| Set | | Sub-set | |
|---|---|---|---|
| Hydrophobic | FWYHKMILVAGC | Aromatic | FWYH |
| | | Aliphatic | ILV |

-continued

| Set | | Sub-set | |
|---|---|---|---|
| Polar | WYHKREDCSTNQ | Charged | HKRED |
| | | Positively charged | HKR |
| | | Negatively charged | ED |
| Small | VCAGSPTND | Tiny | AGS |

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent," "therapeutic capable agent," or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)), the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Homology modelling: Corresponding residues in other Cas9 orthologs can be identified by the methods of Zhang et al., 2012 (Nature; 490(7421): 556-60) and Chen et al., 2015 (PLoS Comput Biol; 11(5): e1004248)—a computational protein-protein interaction (PPI) method to predict interactions mediated by domain-motif interfaces. PrePPI (Predicting PPI), a structure based PPI prediction method, combines structural evidence with non-structural evidence using a Bayesian statistical framework. The method involves taking a pair a query proteins and using structural alignment to identify structural representatives that correspond to either their experimentally determined structures or homology models. Structural alignment is further used to identify both close and remote structural neighbors by considering global and local geometric relationships. Whenever two neighbors of the structural representatives form a complex reported in the Protein Data Bank, this defines a template for modelling the interaction between the two query proteins. Models of the complex are created by superimposing the representative structures on their corresponding structural neighbor in the template. This approach is further described in Dey et al., 2013 (Prot Sci; 22: 359-66).

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically comprises, consists essentially of, or consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 48). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA).

In some embodiments, a loop in the guide RNA is provided. This may be a stem loop or a tetra loop. The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit Pβ-globin (Proc. Natl. Acad. Sci. USA., Vol. 78(3), p.

1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491, 026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g., nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRITS (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula. MAethanobacterium, Methanococcus, Methanosarcina, Methanopyrus, Pyrococcus, Picrophilus, Thermoplasma, Corynebacterium, Mycobacterium, Streptomyces, Apquifex, Porphyromonas, Chlorobium, Thermus, Bacillus, Listeria, Staphylococcus, Clostridium, hermoanaerobacter, Mycoplasma, Fusobacterium, Azarcus, Chromobacterium, Neisseria, Nitrosomonas, Desulfovibrio, Geobacter, Mvxococcus, Campylobacter. Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "nucleic acid-targeting system" as used in the present application refers collectively to transcripts and other elements involved in the expression of or directing the activity of nucleic acid-targeting CRISPR-associated ("Cas") genes (also referred to herein as an effector protein), including sequences encoding a nucleic acid-targeting Cas9 (effector) protein and a guide RNA (comprising crRNA sequence and a trans-activating CRISPR-Cas9 system RNA (tracrRNA) sequence), or other sequences and transcripts from a nucleic acid-targeting CRISPR locus. In some embodiments, one or more elements of a nucleic acid-targeting system are derived from a Type II nucleic acid-targeting CRISPR system. In some embodiments, one or more elements of a nucleic acid-targeting system is derived from a particular organism comprising an endogenous nucleic acid-targeting CRISPR system. In general, a nucleic acid-targeting system is characterized by elements that promote the formation of a nucleic acid-targeting complex at the site of a target sequence. In the context of formation of a nucleic acid-targeting complex, "target sequence" refers to a sequence to which a guide sequence is designed to have complementarity, where hybridization between a target sequence and a guide RNA promotes the formation of a DNA or RNA-targeting complex. Full complementarity is not necessarily required, provided there is sufficient complementarity to cause hybridization and promote formation of a nucleic acid-targeting complex. A target sequence may comprise RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing RNA" or "editing sequence". In aspects of the invention, an exogenous template RNA may be referred to as an editing template. In an aspect of the invention the recombination is homologous recombination.

Typically, in the context of an endogenous nucleic acid-targeting system, formation of a nucleic acid-targeting complex (comprising a guide RNA hybridized to a target sequence and complexed with one or more nucleic acid-targeting effector proteins) results in cleavage of one or both RNA strands in or near (e.g. within 1, 2, 3, 4, 5, 6, 7, 8, 9, 10, 20, 50, or more base pairs from) the target sequence. In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector protein and a guide RNA could each be operably linked to separate regulatory elements on separate vectors. Alternatively, two or more of the elements expressed from the same or different regulatory elements, may be combined in a single vector, with one or more additional vectors providing any components of the nucleic acid-targeting system not included in the first vector. nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector protein and a guide RNA embedded within one or more intron sequences (e.g. each in a different intron, two or more in at least one intron, or all in a single intron). In some embodiments, the nucleic acid-targeting effector protein and guide RNA are operably linked to and expressed from the same promoter.

In general, a guide sequence is any polynucleotide sequence having sufficient complementarity with a target polynucleotide sequence to hybridize with the target sequence and direct sequence-specific binding of a nucleic acid-targeting complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a nucleic acid-targeting complex to a target sequence may be assessed by any suitable assay. For example, the components of a nucleic acid-targeting system sufficient to form a nucleic acid-targeting complex, including the guide sequence to be tested, may be provided to a host cell having the corresponding target sequence, such as by transfection with vectors encoding the components of the nucleic acid-targeting CRISPR sequence, followed by an assessment of preferential cleavage within or in the vicinity of the target sequence, such as by Surveyor assay as described herein. Similarly, cleavage of a target polynucleotide sequence (or a sequence in the vicinity thereof) may be evaluated in a test tube by providing the target sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art.

A guide sequence may be selected to target any target sequence. In some embodiments, the target sequence is a sequence within a gene transcript or mRNA.

In some embodiments, the target sequence is a sequence within a genome of a cell.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and PA Carr and GM Church, 2009, *Nature Biotechnology* 27(12): 1151-62). Further algorithms may be found in U.S. application Ser. No. 61/836,080; incorporated herein by reference.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. In some embodiments, the nucleic acid-targeting effector protein is part of a fusion protein comprising one or more heterologous protein domains (e.g., about or more than about 1, 2, 3, 4, 5, 6, 7, 8, 9, 10, or more domains in addition to the nucleic acid-targeting effector protein).

In some embodiments, the CRISPR enzyme is part of a fusion protein comprising one or more heterologous protein domains (e.g., about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags. FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283 and WO 2014/018423 and U.S. Pat. Nos. 8,889,418, 8,895,308, US20140186919, US20140242700, US20140273234, US20140335620, WO2014093635, which is hereby incorporated by reference in its entirety.

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a nucleic acid-targeting effector protein in combination with (and optionally complexed with) a guide RNA is delivered to a cell. Conventional viral and non-viral based gene transfer methods can be used to introduce nucleic acids in mammalian cells or target tissues. Such methods can be used to administer nucleic acids encoding components of a nucleic acid-targeting system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Models of Genetic and Epigenetic Conditions

A method of the invention may be used to create a plant, an animal or cell that may be used to model and/or study genetic or epigenetic conditions of interest, such as a through a model of mutations of interest or a as a disease model. As used herein, "disease" refers to a disease, disorder, or indication in a subject. For example, a method of the invention may be used to create an animal or cell that comprises a modification in one or more nucleic acid sequences associated with a disease, or a plant, animal or cell in which the expression of one or more nucleic acid sequences associated with a disease are altered. Such a nucleic acid sequence may encode a disease associated protein sequence or may be a disease associated control sequence. Accordingly, it is understood that in embodiments of the invention, a plant, subject, patient, organism or cell can be a non-human subject, patient, organism or cell. Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants. In the instance where the cell is in cultured, a cell line may be established if appropriate culturing conditions are met and preferably if the cell is suitably adapted for this purpose (for instance a stem cell). Bacterial cell lines produced by the invention are also envisaged. Hence, cell lines are also envisaged.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method comprises modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

In another embodiment, this invention provides a method of developing a biologically active agent that modulates a cell signaling event associated with a disease gene. The method comprises contacting a test compound with a cell comprising one or more vectors that drive expression of one or more of a CRISPR enzyme, a guide sequence linked to a tracr mate sequence, and a tracr sequence, and detecting a change in a readout that is indicative of a reduction or an augmentation of a cell signaling event associated with, e.g., a mutation in a disease gene contained in the cell.

A cell model or animal model can be constructed in combination with the method of the invention for screening a cellular function change. Such a model may be used to study the effects of a genome sequence modified by the CRISPR complex of the invention on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but serve to show the broad applicability of the invention across genes and corresponding models.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorocoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody.

The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2a). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) Clinical Immunology 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme.

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427 both entitled SYSTEMS METHODS AND COMPOSITIONS FOR SEQUENCE MANIPULATION filed on Dec. 12, 2012 and Jan. 2, 2013, respectively, and PCT Application PCT/US2013/074667, entitled DELIVERY, ENGINEERING AND OPTIMIZATION OF SYSTEMS, METHODS AND COMPOSITIONS FOR SEQUENCE MANIPULATION AND THERAPEUTIC APPLICATIONS, filed Dec. 12, 2013, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Genome-Wide Knock-Out Screening

The CRISPR-Cas9 proteins and systems described herein can be used to perform efficient and cost effective functional genomic screens. Such screens can utilize CRISPR-Cas9 genome wide libraries. Such screens and libraries can provide for determining the function of genes, cellular pathways genes are involved in, and how any alteration in gene expression can result in a particular biological process. An advantage of the present invention is that the CRISPR system avoids off-target binding and its resulting side effects. This is achieved using systems arranged to have a high degree of sequence specificity for the target DNA.

A genome wide library may comprise a plurality of CRISPR-Cas9 system guide RNAs, as described herein, comprising guide sequences that are capable of targeting a plurality of target sequences in a plurality of genomic loci in a population of eukaryotic cells. The population of cells may be a population of embryonic stem (ES) cells. The target sequence in the genomic locus may be a non-coding sequence. The non-coding sequence may be an intron, regulatory sequence, splice site, 3' UTR, 5' UTR, or polyadenylation signal. Gene function of one or more gene products may be altered by said targeting. The targeting may result in a knockout of gene function. The targeting of a gene product may comprise more than one guide RNA. A gene product may be targeted by 2, 3, 4, 5, 6, 7, 8, 9, or 10 guide RNAs, preferably 3 to 4 per gene. Off-target modifications may be minimized by exploiting the staggered double strand breaks generated by Cas9 effector protein complexes or by utilizing methods analogous to those used in CRISPR-Cas9 systems. (See, e.g., DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013)), incorporated herein by reference. The targeting may be of about 100 or more sequences. The targeting may be of about 1000 or more sequences. The targeting may be of about 20,000 or more sequences. The targeting may be of the entire genome. The targeting may be of a panel of target sequences focused on a relevant or desirable pathway. The pathway may be an immune pathway. The pathway may be a cell division pathway.

One aspect of the invention comprehends a genome wide library that may comprise a plurality of CRISPR-Cas9 system guide RNAs that may comprise guide sequences that are capable of targeting a plurality of target sequences in a plurality of genomic loci, wherein said targeting results in a knockout of gene function. This library may potentially comprise guide RNAs that target each and every gene in the genome of an organism.

In some embodiments of the invention the organism or subject is a eukaryote (including mammal including human) or a non-human eukaryote or a non-human animal or a non-human mammal. In some embodiments, the organism or subject is a non-human animal, and may be an arthropod, for example, an insect, or may be a nematode. In some methods of the invention the organism or subject is a plant. In some methods of the invention the organism or subject is a mammal or a non-human mammal. A non-human mammal may be for example a rodent (preferably a mouse or a rat), an ungulate, or a primate. In some methods of the invention the organism or subject is algae, including microalgae, or is a fungus.

The knockout of gene function may comprise: introducing into each cell in the population of cells a vector system of one or more vectors comprising an engineered, non-naturally occurring CRISPR-Cas9 system comprising I. a Cas9 protein, and II. one or more guide RNAs, wherein components I and II may be same or on different vectors of the system, integrating components I and II into each cell, wherein the guide sequence targets a unique gene in each cell, wherein the Cas9 protein is operably linked to a regulatory element, wherein when transcribed, the guide RNA comprising the guide sequence directs sequence-specific binding of a CRISPR-Cas9 system to a target sequence in the genomic loci of the unique gene, inducing cleavage of the genomic loci by the Cas9 protein, and confirming different knockout mutations in a plurality of unique genes in each cell of the population of cells thereby generating a gene knockout cell library. The invention comprehends that the population of cells is a population of eukaryotic cells, and in a preferred embodiment, the population of cells is a population of embryonic stem (ES) cells.

The one or more vectors may be plasmid vectors. The vector may be a single vector comprising Cas9, a sgRNA, and optionally, a selection marker into target cells. Not being bound by a theory, the ability to simultaneously deliver Cas9 and sgRNA through a single vector enables application to any cell type of interest, without the need to first generate cell lines that express Cas9. The regulatory element may be an inducible promoter. The inducible promoter may be a doxycycline inducible promoter. In some methods of the invention the expression of the guide sequence is under the control of the T7 promoter and is driven by the expression of T7 polymerase. The confirming of different knockout mutations may be by whole exome sequencing. The knockout mutation may be achieved in 100 or more unique genes. The knockout mutation may be achieved in 1000 or more unique genes. The knockout mutation may be achieved in 20,000 or more unique genes. The knockout mutation may be achieved in the entire genome. The knockout of gene function may be achieved in a plurality of unique genes which function in a particular physiological pathway or condition. The pathway or condition may be an immune pathway or condition. The pathway or condition may be a cell division pathway or condition.

The invention also provides kits that comprise the genome wide libraries mentioned herein. The kit may comprise a single container comprising vectors or plasmids comprising the library of the invention. The kit may also comprise a panel comprising a selection of unique CRISPR-Cas9 system guide RNAs comprising guide sequences from the library of the invention, wherein the selection is indicative of a particular physiological condition. The invention comprehends that the targeting is of about 100 or more sequences, about 1000 or more sequences or about 20,000 or more sequences or the entire genome. Furthermore, a panel of target sequences may be focused on a relevant or desirable pathway, such as an immune pathway or cell division.

In an additional aspect of the invention, a Cas9 enzyme may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (D10 and H840) in the RuvC and HNH catalytic domains, respectively. Further mutations have been characterized. In one aspect of the invention, the functional domain may be a transcriptional activation domain, which may be VP64. In other aspects of the invention, the functional domain may be a transcriptional repressor domain, which may be KRAB or SID4X. Other aspects of the invention relate to the mutated Cas9 enzyme being fused to domains which include but are not limited to a transcriptional activator, repressor, a recombinase, a transposase, a histone remodeler, a demethylase, a DNA methyltransferase, a cryptochrome, a light inducible/controllable domain or a chemically inducible/controllable domain. Some methods of the invention can include inducing expression of targeted genes. In one embodiment, inducing expression by targeting a plurality of target sequences in a plurality of genomic loci in a population of eukaryotic cells is by use of a functional domain.

Useful in the practice of the instant invention, reference is made to:

Genome-Scale CRISPR-Cas9 Knockout Screening in Human Cells. Shalem, O., Sanjana, N E., Hartenian, E., Shi, X., Scott, DA., Mikkelson, T., Heckl, D., Ebert, BL., Root, D E., Doench, JG., Zhang, F. Science Dec. 12. (2013). [Epub ahead of print]; Published in final edited form as: Science. 2014 Jan. 3; 343(6166): 84-87.

Shalem et al. involves a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Reference is also made to US patent publication number US20140357530; and PCT Patent Publication WO2014093701, hereby incorporated herein by reference. Reference is also made to NIH Press Release of Oct. 22, 2015 entitled, "Researchers identify potential alternative to CRISPR-Cas genome editing tools: New Cas enzymes shed light on evolution of CRISPR-Cas systems, which is incorporated by reference.

Functional Alteration and Screening

In another aspect, the present invention provides for a method of functional evaluation and screening of genes. The use of the CRISPR system of the present invention to precisely deliver functional domains, to activate or repress genes or to alter epigenetic state by precisely altering the methylation site on a specific locus of interest, can be with one or more guide RNAs applied to a single cell or population of cells or with a library applied to genome in a pool of cells ex vivo or in vivo comprising the administration or expression of a library comprising a plurality of guide RNAs (sgRNAs) and wherein the screening further comprises use of a Cas9 effector protein, wherein the CRISPR complex comprising the Cas9 effector protein is modified to comprise a heterologous functional domain. In an aspect the invention provides a method for screening a genome comprising the administration to a host or expression in a host in vivo of a library. In an aspect the invention provides a method as herein discussed further comprising an activator administered to the host or expressed in the host. In an aspect the invention provides a method as herein discussed wherein the activator is attached to a Cas9 effector protein. In an aspect the invention provides a method as herein discussed wherein the activator is attached to the N terminus or the C terminus of the Cas9 effector protein. In an aspect the invention provides a method as herein discussed wherein the activator is attached to a sgRNA loop. In an aspect the invention provides a method as herein discussed further comprising a repressor administered to the host or expressed in the host. In an aspect the invention provides a method as herein discussed, wherein the screening comprises affecting and detecting gene activation, gene inhibition, or cleavage in the locus.

In an aspect, the invention provides efficient on-target activity and minimizes off target activity. In an aspect, the invention provides efficient on-target cleavage by Cas9 effector protein and minimizes off-target cleavage by the Cas9 effector protein. In an aspect, the invention provides guide specific binding of Cas9 effector protein at a gene locus without DNA cleavage. Accordingly, in an aspect, the invention provides target-specific gene regulation. In an aspect, the invention provides guide specific binding of Cas9 effector protein at a gene locus without DNA cleavage. Accordingly, in an aspect, the invention provides for cleavage at one gene locus and gene regulation at a different gene locus using a single Cas9 effector protein. In an aspect, the invention provides orthogonal activation and/or inhibition and/or cleavage of multiple targets using one or more Cas9 effector protein and/or enzyme.

In an aspect the invention provides a method as herein discussed, wherein the host is a eukaryotic cell. In an aspect the invention provides a method as herein discussed, wherein the host is a mammalian cell. In an aspect the invention provides a method as herein discussed, wherein the host is a non-human eukaryote. In an aspect the invention provides a method as herein discussed, wherein the non-human eukaryote is a non-human mammal. In an aspect the invention provides a method as herein discussed, wherein the non-human mammal is a mouse. An aspect the invention provides a method as herein discussed comprising the delivery of the Cas9 effector protein complexes or component(s) thereof or nucleic acid molecule(s) coding therefor, wherein said nucleic acid molecule(s) are operatively linked to regulatory sequence(s) and expressed in vivo. In an aspect the invention provides a method as herein discussed wherein the expressing in vivo is via a lentivirus, an adenovirus, or an AAV. In an aspect the invention provides a method as herein discussed wherein the delivery is via a particle, a nanoparticle, a lipid or a cell penetrating peptide (CPP).

In an aspect the invention provides a pair of CRISPR complexes comprising Cas9 effector protein, each comprising a guide RNA (sgRNA) comprising a guide sequence capable of hybridizing to a target sequence in a genomic locus of interest in a cell, wherein at least one loop of each sgRNA is modified by the insertion of distinct RNA sequence(s) that bind to one or more adaptor proteins, and wherein the adaptor protein is associated with one or more functional domains, wherein each sgRNA of each Cas9 effector protein complex comprises a functional domain having a DNA cleavage activity. In an aspect the invention provides paired Cas9 effector protein complexes as herein-discussed, wherein the DNA cleavage activity is due to a Fok1 nuclease.

In an aspect the invention provides a method for cutting a target sequence in a genomic locus of interest comprising delivery to a cell of the Cas9 effector protein complexes or component(s) thereof or nucleic acid molecule(s) coding therefor, wherein said nucleic acid molecule(s) are operatively linked to regulatory sequence(s) and expressed in vivo. In an aspect the invention provides a method as herein-discussed wherein the delivery is via a lentivirus, an adenovirus, or an AAV. In an aspect the invention provides a method as herein-discussed or paired Cas9 effector protein complexes as herein-discussed wherein the target sequence for a first complex of the pair is on a first strand of double stranded DNA and the target sequence for a second complex of the pair is on a second strand of double stranded DNA. In an aspect the invention provides a method as herein-discussed or paired Cas9 effector protein complexes as herein-discussed wherein the target sequences of the first and second complexes are in proximity to each other such that the DNA is cut in a manner that facilitates homology directed repair. In an aspect a herein method can further include introducing into the cell template DNA. In an aspect a herein method or herein paired Cas9 effector protein complexes can involve wherein each Cas9 effector protein complex has a Cas9 effector enzyme that is mutated such that it has no more than about 5% of the nuclease activity of the Cas9 effector enzyme that is not mutated.

In an aspect the invention provides a library, method or complex as herein-discussed wherein the sgRNA is modified to have at least one non-coding functional loop, e.g., wherein the at least one non-coding functional loop is repressive; for instance, wherein the at least one non-coding functional loop comprises Alu.

In one aspect, the invention provides a method for altering or modifying expression of a gene product. The said method may comprise introducing into a cell containing and expressing a DNA molecule encoding the gene product an engineered, non-naturally occurring CRISPR system comprising a Cas9 effector protein and guide RNA that targets the DNA molecule, whereby the guide RNA targets the DNA molecule encoding the gene product and the Cas9 effector protein cleaves the DNA molecule encoding the gene product, whereby expression of the gene product is altered; and, wherein the Cas9 effector protein and the guide RNA do not naturally occur together. The invention comprehends the guide RNA comprising a guide sequence linked to a direct repeat sequence. The invention further comprehends the Cas9 effector protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In some embodiments, one or more functional domains are associated with the CRISPR enzyme, for example a Type II Cas9 enzyme.

In some embodiments, one or more functional domains are associated with an adaptor protein, for example as used with the modified guides of Konnerman et al. (Nature 517, 583-588, 29 Jan. 2015).

In some embodiments, one or more functional domains are associated with an dead sgRNA (dRNA). In some embodiments, a dRNA complex with active cas9 directs gene regulation by a functional domain at on gene locus while an sgRNA directs DNA cleavage by the active cas9 at another locus, for example as described by Dahlman et al., 'Orthogonal gene control with a catalytically active Cas9 nuclease' (in press). In some embodiments, dRNAs are selected to maximize selectivity of regulation for a gene locus of interest compared to off-target regulation. In some embodiments, dRNAs are selected to maximize target gene regulation and minimize target cleavage For the purposes of the following discussion, reference to a functional domain could be a functional domain associated with the CRISPR enzyme or a functional domain associated with the adaptor protein.

In the practice of the invention, loops of the sgRNA may be extended, without colliding with the Cas9 protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease. In some preferred embodiments, the functional domain is a transcriptional activation domain, such as, without limitation, VP64, p65, MyoD1, HSF1, RTA, SET7/9 or a histone acetyltransferase. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. Other references herein to activation (or activator) domains in respect of those associated with the CRISPR enzyme include any known transcriptional activation domain and specifically VP64, p65, MyoD1, HSF1, RTA, SET7/9 or a histone acetyltransferase.

In some embodiments, the one or more functional domains is a transcriptional repressor domain. In some embodiments, the transcriptional repressor domain is a KRAB domain. In some embodiments, the transcriptional repressor domain is a NuE domain, NcoR domain, SID domain or a SID4X domain.

In some embodiments, the one or more functional domains have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains. Histone acetyltransferases are preferred in some embodiments.

In some embodiments, the DNA cleavage activity is due to a nuclease. In some embodiments, the nuclease comprises a Fok1 nuclease. See, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In some embodiments, the one or more functional domains is attached to the CRISPR enzyme so that upon binding to the sgRNA and target the functional domain is in a spatial orientation allowing for the functional domain to function in its attributed function.

In some embodiments, the one or more functional domains is attached to the adaptor protein so that upon binding of the CRISPR enzyme to the sgRNA and target, the functional domain is in a spatial orientation allowing for the functional domain to function in its attributed function.

In an aspect the invention provides a composition as herein discussed wherein the one or more functional domains is attached to the CRISPR enzyme or adaptor protein via a linker, optionally a GlySer linker, as discussed herein.

Endogenous transcriptional repression is often mediated by chromatin modifying enzymes such as histone methyltransferases (HMTs) and deacetylases (HDACs). Repressive histone effector domains are known and an exemplary list is provided below. In the exemplary table, preference was given to proteins and functional truncations of small size to facilitate efficient viral packaging (for instance via AAV). In general, however, the domains may include HDACs, histone methyltransferases (HMTs), and histone acetyltransferase (HAT) inhibitors, as well as HDAC and HMT recruiting proteins. The functional domain may be or include, in some embodiments, HDAC Effector Domains, HDAC Recruiter Effector Domains, Histone Methyltransferase (HMT) Effector Domains, Histone Methyltransferase (HMVT) Recruiter Effector Domains, or Histone Acetyltransferase Inhibitor Effector Domains.

| HDAC Effector Domains | | | | | | | | |
|---|---|---|---|---|---|---|---|---|
| Subtype/Complex | Name | Substrate (if known) | Modification (if known) | Organism | Full size (aa) | Selected truncation (aa) | Final size (aa) | Catalytic domain |
| HDAC I | HDAC8 | — | — | X. laevis | 325 | 1-325 | 325 | 1-272: HDAC |
| HDAC I | RPD3 | — | — | S. cerevisiae | 433 | 19-340 (Vannier) | 322 | 19-331: HDAC |
| HDAC IV | MesoLo4 | — | — | M. loti | 300 | 1-300 (Gregoretti) | 300 | — |
| HDAC IV | HDAC11 | — | — | H. sapiens | 347 | 1-347 (Gao) | 347 | 14-326: HDAC |
| HD2 | HDT1 | — | — | A. thaliana | 245 | 1-211 (Wu) | 211 | — |
| SIRT I | SIRT3 | H3K9Ac H4K16Ac H3K56Ac | — | H. sapiens | 399 | 143-399 (Scher) | 257 | 126-382: SIRT |
| SIRT I | HST2 | — | — | C. albicans | 331 | 1-331 (Hnisz) | 331 | — |
| SIRT I | CobB | — | — | E. coli (K12) | 242 | 1-242 (Landry) | 242 | — |
| SIRT I | HST2 | — | — | S. cerevisiae | 357 | 8-298 (Wilson) | 291 | — |
| SIRT III | SIRT5 | H4K8Ac H4K16Ac | — | H. sapiens | 310 | 37-310 (Gertz) | 274 | 41-309: SIRT |
| SIRT III | Sir2A | — | — | P. falciparum | 273 | 1-273 (Zhu) | 273 | 19-273: SIRT |
| SIRT IV | SIRT6 | H3K9Ac H3K56Ac | — | H. sapiens | 355 | 1-289 (Tennen) | 289 | 35-274: SIRT |

Accordingly, the repressor domains of the present invention may be selected from histone methyltransferases (HMTs), histone deacetylases (HDACs), histone acetyltransferase (HAT) inhibitors, as well as HDAC and HMT recruiting proteins.

The HDAC domain may be any of those in the table above, namely: HDAC8, RPD3, MesoLo4, HDAC11, HDT1, SIRT3, HST2, CobB, HST2, SIRT5, Sir2A, or SIRT6.

In some embodiment, the functional domain may be a HDAC Recruiter Effector Domain. Preferred examples include those in the Table below, namely MeCP2, MBD2b, Sin3a, NcoR, SALL1, RCOR1. NcoR is exemplified in the present Examples and, although preferred, it is envisaged that others in the class will also be useful.

Table of HDAC Recruiter Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeCP2 | — | — | R. norvegicus | 492 | 207-492 (Nan) | 286 | — |
| Sin3a | MBD2b | — | — | H. sapiens | 262 | 45-262 (Boeke) | 218 | — |
| Sin3a | Sin3a | — | — | H. sapiens | 1273 | 524-851 (Laherty) | 328 | 627-829: HDAC1 interaction |
| NcoR | NcoR | — | — | H. sapiens | 2440 | 420-488 (Zhang) | 69 | — |
| NuRD | SALL1 | — | — | M. musculus | 1322 | 1-93 (Lauberth) | 93 | — |
| CoREST | RCOR1 | — | — | H. sapiens | 482 | 81-300 (Gu, Ouyang) | 220 | — |

In some embodiment, the functional domain may be a Methyltransferase (HMT) Effector Domain. Preferred examples include those in the Table below, namely NUE, vSET, EHMT2/G9A, SUV39H1, dim-5, KYP, SUVR4, SET4, SET1, SETD8, and TgSET8. NUE is exemplified in the present Examples and, although preferred, it is envisaged that others in the class will also be useful.

Table of Histone Methyltransferase (HMT) Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| SET | NUE | H2B, H3, H4 | — | C. trachomatis | 219 | 1-219 (Pennini) | 219 | — |
| SET | vSET | — | H3K27me3 | P. bursaria chlorella virus | 119 | 1-119 (Mujtaba) | 119 | 4-112: SET2 |
| SUV39 family | EHMT2/G9A | H1.4K2, H3K9, H3K27 | H3K9me1/2, H1K25me1 | M. musculus | 1263 | 969-1263 (Tachibana) | 295 | 1025-1233: preSET, SET, postSET |
| SUV39 | SUV39H1 | — | H3K9me2/3 | H. sapiens | 412 | 79-412 (Snowden) | 334 | 172-412: preSET, SET, postSET |
| Suvar3-9 | dim-5 | — | H3K9me3 | N. crassa | 331 | 1-331 (Rathert) | 331 | 77-331: preSET, SET, postSET |
| Suvar3-9 (SUVH subfamily) | KYP | — | H3K9me1/2 | A. thaliana | 624 | 335-601 | 267 (Jackson) | — |
| Suvar3-9 (SUVR subfamily) | SUVR4 | H3K9me1 | H3K9me2/3 | A. thaliana | 492 | 180-492 | 313 (Thorstensen) | 192-462: preSET, SET, postSET |
| Suvar4-20 | SET4 | — | H4K20me3 | C. elegans | 288 | 1-288 (Vielle) | 288 | — |
| SET8 | SET1 | — | H4K20me1 | C. elegans | 242 | 1-242 (Vielle) | 242 | — |
| SET8 | SETD8 | — | H4K20me1 | H. sapiens | 393 | 185-393 (Couture) | 209 | 256-382: SET |
| SET8 | TgSET8 | — | H4K20me1/2/3 | T. gondii | 1893 | 1590-1893 (Sautel) | 304 | 1749-1884: SET |

In some embodiment, the functional domain may be a Histone Methyltransferase (HMT) Recruiter Effector Domain. Preferred examples include those in the Table below, namely Hp1a, PHF19, and NIPP1.

Table of Histone Methyltransferase (HMT) Recruiter Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| — | Hp1a | — | H3K9me3 | M. musculus | 191 | 73-191 (Hathaway) | 119 | 121-179: chromoshadow |
| — | PHF19 | — | H3K27me3 | H. sapiens | 580 | (1-250) + GGSG linker (SEQ ID NO: 49) + (500-580) | 335 (Ballaré) | 163-250: PHD2 |
| — | NIPP1 | — | H3K27me3 | H. sapiens | 351 | 1-329 (Jin) | 329 | 310-329: EED |

In some embodiment, the functional domain may be Histone Acetyltransferase Inhibitor Effector Domain. Preferred examples include SET/TAF-1β listed in the Table below.

Table of Histone Acetyltransferase Inhibitor Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| — | SET/TAF-1β | — | — | M. musculus | 289 | 1-289 (Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100 kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100 kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

Histone acetyltransferase (HAT) inhibitors are mentioned herein. However, an alternative in some embodiments is for the one or more functional domains to comprise an acetyltransferase, preferably a histone acetyltransferase. These are useful in the field of epigenomics, for example in methods of interrogating the epigenome. Methods of interrogating the epigenome may include, for example, targeting epigenomic sequences. Targeting epigenomic sequences may include the guide being directed to an epigenomic target sequence. Epigenomic target sequence may include, in some embodiments, include a promoter, silencer or an enhancer sequence.

Use of a functional domain linked to a CRISPR-Cas enzyme as described herein, preferably a dead-Cas9, to target epigenomic sequences can be used to activate or repress promoters, silencer or enhancers.

Examples of acetyltransferases are known but may include, in some embodiments, histone acetyltransferases. In some embodiments, the histone acetyltransferase may comprise the catalytic core of the human acetyltransferase p300 (Gerbasch & Reddy, Nature Biotech 6 Apr. 2015).

In some preferred embodiments, the functional domain is linked to a dead-Cas9 enzyme to target and activate epigenomic sequences such as promoters or enhancers. One or more guides directed to such promoters or enhancers may also be provided to direct the binding of the CRISPR enzyme to such promoters or enhancers.

The term "associated with" is used here in relation to the association of the functional domain to the CRISPR enzyme or the adaptor protein. It is used in respect of how one molecule 'associates' with respect to another, for example between an adaptor protein and a functional domain, or between the CRISPR enzyme and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the CRISPR enzyme or adaptor protein is associated with a functional domain by binding thereto. In other embodiments, the CRISPR enzyme or adaptor protein is associated with a functional domain because the two are fused together, optionally via an intermediate linker.

Attachment of a functional domain or fusion protein can be via a linker, e.g., a flexible glycine-serine (GlyGlyGlySer (SEQ ID NO: 41)) or (GGGS)$_3$ (SEQ ID NO: 46) or a rigid alpha-helical linker such as (Ala(GluAlaAlaAlaLys)Ala (SEQ ID NO: 47)). Linkers such as (GGGGS)$_3$ (SEQ ID NO: 42) are preferably used herein to separate protein or peptide domains. (GGGGS)$_3$ (SEQ ID NO: 42) is preferable because it is a relatively long linker (15 amino acids). The glycine residues are the most flexible and the serine residues enhance the chance that the linker is on the outside of the protein. (GGGGS)$_6$ (SEQ ID NO: 43) (GGGGS)$_9$ (SEQ ID NO: 44) or (GGGGS)$_{12}$ (SEQ ID NO: 45) may preferably be used as alternatives. Other preferred alternatives are (GGGGS)$_1$ (SEQ ID NO: 50), (GGGGS)$_2$ (SEQ ID NO: 51), (GGGGS)$_4$ (SEQ ID NO: 52), (GGGGS)$_5$ (SEQ ID NO: 53), (GGGGS) (SEQ ID NO: 54), (GGGGS)$_8$ (SEQ ID NO: 55), (GGGGS)$_{10}$ (SEQ ID NO: 56), or (GGGGS)$_{11}$ (SEQ ID NO: 57). Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)$_3$ (SEQ ID NO: 42) linker may be used here (or the 6 (SEQ ID NO: 43), 9 (SEQ ID NO: 44), or 12 (SEQ ID NO: 45) repeat versions therefore) or the NLS of nucleoplasmin can be used as a linker between Cas9 and the functional domain.

Saturating Mutagenesis

CRISPR-Cas9 System(s) can be used to perform saturating or deep scanning mutagenesis of genomic loci in conjunction with a cellular phenotype—for instance, for determining critical minimal features and discrete vulnerabilities of functional elements required for gene expression, drug resistance, and reversal of disease. By saturating or deep scanning mutagenesis is meant that every or essentially every DNA base is cut within the genomic loci. A library of CRISPR-Cas9 guide RNAs may be introduced into a population of cells. The library may be introduced, such that each cell receives a single guide RNA (sgRNA). In the case where the library is introduced by transduction of a viral vector, as described herein, a low multiplicity of infection (MOI) is used. The library may include sgRNAs targeting every sequence upstream of a (protospacer adjacent motif) (PAM) sequence in a genomic locus. The library may include at least 100 non-overlapping genomic sequences upstream of a PAM sequence for every 1000 base pairs within the genomic locus. The library may include sgRNAs targeting sequences upstream of at least one different PAM sequence. The CRISPR-Cas9 System(s) may include more than one Cas9 protein. Any Cas9 protein as described herein, including orthologues or engineered Cas9 proteins that recognize different PAM sequences may be used. The frequency of off target sites for a sgRNA may be less than 500. Off target scores may be generated to select sgRNAs with the lowest off target sites. Any phenotype determined to be associated with cutting at a sgRNA target site may be confirmed by using sgRNA's targeting the same site in a single experiment. Validation of a target site may also be performed by using a nickase Cas9, as described herein, and two sgRNAs targeting the genomic site of interest. Not being bound by a theory, a target site is a true hit if the change in phenotype is observed in validation experiments.

The genomic loci may include at least one continuous genomic region. The at least one continuous genomic region may comprise up to the entire genome. The at least one continuous genomic region may comprise a functional element of the genome. The functional element may be within a non-coding region, coding gene, intronic region, promoter, or enhancer. The at least one continuous genomic region may comprise at least 1 kb, preferably at least 50 kb of genomic DNA. The at least one continuous genomic region may comprise a transcription factor binding site. The at least one continuous genomic region may comprise a region of DNase I hypersensitivity. The at least one continuous genomic region may comprise a transcription enhancer or repressor element. The at least one continuous genomic region may comprise a site enriched for an epigenetic signature. The at least one continuous genomic DNA region may comprise an epigenetic insulator. The at least one continuous genomic region may comprise two or more continuous genomic regions that physically interact. Genomic regions that interact may be determined by '4C technology'. 4C technology allows the screening of the entire genome in an unbiased manner for DNA segments that physically interact with a DNA fragment of choice, as is described in Zhao et al. ((2006) *Nat Genet* 38, 1341-7) and in U.S. Pat. No. 8,642,295, both incorporated herein by reference in its entirety. The epigenetic signature may be histone acetylation, histone methylation, histone ubiquitination, histone phosphorylation, DNA methylation, or a lack thereof.

CRISPR-Cas9 System(s) for saturating or deep scanning mutagenesis can be used in a population of cells. The CRISPR-Cas9 System(s) can be used in eukaryotic cells, including but not limited to mammalian and plant cells. The population of cells may be prokaryotic cells. The population of eukaryotic cells may be a population of embryonic stem (ES) cells, neuronal cells, epithelial cells, immune cells, endocrine cells, muscle cells, erythrocytes, lymphocytes, plant cells, or yeast cells.

In one aspect, the present invention provides for a method of screening for functional elements associated with a change in a phenotype. The library may be introduced into a population of cells that are adapted to contain a Cas9 protein. The cells may be sorted into at least two groups based on the phenotype. The phenotype may be expression of a gene, cell growth, or cell viability. The relative representation of the guide RNAs present in each group are determined, whereby genomic sites associated with the change in phenotype are determined by the representation of guide RNAs present in each group. The change in phenotype may be a change in expression of a gene of interest. The gene of interest may be upregulated, downregulated, or knocked out. The cells may be sorted into a high expression group and a low expression group. The population of cells may include a reporter construct that is used to determine the phenotype. The reporter construct may include a detectable marker. Cells may be sorted by use of the detectable marker.

In another aspect, the present invention provides for a method of screening for genomic sites associated with resistance to a chemical compound. The chemical compound may be a drug or pesticide. The library may be introduced into a population of cells that are adapted to contain a Cas9 protein, wherein each cell of the population contains no more than one guide RNA; the population of cells are treated with the chemical compound; and the representation of guide RNAs are determined after treatment with the chemical compound at a later time point as compared to an early time point, whereby genomic sites associated with resistance to the chemical compound are determined by enrichment of guide RNAs. Representation of sgRNAs may be determined by deep sequencing methods.

Useful in the practice of the instant invention, reference is made to the article entitled BCL11A enhancer dissection by Cas9-mediated in situ saturating mutagenesis. Canver, M. C., Smith, E. C., Sher, F., Pinello, L., Sanjana, N. E., Shalem, O., Chen, D. D., Schupp, P. G., Vinjamur, D. S., Garcia, S. P., Luc, S., Kurita, R., Nakamura, Y., Fujiwara, Y., Maeda, T., Yuan, G., Zhang, F., Orkin, S. H., & Bauer, D. E. DOI:10.1038/nature15521, published online Sep. 16, 2015, the article is herein incorporated by reference and discussed briefly below:

> Canver et al. describes novel pooled CRISPR-Cas9 guide RNA libraries to perform in situ saturating mutagenesis of the human and mouse BCL11A erythroid enhancers previously identified as an enhancer associated with fetal hemoglobin (HbF) level and whose mouse ortholog is necessary for erythroid BCL11A expression. This approach revealed critical minimal features and discrete vulnerabilities of these enhancers. Through editing of primary human progenitors and mouse transgenesis, the authors validated the BCL11A erythroid enhancer as a target for HbF reinduction. The authors generated a detailed enhancer map that informs therapeutic genome editing.

Method of Using CRISPR-Cas9 Systems to Modify a Cell or Organism

The invention in some embodiments comprehends a method of modifying a cell or organism. The cell may be a prokaryotic cell or a eukaryotic cell. The cell may be a mammalian cell. The mammalian cell many be a non-human primate, bovine, porcine, rodent or mouse cell. The cell may be a non-mammalian eukaryotic cell such as poultry, fish or shrimp. The cell may also be a plant cell. The plant cell may be of a crop plant such as cassava, corn, sorghum, wheat, or rice. The plant cell may also be of an algae, tree or vegetable. The modification introduced to the cell by the present invention may be such that the cell and progeny of the cell are altered for improved production of biologic products such as an antibody, starch, alcohol or other desired cellular output. The modification introduced to the cell by the present invention may be such that the cell and progeny of the cell include an alteration that changes the biologic product produced.

The system may comprise one or more different vectors. In an aspect of the invention, the Cas9 protein is codon optimized for expression the desired cell type, preferentially a eukaryotic cell, preferably a mammalian cell or a human cell.

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CIR, Rat6, CV1, RPTE, A10, T24, J82, A375, ARH-77, Calu1. SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a nucleic acid-targeting system as described herein (such as by transient transfection of one or more vectors, or transfection with RNA), and modified through the activity of a nucleic acid-targeting complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In one aspect, the invention provides for methods of modifying a target polynucleotide in a eukaryotic cell. In some embodiments, the method comprises allowing a nucleic acid-targeting complex to bind to the target polynucleotide to effect cleavage of said target polynucleotide thereby modifying the target polynucleotide, wherein the nucleic acid-targeting complex comprises a nucleic acid-targeting effector protein complexed with a guide RNA hybridized to a target sequence within said target polynucleotide.

In one aspect, the invention provides a method of modifying expression of a polynucleotide in a eukaryotic cell. In some embodiments, the method comprises allowing a nucleic acid-targeting complex to bind to the polynucleotide such that said binding results in increased or decreased expression of said polynucleotide; wherein the nucleic acid-targeting complex comprises a nucleic acid-targeting effector protein complexed with a guide RNA hybridized to a target sequence within said polynucleotide.

CRISPR Systems can be Used in Plants

CRISPR-Cas9 system(s) (e.g., single or multiplexed) can be used in conjunction with recent advances in crop genomics. Such CRISPR-Cas9 system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas system(s) can be used with regard to plants in Site-Directed Integration (SDI) or Gene Editing (GE) or any Near Reverse Breeding (NRB) or Reverse Breeding (RB) techniques. With respect to use of the CRISPR-Cas9 system in plants, mention is made of the University of Arizona website "CRISPR-PLANT" (http://www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi:10. 1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi: 10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sstl 19. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061-*Agrobacterium*-Mediated Plant Transformation Method; U.S. Pat. No. 7,868,149-Plant Genome Sequences and Uses Thereof and US 2009/0100536-Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent; and, the enzymes herein having reduced off-target effects and systems employing such enzymes can be used in plant applications, including those mentioned herein.

Sugano et al. (Plant Cell Physiol. 2014 March; 55(3):475-81. doi: 10.1093/pcp/pcu014. Epub 2014 Jan. 18) reports the application of CRISPR-Cas9 to targeted mutagenesis in the liverwort *Marchantia polymorpha* L., which has emerged as a model species for studying land plant evolution. The U6 promoter of *M. polymorpha* was identified and cloned to express the gRNA. The target sequence of the gRNA was designed to disrupt the gene encoding auxin response factor 1 (ARF1) in *M. polymorpha*. Using *Agrobacterium*-mediated transformation, Sugano et al. isolated stable mutants in the gametophyte generation of *M. polymorpha*. CRISPR-Cas9-based site-directed mutagenesis in vivo was achieved using either the Cauliflower mosaic virus 35S or *M. polymorpha* EF1a promoter to express Cas9. Isolated mutant individuals showing an auxin-resistant phenotype were not chimeric. Moreover, stable mutants were produced by asexual reproduction of T1 plants. Multiple arfl alleles were easily established using CRIPSR-Cas9-based targeted mutagenesis. The methods of Sugano et al. may be applied to the CRISPR Cas9 system of the present invention.

Kabadi et al. (Nucleic Acids Res. 2014 Oct. 29; 42(19): e147. doi: 10.1093/nar/gku749. Epub 2014 Aug. 13) developed a single lentiviral system to express a Cas9 variant, a reporter gene and up to four sgRNAs from independent RNA polymerase III promoters that are incorporated into the vector by a convenient Golden Gate cloning method. Each sgRNA was efficiently expressed and can mediate multiplex gene editing and sustained transcriptional activation in immortalized and primary human cells. The methods of Kabadi et al. may be applied to the CRISPR Cas9 system of the present invention.

Ling et al. (BMC Plant Biology 2014, 14:327) developed a CRISPR-Cas9 binary vector set based on the pGreen or pCAMBIA backbone, as well as a gRNA This toolkit requires no restriction enzymes besides BsaI to generate final constructs harboring maize-codon optimized Cas9 and one or more gRNAs with high efficiency in as little as one cloning step. The toolkit was validated using maize protoplasts, transgenic maize lines, and transgenic *Arabidopsis* lines and was shown to exhibit high efficiency and specificity. More importantly, using this toolkit, targeted mutations of three *Arabidopsis* genes were detected in transgenic seedlings of the T1 generation. Moreover, the multiple-gene mutations could be inherited by the next generation. (guide RNA) module vector set, as a toolkit for multiplex genome editing in plants. The toolbox of Lin et al. may be applied to the CRISPR Cas9 system of the present invention.

Protocols for targeted plant genome editing via CRISPR-Cas9 are also available in volume 1284 of the series Methods in Molecular Biology pp 239-255 10 Feb. 2015. A detailed procedure to design, construct, and evaluate dual gRNAs for plant codon optimized Cas9 (pcoCas9) mediated genome editing using *Arabidopsis thaliana* and *Nicotiana benthamiana* protoplasts s model cellular systems are described. Strategies to apply the CRISPR-Cas9 system to generating targeted genome modifications in whole plants are also discussed. The protocols described in the chapter may be applied to the CRISPR Cas9 system of the present invention.

Ma et al. (Mol Plant. 2015 Aug. 3; 8(8):1274-84. doi: 10.1016/j.molp.2015.04.007) reports robust CRISPR-Cas9 vector system, utilizing a plant codon optimized Cas9 gene, for convenient and high-efficiency multiplex genome editing in monocot and dicot plants. Ma et al. designed PCR-based procedures to rapidly generate multiple sgRNA expression cassettes, which can be assembled into the binary CRISPR-Cas9 vectors in one round of cloning by Golden Gate ligation or Gibson Assembly. With this system, Ma et al. edited 46 target sites in rice with an average 85.4% rate of mutation, mostly in biallelic and homozygous status. Ma et al. provide examples of loss-of-function gene mutations in T0 rice and T1*Arabidopsis* plants by simultaneous targeting of multiple (up to eight) members of a gene family, multiple genes in a biosynthetic pathway, or multiple sites in a single gene. The methods of Ma et al. may be applied to the CRISPR Cas9 system of the present invention.

Lowder et al. (Plant Physiol. 2015 Aug. 21. pii: pp. 00636.2015) also developed a CRISPR-Cas9 toolbox enables multiplex genome editing and transcriptional regulation of expressed, silenced or non-coding genes in plants. This toolbox provides researchers with a protocol and reagents to quickly and efficiently assemble functional CRISPR/Cas9 T-DNA constructs for monocots and dicots using Golden Gate and Gateway cloning methods. It comes with a full suite of capabilities, including multiplexed gene editing and transcriptional activation or repression of plant endogenous genes. T-DNA based transformation technology is fundamental to modern plant biotechnology, genetics, molecular biology and physiology. As such, Applicants developed a method for the assembly of Cas9 (WT, nickase or dCas9) and gRNA(s) into a T-DNA destination-vector of interest. The assembly method is based on both Golden Gate assembly and MultiSite Gateway recombination. Three modules are required for assembly. The first module is a Cas9 entry vector, which contains promoterless Cas9 or its derivative genes flanked by attL1 and attR5 sites. The second module is a gRNA entry vector which contains entry gRNA expression cassettes flanked by attL5 and attL2 sites. The third module includes attR1-attR2-containing destination T-DNA vectors that provide promoters of choice for Cas9 expression. The toolbox of Lowder et al. may be applied to the CRISPR Cas9 system of the present invention.

In an advantageous embodiment, the plant may be a tree. The present invention may also utilize the herein disclosed CRISPR-Cas9 system for herbaceous systems (see, e.g., Belhaj et al., Plant Methods 9: 39 and Harrison et al., Genes & Development 28: 1859-1872). In a particularly advantageous embodiment, the CRISPR Cas9 system of the present invention may target single nucleotide polymorphisms (SNPs) in trees (see, e.g., Zhou et al., New Phytologist, Volume 208, Issue 2, pages 298-301, October 2015). In the Zhou et al. study, the authors applied a CRISPR Cas9 system in the woody perennial *Populus* using the 4-coumarate:CoA ligase (4CL) gene family as a case study and achieved 100% mutational efficiency for two 4CL genes targeted, with every transformant examined carrying biallelic modifications. In the Zhou et al., study, the CRISPR/Cas9 system was highly sensitive to single nucleotide polymorphisms (SNPs), as cleavage for a third 4CL gene was abolished due to SNPs in the target sequence.

The methods of Zhou et al. (New Phytologist, Volume 208, Issue 2, pages 298-301, October 2015) may be applied to the present invention as follows. Two 4CL genes, 4CL1 and 4CL2, associated with lignin and flavonoid biosynthesis, respectively are targeted for CRISPR/Cas9 editing. The *Populus tremula*×alba clone 717-1B4 routinely used for transformation is divergent from the genome-sequenced *Populus trichocarpa*. Therefore, the 4CL1 and 4CL2 gRNAs designed from the reference genome are interrogated with in-house 717 RNA-Seq data to ensure the absence of SNPs which could limit Cas9 efficiency. A third gRNA designed for 4CL5, a genome duplicate of 4CL1, is also included. The corresponding 717 sequence harbors one SNP in each allele near/within the PAM, both of which are expected to abolish targeting by the 4CL5-gRNA. All three gRNA target sites are located within the first exon. For 717 transformation, the gRNA is expressed from the *Medicago* U6.6 promoter, along with a human codon-optimized Cas9 under control of the CaMV 35S promoter in a binary vector. Transformation with the Cas-only vector can serve as a control. Randomly selected 4CL1 and 4CL2 lines are subjected to amplicon-sequencing. The data is then processed and biallelic mutations are confirmed in all cases.

In plants, pathogens are often host-specific. For example, *Fusarium oxysporum* f. sp. *lycopersici* causes tomato wilt but attacks only tomato, and *F. oxysporum f dianthii Puccinia graminis f.* sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

CRISPR Systems can be Used in Non-Human Organisms/Animals

The present application may also be extended to other agricultural applications such as, for example, farm and production animals. For example, pigs have many features that make them attractive as biomedical models, especially in regenerative medicine. In particular, pigs with severe combined immunodeficiency (SCID) may provide useful models for regenerative medicine, xenotransplantation, and tumor development and will aid in developing therapies for human SCID patients. Lee et al., (Proc Natl Acad Sci USA. 2014 May 20; 111(20):7260-5) utilized a reporter-guided transcription activator-like effector nuclease (TALEN) system to generated targeted modifications of recombination activating gene (RAG) 2 in somatic cells at high efficiency, including some that affected both alleles. CRISPR Cas9 may be applied to a similar system.

The methods of Lee et al., (Proc Natl Acad Sci USA. 2014 May 20; 111(20):7260-5) may be applied to the present invention as follows. Mutated pigs are produced by targeted modification of RAG2 in fetal fibroblast cells followed by SCNT and embryo transfer. Constructs coding for CRISPR Cas9 and a reporter are electroporated into fetal-derived fibroblast cells. After 48 h, transfected cells expressing the green fluorescent protein are sorted into individual wells of a 96-well plate at an estimated dilution of a single cell per well. Targeted modification of RAG2 are screened by amplifying a genomic DNA fragment flanking any CRISPR-Cas9 cutting sites followed by sequencing the PCR products. After screening and ensuring lack of off-site mutations, cells carrying targeted modification of RAG2 are used for SCNT. The polar body, along with a portion of the adjacent cytoplasm of oocyte, presumably containing the metaphase II plate, are removed, and a donor cell are placed in the perivitelline. The reconstructed embryos are then electrically porated to fuse the donor cell with the oocyte and then chemically activated. The activated embryos are incubated in Porcine Zygote Medium 3 (PZM3) with 0.5 µM Scriptaid (S7817; Sigma-Aldrich) for 14-16 h. Embryos are then washed to remove the Scriptaid and cultured in PZM3 until they were transferred into the oviducts of surrogate pigs.

The present invention is also applicable to modifying SNPs of other animals, such as cows. Tan et al. (Proc Natl Acad Sci USA. 2013 Oct. 8; 110(41): 16526-16531) expanded the livestock gene editing toolbox to include transcription activator-like (TAL) effector nuclease (TALEN)- and clustered regularly interspaced short palindromic repeats (CRISPR)/Cas9-stimulated homology-directed repair (HDR) using plasmid, rAAV, and oligonucleotide templates. Gene specific gRNA sequences were cloned into the Church lab gRNA vector (Addgene ID: 41824) according to their methods (Mali P, et al. (2013) RNA-Guided Human Genome Engineering via Cas9. Science 339(6121):823-826). The Cas9 nuclease was provided either by co-transfection of the hCas9 plasmid (Addgene ID: 41815) or mRNA synthesized from RCIScript-hCas9. This RCIScript-hCas9 was constructed by sub-cloning the XbaI-AgeI fragment from the hCas9 plasmid (encompassing the hCas9 cDNA) into the RCIScript plasmid.

Heo et al. (Stem Cells Dev. 2015 Feb. 1; 24(3):393-402. doi: 10.1089/scd.2014.0278. Epub 2014 Nov. 3) reported highly efficient gene targeting in the bovine genome using bovine pluripotent cells and clustered regularly interspaced short palindromic repeat (CRISPR)/Cas9 nuclease. First, Heo et al. generate induced pluripotent stem cells (iPSCs) from bovine somatic fibroblasts by the ectopic expression of yamanaka factors and GSK3β and MEK inhibitor (2i) treatment. Heo et al. observed that these bovine iPSCs are highly similar to naïve pluripotent stem cells with regard to gene expression and developmental potential in teratomas. Moreover, CRISPR/Cas9 nuclease, which was specific for the bovine NANOG locus, showed highly efficient editing of the bovine genome in bovine iPSCs and embryos.

Igenity® provides a profile analysis of animals, such as cows, to perform and transmit traits of economic traits of economic importance, such as carcass composition, carcass quality, maternal and reproductive traits and average daily gain. The analysis of a comprehensive Igenity® profile begins with the discovery of DNA markers (most often single nucleotide polymorphisms or SNPs). All the markers behind the Igenity® profile were discovered by independent scientists at research institutions, including universities, research organizations, and government entities such as USDA. Markers are then analyzed at Igenity® in validation populations. Igenity® uses multiple resource populations that represent various production environments and biological types, often working with industry partners from the seedstock, cow-calf, feedlot and/or packing segments of the beef industry to collect phenotypes that are not commonly available. Cattle genome databases are widely available, see, e.g., the NAGRP Cattle Genome Coordination Program (http://www.animalgenome.org/cattle/maps/db.html). Thus, the present invention maybe applied to target bovine SNPs. One of skill in the art may utilize the above protocols for targeting SNPs and apply them to bovine SNPs as described, for example, by Tan et al. or Heo et al.

Therapeutic Targeting with RNA-Guided Effector Protein Complex

As will be apparent, it is envisaged that the present system can be used to target any polynucleotide sequence of interest. The invention provides a non-naturally occurring or engineered composition, or one or more polynucleotides encoding components of said composition, or vector or delivery systems comprising one or more polynucleotides encoding components of said composition for use in a modifying a target cell in vivo, ex vivo or in vitro and, may be conducted in a manner alters the cell such that once modified the progeny or cell line of the CRISPR modified cell retains the altered phenotype. The modified cells and progeny may be part of a multi-cellular organism such as a plant or animal with ex vivo or in vivo application of CRISPR system to desired cell types. The CRISPR invention may be a therapeutic method of treatment. The therapeutic method of treatment may comprise gene or genome editing, or gene therapy.

Treating Pathogens, Like Bacterial, Fungal and Parasitic Pathogens

The present invention may also be applied to treat bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

Jiang et al. ("RNA-guided editing of bacterial genomes using CRISPR-Cas systems," Nature Biotechnology vol. 31, p. 233-9, March 2013) used a CRISPR-Cas9 system to mutate or kill *S. pneumoniae* and *E. coli*. The work, which introduced precise mutations into the genomes, relied on dual-RNA:Cas9-directed cleavage at the targeted genomic site to kill unmutated cells and circumvented the need for selectable markers or counter-selection systems. CRISPR systems have be used to reverse antibiotic resistance and eliminate the transfer of resistance between strains. Bickard et al. showed that Cas9, reprogrammed to target virulence genes, kills virulent, but not avirulent, *S. aureus*. Reprogramming the nuclease to target antibiotic resistance genes destroyed staphylococcal plasmids that harbor antibiotic resistance genes and immunized against the spread of plasmid-borne resistance genes. (see, Bikard et al., "Exploiting CRISPR-Cas nucleases to produce sequence-specific antimicrobials," Nature Biotechnology vol. 32, 1146-1150, doi: 10.1038/nbt.3043, published online 5 Oct. 2014.) Bikard showed that CRISPR-Cas9 antimicrobials function in vivo to kill *S. aureus* in a mouse skin colonization model. Similarly, Yosef et al used a CRISPR system to target genes encoding enzymes that confer resistance to β-lactam antibiotics (see Yousef et al., "Temperate and lytic bacteriophages programmed to sensitize and kill antibiotic-resistant bacteria," Proc. Natl. Acad. Sci. USA, vol. 112, p. 7267-7272, doi: 10.1073/pnas. 1500107112 published online May 18, 2015).

CRISPR systems can be used to edit genomes of parasites that are resistant to other genetic approaches. For example, a CRISPR-Cas9 system was shown to introduce double-stranded breaks into the in the *Plasmodium yoelii* genome (see, Zhang et al., "Efficient Editing of Malaria Parasite Genome Using the CRISPR/Cas9 System," mBio. vol. 5, e01414-14, July-August 2014). Ghorbal et al. ("Genome editing in the human malaria parasite *Plasmodium* falciparu-musing the CRISPR-Cas9 system," Nature Biotechnology, vol. 32, p. 819-821, doi: 10.1038/nbt.2925, published online Jun. 1, 2014) modified the sequences of two genes, orc1 and kelch13, which have putative roles in gene silencing and emerging resistance to artemisinin, respectively. Parasites that were altered at the appropriate sites were recovered with very high efficiency, despite there being no direct selection for the modification, indicating that neutral or even deleterious mutations can be generated using this system. CRISPR-Cas9 is also used to modify the genomes of other pathogenic parasites, including *Toxoplasma gondii* (see Shen et al., "Efficient gene disruption in diverse strains of *Toxoplasma gondii* using CRISPR/CAS9," mBio vol. 5:e01114-14, 2014, and Sidik el al., "Efficient Genome Engineering of *Toxoplasma gondii* Using CRISPR/Cas9," PLoS One vol. 9, e100450, doi: 10.1371/journal.pone.0100450, published online Jun. 27, 2014).

Vyas et al. ("A *Candida albicans* CRISPR system permits genetic engineering of essential genes and gene families," Science Advances, vol. 1, e1500248, DOI: 10.1126/sciadv.1500248, Apr. 3, 2015) employed a CRISPR system to overcome long-standing obstacles to genetic engineering in *C. albicans* and efficiently mutate in a single experiment both copies of several different genes. In an organism where several mechanisms contribute to drug resistance, Vyas produced homozygous double mutants that no longer displayed the hyper-resistance to fluconazole or cycloheximide displayed by the parental clinical isolate Can90. Vyas also obtained homozygous loss-of-function mutations in essential genes of *C. albicans* by creating conditional alleles. Null alleles of DCR1, which is required for ribosomal RNA processing, are lethal at low temperature but viable at high temperature. Vyas used a repair template that introduced a nonsense mutation and isolated dcr1/dcr1 mutants that failed to grow at 16° C.

The CRISPR system of the present invention for use in *P. falciparum* by disrupting chromosomal loci. Ghorbal et al. ("Genome editing in the human malaria parasite *Plasmodium falciparum* using the CRISPR-Cas9 system", Nature Biotechnology, 32, 819-821 (2014), DOI: 10.1038/nbt.2925, Jun. 1, 2014) employed a CRISPR system to introduce specific gene knockouts and single-nucleotide substitutions in the malaria genome. To adapt the CRISPR-Cas9 system to *P. falciparum*, Ghorbal et al. generated expression vectors for under the control of plasmoidal regulatory elements in the pUF1-Cas9 episome that also carries the drug-selectable marker ydhodh, which gives resistance to DSM1, a *P. falciparum* dihydroorotate dehydrogenase (PfDHODH) inhibitor and for transcription of the sgRNA, used *P. falciparum* U6 small nuclear (sn)RNA regulatory elements placing the guide RNA and the donor DNA template for homologous recombination repair on the same plasmid, pL7. See also, Zhang C. et al. ("Efficient editing of malaria parasite genome using the CRISPR/Cas9 system", MBio, 2014 Jul. 1; 5(4):E01414-14, doi: 10.1128/MbIO.01414-14) and Wagner et al. ("Efficient CRISPR-Cas9-mediated genome editing in *Plasmodium falciparum*, Nature Methods 11, 915-918 (2014), DOI: 10.1038/nmeth.3063).

Treating Pathogens, Like Viral Pathogens Such as HIV

Cas-mediated genome editing might be used to introduce protective mutations in somatic tissues to combat nongenetic or complex diseases. For example, NHEJ-mediated inactivation of the CCR5 receptor in lymphocytes (Lombardo et al., Nat Biotechnol. 2007 November; 25(11): 1298-306) may be a viable strategy for circumventing HIV infection, whereas deletion of PCSK9 (Cohen et al., Nat Genet. 2005 February; 37(2):161-5) orangiopoietin (Musunuru et al., N Engl J Med. 2010 Dec. 2; 363(23):2220-7) may provide therapeutic effects against statin-resistant hypercholesterolemia or hyperlipidemia. Although these targets may be also addressed using siRNA-mediated protein knockdown, a unique advantage of NHEJ-mediated gene inactivation is the ability to achieve permanent therapeutic benefit without the need for continuing treatment. As with all gene therapies, it will of course be important to establish that each proposed therapeutic use has a favorable benefit-risk ratio.

Hydrodynamic delivery of plasmid DNA encoding Cas9 and guide RNA along with a repair template into the liver of an adult mouse model of tyrosinemia was shown to be able to correct the mutant Fah gene and rescue expression of the wild-type Fah protein in ~1 out of 250 cells (Nat Biotechnol. 2014 June; 32(6):551-3). In addition, clinical trials successfully used ZF nucleases to combat HIV infection by ex vivo knockout of the CCR5 receptor. In all patients, HIV DNA levels decreased, and in one out of four patients, HIV RNA became undetectable (Tebas et al., N Engl J Med. 2014 Mar. 6; 370(10):901-10). Both of these results demonstrate the promise of programmable nucleases as a new therapeutic platform.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas9 system of the present invention. A minimum of $2.5 \times 10^6$ CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm² tissue culture flasks coated with fibronectin (25 mg/cm²) (RetroNectin, Takara Bio Inc.).

With the knowledge in the art and the teachings in this disclosure the skilled person can correct HSCs as to immunodeficiency condition such as HIV/AIDS comprising contacting an HSC with a CRISPR-Cas9 system that targets and knocks out CCR5. An guide RNA (and advantageously a dual guide approach, e.g., a pair of different guide RNAs; for instance, guide RNAs targeting of two clinically relevant genes, B2M and CCR5, in primary human CD4+ T cells and CD34+ hematopoietic stem and progenitor cells (HSPCs)) that targets and knocks out CCR5-and-Cas9 protein containing particle is contacted with HSCs. The so contacted cells can be administered; and optionally treated/expanded; cf. Cartier. See also Kiem, "Hematopoietic stem cell-based gene therapy for HIV disease," Cell Stem Cell. Feb. 3, 2012; 10(2): 137-147; incorporated herein by reference along with the documents it cites; Mandal et al, "Efficient Ablation of Genes in Human Hematopoietic Stem and Effector Cells using CRISPR/Cas9," Cell Stem Cell, Volume 15, Issue 5, p643-652, 6 Nov. 2014; incorporated herein by reference along with the documents it cites. Mention is also made of Ebina, "CRISPR/Cas9 system to suppress HIV-1 expression by editing HIV-1 integrated proviral DNA" SCIENTIFIC REPORTS |3: 2510|DOI: 10.1038/srep02510, incorporated herein by reference along with the documents it cites, as another means for combatting HIV/AIDS using a CRISPR-Cas9 system.

The rationale for genome editing for HIV treatment originates from the observation that individuals homozygous for loss of function mutations in CCR5, a cellular co-receptor for the virus, are highly resistant to infection and otherwise healthy, suggesting that mimicking this mutation with genome editing could be a safe and effective therapeutic strategy [Liu, R., et al. Cell 86, 367-377 (1996)]. This idea was clinically validated when an HIV infected patient was given an allogeneic bone marrow transplant from a donor homozygous for a loss of function CCR5 mutation, resulting in undetectable levels of HIV and restoration of normal CD4 T-cell counts [Hutter, G., et al. The New England journal of medicine 360, 692-698 (2009)]. Although bone marrow transplantation is not a realistic treatment strategy for most HIV patients, due to cost and potential graft vs. host disease, HIV therapies that convert a patient's own T-cells into CCR5 are desirable.

Early studies using ZFNs and NHEJ to knockout CCR5 in humanized mouse models of HIV showed that transplantation of CCR5 edited CD4 T cells improved viral load and CD4 T-cell counts [Perez, E. E., et al. Nature biotechnology 26, 808-816 (2008)]. Importantly, these models also showed that HIV infection resulted in selection for CCR5 null cells, suggesting that editing confers a fitness advantage and potentially allowing a small number of edited cells to create a therapeutic effect.

As a result of this and other promising preclinical studies, genome editing therapy that knocks out CCR5 in patient T cells has now been tested in humans [Holt, N., et al. Nature biotechnology 28, 839-847 (2010), Li, L., et al. Molecular therapy: the journal of the American Society of Gene Therapy 21, 1259-1269 (2013)]. In a recent phase I clinical trial, CD4+ T cells from patients with HIV were removed, edited with ZFNs designed to knockout the CCR5 gene, and autologously transplanted back into patients [Tebas, P., et al. The New England journal of medicine 370, 901-910 (2014)].

In another study (Mandal et al., Cell Stem Cell, Volume 15, Issue 5, p643-652, 6 Nov. 2014), CRISPR-Cas9 has targeted two clinical relevant genes, B2M and CCR5, in human CD4+ T cells and CD34+ hematopoietic stem and progenitor cells (HSPCs). Use of single RNA guides led to highly efficient mutagenesis in HSPCs but not in T cells. A dual guide approach improved gene deletion efficacy in both cell types. HSPCs that had undergone genome editing with CRISPR-Cas9 retained multilineage potential. Predicted on- and off-target mutations were examined via target capture sequencing in HSPCs and low levels of off-target mutagenesis were observed at only one site. These results demonstrate that CRISPR-Cas9 can efficiently ablate genes in HSPCs with minimal off-target mutagenesis, which have broad applicability for hematopoietic cell-based therapy.

Wang et al. (PLoS One. 2014 Dec. 26; 9(12):e115987. doi: 10.1371/journal.pone.0115987) silenced CCR5 via CRISPR associated protein 9 (Cas9) and single guided RNAs (guide RNAs) with lentiviral vectors expressing Cas9 and CCR5 guide RNAs. Wang et al. showed that a single round transduction of lentiviral vectors expressing Cas9 and CCR5 guide RNAs into HIV-1 susceptible human CD4+ cells yields high frequencies of CCR5 gene disruption. CCR5 gene-disrupted cells are not only resistant to R5-tropic HIV-1, including transmitted/founder (T/F) HIV-1 isolates, but also have selective advantage over CCR5 gene-undisrupted cells during R5-tropic HIV-1 infection. Genome mutations at potential off-target sites that are highly homologous to these CCR5 guide RNAs in stably transduced cells even at 84 days post transduction were not detected by a T7 endonuclease I assay.

Fine et al. (Sci Rep. 2015 Jul. 1; 5:10777. doi: 10.1038/srep10777) identified a two-cassette system expressing pieces of the *S. pyogenes* Cas9 (SpCas9) protein which splice together in cellula to form a functional protein capable of site-specific DNA cleavage. With specific CRISPR guide strands, Fine et al. demonstrated the efficacy of this system in cleaving the HBB and CCR5 genes in human HEK-293T cells as a single Cas9 and as a pair of Cas9 nickases. The trans-spliced SpCas9 (tsSpCas9) displayed ~35% of the nuclease activity compared with the wild-type SpCas9 (wtSpCas9) at standard transfection doses, but had substantially decreased activity at lower dosing levels. The greatly reduced open reading frame length of the tsSpCas9 relative to wtSpCas9 potentially allows for more complex and longer genetic elements to be packaged into an AAV vector including tissue-specific promoters, multiplexed guide RNA expression, and effector domain fusions to SpCas9.

Li et al. (J Gen Virol. 2015 August; 96(8):2381-93. doi: 10.1099/vir.0.000139. Epub 2015 Apr. 8) demonstrated that CRISPR-Cas9 can efficiently mediate the editing of the CCR5 locus in cell lines, resulting in the knockout of CCR5 expression on the cell surface. Next-generation sequencing revealed that various mutations were introduced around the predicted cleavage site of CCR5. For each of the three most effective guide RNAs that were analyzed, no significant off-target effects were detected at the 15 top-scoring potential sites. By constructing chimeric Ad5F35 adenoviruses carrying CRISPR-Cas9 components, Li et al. efficiently transduced primary CD4+T-lymphocytes and disrupted CCR5 expression, and the positively transduced cells were conferred with HIV-1 resistance.

Mention is made of WO 2015/148670 and through the teachings herein the invention comprehends methods and materials of this document applied in conjunction with the teachings herein. In an aspect of gene therapy, methods and compositions for editing of a target sequence related to or in connection with Human Immunodeficiency Virus (HIV) and Acquired Immunodeficiency Syndrome (AIDS) are comprehended. In a related aspect, the invention described herein comprehends prevention and treatment of HIV infection and AIDS, by introducing one or more mutations in the gene for C—C chemokine receptor type 5 (CCR5). The CCR5 gene is also known as CKR5, CCR-5, CD195, CKR-5, CCCKR5, CMKBR5, IDDM22, and CC-CKR-5. In a further aspect, the invention described herein comprehends provide for prevention or reduction of HIV infection and/or prevention or reduction of the ability for HIV to enter host cells, e.g., in subjects who are already infected. Exemplary host cells for HIV include, but are not limited to, CD4 cells, T cells, gut associated lymphatic tissue (GALT), macrophages, dendritic cells, myeloid precursor cell, and microglia. Viral entry into the host cells requires interaction of the viral glycoproteins gp41 and gp120 with both the CD4 receptor and a co-receptor, e.g., CCR5. If a co-receptor, e.g., CCR5, is not present on the surface of the host cells, the virus cannot bind and enter the host cells. The progress of the disease is thus impeded. By knocking out or knocking down CCR5 in the host cells, e.g., by introducing a protective mutation (such as a CCR5 delta 32 mutation), entry of the HIV virus into the host cells is prevented.

One of skill in the art may utilize the above studies of, for example, Holt, N., et al. Nature biotechnology 28, 839-847 (2010), Li, L., et al. Molecular therapy: the journal of the American Society of Gene Therapy 21, 1259-1269 (2013), Mandal et al., Cell Stem Cell, Volume 15, Issue 5, p643-652, 6 Nov. 2014, Wang et al. (PLoS One. 2014 Dec. 26; 9(12):e115987. doi: 10.1371/journal.pone.0115987), Fine et al. (Sci Rep. 2015 Jul. 1:5:10777. doi: 10.1038/srep10777) and Li et al. (J Gen Virol. 2015 August; 96(8):2381-93. doi: 10.1099/vir.0.000139. Epub 2015 Apr. 8) for targeting CCR5 with the CRISPR Cas9 system of the present invention.

Treating Pathogens, Like Viral Pathogens, Such as HBV

The present invention may also be applied to treat hepatitis B virus (HBV). However, the CRISPR Cas9 system must be adapted to avoid the shortcomings of RNAi, such as the risk of oversatring endogenous small RNA pathways, by for example, optimizing dose and sequence (see, e.g., Grimm et al., Nature vol. 441, 26 May 2006). For example, low doses, such as about 1-10×10$^{14}$ particles per human are contemplated. In another embodiment, the CRISPR Cas9 system directed against HBV may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of CRISPR Cas9 targeted to HBV RNA in a SNALP are contemplated. The daily treatment may be over about three days and then weekly for about five weeks. In another embodiment, the system of Chen et al. (Gene Therapy (2007) 14, 11-19) may be used/and or adapted for the CRISPR Cas9 system of the present invention. Chen et al. use a double-stranded adenoassociated virus 8-pseudotyped vector (dsAAV2/8) to deliver shRNA. A single administration of dsAAV2/8 vector (1×10$^{12}$ vector genomes per mouse), carrying HBV-specific shRNA, effectively suppressed the steady level of HBV protein, mRNA and replicative DNA in liver of HBV transgenic mice, leading to up to 2-3 log$_{10}$ decrease in HBV load in the circulation. Significant HBV suppression sustained for at least 120 days after vector administration. The therapeutic effect of shRNA was target sequence dependent and did not involve activation of interferon. For the present invention, a CRISPR Cas9 system directed to HBV may be cloned into an AAV vector, such as a dsAAV2/8 vector and administered to a human, for example, at a dosage of about 1×10$^{15}$ vector genomes to about 1×10$^{16}$ vector genomes per human. In another embodiment, the method of Wooddell et al. (Molecular Therapy vol. 21 no. 5, 973-985 May 2013) may be used/and or adapted to the CRISPR Cas9 system of the present invention. Wooddell et al. show that simple coinjection of a hepatocyte-targeted, N-acetylgalactosamine-conjugated melittin-like peptide (NAG-MLP) with a liver-tropic cholesterol-conjugated siRNA (chol-siRNA) targeting coagulation factor VII (F7) results in efficient F7 knockdown in mice and nonhuman primates without changes in clinical chemistry or induction of cytokines. Using transient and transgenic mouse models of HBV infection, Wooddell et al. show that a single coinjection of NAG-MLP with potent chol-siRNAs targeting conserved HBV sequences resulted in multilog repression of viral RNA, proteins, and viral DNA with long duration of effect. Intravenous coinjections, for example, of about 6 mg/kg of NAG-MLP and 6 mg/kg of HBV specific CRISPR Cas9 may be envisioned for the present invention. In the alternative, about 3 mg/kg of NAG-MLP and 3 mg/kg of HBV specific CRISPR Cas9 may be delivered on day one, followed by administration of about 2-3 mg/kg of NAG-MLP and 2-3 mg/kg of HBV specific CRISPR Cas9 two weeks later.

Lin et al. (Mol Ther Nucleic Acids. 2014 Aug. 19; 3:e186. doi: 10.1038/mtna.2014.38) designed eight gRNAs against HBV of genotype A. With the HBV-specific gRNAs, the CRISPR-Cas9 system significantly reduced the production of HBV core and surface proteins in Huh-7 cells transfected with an HBV-expression vector. Among eight screened gRNAs, two effective ones were identified. One gRNA targeting the conserved HBV sequence acted against different genotypes. Using a hydrodynamics-HBV persistence mouse model, Lin et al. further demonstrated that this system could cleave the intrahepatic HBV genome-containing plasmid and facilitate its clearance in vivo, resulting in reduction of serum surface antigen levels. These data suggest that the CRISPR-Cas9 system could disrupt the HBV-expressing templates both in vitro and in vivo, indicating its potential in eradicating persistent HBV infection.

Dong et al. (Antiviral Res. 2015 June; 118:110-7. doi: 10.1016/j.antiviral.2015.03.015. Epub 2015 Apr. 3) used the CRISPR-Cas9 system to target the HBV genome and efficiently inhibit HBV infection. Dong et al. synthesized four single-guide RNAs (guide RNAs) targeting the conserved regions of HBV. The expression of these guide RNAS with Cas9 reduced the viral production in Huh7 cells as well as in HBV-replication cell HepG2.2.15. Dong et al. further demonstrated that CRISPR-Cas9 direct cleavage and cleavage-mediated mutagenesis occurred in HBV cccDNA of transfected cells. In the mouse model carrying HBV cccDNA, injection of guide RNA-Cas9 plasmids via rapid tail vein resulted in the low level of cccDNA and HBV protein.

Liu et al. (J Gen Virol. 2015 August; 96(8):2252-61. doi: 10.1099/vir.0.000159. Epub 2015 Apr. 22) designed eight guide RNAs (gRNAs) that targeted the conserved regions of different HBV genotypes, which could significantly inhibit HBV replication both in vitro and in vivo to investigate the possibility of using the CRISPR-Cas9 system to disrupt the HBV DNA templates. The HBV-specific gRNA/Cas9 system could inhibit the replication of HBV of different genotypes in cells, and the viral DNA was significantly reduced by a single gRNA/Cas9 system and cleared by a combination of different gRNA/Cas9 systems.

Wang et al. (World J Gastroenterol. 2015 Aug. 28; 21(32): 9554-65. doi: 10.3748/wjg.v21.i32.9554) designed 15 gRNAs against HBV of genotypes A-D. Eleven combinations of two above gRNAs (dual-gRNAs) covering the regulatory region of HBV were chosen. The efficiency of each gRNA and 11 dual-gRNAs on the suppression of HBV (genotypes A-D) replication was examined by the measurement of HBV surface antigen (HBsAg) or e antigen (HBeAg) in the culture supernatant. The destruction of HBV-expressing vector was examined in HuH7 cells co-transfected with dual-gRNAs and HBV-expressing vector using polymerase chain reaction (PCR) and sequencing method, and the destruction of cccDNA was examined in HepAD38 cells using KCl precipitation, plasmid-safe ATP-dependent DNase (PSAD) digestion, rolling circle amplification and quantitative PCR combined method. The cytotoxicity of these gRNAs was assessed by a mitochondrial tetrazolium assay. All of gRNAs could significantly reduce HBsAg or HBeAg production in the culture supernatant, which was dependent on the region in which gRNA against. All of dual gRNAs could efficiently suppress HBsAg and/or HBeAg production for HBV of genotypes A-D, and the efficacy of dual gRNAs in suppressing HBsAg and/or HBeAg production was significantly increased when compared to the single gRNA used alone. Furthermore, by PCR direct sequencing Applicants confirmed that these dual gRNAs could specifically destroy HBV expressing template by removing the fragment between the cleavage sites of the two used gRNAs. Most importantly, gRNA-5 and gRNA-12 combination not only could efficiently suppressing HBsAg and/or HBeAg production, but also destroy the cccDNA reservoirs in HepAD38 cells.

Karimova et al. (Sci Rep. 2015 Sep. 3; 5:13734. doi: 10.1038/srep13734) identified cross-genotype conserved HBV sequences in the S and X region of the HBV genome that were targeted for specific and effective cleavage by a Cas9 nickase. This approach disrupted not only episomal cccDNA and chromosomally integrated HBV target sites in reporter cell lines, but also HBV replication in chronically and de novo infected hepatoma cell lines.

One of skill in the art may utilize the above studies of, for example, Lin et al. (Mol Ther Nucleic Acids. 2014 Aug. 19; 3:e186. doi: 10.1038/mtna.2014.38), Dong et al. (Antiviral Res. 2015 June; 118:110-7. doi: 10.1016/j.antiviral.2015.03.015. Epub 2015 Apr. 3), Liu et al. (J Gen Virol. 2015 August; 96(8):2252-61. doi: 10.1099/vir.0.000159. Epub 2015 Apr. 22), Wang et al. (World J Gastroenterol. 2015 Aug. 28; 21(32):9554-65. doi: 10.3748/ wjg.v21.i32.9554) and Karimova et al. (Sci Rep. 2015 Sep. 3; 5:13734. doi: 10.1038/srep13734) for targeting HBV with the CRISPR Cas9 system of the present invention.

The present invention may also be applied to treat pathogens, e.g. bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

Jiang et al. ("RNA-guided editing of bacterial genomes using CRISPR-Cas systems," Nature Biotechnology vol. 31, p. 233-9, March 2013) used a CRISPR-Cas9 system to mutate or kill *S. pneumoniae* and *E. coli*. The work, which introduced precise mutations into the genomes, relied on dual-RNA:Cas9-directed cleavage at the targeted genomic site to kill unmutated cells and circumvented the need for selectable markers or counter-selection systems. CRISPR systems have be used to reverse antibiotic resistance and eliminate the transfer of resistance between strains. Bickard et al. showed that Cas9, reprogrammed to target virulence genes, kills virulent, but not avirulent, *S. aureus*. Reprogramming the nuclease to target antibiotic resistance genes destroyed staphylococcal plasmids that harbor antibiotic resistance genes and immunized against the spread of plasmid-borne resistance genes. (see, Bikard et al., "Exploiting CRISPR-Cas nucleases to produce sequence-specific antimicrobials," Nature Biotechnology vol. 32, 1146-1150, doi: 10.1038/nbt.3043, published online 5 Oct. 2014.) Bikard showed that CRISPR-Cas9 antimicrobials function in vivo to kill *S. aureus* in a mouse skin colonization model. Similarly, Yosef et al used a CRISPR system to target genes encoding enzymes that confer resistance to β-lactam antibiotics (see Yousef et al., "Temperate and lytic bacteriophages programmed to sensitize and kill antibiotic-resistant bacteria," Proc. Natl. Acad. Sci. USA, vol. 112, p. 7267-7272, doi: 10.1073/pnas.1500107112 published online May 18, 2015).

CRISPR systems can be used to edit genomes of parasites that are resistant to other genetic approaches. For example, a CRISPR-Cas9 system was shown to introduce double-stranded breaks into the in the *Plasmodium yoelii* genome (see, Zhang et al., "Efficient Editing of Malaria Parasite Genome Using the CRISPR/Cas9 System," mBio. vol. 5, e01414-14, July-August 2014). Ghorbal et al. ("Genome editing in the human malaria parasite *Plasmodium* falciparumusing the CRISPR-Cas9 system," Nature Biotechnology, vol. 32, p. 819-821, doi: 10.1038/nbt.2925, published online Jun. 1, 2014) modified the sequences of two genes, orc1 and kelch13, which have putative roles in gene silencing and emerging resistance to artemisinin, respectively. Parasites that were altered at the appropriate sites were recovered with very high efficiency, despite there being no direct selection for the modification, indicating that neutral or even deleterious mutations can be generated using this system. CRISPR-Cas9 is also used to modify the genomes of other pathogenic parasites, including *Toxoplasma gondii* (see Shen et al., "Efficient gene disruption in diverse strains of *Toxoplasma gondii* using CRISPR/CAS9," mBio vol. 5:e01114-14, 2014; and Sidik et al., "Efficient Genome Engineering of *Toxoplasma gondii* Using CRISPR/Cas9," PLoS One vol. 9, e100450, doi: 10.1371/journal.pone.0100450, published online Jun. 27, 2014).

Vyas et al. ("A *Candida albicans* CRISPR system permits genetic engineering of essential genes and gene families," Science Advances, vol. 1, e1500248, DOI: 10.1126/sciadv.1500248, Apr. 3, 2015) employed a CRISPR system to overcome long-standing obstacles to genetic engineering in *C. albicans* and efficiently mutate in a single experiment both copies of several different genes. In an organism where several mechanisms contribute to drug resistance, Vyas produced homozygous double mutants that no longer displayed the hyper-resistance to fluconazole or cycloheximide displayed by the parental clinical isolate Can90. Vyas also obtained homozygous loss-of-function mutations in essential genes of *C. albicans* by creating conditional alleles. Null alleles of DCR1, which is required for ribosomal RNA processing, are lethal at low temperature but viable at high temperature. Vyas used a repair template that introduced a nonsense mutation and isolated dcr1/dcr1 mutants that failed to grow at 16° C.

Treating Pathogens, Like Viral Pathogens, Such as HSV-1/HSV-2

Mention is made of WO 2015/153789 and WO 2015/153791 and through the teachings herein the invention comprehends methods and materials of these documents applied in conjunction with the teachings herein. In an aspect of gene therapy for viral infections, methods and compositions for treating or preventing herpes simplex virus type 1 (HSV-1) or herpes simplex virus type 2 (HSV-2) or its symptoms, e.g., by knocking out one or more of the HSV-1/HSV-2 viral genes, e.g., by knocking out one or more of UL19, UL30, UL48 and/or UL54 gene(s). In one aspect, the methods and compositions may be used to alter one or more of UL19, UL30, ULA8 and/or UL54 gene(s) to treat or prevent HSV-1 or HSV-2 by targeting the gene, e.g., the non-coding or coding regions, e.g., the promoter region, or a transcribed sequence, e.g., intronic or exonic sequence. In an embodiment, coding sequence, e.g., a coding region, e.g., an early coding region, of one or more of UL19, UL30, UlA8 and/or UL54 gene(s), is targeted for alteration and knockout of expression.

Patient-Specific Screening Methods

A CRISPR-Cas9 system that targets nucleotide, e.g., trinucleotide repeats can be used to screen patients or patent samples for the presence of such repeats. The repeats can be the target of the RNA of the CRISPR-Cas9 system, and if there is binding thereto by the CRISPR-Cas9 system, that binding can be detected, to thereby indicate that such a repeat is present. Thus, a CRISPR-Cas9 system can be used to screen patients or patient samples for the presence of the repeat. The patient can then be administered suitable compound(s) to address the condition; or, can be administered a CRISPR-Cas9 system to bind to and cause insertion, deletion or mutation and alleviate the condition.

Treating Diseases with Genetic or Epigenetic Aspects

The CRISPR-Cas9 systems of the present invention can be used to correct genetic mutations that were previously attempted with limited success using TALEN and ZFN and have been identified as potential targets for Cas9 systems, including as in published applications of Editas Medicine describing methods to use Cas9 systems to target loci to therapeutically address diseases with gene therapy, including, WO 2015/048577 CRISPR-RELATED METHODS AND COMPOSITIONS of Gluckmann et al.; WO 2015/070083 CRISPR-RELATED METHODS AND COMPOSITIONS WITH GOVERNING gRNAS of Glucksmann et al.

Mention is made of WO 2015/153780 CRISPR/CAS-RELATED METHODS AND COMPOSITIONS FOR TREATING USHER SYNDROME AND RETINITIS PIGMENTOSA of Maeder et al. Through the teachings herein the invention comprehends methods and materials of these documents applied in conjunction with the teachings herein. In an aspect of ocular and auditory gene therapy, methods and compositions for treating Usher Syndrome and Retinis-Pigmentosa may be adapted to the CRISPR-Cas9 system of the present invention (see, e.g., WO 2015/134812). In an embodiment, the WO 2015/134812 involves a treatment or delaying the onset or progression of Usher Syndrome type HA (USH2A, USH11A) and retinitis pigmentosa 39 (RP39) by gene editing, e.g., using CRISPR-Cas9 mediated methods to correct the guanine deletion at position 2299 in the USH2A gene (e.g., replace the deleted guanine residue at position 2299 in the USH2A gene). In a related aspect, a mutation is targeted by cleaving with either one or more nuclease, one or more nickase, or a combination thereof, e.g., to induce HDR with a donor template that corrects the point mutation (e.g., the single nucleotide, e.g., guanine, deletion). The alteration or correction of the mutant USH2A gene can be mediated by any mechanism. Exemplary mechanisms that can be associated with the alteration (e.g., correction) of the mutant HSH2A gene include, but are not limited to, non-homologous end joining, microhomology-mediated end joining (MMEJ), homology-directed repair (e.g., endogenous donor template mediated), SDSA (synthesis dependent strand annealing), single-strand annealing or single strand invasion. In an embodiment, the method used for treating Usher Syndrome and Retinis-Pigmentosa can include acquiring knowledge of the mutation carried by the subject, e.g., by sequencing the appropriate portion of the USH2A gene.

Mention is also made of WO 2015/138510 and through the teachings herein the invention (using a CRISPR-Cas9 system) comprehends providing a treatment or delaying the onset or progression of Leber's Congenital Amaurosis 10 (LCA 10). LCA 10 is caused by a mutation in the CEP290 gene, e.g., a c.2991+1655, adenine to guanine mutation in the CEP290 gene which gives rise to a cryptic splice site in intron 26. This is a mutation at nucleotide 1655 of intron 26 of CEP290, e.g., an A to G mutation. CEP290 is also known as: CT87; MKS4; POC3; rd16; BBS14; JBTS5; LCAJO; NPHP6; SLSN6; and 3H11Ag (see, e.g., WO 2015/138510). In an aspect of gene therapy, the invention involves introducing one or more breaks near the site of the LCA target position (e.g., c.2991+1655; A to G) in at least one allele of the CEP290 gene. Altering the LCA10 target position refers to (1) break-induced introduction of an indel (also referred to herein as NHEJ-mediated introduction of an indel) in close proximity to or including a LCA10 target position (e.g., c.2991+1655A to G), or (2) break-induced deletion (also referred to herein as NHEJ-mediated deletion) of genomic sequence including the mutation at a LCA10 target position (e.g., c.2991+1655A to G). Both approaches give rise to the loss or destruction of the cryptic splice site resulting from the mutation at the LCA 10 target position.

In an aspect, the invention (using a CRISPR-Cas9 system) comprehends providing a treatment or delaying the onset or progression of Leber's Congenital Amaurosis 10 (LCA 10). LCA 10 is caused by a mutation in the CEP290 gene, e.g., a c.2991+1655, adenine to guanine mutation in the CEP290 gene which gives rise to a cryptic splice site in intron 26. This is a mutation at nucleotide 1655 of intron 26 of CEP290, e.g., an A to G mutation. CEP290 is also known as: CT87: MKS4; POC3; rd16; BBS14; JBTS5; LCAJO; NPHP6; SLSN6; and 3H11Ag (see, e.g., WO 2015/138510). In an aspect of gene therapy, the invention involves introducing one or more breaks near the site of the LCA target position (e.g., c.2991+1655; A to G) in at least one allele of the CEP290 gene. Altering the LCA10 target position refers to (1) break-induced introduction of an indel (also referred to herein as NHEJ-mediated introduction of an indel) in close proximity to or including a LCA10 target position (e.g., c.2991+1655A to G), or (2) break-induced deletion (also referred to herein as NHEJ-mediated deletion) of genomic sequence including the mutation at a LCA10 target position (e.g., c.2991+1655A to G). Both approaches give rise to the loss or destruction of the cryptic splice site resulting from the mutation at the LCA 10 target position.

Researchers are contemplating whether gene therapies could be employed to treat a wide range of diseases. The CRISPR systems of the present invention based on Cas9 effector protein are envisioned for such therapeutic uses, including, but noted limited to further exemplified targeted areas and with delivery methods as below. Some examples of conditions or diseases that might be usefully treated using the present system are included in the examples of genes and references included herein and are currently associated with those conditions are also provided there. The genes and conditions exemplified are not exhaustive.

Treating Diseases of the Circulatory System

The present invention also contemplates delivering the CRISPR-Cas9 system, specifically the novel CRISPR effector protein systems described herein, to the blood or hematopoetic stem cells. The plasma exosomes of Wahlgren et al. (Nucleic Acids Research, 2012, Vol. 40, No. 17 e130) were previously described and may be utilized to deliver the CRISPR Cas9 system to the blood. The nucleic acid-targeting system of the present invention is also contemplated to treat hemoglobinopathies, such as thalassemias and sickle cell disease. See, e.g., International Patent Publication No. WO 2013/126794 for potential targets that may be targeted by the CRISPR Cas9 system of the present invention.

Drakopoulou, "Review Article, The Ongoing Challenge of Hematopoietic Stem Cell-Based Gene Therapy for β-Thalassemia," Stem Cells International, Volume 2011, Article ID 987980, 10 pages, doi:10.4061/2011/987980, incorporated herein by reference along with the documents it cites, as if set out in full, discuss modifying HSCs using a lentivirus that delivers a gene for β-globin or γ-globin. In contrast to using lentivirus, with the knowledge in the art and the teachings in this disclosure, the skilled person can correct HSCs as to β-Thalassemia using a CRISPR-Cas9 system that targets and corrects the mutation (e.g., with a suitable HDR template that delivers a coding sequence for β-globin or γ-globin, advantageously non-sickling β-globin or γ-globin); specifically, the guide RNA can target mutation that give rise to β-Thalassemia, and the HDR can provide coding for proper expression of β-globin or γ-globin. A guide RNA that targets the mutation-and-Cas9 protein containing particle is contacted with HSCs carrying the mutation. The particle also can contain a suitable HDR template to correct the mutation for proper expression of β-globin or γ-globin; or the HSC can be contacted with a second particle or a vector that contains or delivers the HDR template. The so contacted cells can be administered; and optionally treated/expanded; cf. Cartier. In this regard mention is made of: Cavazzana, "Outcomes of Gene Therapy for β-Thalassemia Major via Transplantation of Autologous Hematopoietic Stem Cells Transduced Ex Vivo with a Lentiviral $\beta^{A-T87Q}$-Globin Vector." tif2014.org/abstractFiles/Jean%20Antoine%20Ribeil_Abstract.pdf; Cavazzana-Calvo, "Transfusion independence and HMGA2 activation after gene therapy of human β-thalassaemia", Nature 467, 318-322 (16 Sep. 2010) doi:10.1038/nature09328; Nienhuis, "Development of Gene Therapy for Thalassemia, Cold Spring Harbor Perspectives in Medicine, doi: 10.1101/cshperspect.a011833 (2012), LentiGlobin BB305, a lentiviral vector containing an engineered fβ-globin gene ($\beta^{A-T87Q}$); and Xie et al., "Seamless gene correction of β-thalassaemia mutations in patient-specific iPSCs using CRISPR/Cas9 and piggyback" Genome Research gr.173427.114 (2014) http://www.genome.org/cgi/doi/10.1101/gr 173427.114 (Cold Spring Harbor Laboratory Press); that is the subject of Cavazzana work involving human β-thalassaemia and the subject of the Xie work, are all incorporated herein by reference, together with all documents cited therein or associated therewith. In the instant invention, the HDR template can provide for the HSC to express an engineered β-globin gene (e.g., $\beta^{A-T87Q}$), or β-globin as in Xie.

Xu et al. (Sci Rep. 2015 Jul. 9; 5:12065. doi: 10.1038/srep12065) have designed TALENs and CRISPR-Cas9 to directly target the intron2 mutation site IVS2-654 in the globin gene. Xu et al. observed different frequencies of double-strand breaks (DSBs) at IVS2-654 loci using TALENs and CRISPR-Cas9, and TALENs mediated a higher homologous gene targeting efficiency compared to CRISPR-Cas9 when combined with the piggyBac transposon donor. In addition, more obvious off-target events were observed for CRISPR-Cas9 compared to TALENs. Finally, TALENs-corrected iPSC clones were selected for erythroblast differentiation using the OP9 co-culture system and detected relatively higher transcription of HBB than the uncorrected cells.

Song et al. (Stem Cells Dev. 2015 May 1; 24(9):1053-65. doi: 10.1089/scd.2014.0347. Epub 2015 Feb. 5) used CRISPR/Cas9 to correct β-Thal iPSCs; gene-corrected cells exhibit normal karyotypes and full pluripotency as human embryonic stem cells (hESCs) showed no off-targeting effects. Then, Song et al. evaluated the differentiation efficiency of the gene-corrected β-Thal iPSCs. Song et al. found that during hematopoietic differentiation, gene-corrected β-Thal iPSCs showed an increased embryoid body ratio and various hematopoietic progenitor cell percentages. More importantly, the gene-corrected β-Thal iPSC lines restored HBB expression and reduced reactive oxygen species production compared with the uncorrected group. Song et al.'s study suggested that hematopoietic differentiation efficiency of β-Thal iPSCs was greatly improved once corrected by the CRISPR-Cas9 system. Similar methods may be performed utilizing the CRISPR-Cas9 systems described herein, e.g. systems comprising Cas9 effector proteins.

Mention is made of WO 2015/148860, through the teachings herein the invention comprehends methods and materials of these documents applied in conjunction with the teachings herein. In an aspect of blood-related disease gene therapy, methods and compositions for treating beta thalassemia may be adapted to the CRISPR-Cas9 system of the present invention (see, e.g., WO 2015/148860). In an embodiment, WO 2015/148860 involves the treatment or prevention of beta thalassemia, or its symptoms, e.g., by altering the gene for B-cell CLL/lymphoma 11A (BCL11A). The BCL11A gene is also known as B-cell CLL/lymphoma 11A, BCL11A-L, BCL11A-S, BCL11AXL, CTIP 1, HBFQTL5 and ZNF. BCL11A encodes a zinc-finger protein that is involved in the regulation of globin gene expression. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating beta thalassemia disease phenotypes.

Sickle cell anemia is an autosomal recessive genetic disease in which red blood cells become sickle-shaped. It is caused by a single base substitution in the β-globin gene, which is located on the short arm of chromosome 11. As a result, valine is produced instead of glutamic acid causing the production of sickle hemoglobin (HbS). This results in the formation of a distorted shape of the erythrocytes. Due to this abnormal shape, small blood vessels can be blocked, causing serious damage to the bone, spleen and skin tissues. This may lead to episodes of pain, frequent infections, hand-foot syndrome or even multiple organ failure. The distorted erythrocytes are also more susceptible to hemolysis, which leads to serious anemia. As in the case of β-thalassaemia, sickle cell anemia can be corrected by modifying HSCs with the CRISPR-Cas9 system. The system allows the specific editing of the cell's genome by cutting its DNA and then letting it repair itself. The Cas9 protein is inserted and directed by a RNA guide to the mutated point and then it cuts the DNA at that point. Simultaneously, a healthy version of the sequence is inserted. This sequence is used by the cell's own repair system to fix the induced cut. In this way, the CRISPR-Cas9 allows the correction of the mutation in the previously obtained stem cells. With the knowledge in the art and the teachings in this disclosure, the skilled person can correct HSCs as to sickle cell anemia using a CRISPR-Cas9 system that targets and corrects the mutation (e.g., with a suitable HDR template that delivers a coding sequence for β-globin, advantageously non-sickling β-globin); specifically, the guide RNA can target mutation that give rise to sickle cell anemia, and the HDR can provide coding for proper expression of β-globin. An guide RNA that targets the mutation-and-Cas9 protein containing particle is contacted with HSCs carrying the mutation. The particle also can contain a suitable HDR template to correct the mutation for proper expression of β-globin; or the HSC can be contacted with a second particle or a vector that contains or delivers the HDR template. The so contacted cells can be administered; and optionally treated/expanded; cf. Cartier. The HDR template can provide for the HSC to express an engineered Jβ-globin gene (e.g., βA-T87Q), or β-globin as in Xie.

Mention is also made of WO 2015/148863 and through the teachings herein the invention comprehends methods and materials of these documents which may be adapted to the CRISPR-Cas9 system of the present invention. In an aspect of treating and preventing sickle cell disease, which is an inherited hematologic disease, WO 2015/148863 comprehends altering the BCL11A gene. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating sickle cell disease phenotypes.

Williams, "Broadening the Indications for Hematopoietic Stem Cell Genetic Therapies," Cell Stem Cell 13:263-264 (2013), incorporated herein by reference along with the documents it cites, as if set out in full, report lentivirus-mediated gene transfer into HSC/P cells from patients with the lysosomal storage disease metachromatic leukodystrophy disease (MLD), a genetic disease caused by deficiency of arylsulfatase A (ARSA), resulting in nerve demyelination; and lentivirus-mediated gene transfer into HSCs of patients with Wiskott-Aldrich syndrome (WAS) (patients with defective WAS protein, an effector of the small GTPase CDC42 that regulates cytoskeletal function in blood cell lineages and thus suffer from immune deficiency with recurrent infections, autoimmune symptoms, and thrombocytopenia with abnormally small and dysfunctional platelets leading to excessive bleeding and an increased risk of leukemia and lymphoma). In contrast to using lentivirus, with the knowledge in the art and the teachings in this disclosure, the skilled person can correct HSCs as to MLD (deficiency of arylsulfatase A (ARSA)) using a CRISPR-Cas9 system that targets and corrects the mutation (deficiency of arylsulfatase A (ARSA)) (e.g., with a suitable HDR template that delivers a coding sequence for ARSA); specifically, the guide RNA can target mutation that gives rise to MLD (deficient ARSA), and the HDR can provide coding for proper expression of ARSA. A guide RNA that targets the mutation-and-Cas9 protein containing particle is contacted with HSCs carrying the mutation. The particle also can contain a suitable HDR template to correct the mutation for proper expression of ARSA; or the HSC can be contacted with a second particle or a vector that contains or delivers the HDR template. The so contacted cells can be administered; and optionally treated/expanded; cf. Cartier. In contrast to using lentivirus, with the knowledge in the art and the teachings in this disclosure, the skilled person can correct HSCs as to WAS using a CRISPR-Cas9 system that targets and corrects the mutation (deficiency of WAS protein) (e.g., with a suitable HDR template that delivers a coding sequence for WAS protein); specifically, the guide RNA can target mutation that gives rise to WAS (deficient WAS protein), and the HDR can provide coding for proper expression of WAS protein. A guide RNA that targets the mutation-and-Cas9 protein containing particle is contacted with HSCs carrying the mutation. The particle also can contain a suitable HDR template to correct the mutation for proper expression of WAS protein; or the HSC can be contacted with a second particle or a vector that contains or delivers the HDR template. The so contacted cells can be administered; and optionally treated/expanded; cf. Cartier.

In an aspect of the invention, methods and compositions which involve editing a target nucleic acid sequence, or modulating expression of a target nucleic acid sequence, and applications thereof in connection with cancer immunotherapy are comprehended by adapting the CRISPR-Cas9 system of the present invention. Reference is made to the application of gene therapy in WO 2015/161276 which involves methods and compositions which can be used to affect T-cell proliferation, survival and/or function by altering one or more T-cell expressed genes, e.g., one or more of FAS, BID, CTLA4, PDCD1, CBLB, PTPN6, TRAC and/or TRBC genes. In a related aspect, T-cell proliferation can be affected by altering one or more T-cell expressed genes, e.g., the CBLB and/or PTPN6 gene, FAS and/or BID gene, CTLA4 and/or PDCD1 and/or TRAC and/or TRBC gene.

Chimeric antigen receptor (CAR)19 T-cells exhibit anti-leukemic effects in patient malignancies. However, leukemia patients often do not have enough T-cells to collect, meaning that treatment must involve modified T cells from donors. Accordingly, there is interest in establishing a bank of donor T-cells. Qasim et al. ("First Clinical Application of Talen Engineered Universal CAR19 T Cells in B-ALL" ASH 57th Annual Meeting and Exposition, Dec. 5-8, 2015, Abstract 2046 (https://ash.confex.com/ash/2015/webprogram/Paper81653.html published online November 2015) discusses modifying CAR19 T cells to eliminate the risk of graft-versus-host disease through the disruption of T-cell receptor expression and CD52 targeting. Furthermore, CD52 cells were targeted such that they became insensitive to Alemtuzumab, and thus allowed Alemtuzumab to prevent host-mediated rejection of human leukocyte antigen (HLA) mismatched CAR19 T-cells. Investigators used third generation self-inactivating lentiviral vector encoding a 4 g7 CAR19 (CD19 scFv-4-1BB-CD3ζ) linked to RQR8, then electroporated cells with two pairs of TALEN mRNA for multiplex targeting for both the T-cell receptor (TCR) alpha constant chain locus and the CD52 gene locus. Cells which were still expressing TCR following ex vivo expansion were depleted using CliniMacs α/β TCR depletion, yielding a T-cell product (UCART19) with <1% TCR expression, 85% of which expressed CAR19, and 64% becoming CD52 negative. The modified CAR19 T cells were administered to treat a patient's relapsed acute lymphoblastic leukemia. The teachings provided herein provide effective methods for modifying cells, for example to remove or modulate CD52 or other targets, thus can be used in conjunction with modification of administration of T cells or other cells to patients to treat malignancies.

Watts, "Hematopoietic Stem Cell Expansion and Gene Therapy" Cytotherapy 13(10):1164-1171. doi:10.3109/14653249.2011.620748 (2011), incorporated herein by reference along with the documents it cites, as if set out in full, discusses hematopoietic stem cell (HSC) gene therapy, e.g., virus-mediated HSC gene therapy, as an highly attractive treatment option for many disorders including hematologic conditions, immunodeficiencies including HIV/AIDS, and other genetic disorders like lysosomal storage diseases, including SCID-X1, ADA-SCID, β-thalassemia, X-linked CGD, Wiskott-Aldrich syndrome, Fanconi anemia, adrenoleukodystrophy (ALD), and metachromatic leukodystrophy (MLD).

US Patent Publication Nos. 20110225664, 20110091441, 20100229252, 20090271881 and 20090222937 assigned to Cellectis, relates to CREI variants, wherein at least one of the two I-CreI monomers has at least two substitutions, one in each of the two functional subdomains of the LAGLI-DADG core domain (SEQ ID NO: 58) situated respectively from positions 26 to 40 and 44 to 77 of I-CreI, said variant being able to cleave a DNA target sequence from the human interleukin-2 receptor gamma chain (IL2RG) gene also named common cytokine receptor gamma chain gene or gamma C gene. The target sequences identified in US Patent Publication Nos. 20110225664, 20110091441, 20100229252, 20090271881 and 20090222937 may be utilized for the nucleic acid-targeting system of the present invention.

Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-109). Overall incidence is estimated to 1 in 75 000 births. Patients with untreated SCID are subject to multiple opportunist micro-organism infections, and do generally not live beyond one year. SCID can be treated by allogenic hematopoietic stem cell transfer, from a familial donor. Histocompatibility with the donor can vary widely. In the case of Adenosine Deaminase (ADA) deficiency, one of the SCID forms, patients can be treated by injection of recombinant Adenosine Deaminase enzyme.

Since the ADA gene has been shown to be mutated in SCID patients (Giblett et al., Lancet, 1972, 2, 1067-1069), several other genes involved in SCID have been identified (Cavazzana-Calvo et al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., Annu. Rev. Med., 2005, 56, 585-602; Fischer et al., Immunol. Rev., 2005, 203, 98-109). Since when their genetic bases have been identified, the different SCID forms have become a paradigm for gene therapy approaches (Fischer et al., Immunol. Rev., 2005, 203, 98-109) for two major reasons. First, as in all blood diseases, an ex vivo treatment can be envisioned. Hematopoietic Stem Cells (HSCs) can be recovered from bone marrow, and keep their pluripotent properties for a few cell divisions. Therefore, they can be treated in vitro, and then reinjected into the patient, where they repopulate the bone marrow. Second, since the maturation of lymphocytes is impaired in SCID patients, corrected cells have a selective advantage. Therefore, a small number of corrected cells can restore a functional immune system. This hypothesis was validated several times by (i) the partial restoration of immune functions associated with the reversion of mutations in SCID patients (Hirschhorn et al., Nat. Genet., 1996, 13, 290-295; Stephan et al., N. Engl. J. Med., 1996, 335, 1563-1567; Bousso et al., Proc. Natl., Acad. Sci. USA, 2000, 97, 274-278; Wada et al., Proc. Natl. Acad. Sci. USA, 2001, 98, 8697-8702; Nishikomori et al., Blood, 2004, 103, 4565-4572), (ii) the correction of SCID-X1 deficiencies in vitro in hematopoietic cells (Candotti et al., Blood, 1996, 87, 3097-3102; Cavazzana-Calvo et al., Blood, 1996, Blood, 88, 3901-3909; Taylor et al., Blood, 1996, 87, 3103-3107; Hacein-Bey et al., Blood, 1998, 92, 4090-4097), (iii) the correction of SCID-X1 (Soudais et al., Blood, 2000, 95, 3071-3077; Tsai et al., Blood, 2002, 100, 72-79), JAK-3 (Bunting et al., Nat. Med., 1998, 4, 58-64; Bunting et al., Hum. Gene Ther., 2000, 11, 2353-2364) and RAG2 (Yates et al., Blood, 2002, 100, 3942-3949) deficiencies in vivo in animal models and (iv) by the result of gene therapy clinical trials (Cavazzana-Calvo et al., Science, 2000, 288, 669-672; Aiuti et al., Nat. Med., 2002; 8, 423-425, Gaspar et al., Lancet, 2004, 364, 2181-2187).

US Patent Publication No. 20110182867 assigned to the Children's Medical Center Corporation and the President and Fellows of Harvard College relates to methods and uses of modulating fetal hemoglobin expression (HbF) in a hematopoietic progenitor cells via inhibitors of BCL11A expression or activity, such as RNAi and antibodies. The targets disclosed in US Patent Publication No. 20110182867, such as BCL11A, may be targeted by the CRISPR Cas9 system of the present invention for modulating fetal hemoglobin expression. See also Bauer et al. (Science 11 Oct. 2013: Vol. 342 no. 6155 pp. 253-257) and Xu et al. (Science 18 Nov. 2011: Vol. 334 no. 6058 pp. 993-996) for additional BCL11A targets.

With the knowledge in the art and the teachings in this disclosure, the skilled person can correct HSCs as to a genetic hematologic disorder, e.g., β-Thalassemia, Hemophilia, or a genetic lysosomal storage disease.

Treating Disease of the Brain, Central Nervous and Immune Systems

The present invention also contemplates delivering the CRISPR-Cas9 system to the brain or neurons. For example, RNA interference (RNAi) offers therapeutic potential for this disorder by reducing the expression of HTT, the disease-causing gene of Huntington's disease (see, e.g., McBride et al., Molecular Therapy vol. 19 no. 12 Dec. 2011, pp. 2152-2162), therefore Applicant postulates that it may be used/and or adapted to the CRISPR-Cas9 system. The CRISPR-Cas9 system may be generated using an algorithm to reduce the off-targeting potential of antisense sequences. The CRISPR-Cas9 sequences may target either a sequence in exon 52 of mouse, rhesus or human huntingtin and expressed in a viral vector, such as AAV. Animals, including humans, may be injected with about three microinjections per hemisphere (six injections total): the first 1 mm rostral to the anterior commissure (12 µl) and the two remaining injections (12 µl and 10 µl, respectively) spaced 3 and 6 mm caudal to the first injection with 1e12 vg/ml of AAV at a rate of about 1 µl/minute, and the needle was left in place for an additional 5 minutes to allow the injectate to diffuse from the needle tip.

DiFiglia et al. (PNAS, Oct. 23, 2007, vol. 104, no. 43, 17204-17209) observed that single administration into the adult striatum of an siRNA targeting Htt can silence mutant Htt, attenuate neuronal pathology, and delay the abnormal behavioral phenotype observed in a rapid-onset, viral transgenic mouse model of HD. DiFiglia injected mice intrastriatally with 2 µl of Cy3-labeled cc-siRNA-Htt or unconjugated siRNA-Htt at 10 µM. A similar dosage of CRISPR Cas9 targeted to Htt may be contemplated for humans in the present invention, for example, about 5-10 ml of 10 µM CRISPR Cas9 targeted to Htt may be injected intrastriatally.

In another example, Boudreau et al. (Molecular Therapy vol. 17 no. 6 Jun. 2009) injects 5 µl of recombinant AAV serotype 2/1 vectors expressing htt-specific RNAi virus (at $4 \times 10^{12}$ viral genomes/ml) into the striatum. A similar dosage of CRISPR Cas9 targeted to Htt may be contemplated for humans in the present invention, for example, about 10-20 ml of $4 \times 10^{12}$ viral genomes/ml) CRISPR Cas9 targeted to Htt may be injected intrastriatally.

In another example, a CRISPR Cas9 targeted to HTT may be administered continuously (see, e.g., Yu et al., Cell 150, 895-908, Aug. 31, 2012). Yu et al. utilizes osmotic pumps delivering 0.25 ml/hr (Model 2004) to deliver 300 mg/day of ss-siRNA or phosphate-buffered saline (PBS) (Sigma Aldrich) for 28 days, and pumps designed to deliver 0.5 µl/hr (Model 2002) were used to deliver 75 mg/day of the positive control MOE ASO for 14 days. Pumps (Durect Corporation) were filled with ss-siRNA or MOE diluted in sterile PBS and then incubated at 37 C for 24 or 48 (Model 2004) hours prior to implantation. Mice were anesthetized with 2.5% isofluorane, and a midline incision was made at the base of the skull. Using stereotaxic guides, a cannula was implanted into the right lateral ventricle and secured with Loctite adhesive. A catheter attached to an Alzet osmotic mini pump was attached to the cannula, and the pump was placed subcutaneously in the midscapular area. The incision was closed with 5.0 nylon sutures. A similar dosage of CRISPR Cas9 targeted to Htt may be contemplated for humans in the present invention, for example, about 500 to 1000 g/day CRISPR Cas9 targeted to Htt may be administered.

In another example of continuous infusion, Stiles et al. (Experimental Neurology 233 (2012) 463-471) implanted an intraparenchymal catheter with a titanium needle tip into the right putamen. The catheter was connected to a SynchroMed® II Pump (Medtronic Neurological, Minneapolis, Minn.) subcutaneously implanted in the abdomen. After a 7 day infusion of phosphate buffered saline at 6 µL/day, pumps were re-filled with test article and programmed for continuous delivery for 7 days. About 2.3 to 11.52 mg/d of siRNA were infused at varying infusion rates of about 0.1 to 0.5 µL/min. A similar dosage of CRISPR Cas9 targeted to Htt may be contemplated for humans in the present invention, for example, about 20 to 200 mg/day CRISPR Cas9 targeted to Htt may be administered. In another example, the methods of US Patent Publication No. 20130253040 assigned to Sangamo may also be be also be adapted from TALES to the nucleic acid-targeting system of the present invention for treating Huntington's Disease.

A further aspect of the invention relates to utilizing the CRISPR-Cas9 system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas9 system and the underlying genetics is further described in Genetics of Epilepsy and Genetic Epilepsies, edited by Giuliano Avanzini, Jeffrey L. Noebels, Mariani Foundation Paediatric Neurology:20; 2009).

The methods of US Patent Publication No. 20110158957 assigned to Sangamo BioSciences, Inc. involved in inactivating T cell receptor (TCR) genes may also be modified to the CRISPR Cas9 system of the present invention. In another example, the methods of US Patent Publication No. 20100311124 assigned to Sangamo BioSciences, Inc. and US Patent Publication No. 20110225664 assigned to Cellectis, which are both involved in inactivating glutamine synthetase gene expression genes may also be modified to the CRISPR Cas9 system of the present invention.

Treating Hearing Diseases

The present invention also contemplates delivering the CRISPR-Cas9 system to one or both ears.

Researchers are looking into whether gene therapy could be used to aid current deafness treatments—namely, cochlear implants. Deafness is often caused by lost or damaged hair cells that cannot relay signals to auditory neurons. In such cases, cochlear implants may be used to respond to sound and transmit electrical signals to the nerve cells. But these neurons often degenerate and retract from the cochlea as fewer growth factors are released by impaired hair cells.

US patent application 20120328580 describes injection of a pharmaceutical composition into the ear (e.g., auricular administration), such as into the luminae of the cochlea (e.g., the Scala media, Sc vestibulae, and Sc tympani), e.g., using a syringe, e.g., a single-dose syringe. For example, one or more of the compounds described herein can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, Drug Discovery Today, 10: 1299-1306, 2005).

In another mode of administration, the pharmaceutical composition can be administered in situ, via a catheter or pump. A catheter or pump can, for example, direct a pharmaceutical composition into the cochlear luminae or the round window of the ear and/or the lumen of the colon. Exemplary drug delivery apparatus and methods suitable for administering one or more of the compounds described herein into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a patient during a surgical procedure. In some embodiments, a catheter or pump can be positioned, e.g., in the ear (e.g., the outer, middle, and/or inner ear) of a patient without the need for a surgical procedure.

Alternatively or in addition, one or more of the compounds described herein can be administered in combination with a mechanical device such as a cochlear implant or a hearing aid, which is worn in the outer ear. An exemplary cochlear implant that is suitable for use with the present invention is described by Edge et al., (U.S. Publication No. 2007/0093878).

In some embodiments, the modes of administration described above may be combined in any order and can be simultaneous or interspersed.

Alternatively or in addition, the present invention may be administered according to any of the Food and Drug Administration approved methods, for example, as described in CDER Data Standards Manual, version number 004 (which is available at fda.give/cder/dsm/DRG/drg00301.htm).

In general, the cell therapy methods described in US patent application 20120328580 can be used to promote complete or partial differentiation of a cell to or towards a mature cell type of the inner ear (e.g., a hair cell) in vitro. Cells resulting from such methods can then be transplanted or implanted into a patient in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Cells suitable for use in the present invention include, but are not limited to, cells that are capable of differentiating completely or partially into a mature cell of the inner ear, e.g., a hair cell (e.g., an inner and/or outer hair cell), when contacted, e.g., in vitro, with one or more of the compounds described herein. Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, iPS cells, and fat derived stem cells), progenitor cells (e.g., inner ear progenitor cells), support cells (e.g., Deiters' cells, pillar cells, inner phalangeal cells, tectal cells and Hensen's cells), and/or germ cells. The use of stem cells for the replacement of inner ear sensory cells is described in Li et al., (U.S. Publication No. 2005/0287127) and Li et al., (U.S. patent Ser. No. 11/953, 797). The use of bone marrow derived stem cells for the replacement of inner ear sensory cells is described in Edge et al., PCT/US2007/084654. iPS cells are described, e.g., at Takahashi et al., Cell, Volume 131, Issue 5, Pages 861-872 (2007); Takahashi and Yamanaka, Cell 126, 663-76 (2006); Okita et al., Nature 448, 260-262 (2007); Yu, J. et al., Science 318(5858):1917-1920 (2007); Nakagawa et al., Nat. Biotechnol. 26:101-106 (2008); and Zaehres and Scholer, Cell 131(5):834-835 (2007). Such suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

The CRISPR Cas9 molecules of the present invention may be delivered to the ear by direct application of pharmaceutical composition to the outer ear, with compositions modified from US Published application, 20110142917. In some embodiments the pharmaceutical composition is applied to the ear canal. Delivery to the ear may also be referred to as aural or optic delivery.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example Tolentino et al., Retina 24(4):660 which may also be applied to the present invention).

Qi et al. discloses methods for efficient siRNA transfection to the inner ear through the intact round window by a novel proteidic delivery technology which may be applied to the nucleic acid-targeting system of the present invention (see, e.g., Qi et al., Gene Therapy (2013), 1-9). In particular, a TAT double stranded RNA-binding domains (TAT-DRBDs), which can transfect Cy3-labeled siRNA into cells of the inner ear, including the inner and outer hair cells, *crista ampullaris*, macula utriculi and macula sacculi, through intact round-window permeation was successful for delivering double stranded siRNAs in vivo for treating various inner ear ailments and preservation of hearing function. About 40 µl of 10 mM RNA may be contemplated as the dosage for administration to the ear.

According to Rejali et al. (Hear Res. 2007 June; 228(1-2):180-7), cochlear implant function can be improved by good preservation of the spiral ganglion neurons, which are the target of electrical stimulation by the implant and brain derived neurotrophic factor (BDNF) has previously been shown to enhance spiral ganglion survival in experimentally deafened ears. Rejali et al. tested a modified design of the cochlear implant electrode that includes a coating of fibroblast cells transduced by a viral vector with a BDNF gene insert. To accomplish this type of ex vivo gene transfer, Rejali et al. transduced guinea pig fibroblasts with an adenovirus with a BDNF gene cassette insert, and determined that these cells secreted BDNF and then attached BDNF-secreting cells to the cochlear implant electrode via an agarose gel, and implanted the electrode in the scala tympani. Rejali et al. determined that the BDNF expressing electrodes were able to preserve significantly more spiral ganglion neurons in the basal turns of the cochlea after 48 days of implantation when compared to control electrodes and demonstrated the feasibility of combining cochlear implant therapy with ex vivo gene transfer for enhancing spiral ganglion neuron survival. Such a system may be applied to the nucleic acid-targeting system of the present invention for delivery to the ear.

Mukherjea et al. (Antioxidants & Redox Signaling, Volume 13, Number 5, 2010) document that knockdown of NOX3 using short interfering (si) RNA abrogated cisplatin ototoxicity, as evidenced by protection of OHCs from damage and reduced threshold shifts in auditory brainstem responses (ABRs). Different doses of siNOX3 (0.3, 0.6, and 0.9 µg) were administered to rats and NOX3 expression was evaluated by real time RT-PCR. The lowest dose of NOX3 siRNA used (0.3 µg) did not show any inhibition of NOX3 mRNA when compared to transtympanic administration of scrambled siRNA or untreated *cochleae*. However, administration of the higher doses of NOX3 siRNA (0.6 and 0.9 µg) reduced NOX3 expression compared to control scrambled siRNA. Such a system may be applied to the CRISPR Cas9 system of the present invention for transtympanic administration with a dosage of about 2 mg to about 4 mg of CRISPR Cas9 for administration to a human.

Jung et al. (Molecular Therapy, vol. 21 no. 4, 834-841 April 2013) demonstrate that HesS levels in the utricle decreased after the application of siRNA and that the number of hair cells in these utricles was significantly larger than following control treatment. The data suggest that siRNA technology may be useful for inducing repair and regeneration in the inner ear and that the Notch signaling pathway is a potentially useful target for specific gene expression inhibition. Jung et al. injected 8 µg of HesS siRNA in 2 µl volume, prepared by adding sterile normal saline to the lyophilized siRNA to a vestibular epithelium of the ear. Such a system may be applied to the nucleic acid-targeting system of the present invention for administration to the vestibular epithelium of the ear with a dosage of about 1 to about 30 mg of CRISPR Cas9 for administration to a human.

Treating Diseases of the Eye

The present invention also contemplates delivering the CRISPR-Cas9 system to one or both eyes.

In yet another aspect of the invention, the CRISPR-Cas9 system may be used to correct ocular defects that arise from several genetic mutations further described in Genetic Diseases of the Eye, Second Edition, edited by Elias I. Traboulsi, Oxford University Press, 2012.

For administration to the eye, lentiviral vectors, in particular equine infectious anemia viruses (EIAV) are particularly preferred.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285, Published online 21 Nov. 2005 in Wiley InterScience (www.interscience.wiley.com). DOI: 10.1002/jgm.845). The vectors are contemplated to have cytomegalovirus (CMV) promoter driving expression of the target gene. Intracameral, subretinal, intraocular and intravitreal injections are all contemplated (see, e.g., Balagaan, J Gene Med 2006; 8: 275-285, Published online 21 Nov. 2005 in Wiley InterScience (www.interscience.wiley.com). DOI: 10.1002/jgm.845). Intraocular injections may be performed with the aid of an operating microscope. For subretinal and intravitreal injections, eyes may be prolapsed by gentle digital pressure and fundi visualised using a contact lens system consisting of a drop of a coupling medium solution on the cornea covered with a glass microscope slide coverslip. For subretinal injections, the tip of a 10-mm 34-gauge needle, mounted on a 5-µl Hamilton syringe may be advanced under direct visualisation through the superior equatorial sclera tangentially towards the posterior pole until the aperture of the needle was visible in the subretinal space. Then, 2 µl of vector suspension may be injected to produce a superior bullous retinal detachment, thus confirming subretinal vector administration. This approach creates a self-sealing sclerotomy allowing the vector suspension to be retained in the subretinal space until it is absorbed by the RPE, usually within 48 h of the procedure. This procedure may be repeated in the inferior hemisphere to produce an inferior retinal detachment. This technique results in the exposure of approximately 70% of neurosensory retina and RPE to the vector suspension. For intravitreal injections, the needle tip may be advanced through the sclera 1 mm posterior to the corneoscleral limbus and 2 µl of vector suspension injected into the vitreous cavity. For intracameral injections, the needle tip may be advanced through a corneoscleral limbal paracentesis, directed towards the central cornea, and 2 µl of vector suspension may be injected. For intracameral injections, the needle tip may be advanced through a corneoscleral limbal paracentesis, directed towards the central cornea, and 2 µl of vector suspension may be injected. These vectors may be injected at titres of either $1.0$-$1.4 \times 10^{10}$ or $1.0$-$1.4 \times 10^{9}$ transducing units (TU)/ml.

In another embodiment, RetinoStat®, an equine infectious anemia virus-based lentiviral gene therapy vector that expresses angiostatic proteins endostain and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for the CRISPR-Cas9 system of the present invention. Each eye may be treated with either RetinoStat® at a dose of $1.1 \times 10^5$ transducing units per eye (TU/eye) in a total volume of 100 µl.

In an embodiment, mention is made of WO 2015/153780 which comprehends providing a treatment or prevention of Primary Open Angle Glaucoma (POAG) by targeting the coding sequence of the MYOC gene. Some of the target mutations which give rise to POAG include, but are not limited to, P370 (e.g. P370L); 1477 (e.g., I477N or I477S): T377 (e.g., TE77R); Q368 (Q368stop)—all in the MYOC gene. The target mutation also may include a mutational hotspot between amino acid sequence positions 246-252 in the MYOC gene. In an embodiment, the target mutation is a mutational hotspot between amino acid sequence positions, e.g., amino acids 368-380, amino acids 368-370+377-380, amino acids 364-380, or amino acids 347-380 in the MYOC gene. In an embodiment, the target mutation is a mutational hotspot between amino acid sequence positions 423-437 (e.g., amino acids 423-426, amino acids 423-427 and amino acids 423-437) in the MYOC gene. In an embodiment, the target mutation is a mutational hotspot between amino acid sequence positions 477-502 in the MYOC gene (see, e.g., WO 2015/153780).

In another embodiment, an E1-, partial E3-, E4-deleted adenoviral vector may be contemplated for delivery to the eye. Twenty-eight patients with advanced neovascular age related macular degeneration (AMD) were given a single intravitreous injection of an E1-, partial E3-, E4-deleted adenoviral vector expressing human pigment epithelium-derived factor (AdPEDF.11) (see, e.g., Campochiaro et al., Human Gene Therapy 17:167-176 (February 2006)). Doses ranging from $10^6$ to $10^{9.5}$ particle units (PU) were investigated and there were no serious adverse events related to AdPEDF.11 and no dose-limiting toxicities (see, e.g., Campochiaro et al., Human Gene Therapy 17:167-176 (February 2006)). Adenoviral vector mediated ocular gene transfer appears to be a viable approach for the treatment of ocular disorders and could be applied to the CRISPR Cas9 system.

In another embodiment, the sd-rxRNA® system of RXi Pharmaceuticals may be used/and or adapted for delivering CRISPR Cas9 to the eye. In this system, a single intravitreal administration of 3 gig of sd-rxRNA results in sequence-specific reduction of PPIB mRNA levels for 14 days. The sd-rxRNA® system may be applied to the nucleic acid-targeting system of the present invention, contemplating a dose of about 3 to 20 mg of CRISPR administered to a human.

Millington-Ward et al. (Molecular Therapy, vol. 19 no. 4, 642-649 April 2011) describes adeno-associated virus (AAV) vectors to deliver an RNA interference (RNAi)-based rhodopsin suppressor and a codon-modified rhodopsin replacement gene resistant to suppression due to nucleotide alterations at degenerate positions over the RNAi target site. An injection of either $6.0 \times 10^8$ vp or $1.8 \times 10^{10}$ vp AAV were subretinally injected into the eyes by Millington-Ward et al. The AAV vectors of Millington-Ward et al. may be applied to the CRISPR Cas9 system of the present invention, contemplating a dose of about $2 \times 10^1$ to about $6 \times 10^{13}$ vp administered to a human.

Dalkara et al. (Sci Transl Med 5, 189ra76 (2013)) also relates to in vivo directed evolution to fashion an AAV vector that delivers wild-type versions of defective genes throughout the retina after noninjurious injection into the eyes' vitreous humor. Dalkara describes a 7mer peptide display library and an AAV library constructed by DNA shuffling of cap genes from AAV1, 2, 4, 5, 6, 8, and 9. The rcAAV libraries and rAAV vectors expressing GFP under a CAG or Rho promoter were packaged and deoxyribonuclease-resistant genomic titers were obtained through quantitative PCR. The libraries were pooled, and two rounds of evolution were performed, each consisting of initial library diversification followed by three in vivo selection steps. In each such step, P30 rho-GFP mice were intravitreally injected with 2 ml of iodixanol-purified, phosphate-buffered saline (PBS)-dialyzed library with a genomic titer of about $1 \times 10^{12}$ vg/ml. The AAV vectors of Dalkara et al. may be applied to the nucleic acid-targeting system of the present invention, contemplating a dose of about $1 \times 10^{15}$ to about $1 \times 10^{16}$ vg/ml administered to a human.

In another embodiment, the rhodopsin gene may be targeted for the treatment of retinitis pigmentosa (RP), wherein the system of US Patent Publication No. 20120204282 assigned to Sangamo BioSciences, Inc. may be modified in accordance of the CRISPR Cas9 system of the present invention.

In another embodiment, the methods of US Patent Publication No. 20130183282 assigned to Cellectis, which is directed to methods of cleaving a target sequence from the human rhodopsin gene, may also be modified to the nucleic acid-targeting system of the present invention.

US Patent Publication No. 20130202678 assigned to Academia Sinica relates to methods for treating retinopathies and sight-threatening ophthalmologic disorders relating to delivering of the Puf-A gene (which is expressed in retinal ganglion and pigmented cells of eye tissues and displays a unique anti-apoptotic activity) to the sub-retinal or intravitreal space in the eye. In particular, desirable targets are zgc:193933, prdm1a, spata2, tex10, rbb4, ddx3, zp2.2, Blimp-1 and HtrA2, all of which may be targeted by the nucleic acid-targeting system of the present invention.

Wu (Cell Stem Cell, 13:659-62, 2013) designed a guide RNA that led Cas9 to a single base pair mutation that causes cataracts in mice, where it induced DNA cleavage. Then using either the other wild-type allele or oligos given to the zygotes repair mechanisms corrected the sequence of the broken allele and corrected the cataract-causing genetic defect in mutant mouse.

US Patent Publication No. 20120159653, describes use of zinc finger nucleases to genetically modify cells, animals and proteins associated with macular degeneration (MD). Macular degeneration (MD) is the primary cause of visual impairment in the elderly, but is also a hallmark symptom of childhood diseases such as Stargardt disease, Sorsby fundus, and fatal childhood neurodegenerative diseases, with an age of onset as young as infancy. Macular degeneration results in a loss of vision in the center of the visual field (the macula) because of damage to the retina. Currently existing animal models do not recapitulate major hallmarks of the disease as it is observed in humans. The available animal models comprising mutant genes encoding proteins associated with MD also produce highly variable phenotypes, making translations to human disease and therapy development problematic.

One aspect of US Patent Publication No. 20120159653 relates to editing of any chromosomal sequences that encode proteins associated with MD which may be applied to the nucleic acid-targeting system of the present invention. The proteins associated with MD are typically selected based on an experimental association of the protein associated with MD to an MD disorder. For example, the production rate or circulating concentration of a protein associated with MD may be elevated or depressed in a population having an MD disorder relative to a population lacking the MD disorder. Differences in protein levels may be assessed using proteomic techniques including but not limited to Western blot, immunohistochemical staining, enzyme linked immunosorbent assay (ELISA), and mass spectrometry. Alternatively, the proteins associated with MD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with MD include but are not limited to the following proteins: (ABCA4) ATP-binding cassette, sub-family A (ABC1), member 4 ACHMI achromatopsia (rod monochromacy) 1 ApoE Apolipoprotein E (ApoE) C1QTNF5 (CTRP5) C1q and tumor necrosis factor related protein 5 (C1QTNF5) C2 Complement component 2 (C2) C3 Complement components (C3) CCL2 Chemokine (C—C motif) Ligand 2 (CCL2) CCR2 Chemokine (C—C motif) receptor 2 (CCR2) CD36 Cluster of Differentiation 36 CFB Complement factor B CFH Complement factor CFH H CFHR1 complement factor H-related 1 CFHR3 complement factor H-related 3 CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair crosscomplementing rodent repair deficiency, complementation group 6 FBLN5 Fibulin-5 FBLN5 Fibulin 5 FBLN6 Fibulin 6 FSCN2 fascin (FSCN2) HMCN1 Hemicentrin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domain containing family A member 1 (PLEKHA1) PROM1 Prominin 1 (PROM1 or CD133) PRPH2 Peripherin-2 RPGR retinitis pigmentosa GTPase regulator SERPING1 serpin peptidase inhibitor, clade G, member 1 (C1-inhibitor) TCOF1 Treacle TIMP3 Metalloproteinase inhibitor 3 (TIMP3) TLR3 Toll-like receptor 3.

The identity of the protein associated with MD whose chromosomal sequence is edited can and will vary. In preferred embodiments, the proteins associated with MD whose chromosomal sequence is edited may be the ATP-binding cassette, sub-family A (ABC1) member 4 protein (ABCA4) encoded by the ABCR gene, the apolipoprotein E protein (APOE) encoded by the APOE gene, the chemokine (C—C motif) Ligand 2 protein (CCL2) encoded by the CCL2 gene, the chemokine (C—C motif) receptor 2 protein (CCR2) encoded by the CCR2 gene, the ceruloplasmin protein (CP) encoded by the CP gene, the cathepsin D protein (CTSD) encoded by the CTSD gene, or the metalloproteinase inhibitor 3 protein (TIMP3) encoded by the TIMP3 gene. In an exemplary embodiment, the genetically modified animal is a rat, and the edited chromosomal sequence encoding the protein associated with MD may be: (ABCA4) ATPbinding cassette, NM_000350 sub-family A (ABC1), member 4 APOE Apolipoprotein E NM_138828 (APOE) CCL2 Chemokine (C—C NM_031530 motif) Ligand 2 (CCL2) CCR2 Chemokine (C—C NM_021866 motif) receptor 2 (CCR2) CP ceruloplasmin (CP) NM_012532 CTSD Cathepsin D (CTSD) NM_134334 TIMP3 Metalloproteinase NM_012886 inhibitor 3 (TIMP3) The animal or cell may comprise 1, 2, 3, 4, 5, 6, 7 or more disrupted chromosomal sequences encoding a protein associated with MD and zero, 1, 2, 3, 4, 5, 6, 7 or more chromosomally integrated sequences encoding the disrupted protein associated with MD.

The edited or integrated chromosomal sequence may be modified to encode an altered protein associated with MD. Several mutations in MD-related chromosomal sequences have been associated with MD. Non-limiting examples of mutations in chromosomal sequences associated with MD include those that may cause MD including in the ABCR protein, E471K (i.e. glutamate at position 471 is changed to lysine), R1129L (i.e. arginine at position 1129 is changed to leucine). T1428M (i.e. threonine at position 1428 is changed to methionine), R1517S (i.e. arginine at position 1517 is changed to serine), I1562T (i.e. isoleucine at position 1562 is changed to threonine), and G1578R (i.e. glycine at position 1578 is changed to arginine); in the CCR2 protein, V64I (i.e. valine at position 192 is changed to isoleucine); in CP protein, G969B (i.e. glycine at position 969 is changed to asparagine or aspartate); in TIMP3 protein, S156C (i.e. serine at position 156 is changed to cysteine), G166C (i.e. glycine at position 166 is changed to cysteine), G167C (i.e. glycine at position 167 is changed to cysteine), Y168C (i.e. tyrosine at position 168 is changed to cysteine), S170C (i.e. serine at position 170 is changed to cysteine), Y172C (i.e. tyrosine at position 172 is changed to cysteine) and S181C (i.e. serine at position 181 is changed to cysteine). Other associations of genetic variants in MD-associated genes and disease are known in the art.

Treating Circulatory and Muscular Diseases

The present invention also contemplates delivering the CRISPR-Cas9 system described herein, e.g. Cas9 effector protein systems, to the heart. For the heart, a myocardium tropic adena-associated virus (AAVM) is preferred, in particular AAVM41 which showed preferential gene transfer in the heart (see, e.g., Lin-Yanga et al., PNAS, Mar. 10, 2009, vol. 106, no. 10). Administration may be systemic or local. A dosage of about $1$-$10 \times 10^{14}$ vector genomes are contemplated for systemic administration. See also, e.g., Eulalio et al. (2012) Nature 492: 376 and Somasuntharam et al. (2013) Biomaterials 34: 7790.

For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. Any chromosomal sequence involved in cardiovascular disease or the protein encoded by any chromosomal sequence involved in cardiovascular disease may be utilized in the methods described in this disclosure. The cardiovascular-related proteins are typically selected based on an experimental association of the cardiovascular-related protein to the development of cardiovascular disease. For example, the production rate or circulating concentration of a cardiovascular-related protein may be elevated or depressed in a population having a cardiovascular disorder relative to a population lacking the cardiovascular disorder. Differences in protein levels may be assessed using proteomic techniques including but not limited to Western blot, immunohistochemical staining, enzyme linked immunosorbent assay (ELISA), and mass spectrometry. Alternatively, the cardiovascular-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Treating Diseases of the Liver and Kidney

The present invention also contemplates delivering the CRISPR-Cas9 system described herein, e.g. Cas9 effector protein systems, to the liver and/or kidney. Delivery strategies to induce cellular uptake of the therapeutic nucleic acid include physical force or vector systems such as viral-, lipid- or complex-based delivery, or nanocarriers. From the initial applications with less possible clinical relevance, when nucleic acids were addressed to renal cells with hydrodynamic high pressure injection systemically, a wide range of gene therapeutic viral and non-viral carriers have been applied already to target posttranscriptional events in different animal kidney disease models in vivo (Csaba Revesz and Peter Hamar (2011). Delivery Methods to Target RNAs in the Kidney, Gene Therapy Applications, Prof. Chunsheng Kang (Ed.), ISBN: 978-953-307-541-9, InTech, Available from: http://www.intechopen.com/books/gene-therapy-applications/delivery-methods-to-target-rnas-inthe-kidney).

Delivery methods to the kidney may include those in Yuan et al. (Am J Physiol Renal Physiol 295: F605-F617, 2008) investigated whether in vivo delivery of small interfering RNAs (siRNAs) targeting the 12/15-lipoxygenase (12/15-LO) pathway of arachidonate acid metabolism can ameliorate renal injury and diabetic nephropathy (DN) in a streptozotocininjected mouse model of type 1 diabetes. To achieve greater in vivo access and siRNA expression in the kidney, Yuan et al. used double-stranded 12/15-LO siRNA oligonucleotides conjugated with cholesterol. About 400 µg of siRNA was injected subcutaneously into mice. The method of Yuang et al. may be applied to the CRISPR Cas9 system of the present invention contemplating a 1-2 g subcutaneous injection of CRISPR Cas9 conjugated with cholesterol to a human for delivery to the kidneys.

Molitoris et al. (J Am Soc Nephrol 20: 1754-1764, 2009) exploited proximal tubule cells (PTCs), as the site of oligonucleotide reabsorption within the kidney to test the efficacy of siRNA targeted to p53, a pivotal protein in the apoptotic pathway, to prevent kidney injury. Naked synthetic siRNA to p53 injected intravenously 4 h after ischemic injury maximally protected both PTCs and kidney function. Molitoris et al.'s data indicates that rapid delivery of siRNA to proximal tubule cells follows intravenous administration. For dose-response analysis, rats were injected with doses of siP53, 0.33; 1, 3, or 5 mg/kg, given at the same four time points, resulting in cumulative doses of 1.32; 4, 12, and 20 mg/kg, respectively. All siRNA doses tested produced a SCr reducing effect on day one with higher doses being effective over approximately five days compared with PBS-treated ischemic control rats. The 12 and 20 mg/kg cumulative doses provided the best protective effect. The method of Molitoris et al. may be applied to the nucleic acid-targeting system of the present invention contemplating 12 and 20 mg/kg cumulative doses to a human for delivery to the kidneys.

Thompson et al. (Nucleic Acid Therapeutics, Volume 22, Number 4, 2012) reports the toxicological and pharmacokinetic properties of the synthetic, small interfering RNA I5NP following intravenous administration in rodents and nonhuman primates. I5NP is designed to act via the RNA interference (RNAi) pathway to temporarily inhibit expression of the pro-apoptotic protein p53 and is being developed to protect cells from acute ischemia/reperfusion injuries such as acute kidney injury that can occur during major cardiac surgery and delayed graft function that can occur following renal transplantation. Doses of 800 mg/kg I5NP in rodents, and 1,000 mg/kg I5NP in nonhuman primates, were required to elicit adverse effects, which in the monkey were isolated to direct effects on the blood that included a sub-clinical activation of complement and slightly increased clotting times. In the rat, no additional adverse effects were observed with a rat analogue of I5NP, indicating that the effects likely represent class effects of synthetic RNA duplexes rather than toxicity related to the intended pharmacologic activity of I5NP. Taken together, these data support clinical testing of intravenous administration of I5NP for the preservation of renal function following acute ischemia/reperfusion injury. The no observed adverse effect level (NOAEL) in the monkey was 500 mg/kg. No effects on cardiovascular, respiratory, and neurologic parameters were observed in monkeys following i.v. administration at dose levels up to 25 mg/kg. Therefore, a similar dosage may be contemplated for intravenous administration of CRISPR Cas9 to the kidneys of a human.

Shimizu et al. (J Am Soc Nephrol 21: 622-633, 2010) developed a system to target delivery of siRNAs to glomeruli via poly(ethylene glycol)-poly(L-lysine)-based vehicles. The siRNA/nanocarrier complex was approximately 10 to 20 nm in diameter, a size that would allow it to move across the fenestrated endothelium to access to the mesangium. After intraperitoneal injection of fluorescence-labeled siRNA/nanocarrier complexes, Shimizu et al. detected siRNAs in the blood circulation for a prolonged time. Repeated intraperitoneal administration of a mitogen-activated protein kinase 1 (MAPK1) siRNA/nanocarrier complex suppressed glomerular MAPK1 mRNA and protein expression in a mouse model of glomerulonephritis. For the investigation of siRNA accumulation, Cy5-labeled siRNAs complexed with PIC nanocarriers (0.5 ml, 5 nmol of siRNA content), naked Cy5-labeled siRNAs (0.5 ml, 5 nmol), or Cy5-labeled siRNAs encapsulated in HVJ-E (0.5 ml, 5 nmol of siRNA content) were administered to BALBc mice. The method of Shimizu et al. may be applied to the nucleic acid-targeting system of the present invention contemplating a dose of about of 10-20 µmol CRISPR Cas9 complexed with nanocarriers in about 1-2 liters to a human for intraperitoneal administration and delivery to the kidneys.

Treating Epithelial and Lung Diseases

The present invention also contemplates delivering the CRISPR-Cas9 system described herein, e.g. Cas9 systems, to one or both lungs.

Although AAV-2-based vectors were originally proposed for CFTR delivery to CF airways, other serotypes such as AAV-1, AAV-5, AAV-6, and AAV-9 exhibit improved gene transfer efficiency in a variety of models of the lung epithelium (see, e.g., Li et al., Molecular Therapy, vol. 17 no. 12, 2067-277 December 2009). AAV-1 was demonstrated to be ~100-fold more efficient than AAV-2 and AAV-5 at transducing human airway epithelial cells in vitro, 5 although AAV-1 transduced murine tracheal airway epithelia in vivo with an efficiency equal to that of AAV-5. Other studies have shown that AAV-5 is 50-fold more efficient than AAV-2 at gene delivery to human airway epithelium (HAE) in vitro and significantly more efficient in the mouse lung airway epithelium in vivo. AAV-6 has also been shown to be more efficient than AAV-2 in human airway epithelial cells in vitro and murine airways in vivo.8 The more recent isolate, AAV-9, was shown to display greater gene transfer efficiency than AAV-5 in murine nasal and alveolar epithelia in vivo with gene expression detected for over 9 months suggesting AAV may enable long-term gene expression in vivo, a desirable property for a CFTR gene delivery vector. Furthermore, it was demonstrated that AAV-9 could be readministered to the murine lung with no loss of CFTR expression and minimal immune consequences. CF and non-CF HAE cultures may be inoculated on the apical surface with 100 µl of AAV vectors for hours (see, e.g., Li et al., Molecular Therapy, vol. 17 no. 12, 2067-277 December 2009). The MOI may vary from $1 \times 10^3$ to $4 \times 10^5$ vector genomes/cell, depending on virus concentration and purposes of the experiments. The above cited vectors are contemplated for the delivery and/or administration of the invention.

Zamora et al. (Am J Respir Crit Care Med Vol 183. pp 531-538, 2011) reported an example of the application of an RNA interference therapeutic to the treatment of human infectious disease and also a randomized trial of an antiviral drug in respiratory syncytial virus (RSV)-infected lung transplant recipients. Zamora et al. performed a randomized, double-blind, placebo controlled trial in LTX recipients with RSV respiratory tract infection. Patients were permitted to receive standard of care for RSV. Aerosolized ALN-RSV01 (0.6 mg/kg) or placebo was administered daily for 3 days. This study demonstrates that an RNAi therapeutic targeting RSV can be safely administered to LTX recipients with RSV infection. Three daily doses of ALN-RSV01 did not result in any exacerbation of respiratory tract symptoms or impairment of lung function and did not exhibit any systemic proinflammatory effects, such as induction of cytokines or CRP. Pharmacokinetics showed only low, transient systemic exposure after inhalation, consistent with preclinical animal data showing that ALN-RSVOI, administered intravenously or by inhalation, is rapidly cleared from the circulation through exonuclease mediated digestion and renal excretion. The method of Zamora et al. may be applied to the nucleic acid-targeting system of the present invention and an aerosolized CRISPR Cas, for example with a dosage of 0.6 mg/kg, may be contemplated for the present invention.

Schwank et al. (Cell Stem Cell, 13:653-58, 2013) used CRISPR-Cas9 to correct a defect associated with cystic fibrosis in human stem cells. The team's target was the gene for an ion channel, cystic fibrosis transmembrane conductor receptor (CFTR). A deletion in CFTR causes the protein to misfold in cystic fibrosis patients. Using cultured intestinal stem cells developed from cell samples from two children with cystic fibrosis, Schwank et al. were able to correct the defect using CRISPR along with a donor plasmid containing the reparative sequence to be inserted. The researchers then grew the cells into intestinal "organoids," or miniature guts, and showed that they functioned normally. In this case, about half of clonal organoids underwent the proper genetic correction.

Treating Diseases of the Muscular System

The present invention also contemplates delivering the CRISPR-Cas9 system described herein, e.g. Cas9 systems, to muscle(s).

Bortolanza et al. (Molecular Therapy vol. 19 no. 11, 2055-264 November 2011) shows that systemic delivery of RNA interference expression cassettes in the FRG1 mouse, after the onset of facioscapulohumeral muscular dystrophy (FSHD), led to a dose-dependent long-term FRG1 knockdown without signs of toxicity. Bortolanza et al. found that a single intravenous injection of $5\times10^{12}$ vg of rAAV6-sh1FRG1 rescues muscle histopathology and muscle function of FRG1 mice. In detail, 200 μl containing $2\times10^{12}$ or $5\times10^{12}$ vg of vector in physiological solution were injected into the tail vein using a 25-gauge Terumo syringe. The method of Bortolanza et al. may be applied to an AAV expressing CRISPR Cas9 and injected into humans at a dosage of about $2\times10^{15}$ or $2\times10^{16}$ vg of vector.

Dumonceaux et al. (Molecular Therapy vol. 18 no. 5, 881-887 May 2010) inhibit the myostatin pathway using the technique of RNA interference directed against the myostatin receptor AcvRIIb mRNA (sh-AcvRIIb). The restoration of a quasi-dystrophin was mediated by the vectorized U7 exon-skipping technique (U7-DYS). Adeno-associated vectors carrying either the sh-AcvrIIb construct alone, the U7-DYS construct alone, or a combination of both constructs were injected in the tibialis anterior (TA) muscle of dystrophic mdx mice. The injections were performed with $10^{11}$ AAV viral genomes. The method of Dumonceaux et al. may be applied to an AAV expressing CRISPR Cas9 and injected into humans, for example, at a dosage of about $10^{14}$ to about $10^{15}$ vg of vector.

Kinouchi et al. (Gene Therapy (2008) 15, 1126-1130) report the effectiveness of in vivo siRNA delivery into skeletal muscles of normal or diseased mice through nanoparticle formation of chemically unmodified siRNAs with atelocollagen (ATCOL). ATCOL-mediated local application of siRNA targeting myostatin, a negative regulator of skeletal muscle growth, in mouse skeletal muscles or intravenously, caused a marked increase in the muscle mass within a few weeks after application. These results imply that ATCOL-mediated application of siRNAs is a powerful tool for future therapeutic use for diseases including muscular atrophy. MstsiRNAs (final concentration, 10 mM) were mixed with ATCOL (final concentration for local administration, 0.5%) (AteloGene, Kohken, Tokyo, Japan) according to the manufacturer's instructions. After anesthesia of mice (20-week-old male C57BL/6) by Nembutal (25 mg/kg, i.p.), the Mst-siRNA/ATCOL complex was injected into the masseter and biceps femoris muscles. The method of Kinouchi et al. may be applied to CRISPR Cas9 and injected into a human, for example, at a dosage of about 500 to 1000 ml of a 40 μM solution into the muscle. Hagstrom et al. (Molecular Therapy Vol. 10, No. 2, August 2004) describe an intravascular, nonviral methodology that enables efficient and repeatable delivery of nucleic acids to muscle cells (myofibers) throughout the limb muscles of mammals. The procedure involves the injection of naked plasmid DNA or siRNA into a distal vein of a limb that is transiently isolated by a tourniquet or blood pressure cuff. Nucleic acid delivery to myofibers is facilitated by its rapid injection in sufficient volume to enable extravasation of the nucleic acid solution into muscle tissue. High levels of transgene expression in skeletal muscle were achieved in both small and large animals with minimal toxicity. Evidence of siRNA delivery to limb muscle was also obtained. For plasmid DNA intravenous injection into a rhesus monkey, a threeway stopcock was connected to two syringe pumps (Model PHD 2000; Harvard Instruments), each loaded with a single syringe. Five minutes after a papaverine injection, pDNA (15.5 to 25.7 mg in 40-100 ml saline) was injected at a rate of 1.7 or 2.0 ml/s. This could be scaled up for plasmid DNA expressing CRISPR Cas9 of the present invention with an injection of about 300 to 500 mg in 800 to 2000 ml saline for a human. For adenoviral vector injections into a rat, $2\times10^9$ infectious particles were injected in 3 ml of normal saline solution (NSS). This could be scaled up for an adenoviral vector expressing CRISPR Cas9 of the present invention with an injection of about $1\times10^{13}$ infectious particles were injected in 10 liters of NSS for a human. For siRNA, a rat was injected into the great saphenous vein with 12.5 μg of a siRNA and a primate was injected into the great saphenous vein with 750 μg of a siRNA. This could be scaled up for a CRISPR Cas9 of the present invention, for example, with an injection of about 15 to about 50 mg into the great saphenous vein of a human.

See also, for example, WO2013163628 A2, Genetic Correction of Mutated Genes, published application of Duke University describes efforts to correct, for example, a frameshift mutation which causes a premature stop codon and a truncated gene product that can be corrected via nuclease mediated non-homologous end joining such as those responsible for Duchenne Muscular Dystrophy, ("DMD") a recessive, fatal, X-linked disorder that results in muscle degeneration due to mutations in the dystrophin gene. The majority of dystrophin mutations that cause DMD are deletions of exons that disrupt the reading frame and cause premature translation termination in the dystrophin gene. Dystrophin is a cytoplasmic protein that provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

The methods of US Patent Publication No. 20130145487 assigned to Cellectis, which relates to meganuclease variants to cleave a target sequence from the human dystrophin gene (DMD), may also be modified to for the nucleic acid-targeting system of the present invention.

Treating Diseases of the Skin

The present invention also contemplates delivering the CRISPR-Cas9 system described herein, e.g. Cas9 effector protein systems, to the skin.

Hickerson et al. (Molecular Therapy-Nucleic Acids (2013) 2, e129) relates to a motorized microneedle array skin delivery device for delivering self-delivery (sd)-siRNA to human and murine skin. The primary challenge to translating siRNA-based skin therapeutics to the clinic is the development of effective delivery systems. Substantial effort has been invested in a variety of skin delivery technologies with limited success. In a clinical study in which skin was treated with siRNA, the exquisite pain associated with the hypodermic needle injection precluded enrollment of additional patients in the trial, highlighting the need for improved, more "patient-friendly" (i.e., little or no pain) delivery approaches. Microneedles represent an efficient way to deliver large charged cargos including siRNAs across the primary barrier, the stratum corneum, and are generally regarded as less painful than conventional hypodermic needles. Motorized "stamp type" microneedle devices, including the motorized microneedle array (MMNA) device used by Hickerson et al., have been shown to be safe in hairless mice studies and cause little or no pain as evidenced by (i) widespread use in the cosmetic industry and (ii) limited testing in which nearly all volunteers found use of the device to be much less painful than a flushot, suggesting siRNA delivery using this device will result in much less pain than was experienced in the previous clinical trial using hypodermic needle injections. The MMNA device (marketed as Triple-M or Tri-M by Bomtech Electronic Co, Seoul, South Korea) was adapted for delivery of siRNA to mouse and human skin. sd-siRNA solution (up to 300 μl of 0.1 mg/ml RNA) was introduced into the chamber of the disposable Tri-M needle cartridge (Bomtech), which was set to a depth of 0.1 mm. For treating human skin, deidentified skin (obtained immediately following surgical procedures) was manually stretched and pinned to a cork platform before treatment. All intradermal injections were performed using an insulin syringe with a 28-gauge 0.5-inch needle. The MMNA device and method of Hickerson et al. could be used and/or adapted to deliver the CRISPR Cas9 of the present invention, for example, at a dosage of up to 300 μl of 0.1 mg/ml CRISPR Cas9 to the skin.

Leachman et al. (Molecular Therapy, vol. 18 no. 2, 442-446 February 2010) relates to a phase Ib clinical trial for treatment of a rare skin disorder pachyonychia congenita (PC), an autosomal dominant syndrome that includes a disabling plantar keratoderma, utilizing the first short-interfering RNA (siRNA)-based therapeutic for skin. This siRNA, called TD101, specifically and potently targets the keratin 6a (K6a) N171K mutant mRNA without affecting wild-type K6a mRNA.

Zheng et al. (PNAS, Jul. 24, 2012, vol. 109, no. 30, 11975-11980) show that spherical nucleic acid nanoparticle conjugates (SNA-NCs), gold cores surrounded by a dense shell of highly oriented, covalently immobilized siRNA, freely penetrate almost 100% of keratinocytes in vitro, mouse skin, and human epidermis within hours after application. Zheng et al. demonstrated that a single application of 25 nM epidermal growth factor receptor (EGFR) SNA-NCs for 60 h demonstrate effective gene knockdown in human skin. A similar dosage may be contemplated for CRISPR Cas9 immobilized in SNA-NCs for administration to the skin.

General Gene Therapy Considerations

Examples of disease-associated genes and polynucleotides and disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web.

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex of the present invention.

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA•DNA hybrids. McIvor E I, Polak U, Napierala M. RNA Biol. 2010 September-October; 7(5):551-8). The present effector protein systems may be harnessed to correct these defects of genomic instability.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

The present invention may be further illustrated and extended based on aspect of CISPR-Cas9 development and use as set forth in the following articles hereby incorporated herein by reference and particularly as relates to delivery of a CRISPR protein complex and uses of an RNA guided endonuclease in cells and organisms:

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546): 186-91(2015).

*High-throughput functional genomics using CRISPR-Cas9*, Shalem et al., Nature Reviews Genetics 16, 299-311 (May 2015).

*Sequence determinants of improved CRISPR sgRNA design*, Xu et al., Genome Research 25, 1147-1157 (August 2015).

*A Genome-wide CRISPR Screen in Primary Immune Cells to Dissect Regulatory Networks*, Parnas et al., Cell 162, 675-686 (Jul. 30, 2015).

*CRISPR/Cas9 cleavage of viral DNA efficiently suppresses hepatitis B virus*, Ramanan et al., Scientific Reports 5:10833. doi: 10.1038/srep10833 (Jun. 2, 2015).

*Crystal Structure of Staphylococcus aureus Cas9*, Nishimasu et al., Cell 162, 1113-1126 (Aug. 27, 2015).

*BCL11A enhancer dissection by Cas9-mediated in situ saturating mutagenesis*, Canver et al., Nature 527(7577): 192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 2015 Dec. 1. pii: aad5227. [Epub ahead of print]

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crR- NAs enabled multiplex mutagenesis. Furthermore, when the approach was used in combination with recombineering, in S. pneumoniae, nearly 10% of cells that were recovered using the described approach contained the desired mutation, and in E. coli, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of Streptococcus pyogenes Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from Streptococcus pyogenes loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* 1/112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2015) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Also, "Dimeric CRISPR RNA-guided Fok1 nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR-Cas9 Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641, US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830. Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013: Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/835,973, 61/836,080, 61/836,101, and 61/836,127, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT/US2014/62558 filed Oct. 28, 2014, and U.S. Provisional Patent Applications Ser. Nos. 61/915,148, 61/915,150, 61/915,153, 61/915,203, 61/915,251, 61/915,301, 61/915,267, 61/915,260, and 61/915,397, each filed Dec. 12, 2013; 61/757,972 and 61/768,959, filed on Jan. 29, 2013 and Feb. 25, 2013; 62/010,888 and 62/010,879, both filed Jun. 11, 2014; 62/010,329, 62/010,439 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/055,484, 62/055,460 and 62/055,487, each filed Sep. 25, 2014; and 62/069,243, filed Oct. 27, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to PCT application designating, inter alia, the United States, application No. PCT/US14/41806, filed Jun. 10, 2014.

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPO- NENTS; U.S. application 61/939,154, 12-F EB-14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, filed 22 Oct. 2015, NOVEL CRISPR ENZYMES AND SYSTEMS, U.S. application 62/232,067, 24 Sep. 2015, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30 C, e.g., 20-25 C, e.g., room temperature, for a suitable time, e.g., 15-45, such as 30 minutes, advantageously in sterile, nuclease free buffer, e.g., 1X PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP: DMPC: PEG: Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

The present invention will be further illustrated in the following Examples which are given for illustration purposes only and are not intended to limit the invention in any way.

The invention will now be further described by way of the following non-limiting examples.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Further Characterization of Protected Guide RNAs

Applicants tested a library with a larger range of exposed (0, 4, 8, 12, 14, 16, 18) and extended lengths (0, 4, 8, 12) on the original 20 bp EMX1.3 sgRNA and a truncated 18 bp version. Applicants measured indel rates at the EMX1.3 locus as well as three off-target loci (OT 14, 25, and 46). The results are summarized in FIG. 14 while the actual cutting rates at each of these loci for each construct are indicated in FIG. 16.

Applicants first started by analyzing the on-target cutting to off-target (sum of the three OT sites) cutting ratio as a measure of specificity and determined how it varied against the Exposed Length/Total Sequence Ratio, which is a measure of how many double stranded bases there are in the protected guide. Applicants hypothesized there might be a relationship here because based on predictions of thermodynamic model, the number of double stranded bases is an important determinant of specificity since more double stranded bases makes the displacement of the protector strand for the target DNA less favorable if mismatches are present. Applicants determined that there was a relationship between both the on-target/off-target ratio (FIG. 14A) and just on-target activity (FIG. 14B) to the exposed length ratio. This data suggested that exposed length is important to allow for target binding and sufficient on-target activity and for improving specificity.

Figure 14A:
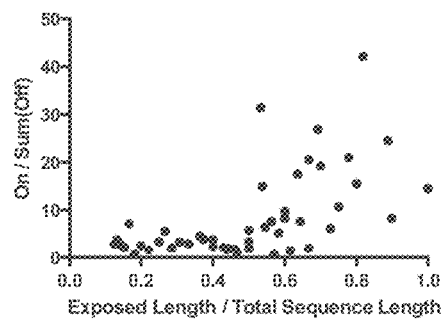
FIG. 14A-14F: Effect of varying the exposed length (EpL) and extended length (ExL) on on-target indel formation and specificity. The on-target/off-target cutting ratio (A) and on-target cutting percent (B) increases as the exposed length to total sequence length ratio increases. C) On-target activity increases as exposed length increases. D-E) The distribution of on-target/off-target cutting activity for the four extended lengths designed (D) and for the total length of sequence (E). F) The on-target/off-target cutting ratio for the control guides, showing a flattened distribution of specificity.
Figure 14B:
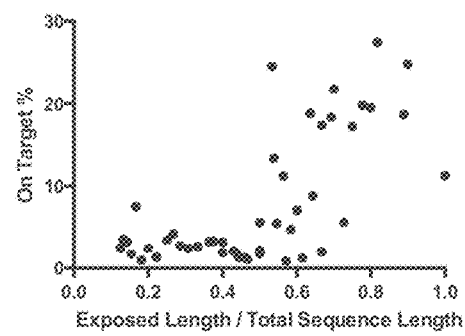
Figure 14C:
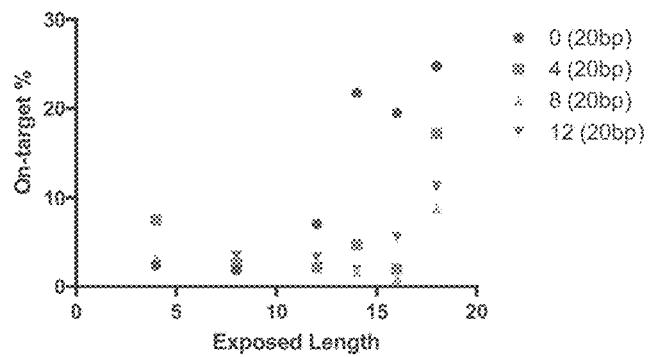
Figure 14D:
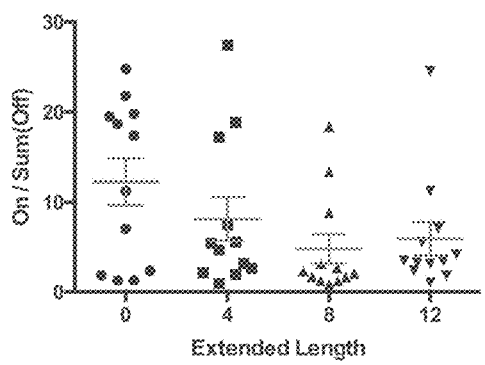
Figure 14E:
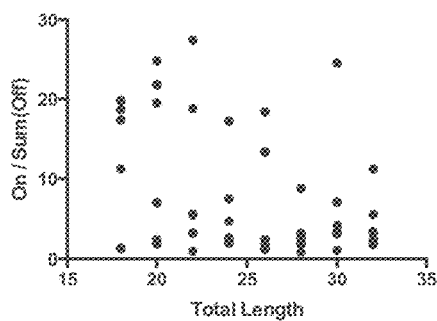
Figure 14F:
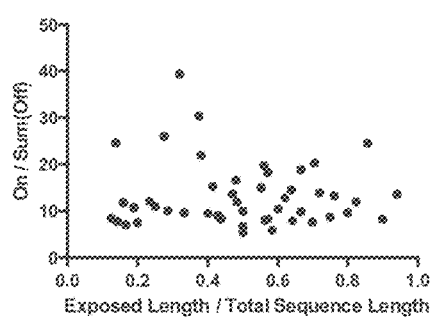
Figure 15:
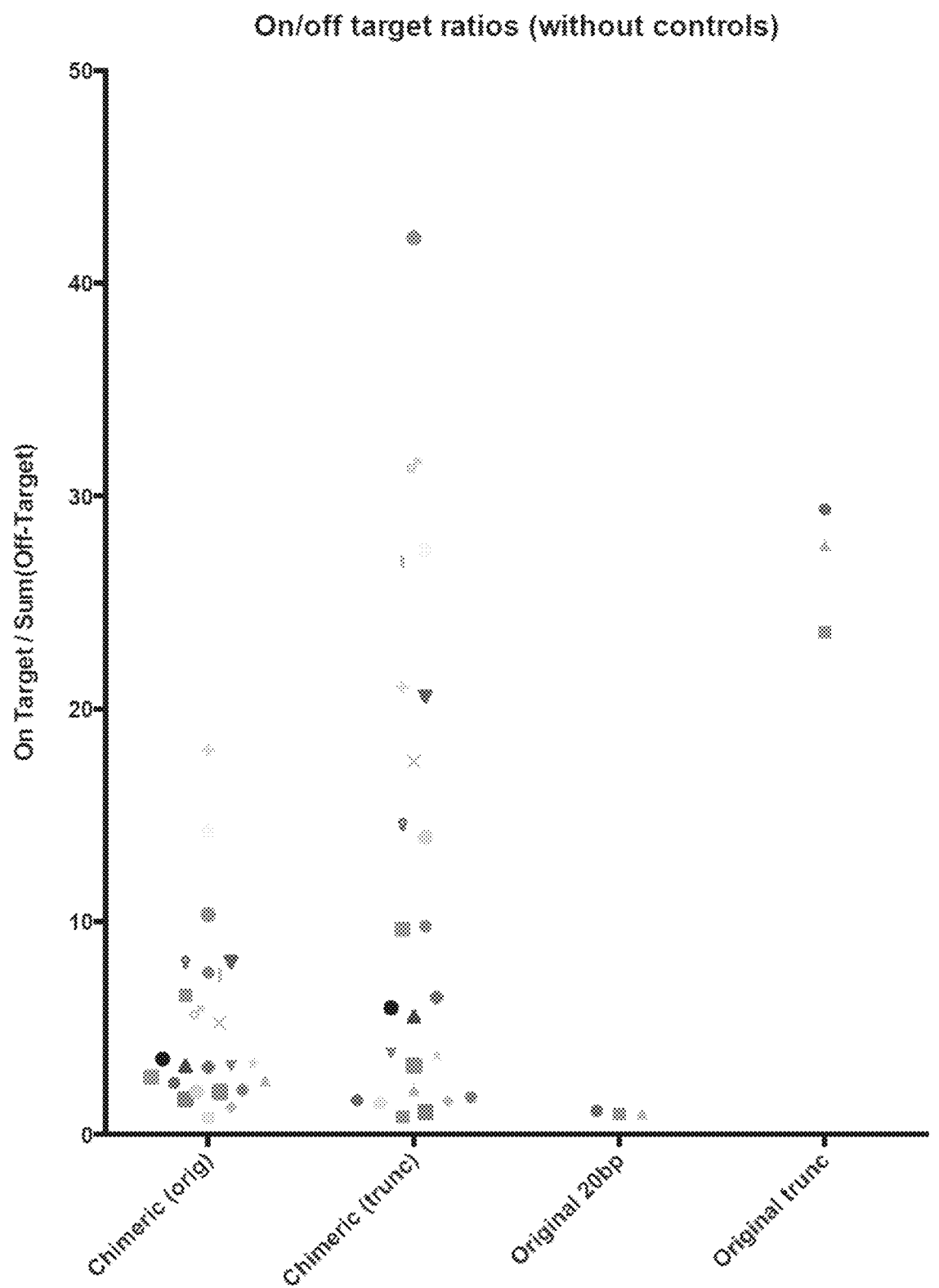
FIG. 15: A graphical representation of the On-target to off-target ratio scores (without controls).

Applicants also found that the extended length can affect on-target activity and the on-target/off-target ratio. The most effective constructs had protector lengths of 0 or 4 with longer extended lengths causing lower on-target cutting percent (FIG. 14C). The on-target/off-target ratio also showed this relationship showing skewed distributions toward greater specificity for extended lengths of 0 and 4 (see FIG. 14D). Applicants also found that the on-target/off-target ratio decreases with increasing length of the guide (20 or 18 bp+extended length) (FIG. 14E), likely due to less on-target activity.

For each protected guide Applicants designed, a control construct where the bases in the complementary protector strand were flipped such that the protector could no longer bind and form secondary structure was also designed. Applicants found that these control constructs did not show the trends determined in the experiments herein (FIG. 14F) and displayed a flattened specificity distribution indicating that the secondary structure was no longer present and the design rules no longer applied. Because there is no secondary structure present in these controls, they are likely processed and chewed back by exonuclease activity. Applicants further confirm this phenomenon by performing RNA-sequencing on the constructs. An advantageous aspect of the invention is that secondary structure can protect against exonuclease activity and allow for 5' additions to the sgRNA.

Shown in FIG. 16 are the raw results that are summarized in FIG. 14. These results indicate the constructs that may be selected for both specificity and in retained on-target activity.

Figure 17:
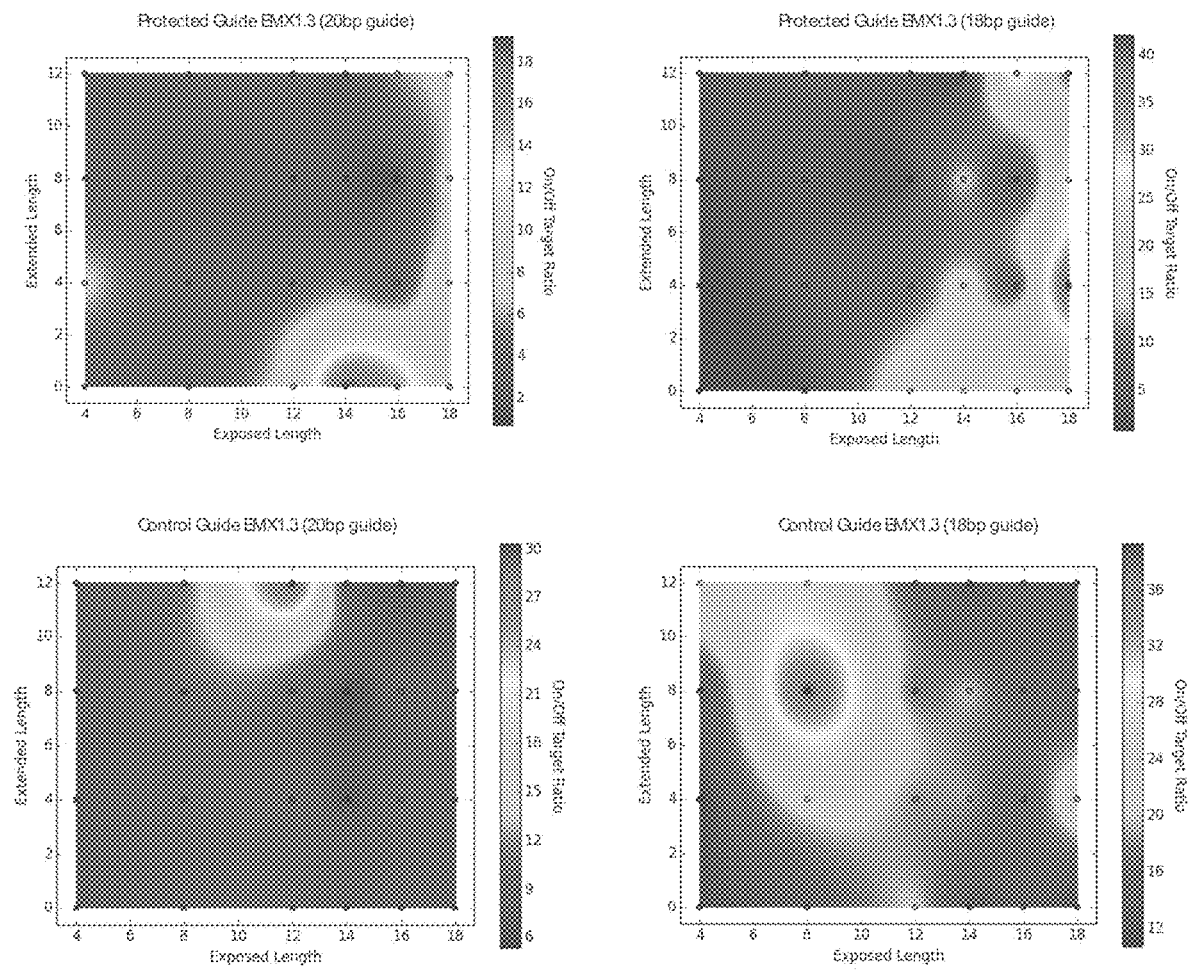
FIG. 17: Contour maps showing the distribution of on-target/off-target activity ratio for protected guides of varying exposed and extended lengths. The protected guides using the original 20 bp (top left) and truncated 18 bp (top right) EMX0.3 guide sequence display maximal specificity at greater exposed lengths and shorter extended lengths. This trend is lost in the control 20 bp (bottom right) and truncated (18 bp) samples where the distribution of activity is flatter and only peaked at specific outliers.
Figure 18:
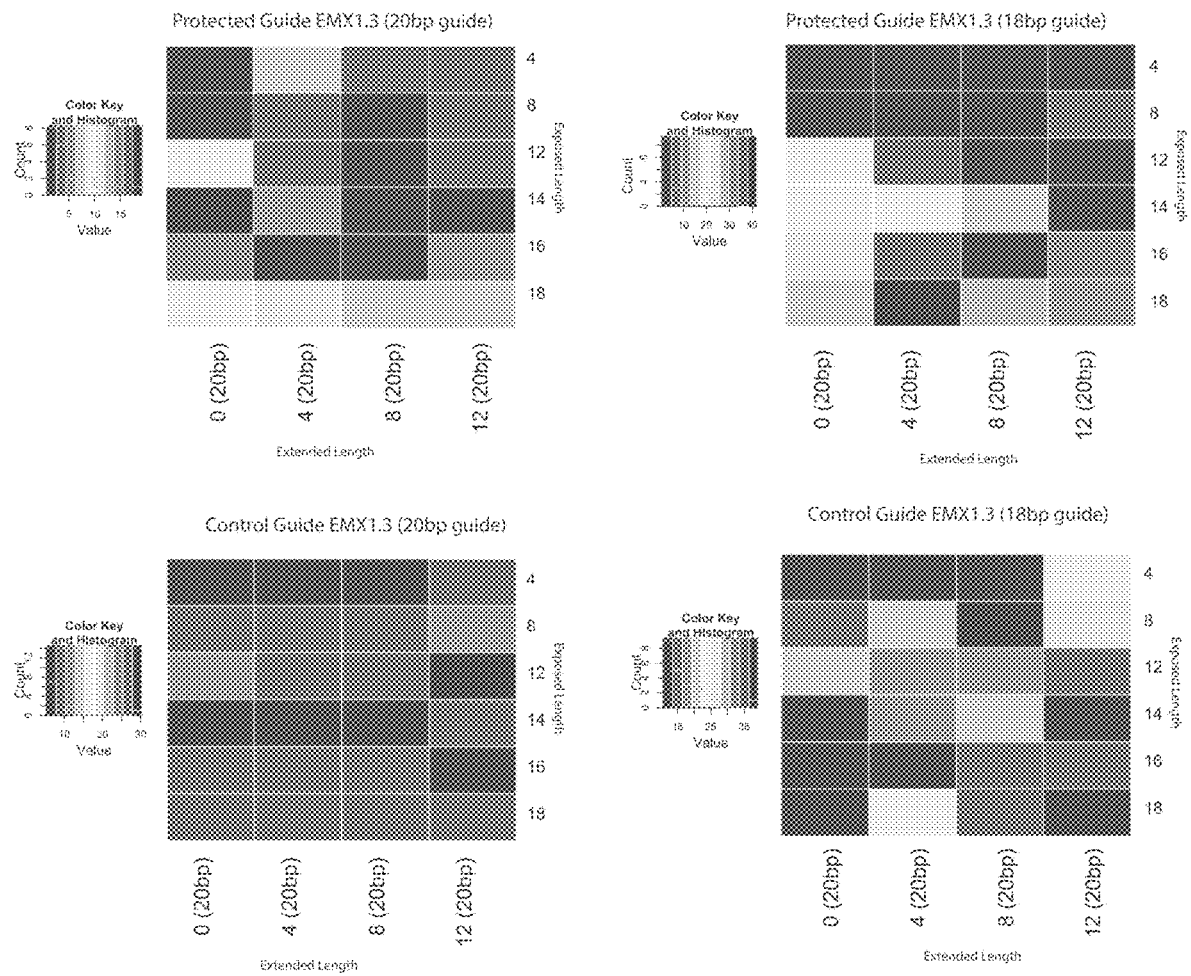
FIG. 18: Heatmaps showing the on-target/off-target activity ratio for protected guides of varying exposed and extended lengths. The protected guides using the original 20 bp (top left) and truncated 18 bp (top right) EMX1.3 guide sequence display maximal specificity at greater exposed lengths and shorter extended lengths. This trend is lost in the control 20 bp (bottom right) and truncated (18 bp) samples where the distribution of activity is flatter and only peaked at specific outliers. Red: higher ratio. Blue: lower ratio.

Applicants have shown the activity and specificity in contour maps (FIG. 17) and heatmaps (FIG. 18) to better indicate the effect of varying these two parameters. Applicants found similar trends where the protected 20 bp and truncated 18 bp guides show maximal activity and specificity at greater exposed lengths and shorter extended lengths. The protected 18 bp guides seem to have good specificity at longer extended lengths as well. These trends are not seen in control versions of these protected guides where the bases of the protector are flipped such that the complementary protector strand cannot bind and form secondary structure. The control data may indicate a peak in activity/specificity for certain outliers, but this does not happen at expected regions and there is no trend with respect to the design parameters selected (ExL and EpL).

Materials and Methods:

The sgRNA constructs were synthesized as 4 nm ultramers from IDT and then PCR prepped and purified for transfection. HEK293 cells were plated in 96 well plates and 24 hours later 75 ng of Cas9 plasmid (px165) and 25 ng of the protected sgRNA were transfected into each well using lipofectamine.

48 hours after transfection genome DNA was extracted using Quick Extract. The relevant loci (on target and off-target sites) were PCR amplified and barcoded for NGS analysis. The samples were loaded on an Illumina MiSeq instrument and data was processed using a custom indel analysis script.

Example 2: Further Applications of pgRNAs

Applicants created a Cas9 system for 1) increased specificity by tuning thermodynamic parameters involved in double stranded displacement reactions and 2) 5' secondary structure protection from exonuclease degradation of 5' extensions to the sgRNA. This system can be utilized for the following applications.

In one aspect, the system is used for allelic CRISPR sensing such that the sgRNA can sense allelic regions with SNPs or mutations that differ from the other allele. The system can target mutations or SNPs involved in disease. For instance, if one wanted to target the KRAS mutation involved in a tumor, the protected sgRNA would be much more specific for the mutated sequence (even though it's only one nucleotide different) and so the WT allele would be untouched and there would be significantly reduced toxicity since if the delivered constructs enter normal cells in vivo, they would not target the WT KRAS gene found in these cells.

Figure 19:
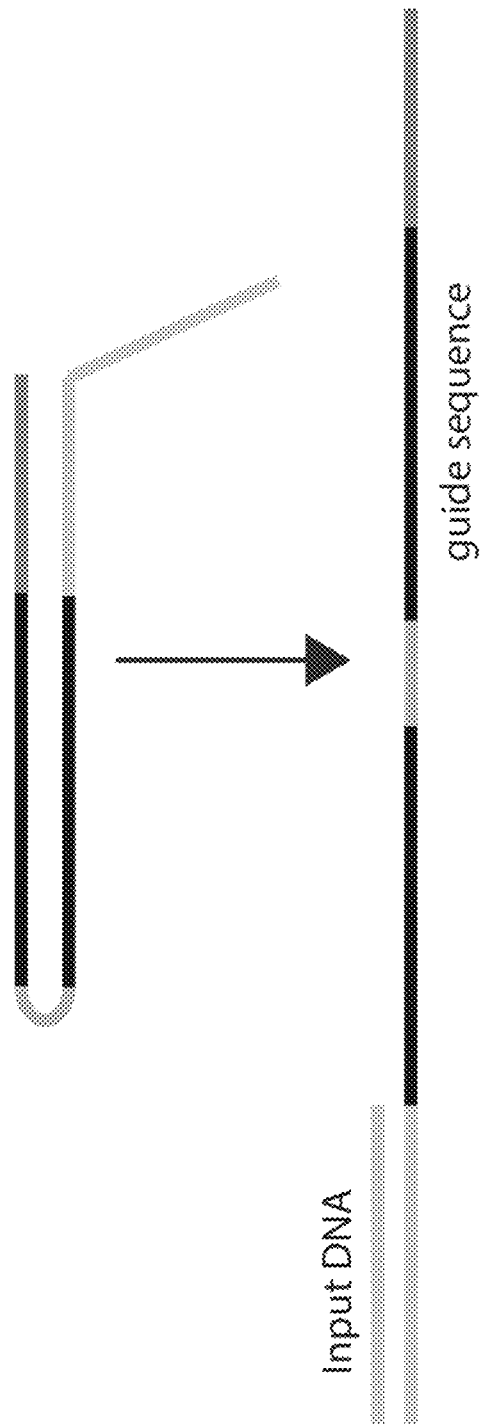
FIG. 19: An example of using protector toe-holds for generating an inducible Cas9 for synthetic biology applications.

In one aspect, the system is used for toehold-based logic for synthetic biology and smart therapeutics using inducible Cas9 (see FIG. 19). By extending the protection such that there is zero exposed length, the on-target activity is significantly diminished, rendering an inactive Cas9-sgRNA complex. This system is used to make an inducible Cas9 active only when specific oligos are introduced complementary to the toehold (such as synthetic oligos or endogenous oligos like lincRNAs or miRNAs).

Figure 20:
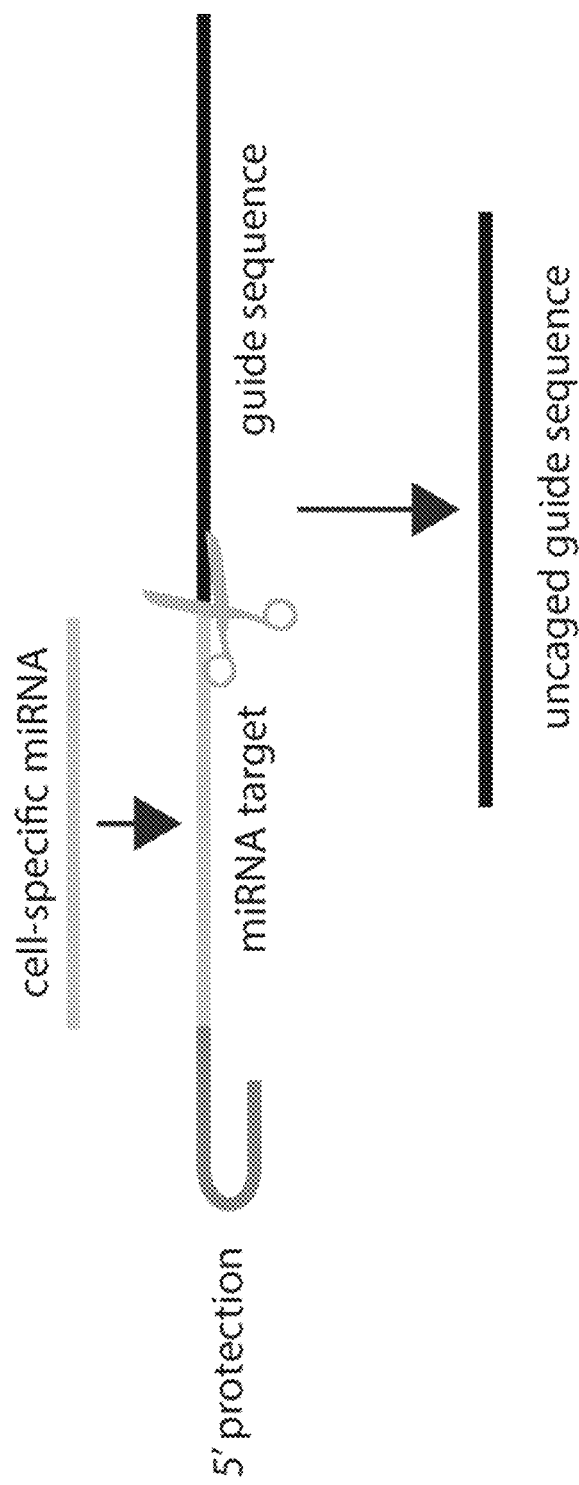
FIG. 20: Example of using secondary structure for protection from exonuclease activity.

In one aspect, the system is used for secondary structure protection for 5' extensions to the sgRNA. For example, Applicants extend the sgRNA such that a miRNA binding site is introduced to make the sgRNA only active when the miRNA binding site is processed and cleaved by the RISC complex machinery (FIG. 20). This would not be possible without secondary structure protection since exonuclease processing would start from the 5' end and cut back towards the sgRNA. By adding a small secondary structure loop 5' to the added miRNA site, then miRNA may be protected from exonuclease chew back.

The invention is further described by the following numbered paragraphs:

1. An engineered, non-naturally occurring composition comprising a Clustered Regularly Interspaced Short Palindromic Repeats (CRISPR)-CRISPR associated (Cas) (CRISPR-Cas) system comprising a protected guide RNA (pgRNA) polynucleotide sequence comprising (a) a protector sequence, (b) a guide sequence capable of hybridizing to a target sequence in a eukaryotic cell, (c) a tracr mate sequence, and (d) a tracr sequence wherein (a), (b), (c) and (d) are arranged in a 5' to 3' orientation, wherein the protector sequence comprises two or more nucleotides that are non-complementary to the target sequence, wherein when transcribed, the tracr mate sequence hybridizes to the tracr sequence and the guide sequence directs sequence-specific binding of a CRISPR complex to the target sequence, wherein the CRISPR complex comprises a Type II Cas9 protein complexed with (1) the guide sequence that is hybridized to the target sequence, and (2) the tracr mate sequence that is hybridized to the tracr sequence and wherein in the polynucleotide sequence, one or more of the guide, tracr and tracr mate sequences are modified.

2. The composition of numbered paragraph 1., wherein the protected modified guide RNA comprises a chimeric guide sequence and a tracr sequence.

3. The composition of numbered paragraph 1, wherein the modification comprises an engineered secondary structure.

4. The composition of any one of numbered paragraphs 1-3, wherein the protected guide RNA improves specificity of target binding as compared to the naturally occurring CRISPR-Cas system.

5. The composition of any one of numbered paragraphs 1-4, wherein the guide sequence is modified and the protected modified guide RNA improves stability as compared to a naturally occurring CRISPR-Cas.

6. The composition of any one of numbered paragraphs 1-5, wherein the protector sequence has a length between 3 and 120 nucleotides and comprises 3 or more contiguous nucleotides complementary to another sequence within the guide or protector and wherein the modification comprises or allows for hairpin formation.

7. The composition of any one of numbered paragraphs 1-6, wherein the guide sequence is 10-30 nucleotides long.

8. The composition of any one of numbered paragraphs 1-7, wherein the guide sequence further comprises a protected sequence and an exposed sequence.

9. The composition of numbered paragraph 8, wherein the exposed sequence is 1 to 19 nucleotides.

10. The composition of numbered paragraph 8 or 9, wherein the exposed sequence is at least 75%, at least 90% or about 100% complementary to the target sequence.

11. The composition of any one of numbered paragraphs 1-10, wherein the guide sequence is at least 90% or about 100% complementary to the protector strand.

12. The composition of any one of numbered paragraphs 1-11, wherein the guide sequence is at least 75%, at least 90% or about 100% complementary to the target sequence.

13. The composition of any one of numbered paragraphs 1-12, wherein the tracr mate sequence is at least 75%, at least 90% or about 100% complementary to the tracr sequence.

14. The composition of any one of numbered paragraphs 1-13 further comprising an extension sequence.

15. The composition of numbered paragraph 14, wherein the extension sequence is operably linked to the 5' end of the protected guide sequence, and optionally directly linked to the 5' end of the protected guide sequence.

16. The composition of numbered paragraph 14 or 15, wherein the extension sequence is 0-12 nucleotides.

17. The composition of any one of numbered paragraphs 14-16, wherein the extension sequence is operably linked to the guide sequence at the 5' end of the protected guide sequence and the 3' end of the protector strand and optionally directly linked to the 5' end of the protected guide sequence and the 3' end of the protector strand, wherein the extension sequence is a linking sequence between the protected sequence and the protector strand.

18. The composition of any one of numbered paragraphs 14-17, wherein the extension sequence is 100% not complementary (0% complementary) to the protector strand, optionally at least 95%, at least 9/0%, at least 80%, at least 70%, at least 60%, or at least 50% not complementary to the protector strand.

19. The composition of any one of numbered paragraphs 1, 2 or 4-18, wherein the guide sequence further comprises mismatches appended to the end of the guide sequence, wherein the mismatches thermodynamically optimize specificity.

20. A non-naturally occurring or engineered CRISPR-Cas complex composition comprising the pgRNA of any one of numbered paragraphs 1-19 and a CRISPR enzyme, wherein optionally the CRISPR enzyme comprises at least one mutation, such that the CRISPR enzyme has no more than 5% of the nuclease activity of the CRISPR enzyme not having the at least one mutation, and optionally comprising at least one or more nuclear localization sequences.

21. The pgRNA of any one of numbered paragraphs 1-19 or the CRISPR-Cas complex of numbered paragraph 18 including a non-naturally occurring or engineered composition comprising two or more adaptor proteins, wherein each protein is associated with one or more functional domains and wherein the adaptor protein binds to the distinct RNA sequence(s) inserted into the at least one loop of the sgRNA.

22. A non-naturally occurring or engineered composition comprising the protected guide RNA (pgRNA) of any one of numbered paragraphs 1-19, a CRISPR enzyme comprising at least one or more nuclear localization sequences, wherein the CRISPR enzyme comprises at least one mutation, such that the CRISPR enzyme has no more than 5% of the nuclease activity of the CRISPR enzyme not having the at least one mutation.

23. The composition of any one of numbered paragraphs 20-22, wherein the CRISPR enzyme has a diminished nuclease activity of at least 97%, or 100% as compared with the CRISPR enzyme not having the at least one mutation.

24. The composition of any one of numbered paragraphs 20-23, wherein the CRISPR enzyme comprises two or more mutations wherein two or more of D10, E762, H840, N854, N863, or D986 according to SpCas9 protein or any corresponding ortholog are mutated, or the CRISPR enzyme comprises at least one mutation wherein at least H840 is mutated.

25. The composition of numbered paragraph 24 wherein the CRISPR enzyme comprises two or more mutations comprising D10A, E762A, H840A, N854A, N863A or D986A according to SpCas9 protein or any corresponding ortholog, or at least one mutation comprising H840A.

26. The composition of any one of numbered paragraphs 20-23, wherein the CRISPR enzyme comprises H840A, or D10A and H840A, or D10A and N863A, according to SpCas9 protein or any corresponding ortholog.

27. The composition of any one of numbered paragraphs 21-26, wherein the CRISPR enzyme is associated with one or more functional domains.

28. The composition of numbered paragraph 27, wherein the one or more functional domains associated with the adaptor protein is a heterologous functional domain.

29. The composition of numbered paragraph 27, wherein the one or more functional domains associated with the CRISPR enzyme is a heterologous functional domain.

30. The composition of any one of numbered paragraphs 21-29, wherein the adaptor protein is a fusion protein comprising the functional domain.

31. The composition of any one of numbered paragraphs 21-30, wherein the one or more functional domains associated with the adaptor protein is a transcriptional activation domain.

32. The composition of any one of numbered paragraphs 21-31, wherein the one or more functional domains associated with the CRISPR enzyme is a transcriptional activation domain.

33. The composition of any one of numbered paragraphs 21-32, wherein the one or more functional domains associated with the adaptor protein is a transcriptional activation domain comprising VP64, p65, MyoD1 or HSF1.

34. The composition of any one of numbered paragraphs 21-33, wherein the one or more functional domains associated with the CRISPR enzyme is a transcriptional activation domain comprises VP64, p65, MyoD1 or HSF1.

35. The composition of any one of numbered paragraphs 21-30, wherein the one or more functional domains associated with the adaptor protein is a transcriptional repressor domain.

36. The composition of any one of numbered paragraphs 21-30, wherein the one or more functional domains associated with the CRISPR enzyme is a transcriptional repressor domain.

37. The composition of numbered paragraph 35 or 36, wherein the transcriptional repressor domain is a KRAB domain.

38. The composition of numbered paragraph 35 or 36, wherein the transcriptional repressor domain is a SID domain or a SID4X domain.

39. The composition of any one of numbered paragraphs 21-30, wherein at least one of the one or more functional domains associated with the adaptor protein have one or more activities comprising methylase activity, demethylase activity, transcription activation activity, transcription repression activity, transcription release factor activity, histone modification activity, RNA cleavage activity, DNA cleavage activity or nucleic acid binding activity.

40. The composition of any one of numbered paragraphs 21-30, wherein the one or more functional domains associated with the CRISPR enzyme have one or more activities comprising methylase activity, demethylase activity, transcription activation activity, transcription repression activity, transcription release factor activity, histone modification activity, RNA cleavage activity, DNA cleavage activity, nucleic acid binding activity, or molecular switch activity or chemical inducibility or light inducibility.

41. The composition of any one of numbered paragraphs 39-40, wherein the DNA cleavage activity is due to a Fok1 nuclease.

42. The composition of any one of numbered paragraphs 21-41, wherein the one or more functional domains is attached to the CRISPR enzyme so that upon binding to the sgRNA and target the functional domain is in a spatial orientation allowing for the functional domain to function in its attributed function.

43. The composition of any one of numbered paragraphs 21-41, wherein the sgRNA is modified so that, after sgRNA binds the adaptor protein and further binds to the CRISPR enzyme and target, the functional domain is in a spatial orientation allowing for the functional domain to function in its attributed function.

44. The composition of any one of numbered paragraphs 21-41, wherein the one or more functional domains associated with the CRISPR enzyme is attached to the Red domain, the Rec2 domain, the HNH domain, or the PI domain of the SpCas9 protein or any ortholog corresponding to these domains.

45. The composition of any one of numbered paragraphs 21-44, wherein the one or more functional domains associated with the CRISPR enzyme is attached to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains.

46. The composition of any one of numbered paragraphs 21-45, wherein the one or more functional domains associated with the CRISPR enzyme is attached to the Red domain or the Rec2 domain, of the SpCas9 protein or any ortholog corresponding to these domains.

47. The composition of any one of numbered paragraphs 21-46, wherein the one or more functional domains associated with the CRISPR enzyme is attached to the Rec2 domain of the SpCas9 protein or any ortholog corresponding to this domain.

48. The composition of any one of numbered paragraphs 21-47, wherein the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s or PRR1.

49. The composition of any one of numbered paragraphs 20-47 wherein the composition is in a cell or progeny thereof.

50. The composition of numbered paragraph 49, wherein the cell is a eukaryotic cell or progeny thereof 51. The composition of numbered paragraph 50, wherein the eukaryotic cell is a mammalian cell or progeny thereof 52. The composition of numbered paragraph 51, wherein the mammalian cell is a human cell or progeny thereof.

53. The composition of any one of numbered paragraphs 21-52, wherein a first adaptor protein is associated with a p65 domain and a second adaptor protein is associated with a HSF1 domain.

54. The composition of any one of numbered paragraphs 20-53, wherein the composition comprises a CRISPR-Cas complex having at least three functional domains, at least one of which is associated with the CRISPR enzyme and at least two of which are associated with sgRNA.

55. A method for introducing a genomic locus event comprising the administration to a host or expression in a host in vivo of one or more of the compositions according to any one of numbered paragraphs 1-54.

56. The method according to numbered paragraph 55, wherein the genomic locus event comprises affecting gene activation, gene inhibition, or cleavage in the locus.

57. The method according to numbered paragraphs 55 or 56, wherein the host is a eukaryotic cell or progeny thereof.

58. The method according to numbered paragraph 57, wherein the host is a mammalian cell or progeny thereof 59. The method according to numbered paragraphs 55 or 56, wherein the host is a non-human eukaryote or progeny thereof.

60. The method according to numbered paragraph 59, wherein the non-human eukaryote is a non-human mammal or progeny thereof.

61. The method according to numbered paragraph 60, wherein the non-human mammal is a mouse or progeny thereof.

62. A method of modifying a genomic locus of interest to change gene expression in a cell or progeny thereof by introducing or expressing in a cell the composition of any one of numbered paragraphs 1-54.

63. The method according to any one of numbered paragraphs 55-62 comprising the delivery of the composition or nucleic acid molecule(s) coding therefor, wherein said nucleic acid molecule(s) are operatively linked to regulatory sequence(s) and expressed in vivo.

64. The method according to numbered paragraph 63 wherein the expression in vivo is via a lentivirus, an adenovirus, or an AAV.

65. The pgRNA as defined in any one of numbered paragraphs 1-19 or 21, wherein the extension sequence comprises chemically modified bases.

66. The pgRNA as defined in any one of numbered paragraphs 1-19 or 21, wherein the protector sequence comprise chemically modified bases.

67. The pgRNA as defined in any one of numbered paragraphs 1-19 or 21, wherein the guide sequence comprise chemically modified bases.

68. The pgRNA as defined in any one of numbered paragraphs 1-19 or 21, wherein both extension sequence and the protector sequence comprise chemically modified bases.

69. The pgRNA as defined in any one of numbered paragraphs 1-19 or 21, wherein the extension sequence, the protector sequence, and the guide sequence comprise chemically modified bases.

70. The pgRNA as defined in any one of numbered paragraphs 1-19, 21 or 65-69, wherein the binding free energy of the protector sequence is designed so that the overall free energy of the reaction is in a range of no more than +/−10% from zero.

71. The pgRNA as defined in any one of numbered paragraphs 1-19, 21 or 65-70, wherein the binding free energy of the protector sequence is designed so that the overall free energy of the reaction is in a range of no more than +/−5% from zero.

72. The pgRNA as defined in any one of numbered paragraphs 1-19, 21 or 65-71, wherein the binding free energy of the protector sequence is designed so that the overall free energy of the reaction is in a range of no more than +/−2% from zero.

73. The pgRNA as defined in any one of numbered paragraphs 1-19, 21 or 65-72, wherein the binding free energy of the protector sequence is designed so that the overall free energy of the reaction is zero.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. An engineered, non-naturally occurring composition comprising a CRISPR Cas system comprising:
   (I) a Cas9 protein or a polynucleotide encoding the Cas9 protein; and
   (II) a protected guide or a polynucleotide encoding the protected guide, wherein the protected guide comprising, from 5' to 3', (a) a protector sequence, (b) a guide sequence capable of hybridizing to a target sequence in a eukaryotic cell and directing sequence-specific binding of a CRISPR complex to the target sequence, (c) a tracr mate sequence, and (d) a tracr sequence capable of hybridizing to the tracr mate sequence, wherein the protector sequence comprises three or more nucleotides that are complementary to the guide sequence and two or more nucleotides that are non-complementary to the target sequence, and wherein the protected guide comprises a hairpin formed by hybridization between the protector sequence and the guide sequence.

2. The composition of claim 1, wherein the protected guide is a chimeric RNA.

3. The composition of claim 1, wherein the protector sequence has a length between 3 and 120 nucleotides.

4. The composition of claim 1, wherein the guide sequence comprises a protected part and an exposed part, and the exposed part is 1 to 19 nucleotides.

5. The composition of claim 1, wherein the guide sequence is at least 90% or about 100% complementary to the protector sequence.

6. The composition of claim 1, wherein the protected guide further comprises an extension sequence between the 5' end of the guide sequence and the 3' end of the protector sequence.

7. The composition of claim 6, wherein the extension sequence is 100% not complementary to the protector sequence.

8. The composition of claim 1, wherein the guide sequence further comprises mismatches appended to the end of the guide sequence, and wherein the mismatches thermodynamically optimize specificity.

9. The composition of claim 1, wherein the Cas9 comprises one or more nuclear localization sequences.

10. An isolated cell comprising the composition of claim 9.

11. The isolated cell of claim 10, wherein the cell is a eukaryotic cell.

12. The isolated cell of claim 11, wherein the eukaryotic cell is a mammalian cell.

13. The isolated cell of claim 12, wherein the mammalian cell is a human cell.

14. The composition of claim 1, wherein the protector sequence is 10-30 nucleotides.

15. The composition of claim 1, wherein the guide sequence is 10-30 nucleotides.

16. The composition of claim 1, wherein the guide sequence is at least 75% complementary to the target sequence.

17. The composition of claim 1, wherein the guide sequence is at least 90% complementary to the target sequence.

18. The composition of claim 1, wherein the guide sequence is about 100% complementary to the target sequence.

19. The composition of claim 1, wherein the tracr mate sequence is at least 75% complementary to the tracr sequence.

20. The composition of claim 1, wherein the tracr mate sequence is at least 90% complementary to the tracr sequence.

21. The composition of claim 1, wherein the tracr mate sequence is about 100% complementary to the tracr sequence.

22. The composition of claim 4, wherein the exposed part of the guide sequence is at least 75% complementary to the target sequence.

23. The composition of claim 4, wherein the exposed part of the guide sequence is at least 90% complementary to the target sequence.

24. The composition of claim 6, wherein the extension sequence is 12 nucleotides or less.

25. The composition of claim 6, wherein the extension sequence is at least 70% not complementary to the protector sequence.

26. The composition of claim 6, wherein the extension sequence is at least 80% not complementary to the protector sequence.

27. The composition of claim 6, wherein the extension sequence is at least 90% not complementary to the protector sequence.

28. The composition of claim 9, wherein the Cas9 comprises at least one mutation in the RuvC and/or HNH domain and has no more than 5% of the nuclease activity of a corresponding wild-type Cas9.

29. The composition of claim 9, wherein the Cas9 comprises at least two mutations in the RuvC and/or HNH domain and has diminished nuclease activity of at least 97% or 100% as compared with a corresponding wild-type Cas9.

* * * * *

SEQUENCE LISTING

```
<160> NUMBER OF SEQ ID NOS: 70

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"
```

```
<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 3

Pro Ala Ala Lys Arg Val Lys Leu Asp
1               5

<210> SEQ ID NO 4
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 4

Arg Gln Arg Arg Asn Glu Leu Lys Arg Ser Pro
1               5                   10

<210> SEQ ID NO 5
<211> LENGTH: 38
<212> TYPE: PRT
<213> ORGANISM: Homo sapiens

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
                20                  25                  30

Arg Asn Gln Gly Gly Tyr
            35

<210> SEQ ID NO 6
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 7
<211> LENGTH: 8
<212> TYPE: PRT
<213> ORGANISM: Unknown
<220> FEATURE:
```

```
<221> NAME/KEY: source
<223> OTHER INFORMATION: /note="Description of Unknown:
      Myoma T protein sequence"

<400> SEQUENCE: 7

Val Ser Arg Lys Arg Pro Arg Pro
1               5

<210> SEQ ID NO 8
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 8

Pro Pro Lys Lys Ala Arg Glu Asp
1               5

<210> SEQ ID NO 9
<211> LENGTH: 8
<212> TYPE: PRT
<213> ORGANISM: Homo sapiens

<400> SEQUENCE: 9

Pro Gln Pro Lys Lys Lys Pro Leu
1               5

<210> SEQ ID NO 10
<211> LENGTH: 12
<212> TYPE: PRT
<213> ORGANISM: Mus musculus

<400> SEQUENCE: 10

Ser Ala Leu Ile Lys Lys Lys Lys Lys Met Ala Pro
1               5                   10

<210> SEQ ID NO 11
<211> LENGTH: 5
<212> TYPE: PRT
<213> ORGANISM: Influenza virus

<400> SEQUENCE: 11

Asp Arg Leu Arg Arg
1               5

<210> SEQ ID NO 12
<211> LENGTH: 7
<212> TYPE: PRT
<213> ORGANISM: Influenza virus

<400> SEQUENCE: 12

Pro Lys Gln Lys Lys Arg Lys
1               5

<210> SEQ ID NO 13
<211> LENGTH: 10
<212> TYPE: PRT
<213> ORGANISM: Hepatitis delta virus

<400> SEQUENCE: 13

Arg Lys Leu Lys Lys Lys Ile Lys Lys Leu
1               5                   10
```

```
<210> SEQ ID NO 14
<211> LENGTH: 10
<212> TYPE: PRT
<213> ORGANISM: Mus musculus

<400> SEQUENCE: 14

Arg Glu Lys Lys Lys Phe Leu Lys Arg Arg
1               5                   10

<210> SEQ ID NO 15
<211> LENGTH: 20
<212> TYPE: PRT
<213> ORGANISM: Homo sapiens

<400> SEQUENCE: 15

Lys Arg Lys Gly Asp Glu Val Asp Gly Val Asp Glu Val Ala Lys Lys
1               5                   10                  15

Lys Ser Lys Lys
            20

<210> SEQ ID NO 16
<211> LENGTH: 17
<212> TYPE: PRT
<213> ORGANISM: Homo sapiens

<400> SEQUENCE: 16

Arg Lys Cys Leu Gln Ala Gly Met Asn Leu Glu Ala Arg Lys Thr Lys
1               5                   10                  15

Lys

<210> SEQ ID NO 17
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 17
nnnnnnnnnn nnnnnnnnnn ngg                                      23

<210> SEQ ID NO 18
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 18
```
nnnnnnnnnn nnngg                                              15

<210> SEQ ID NO 19
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 19
nnnnnnnnnn nnnnnnnnnn ngg                                     23

<210> SEQ ID NO 20
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 20
nnnnnnnnnn nngg                                               14

<210> SEQ ID NO 21
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 21
nnnnnnnnnn nnnnnnnnnn nnagaaw                                 27

<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

```
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 22
nnnnnnnnnn nnnnagaaw                                              19

<210> SEQ ID NO 23
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 23
nnnnnnnnnn nnnnnnnnnn nnagaaw                                     27

<210> SEQ ID NO 24
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 24
nnnnnnnnnn nnnagaaw                                               18

<210> SEQ ID NO 25
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 25
```
nnnnnnnnnn nnnnnnnnnn nggng					25

<210> SEQ ID NO 26
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 26
nnnnnnnnnn nnnggng					17

<210> SEQ ID NO 27
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 27
nnnnnnnnnn nnnnnnnnnn nggng					25

<210> SEQ ID NO 28
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 28
nnnnnnnnnn nnggng                                               16

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
atcgatcgat cgatcgatcg                                           20

<210> SEQ ID NO 30
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
cgatcgatcg atcg                                                 14

<210> SEQ ID NO 31
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
gaaatagcta                                                      10

<210> SEQ ID NO 32
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 32
nnnnnnnnnn nnnnnnnnnn gtttttgtac tctcaagatt tagaaataaa tcttgcagaa    60
gctacaaaga taaggcttca tgccgaaatc aacaccctgt catttatgg cagggtgttt    120 tcgttattta attttt                                                   137

<210> SEQ ID NO 33
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 33
nnnnnnnnnn nnnnnnnnnn gttttttgtac tctcagaaat gcagaagcta caaagataag    60
gcttcatgcc gaaatcaaca ccctgtcatt ttatggcagg gtgttttcgt tatttaattt   120
ttt                                                                  123

<210> SEQ ID NO 34
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 34
nnnnnnnnnn nnnnnnnnnn gttttttgtac tctcagaaat gcagaagcta caaagataag    60
gcttcatgcc gaaatcaaca ccctgtcatt ttatggcagg gtgtttttt                110

<210> SEQ ID NO 35
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 35
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 36
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 36
nnnnnnnnnn nnnnnnnnnn gttttagagc tagaaatagc aagttaaaat aaggctagtc    60
cgttatcaac ttgaaaaagt gtttttt                                        88

<210> SEQ ID NO 37
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

```
<221> NAME/KEY: modified_base
<222> LOCATION: (1)..(20)
<223> OTHER INFORMATION: a, c, t, g, unknown or other

<400> SEQUENCE: 37
nnnnnnnnnn nnnnnnnnnn gttttagagc tagaaatagc aagttaaaat aaggctagtc    60
cgttatcatt tttttt                                                   76

<210> SEQ ID NO 38
<211> LENGTH: 20
<212> TYPE: DNA
<213> ORGANISM: Homo sapiens

<400> SEQUENCE: 38
gagtccgagc agaagaagaa                                               20

<210> SEQ ID NO 39
<211> LENGTH: 20
<212> TYPE: DNA
<213> ORGANISM: Homo sapiens

<400> SEQUENCE: 39
gagtcctagc aggagaagaa                                               20

<210> SEQ ID NO 40
<211> LENGTH: 20
<212> TYPE: DNA
<213> ORGANISM: Homo sapiens

<400> SEQUENCE: 40
gagtctaagc agaagaagaa                                               20

<210> SEQ ID NO 41
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Gly Gly Ser
1

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 43

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25                  30

<210> SEQ ID NO 44
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser
        35                  40                  45

<210> SEQ ID NO 45
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly
        35                  40                  45

Gly Ser Gly Gly Gly Gly Ser Gly Gly Gly Ser
    50                  55                  60

<210> SEQ ID NO 46
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Gly Gly Ser Gly Gly Gly Ser Gly Gly Gly Ser
1               5                   10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 47

Ala Glu Ala Ala Ala Lys Ala
1               5

<210> SEQ ID NO 48
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
guuuuagagc ua                                                          12

<210> SEQ ID NO 49
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Gly Ser Gly
1

<210> SEQ ID NO 50
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gly Gly Gly Gly Ser
1               5

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gly Gly Gly Gly Ser Gly Gly Gly Gly Ser
1               5                   10

<210> SEQ ID NO 52
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gly Gly Gly Gly Ser Gly Gly Gly Gly Ser Gly Gly Gly Gly Ser Gly
1               5                   10                  15
```

Gly Gly Gly Ser
        20

<210> SEQ ID NO 53
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 54
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 55
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 56
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly

```
            20                  25                  30

Gly Gly Ser Gly Gly Gly Ser Gly Gly Gly Ser Gly Gly Gly
        35                  40                  45

Gly Ser
    50

<210> SEQ ID NO 57
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser Gly Gly Gly Gly Ser
    50                  55

<210> SEQ ID NO 58
<211> LENGTH: 9
<212> TYPE: PRT
<213> ORGANISM: Homo sapiens

<400> SEQUENCE: 58

Leu Ala Gly Leu Ile Asp Ala Asp Gly
1               5

<210> SEQ ID NO 59
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
caaacggcag aagctggagg aggaagggcc tgagtccgag cagaagaaga agggctccca    60
t                                                                    61

<210> SEQ ID NO 60
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
gcaaatagag ccctttattc atagtagaca agagtctaag cagaagaaga agagagccac    60
t                                                                    61

<210> SEQ ID NO 61
<211> LENGTH: 30
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
ggaagggcct gagtccgagc agaagaagaa                                    30

<210> SEQ ID NO 62
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
tcatccgagc agaagaagaa                                               20

<210> SEQ ID NO 63
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
ggtcatccga gcagaagaag aa                                            22

<210> SEQ ID NO 64
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(10)
<223> OTHER INFORMATION: a, c, t, g, unknown or other

<400> SEQUENCE: 64
nnnnnnnnnn gagtccgagc agaagaagaa                                    30

<210> SEQ ID NO 65
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other

<400> SEQUENCE: 65
nngagtccga gcagaagaag aa                                            22

<210> SEQ ID NO 66
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: a, c, t, g, unknown or other

<400> SEQUENCE: 66
ngagtccgag cagaagaaga a                                             21

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
gtcacctcca atgactaggg                                               20

<210> SEQ ID NO 68
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
gagtccgagc agaagaagaa                                               20

<210> SEQ ID NO 69
<211> LENGTH: 102
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
gucaccucca augacuaggg guuuuagagc uagaaauagc aaguuaaaau aaggcuaguc   60
cguuaucaac uugaaaaagu ggcaccgagu cggugcuuuu uu                    102

<210> SEQ ID NO 70
<211> LENGTH: 117
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70
ggggaggaca ucgaugucac cuccaaugac uagggguuuu agagcuagaa auagcaaguu   60
aaaauaaggc uaguccguua ucaacuugaa aaaguggcac cgagucggug cuuuuuu    117
```